(12) United States Patent     (10) Patent No.:   US 12,686,725 B2

Hassanzadeh Ghassabeh et al.     (45) Date of Patent:    Jul. 21, 2026

(54) ANTI-DLL3 ANTIBODIES AND METHODS OF USE

(71) Applicant: Mythic Therapeutics, Inc., Waltham, MA (US)

(72) Inventors: Gholamreza Hassanzadeh Ghassabeh, Ghent (BE); Lorena Lerner, Andover, MA (US); Sonia Feau, Chestnut Hill, MA (US); Christophe Quéva, Cambridge, MA (US)

(73) Assignee: Mythic Therapeutics, Inc., Waltham, MA (US)

( * ) Notice: Subject to any disclaimer, the term of this patent is extended or adjusted under 35 U.S.C. 154(b) by 666 days.

(21) Appl. No.: 17/997,907

(22) PCT Filed: May 5, 2021

(86) PCT No.: PCT/US2021/030836

§ 371 (c)(1),
(2) Date: Nov. 3, 2022

(87) PCT Pub. No.: WO2021/226204

PCT Pub. Date: Nov. 11, 2021

(65) Prior Publication Data

US 2023/0227577 A1    Jul. 20, 2023

Related U.S. Application Data

(60) Provisional application No. 63/020,444, filed on May 5, 2020.

(51) Int. Cl.

| | |
|---|---|
| *C07K 16/30* | (2006.01) |
| *A61P 35/00* | (2006.01) |
| *C07K 16/28* | (2006.01) |
| *C12N 15/63* | (2006.01) |

(52) U.S. Cl.

CPC .......... *C07K 16/3023* (2013.01); *A61P 35/00* (2018.01); *C07K 16/2809* (2013.01); *C12N 15/63* (2013.01); *C07K 2317/31* (2013.01); *C07K 2317/52* (2013.01); *C07K 2317/565* (2013.01)

(58) Field of Classification Search

CPC . C07K 16/3023; C07K 16/2809; A61P 35/00; C12N 15/63

See application file for complete search history.

(56) References Cited

U.S. PATENT DOCUMENTS

| | | | |
|---|---|---|---|
| 4,579,821 | A | 4/1986 | Palmiter et al. |
| 4,656,134 | A | 4/1987 | Ringold |
| 4,713,339 | A | 12/1987 | Levinson et al. |
| 4,784,950 | A | 11/1988 | Hagen et al. |
| 4,946,778 | A | 8/1990 | Ladner et al. |
| 5,037,743 | A | 8/1991 | Welch et al. |
| 5,091,513 | A | 2/1992 | Huston et al. |
| 5,132,405 | A | 7/1992 | Huston et al. |
| 5,143,830 | A | 9/1992 | Holland et al. |
| 5,283,173 | A | 2/1994 | Fields et al. |
| 5,468,614 | A | 11/1995 | Fields et al. |
| 7,078,387 | B1 | 7/2006 | Leiden et al. |
| 8,088,376 | B2 | 1/2012 | Chamberlain et al. |
| 8,188,223 | B2 | 5/2012 | Beirnaert et al. |
| 8,394,925 | B2 | 3/2013 | Chamberlain et al. |
| 9,233,125 | B2 | 1/2016 | Davila et al. |
| 9,624,279 | B2 | 4/2017 | Nonaka et al. |
| 9,701,750 | B2 | 7/2017 | Hoffmann et al. |
| 10,174,124 | B2 | 1/2019 | Chen et al. |
| 10,308,721 | B2 | 6/2019 | Williams et al. |
| 10,336,818 | B2 | 7/2019 | Chamberlain et al. |
| 10,344,087 | B2 | 7/2019 | Bonnafous et al. |
| 2008/0145362 | A1 | 6/2008 | Kipriyanov et al. |
| 2013/0095097 | A1 | 4/2013 | Blankenship et al. |
| 2013/0129723 | A1 | 5/2013 | Blankenship et al. |
| 2013/0156770 | A1 | 6/2013 | Kufer et al. |
| 2013/0243775 | A1 | 9/2013 | Papadopoulos et al. |
| 2013/0287748 | A1 | 10/2013 | June et al. |
| 2015/0238631 | A1 | 8/2015 | Kim et al. |
| 2016/0083449 | A1 | 3/2016 | Schmitt et al. |
| 2016/0176973 | A1 | 6/2016 | Kufer et al. |
| 2017/0007715 | A1 | 1/2017 | Andreev et al. |
| 2017/0191055 | A1 | 7/2017 | Short et al. |
| 2017/0210802 | A1 | 7/2017 | Gauthier et al. |

(Continued)

FOREIGN PATENT DOCUMENTS

| | | |
|---|---|---|
| EP | 2552955 | 2/2013 |
| KR | 10-2018-0025865 | 3/2018 |

(Continued)

OTHER PUBLICATIONS

"Tolerance to Single, but Not Multiple, Amino Acid Replacements in Antibody VH CDR2," Brown et al, J. Immunology, 156(9), 3285-3291. (Year: 1996).*

"Progress and Challenges in the Design and Clinical Development of Antibodies for Cancer Therapy," Almagro et al, Frontiers in Immunology, vol. 8 (Year: 2018).*

Ahmed et al., "Human Epidermal Growth Factor Receptor 2 (HER2)—Specific Chimeric Antigen Receptor-Modified T Cells for the Immunotherapy of HER2-Positive Sarcoma," Journal of Clinical Oncology, May 2015, 33(15):1688-1696.

(Continued)

*Primary Examiner* — Julie Wu

(74) *Attorney, Agent, or Firm* — Fish & Richardson P.C.

(57) ABSTRACT

The present disclosure provides anti-DLL3 binding constructs, such as anti-DLL3 single domain antibodies, as well as polynucleotide encoding the same. Further provided are multispecific binding constructs comprising the DLL3 binding domains described herein and polynucleotides encoding the same. Methods of production of the anti-DLL3 binding constructs and their use in the treatment of cancer are also provided herein.

24 Claims, 12 Drawing Sheets

Specification includes a Sequence Listing.

(56)　　　　References Cited

U.S. PATENT DOCUMENTS

| 2018/0104354 A1 | 4/2018 | Kim et al. |
| 2018/0208658 A1 | 7/2018 | Liu et al. |
| 2018/0243435 A1 | 8/2018 | Dylla et al. |
| 2018/0355038 A1 | 12/2018 | Smith et al. |
| 2019/0024078 A1 | 1/2019 | Short et al. |
| 2019/0040135 A1 | 2/2019 | Huang et al. |
| 2019/0046656 A1 | 2/2019 | Stull et al. |
| 2019/0263907 A1 | 8/2019 | Raum et al. |
| 2019/0270817 A1 | 9/2019 | Ali et al. |
| 2020/0010547 A1 | 1/2020 | Koch et al. |
| 2020/0071405 A1 | 3/2020 | Xiao et al. |
| 2021/0380679 A1* | 12/2021 | Eckelman .............. C07K 16/28 |

FOREIGN PATENT DOCUMENTS

| WO | WO 1993/003769 | 3/1993 |
| WO | WO 1993/009239 | 5/1993 |
| WO | WO 1993/011161 | 6/1993 |
| WO | WO 1993/019191 | 9/1993 |
| WO | WO 1994/012649 | 6/1994 |
| WO | WO 1994/013804 | 6/1994 |
| WO | WO 1994/028938 | 12/1994 |
| WO | WO 1995/000655 | 1/1995 |
| WO | WO 1995/011984 | 5/1995 |
| WO | WO 1997/009433 | 3/1997 |
| WO | WO 2006/079372 | 8/2006 |
| WO | WO 2008/119567 | 10/2008 |
| WO | WO 2009/091826 | 7/2009 |
| WO | WO 2011/111007 | 9/2011 |
| WO | WO 2011/122011 | 10/2011 |
| WO | WO 2013/138400 | 9/2013 |
| WO | WO 2014/055657 | 4/2014 |
| WO | WO 2014/177595 | 11/2014 |
| WO | WO 2014/207063 | 12/2014 |
| WO | WO 2015/090229 | 6/2015 |
| WO | WO 2015/142675 | 9/2015 |
| WO | WO 2017/055398 | 4/2017 |
| WO | WO 2017/134197 | 8/2017 |
| WO | WO 2018/044619 | 3/2018 |
| WO | WO 2018/136455 | 7/2018 |
| WO | WO 2019/016237 | 1/2019 |
| WO | WO 2019/222278 | 11/2019 |
| WO | WO 2019/222282 | 11/2019 |
| WO | WO 2019/222283 | 11/2019 |

OTHER PUBLICATIONS

Ahmed et al., "Immunotherapy for Osteosarcoma: Genetic Modification of T cells Overcomes Low Levels of Tumor Antigen Expression," Molecular Therapy, Oct. 2009, 17(10):1779-1787.

Ali et al., "Adeno-associated virus gene transfer to mouse retina," Human Gene Therapy, Jan. 1998, 9(1):81-86.

Ali et al., "Gene transfer into the mouse retina mediated by an adeno-associated viral vector," Human Molecular Genetics, Jan. 1996, 5(5):591-594.

Arduin et al., "Highly reduced binding to high and low affinity mouse Fc gamma receptors by L234A/L235A and N297A Fc mutations engineered into mouse IgG2a," Molecular Immunology, 2015, 63(2):456-463.

Augustyn et al., "ASCL1 is a lineage oncogene providing therapeutic targets for high-grade neuroendocrine lung cancers," Proc Natl Acad Science USA, Oct. 2014, 111(41):14788-14793.

Bennett et al., "Real-Time, Noninvasive In Vivo Assessment of Adeno-Associated Virus-Mediated Retinal Transduction," Investigative Ophthalmology & Visual Science, Dec. 1997, 38(13):2857 2863.

Bird et al., "Single-chain antigen-binding proteins," Science, Oct. 1988, 242:423-426.

Bonvin et al., "De novo isolation of antibodies with pH-dependent binding properties," MABS, 2015, 7(2):294-302.

Borras et al., "Adenoviral reporter gene transfer to the human trabecular meshwork does not alter aqueous humor outflow. Relevance for potential gene therapy of glaucoma," Gene Therapy, Apr. 1999, 6:515-524.

Borrok et al., "pH-dependent Binding Engineering Reveals an FcRn Affinity Threshold That Governs IgG Recycling," The Journal of Biological Chemistry, Feb. 13, 2015, 290(7):4282-4290.

Borromeo et al., "ASCL1 and NEUROD1 Reveal Heterogeneity in Pulmonary Neuroendocrine Tumors and Regulate Distinct Genetic Programs," Cell Reports, Aug. 2016, 16(5):1259-1272.

Brando et al., "Receptors and lytic mediators regulating anti-tumor activity by the leukemic killer T cell line TALL-104," Journal of Leukocyte Biology, Aug. 2005, 78:359-371.

Brown et al., "Bioactivity and Safety of IL13Ra2-Redirected Chimeric Antigen Receptor CD8 T Cells in Patients with Recurrent Glioblastoma," Clinical Cancer Research, Jun. 2015, 21(18):4062-4072.

Caruana et al., "Heparanase promotes tumor infiltration and anti-tumor activity of CAR-redirected T lymphocytes," Nature Medicine, May 2015, 21(5):524-529.

Cheong et al., "Diagnostic and therapeutic potential of shark variable new antigen receptor (VNAR) single domain antibody," International Journal of Biological Macromolecules, Mar. 2020, 147:369-375.

Co, et al., "Humanized antibodies for antiviral therapy," Proc Natl. Acad. Sci. USA, Apr. 1991, 88:2869-2873.

Corsaro et al., "Enhancing the efficiency of DNA-mediated gene transfer in mammalian cells," Somatic Cell Genetics, Sep. 1981, 7(5):603-616.

Debets et al., "TCR-engineered T cells to treat tumors: Seeing but not touching?" Seminars in Immunology, Feb. 2016, 28(1):10-21.

Ehrlich et al., "Isolation of an active heavy-chain variable domain from a homogeneous rabbit antibody by cathepsin B digestion of the aminoethylated heavy chain," Biochemistry, Aug. 1980, 19(17):4091-4096.

El-Sherbiny et al., "The Requirement for DNAM-1, NKG2D, and NKp46 in the Natural Killer Cell-Mediated Killing of Myeloma Cells," Cancer Research, Sep. 2007, 67(18):8444-9.

Flannery et al., "Efficient photoreceptor-targeted gene expression in vivo by recombinant adeno-associated virus," Proc. Natl. Acad. Sci. USA, Jun. 1997, 94:6916-6921.

Flotte et al., "Stable in vivo expression of the cystic fibrosis transmembrane conductance regulator with an adeno-associated virus vector," Proc. Natl. Acad. Sci. USA, Nov. 1993, 90:10613-10617.

Furuta et al., "DLL3 regulates the migration and invasion of small cell lung cancer by modulating Snail," Cancer Science, Apr. 2019, 110(5):1599-1608.

Grada et al., "TanCAR: A Novel Bispecific Chimeric Antigen Receptor for Cancer Immunotherapy," Molecular Therapy—Nucleic Acids, Jul. 2013, 2(7) 11 pages.

Graham et al., "A New Technique for the Assay of Infectivity of Human Adenovirus 5 DNA," Virology, Apr. 1973, 52(2):456-467.

Hochman et al., "Folding and interaction of subunits at the antibody combining site," Biochemistry, Jun. 1976, 15(12):2706-2710.

Holliger et al., "Diabodies: small bivalent and bispecific antibody fragments," Proc. Natl. Acad. Sci. USA, Jul. 1993, 90(14):6444-6448.

Horton et al., "Potent In vitro and In vivo Activity of an Fc-Engineered Anti-CD19 Monoclonal Antibody against Lymphoma and Leukemia," Cancer Research, Oct. 2008, 68(19):8049-57.

Hu et al., "Minibody: A Novel Engineered Anti Carcinoembryonic Antigen Antibody Fragment (Single-Chain Fv-CH3) Which Exhibits Rapid, High-Level Targeting of Xenografts1," Cancer Research, Jul. 1996, 56(13):3055-3061.

Huston et al., "Protein engineering of antibody binding sites: Recovery of specific activity in an anti-digoxin single-chain Fv analogue produced in *Escherichia coli*," Proc. Nat. Acad. Sci. USA, Aug. 1988, 85(16):5879-5883.

Igawa et al., "pH-dependent antigen-binding antibodies as a novel therapeutic modality," Biochimica et Biophysica Acta (BBA)—Proteins and Proteomics, Nov. 2014, 1844(11):1943-1950.

(56)                  References Cited

OTHER PUBLICATIONS

Inbar et al., "Localization of Antibody-Combining Sites within the Variable Portions of Heavy and Light Chains," Proc. Nat. Acad. Sci. USA, Sep. 1972, 69(9):2659-2662.

International Preliminary Report on Patentability in International Appln. No. PCT/US2021/030836, mailed on Nov. 22, 2021, 8 pages.

International Search Report in International Appln. No. PCT/US2021/030836, mailed on Nov. 22, 2022, 5 pages.

Irions et al., "Identification and targeting of the ROSA26 locus in human embryonic stem cells,"Nature Biotechnology, Dec. 2007, 25(12):1477-1482.

Johnson et al., "Gene therapy with human and mouse T-cell receptors mediates cancer regression and targets normal tissues expressing cognate antigen," Blood, Jul. 2009, 114(3):535-546.

Jomary et al., "Rescue of photoreceptor function by AAV-mediated gene transfer in a mouse model of inherited retinal degeneration," Gene Therapy, Mar. 1997, 4:683-690.

Jones et al., "Replacing the complementarity-determining regions in a human antibody with those from a mouse," Nature, May 1986, 321:522.

Karlin et al., Applications and statistics for multiple high-scoring segments in molecular sequences, Proc. Natl. Acad. Sci. USA, Jun. 1993, 90(12):5873-5877.

Katz et al., "Phase I Hepatic Immunotherapy for Metastases Study of Intra-Arterial Chimeric Antigen Receptor-Modified T-cell Therapy for CEA+ Liver Metastases," Clinical Cancer Research, Jul. 2015, 21(14):3149-3159.

Kershaw et al., "A phase I study on adoptive immunotherapy using gene-modified T cells for ovarian cancer," Clinical Cancer Research, Oct. 2006, 12(20):6106-6015.

Kobold et al., "Selective Bispecific T Cell Recruiting Antibody and Antitumor Activity of Adoptive T Cell Transfer," Journal of the National Cancer Institute, Jan. 2014, 107(1):364.

Kunnimalaiyaan et al., "Tumor Suppressor Role of Notch-1 Signaling in Neuroendocrine Tumors," Oncologist, May 2007, 12(5):535-542.

Lamers et al., "Treatment of metastatic renal cell carcinoma (mRCC) with CAIX CAR-engineered T-cells—A completed study overview," Biochem Soc Trans, Jun. 2016, 44(3):951-959.

Lehman et al., "Immunotherapy and Targeted Therapy for Small Cell Lung Cancer: There Is Hope," Curr Oncol Rep., Jul. 2017, 19(7):49.

Li et al., "Chimeric antigen receptor T cell (CAR-T) immunotherapy for solid tumors: lessons learned and strategies for moving forward," Journal of Hematology and Oncology, Feb. 2018, 11(1) 18 pages.

Li et al., "In Vivo Transfer of a Reporter Gene to the Retina Mediated by an Adenoviral Vector," Investigative Ophthalmology & Visual Science, Apr. 1994, 35(5):2543-2549.

Li et al., "Phenotype correction in retinal pigment epithelium in murine mucopolysaccharidosis VII by adenovirus-mediated gene transfer," PNAS, Aug. 1995, 92(17):7700-7704.

Linette et al., "Cardiovascular toxicity and titin cross-reactivity of affinity-enhanced T cells in myeloma and melanoma," Blood, Aug. 2013, 122(6):227-242.

Louis et al., "Antitumor activity and long-term fate of chimeric antigen receptor-positive T cells in patients with neuroblastoma," Blood, Dec. 2011, 118(23):6050-6056.

Luo et al., "Bifunctional αHER2/CD3 RNA-engineered CART-like human T cells specifically eliminate HER2(+) gastric cancer," Cell Research, Jun. 2016, 26(7):850-853.

Mendelson et al., "Expression and rescue of a nonselected marker from an integrated AAV vector," Virology, Sep. 1988, 166:154-165.

Miyoshi et al., "Stable and efficient gene transfer into the retina using an HIV-based lentiviral vector," PNAS, Sep. 1997, 94(19):10319-23.

Molgaard et al., "Bispecific light T-cell engagers for gene-based immunotherapy of epidermal growth factor receptor (EGFR)-positive malignancies," Cancer Immunol Immunother., Aug. 2018, 67(8):1251-1260.

Moon et al, "Expression of a Functional CCR2 Receptor Enhances Tumor Localization and Tumor Eradication by Retargeted Human T cells Expressing a Mesothelin-Specific Chimeric Antibody Receptor," Clinical Cancer Research, May 2011, 17(14):4719-30.

Moon et al., "Blockade of Programmed Death 1 Augments the Ability of Human T Cells Engineered to Target NY-ESO-1 to Control Tumor Growth after Adoptive Transfer," Clinical Cancer Research, Jan. 2016, 22(2):436-447.

Morgan et al., "Cancer regression and neurologic toxicity following anti-MAGE A3 TCR gene therapy," J Immunother, Feb. 2013, 36:133-151.

Morgan et al., "Cancer Regression in Patients After Transfer of Genetically Engineered Lymphocytes," Science, Oct. 2006, 314:126-129.

Morgan et al., "Case Report of a Serious Adverse Event Following the Administration of T Cells Transduced With a Chimeric Antigen Receptor Recognizing ErbB2," Molecular Therapy, Apr. 2010, 18(4):843-851.

Morgan et al., "Recognition of glioma stem cells by genetically modified T cells targeting EGFRvIII and development of adoptive cell therapy for glioma," Human Gene Therapy, Sep. 2012, 23(10):1043-1053.

Nakazawa et al., "PiggyBac-mediated Cancer Immunotherapy Using EBV-specific Cytotoxic T-cells Expressing HER2-specific Chimeric Antigen Receptor," Molecular Therapy, Dec. 2011, 19(12):2133-2143.

Neumann et al., "Gene transfer into mouse lyoma cells by electroporation in high electric fields," The EMBO Journal, Jan. 1982, 1(7):841-845.

Nolte-'t Hoen et al., "Increased surveillance of cells in mitosis by human NK cells suggests a novel strategy for limiting tumor growth and viral replication," Blood, Jan. 2007, 109(2):670-673.

Padlan, "Anatomy of the Antibody Molecule," Molecular Immunology, Feb. 1994, 31(3):169-217.

Park et al., "Adoptive Transfer of Chimeric Antigen Receptor Re-directed Cytolytic T Lymphocyte Clones in Patients with Neuroblastoma," Molecular Therapy, Apr. 2007, 15(4):825-833.

Parkhurst et al., "T Cells Targeting Carcinoembryonic Antigen Can Mediate Regression of Metastatic Colorectal Cancer but Induce Severe Transient Colitis," Molecular Therapy, Mar. 2011, 19(3):620-626.

Pereira et al., "The "less-is-more" in therapeutic antibodies: Afucosylated anti-cancer antibodies with enhanced antibody-dependent cellular cytotoxicity," Mabs, Jul. 2018, 10(5):693-711.

Pessino et al., "Molecular Cloning of NKp46: A Novel Member of the Immunoglobulin Superfamily Involved in Triggering of Natural Cytotoxicity," Journal of Experimental Medicine, Sep. 1998, 188(5):953-960.

Poljak et al., "Production and structure of diabodies," Structure, Dec. 1994, 2:1121-23.

Queen et al., "A humanized antibody that binds to the interleukin 2 receptor," Proc. Natl. Acad. Sci. USA, Dec. 1989, 86:10029-10033.

Rapoport et al., "NY-ESO-1-specific TCR-engineered T cells mediate sustained antigen-specific antitumor effects in myeloma," Nature Medicine, Aug. 2015, 21:914-921.

Reiter et al., "Engineering antibody Fv fragments for cancer detection and therapy: disulfide-stabilized Fv fragments," Nature Biotechnology, Oct. 1996, 14(10):1239-1245.

Riechmann, et al., "Reshaping human antibodies for therapy," Nature, Mar. 1988, 332:323-327.

Robbins et al., "A Pilot Trial Using Lymphocytes Genetically Engineered with an NY-ESO-1-Reactive T-cell Receptor: Long-term Follow-up and Correlates with Response," Clinical Cancer Research, Mar. 2015, 21(5):1019-1027.

Robbins et al., "Tumor Regression in Patients With Metastatic Synovial Cell Sarcoma and Melanoma Using Genetically Engineered Lymphocytes Reactive With NY-ESO-1," Journal of Clinical Oncology, Mar. 2011, 29(7):917-924.

(56)     References Cited

OTHER PUBLICATIONS

Rolling et al., "Evaluation of Adeno-Associated Virus-Mediated Gene Transfer into the Rat Retina by Clinical Fluorescence Photography," Hum Gene Ther., Mar. 1999, 10:641-648.

Runcie et al., "Bi-specific and tri-specific antibodies—the next big thing in solid tumor therapeutics," Molecular Medicine, Sep. 2018, 24, 16 pages.

Sabari et al., "Unravelling the biology of SCLC: implications for therapy," Nature Reviews Clinical Oncology, May 2017, 14(9):549-561.

Sakamoto et al., "A vitrectomy improves the transfection efficiency of adenoviral vector-mediated gene transfer to Muller cells," Gene Therapy, Aug. 1998, 5(8):1088-1097.

Samulski et al., "Helper-free stocks of recombinant adeno-associated viruses: normal integration does not require viral gene expression," Journal of Virology, Sep. 1989, 63:3822-3828.

Saunders et al., "A DLL3-targeted antibody-drug conjugate eradicates high-grade pulmonary neuroendocrine tumor-initiating cells in vivo," Sci Transl Med., Aug. 2015, 7(302):302ra136.

Scatchard et al., "The Attractions of Proteins for Small Molecules and Ions," Annals of the New York Academy of Science, May 1949, 51(4):660-672.

Shields et al., "High Resolution Mapping of the Binding Site on Human IgG1 for FcgRI, FcgRII, FcgRIII, and FcRn and Design of IgG1 Variants with Improved Binding to the FcgR," The Journal of Biological Chemistry, Mar. 2001, 276:9;6591-6604.

Sivori et al., "NKp46 is the major triggering receptor involved in the natural cytotoxicity of fresh or cultured human NK cells. Correlation between surface density ofNKp46 and natural cytotoxicity against autologous, allogeneic or xenogeneic target cells," Eur J Immunol, May 1999, 29:1656-1666.

Takahashi et al., "Rescue from Photoreceptor Degeneration in the rd Mouse by Human Immunodeficiency Virus Vector-Mediated Gene Transfer," Journal of Virology, Sep. 1999, 73(9):7812-7816.

Tempest, et al., "Reshaping a human monoclonal antibody to inhibit human respiratory syncytial virus infection in vivo," Bio/Technol., Mar. 1991, 9(3):266-271.

UniProt Accession No. M0R177, "Delta like canonical Notch ligand 3," Dec. 5, 2018, 2 pages.

UniProt Accession No. O88516, "Delta-like protein 3," Feb. 13, 2019, 4 pages.

UniProt Accession No. P53708, "Integrin alpha-8," Feb. 13, 2019, 7 pages.

UniProt Accession No. Q02223, "Tumor necrosis factor receptor superfamily member 17," 6 pages.

UniProt Accession No. Q68SN8, "Fc receptor-like protein 5," Apr. 10, 2019, 4 pages.

UniProt Accession No. Q9NQ25, "Slam family member 7," Apr. 10, 2019, 8 pages.

UniProt Accession No. Q9NYJ7, "Delta-like protein 3," Feb. 13, 2019, 5 pages.

UniProt Accession No. Q9NYL4, "Peptidyl-prolyl cis-trans isomerase FKBP11," Feb. 13, 2019, 4 pages.

UniProt Accession No. Q9NZD1, "G-protein coupled receptor family C group 5 member D," Apr. 10, 2019, 3 pages.

Urlaub et al., "Effect of Gamma Rays at the Dihydrofolate Reductase Locus: Deletions and Inversions," Somatic Cell and Molecular Genetics, Jul. 1986, 12(6):555-566.

Vafa et al., "An engineered Fc variant of an IgG eliminates all immune effector functions via structural perturbations," Methods, Jul. 2013, 65:1;114-126.

Van den Berg et al., "Case Report of a Fatal Serious Adverse Event Upon Administration of T Cells Transduced With a MART-1-specific T-cell Receptor," Molecular Therapy, Sep. 2015, 23(9):1541-1550.

Vanseggelen et al., "T Cells Engineered With Chimeric Antigen Receptors Targeting NKG2D Ligands Display Lethal Toxicity in Mice," Molecular Therapy, Oct. 2015, 23(10):1600-1610.

Verhoeyen, et al., "Reshaping human antibodies: grafting an antilysozyme activity," Science, Mar. 1988, 239:1534-1536.

Wang et al., "Targeting Fibroblast Activation Protein in Tumor Stroma with Chimeric Antigen Receptor T Cells Can Inhibit Tumor Growth and Augment Host Immunity without Severe Toxicity," Cancer Immunology Research, Feb. 2014, 2(2):154-166.

Ward et al., "Binding activities of a repertoire of single immunoglobulin variable domains secreted from *Escherichia coli*," Nature, Oct. 1989, 341(6242):544-546.

Wigler et al., "Biochemical transfer of single-copy eucaryotic genes using total cellular DNA as donor," Cell, Jul. 1978, 14(3):725-731.

Wilkie et al., "Dual Targeting of ErbB2 and MUC1 in Breast Cancer Using Chimeric Antigen Receptors Engineered to Provide Complementary Signaling," Journal of Clinical Immunology, Oct. 2012, 32(5):1059-1070.

Wu et al., "Building blocks for bispecific and trispecific antibodies," Methods, Feb. 2019, 154:3-9.

Wu et al., "Trispecific antibodies enhance the therapeutic efficacy of tumor-directed T cells through T cell receptor co-stimulation," Nature Cancer, Jan. 2020, 1(1):86-98.

* cited by examiner

Fig. 3

| anti-hDLL3 Nb | $K_D$ (M) | $K_D$ error | $k_{on}$ (1/Ms) | $k_{on}$ error | $k_{off}$ (1/s) | $k_{off}$ error | Full $R^2$ |
|---|---|---|---|---|---|---|---|
| 2HCE27 | 7.89E-09 | 1.39E-11 | 8.09E+04 | 1.20E+02 | 6.38E-04 | 6.05E-07 | 0.9994 |
| 3HCE4 | 5.15E-09 | 2.22E-11 | 2.49E+05 | 9.86E+02 | 1.28E-03 | 2.13E-06 | 0.9955 |
| 3HCE56 | 2.13E-08 | 1.90E-10 | 6.85E+04 | 5.82E+02 | 1.46E-03 | 4.12E-06 | 0.9862 |
| 3HCE87 | 5.35E-09 | 7.00E-11 | 1.92E+05 | 2.27E+03 | 1.03E-03 | 5.76E-06 | 0.9522 |
| 2HCE117 | 1.01E-07 | 1.32E-09 | 5.96E+03 | 7.26E+01 | 6.00E-04 | 2.95E-06 | 0.9111 |

Binding results on CHO cells

| anti-hDLL3 Nb | CDR3 Group | ELISA DLL3 | ELISA control | DLL3 / control | Human-DLL3-CHO | Cyno-DLL3-CHO | Mouse-DLL3-CHO |
|---|---|---|---|---|---|---|---|
| 2HCE27 | 27 | 4.7384 | 0.1421 | 33.3455 | YES | YES | YES |
| 3HCE4 | 8 | 5.2586 | 0.0801 | 65.6504 | YES | YES | YES |
| 3HCE56 | 29 | 4.0625 | 0.2196 | 18.4995 | YES | YES | YES |
| 3HCE87 | 30 | 4.6909 | 0.25 | 18.7636 | YES | YES | YES |
| 2HCE117 | 17 | 5.8372 | 0.1983 | 29.4362 | YES | YES | YES |

Fig. 8A

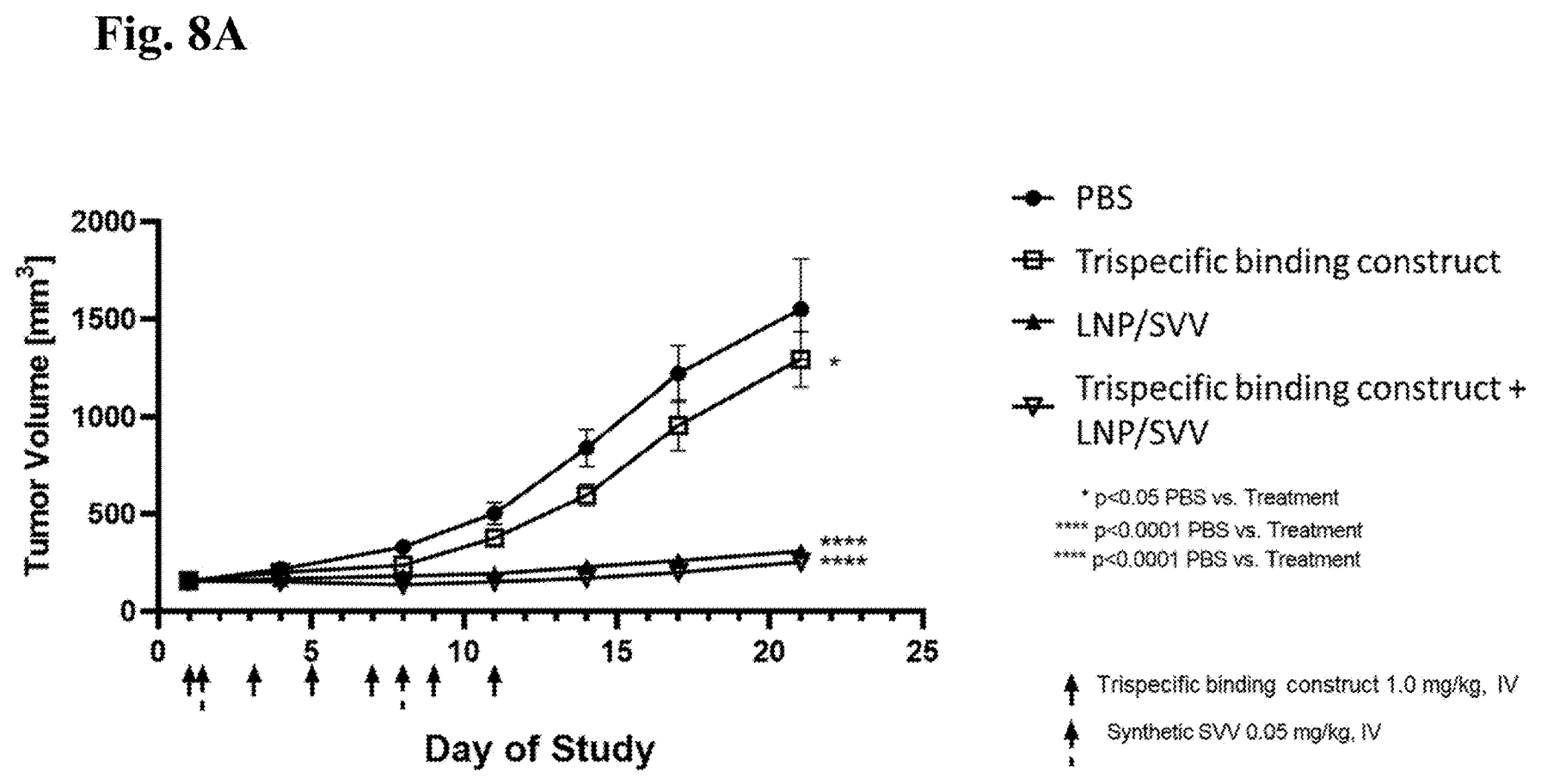

PBS

Trispecific binding construct

LNP/SVV

Trispecific binding construct + LNP/SVV

* p<0.05 PBS vs. Treatment
**** p<0.0001 PBS vs. Treatment
**** p<0.0001 PBS vs. Treatment Trispecific binding construct 1.0 mg/kg, IV Synthetic SVV 0.05 mg/kg, IV Tumor Volume [mm³]

Day of Study

SEQUENCE LISTING

```
<160> NUMBER OF SEQ ID NOS: 761

<210> SEQ ID NO 1
<211> LENGTH: 8
<212> TYPE: PRT
<213> ORGANISM: Artificial Sequence
<220> FEATURE:
<223> OTHER INFORMATION: VH-CDR1

<400> SEQUENCE: 1

Gly Ser Ile Val Gly Asp Tyr Ala
1               5

<210> SEQ ID NO 2
<211> LENGTH: 7
<212> TYPE: PRT
<213> ORGANISM: Artificial Sequence
<220> FEATURE:
<223> OTHER INFORMATION: VH-CDR2

<400> SEQUENCE: 2

Ile Gly Ser Glu Gly Ser Arg
1               5
```

-continued

```
<210> SEQ ID NO 3
<211> LENGTH: 9
<212> TYPE: PRT
<213> ORGANISM: Artificial Sequence
<220> FEATURE:
<223> OTHER INFORMATION: VH-CDR3

<400> SEQUENCE: 3

Phe Leu Tyr Asn Ser Gly Glu Asp Tyr
1               5

<210> SEQ ID NO 4
<211> LENGTH: 115
<212> TYPE: PRT
<213> ORGANISM: Artificial Sequence
<220> FEATURE:
<223> OTHER INFORMATION: 2DLT10

<400> SEQUENCE: 4

Gln Val Gln Leu Gln Glu Ser Gly Gly Gly Leu Val Gln Pro Gly Glu
1               5                   10                  15

Ser Leu Arg Leu Ser Cys Ala Ala Ser Gly Ser Ile Val Gly Asp Tyr
            20                  25                  30

Ala Met Gly Trp Tyr Arg Gln Ala Pro Gly Lys Lys Arg Glu Leu Val
        35                  40                  45

Ala Gly Ile Gly Ser Glu Gly Ser Arg Asp Tyr Ala Asp Ser Val Lys
    50                  55                  60

Gly Arg Phe Thr Ile Ser Arg Asp Asn Ala Lys Arg Thr Leu Tyr Leu
65                  70                  75                  80

Gln Met Asn Ser Leu Lys Ser Glu Asp Thr Ala Val Tyr Ile Cys Phe
            85                  90                  95

Leu Tyr Asn Ser Gly Glu Asp Tyr Trp Gly Gln Gly Thr Gln Val Thr
            100                 105                 110

Val Ser Ser
        115

<210> SEQ ID NO 5
<211> LENGTH: 115
<212> TYPE: PRT
<213> ORGANISM: Artificial Sequence
<220> FEATURE:
<223> OTHER INFORMATION: 1DLT176

<400> SEQUENCE: 5

Gln Val Gln Leu Gln Glu Ser Gly Gly Gly Leu Val Gln Pro Gly Gly
1               5                   10                  15

Ser Leu Arg Leu Ala Cys Ala Ala Ser Gly Ser Ile Val Gly Asp Tyr
            20                  25                  30

Ala Met Gly Trp Tyr Arg Gln Ala Pro Gly Lys Lys Arg Glu Leu Val
        35                  40                  45

Ala Gly Ile Gly Ser Glu Gly Ser Arg Asp Tyr Ala Asp Ser Val Lys
    50                  55                  60

Gly Arg Phe Thr Ile Ser Arg Asp Asn Ala Lys Arg Thr Leu Tyr Leu
65                  70                  75                  80

Gln Met Asn Ser Leu Lys Ser Glu Asp Thr Ala Val Tyr Ile Cys Phe
            85                  90                  95

Leu Tyr Asn Ser Gly Glu Asp Tyr Trp Gly Gln Gly Thr Gln Val Thr
            100                 105                 110
```

```
Val Ser Ser
        115

<210> SEQ ID NO 6
<211> LENGTH: 8
<212> TYPE: PRT
<213> ORGANISM: Artificial Sequence
<220> FEATURE:
<223> OTHER INFORMATION: VH-CDR1

<400> SEQUENCE: 6

Gly Phe Thr Thr Asp Asp Tyr Gly
1               5

<210> SEQ ID NO 7
<211> LENGTH: 7
<212> TYPE: PRT
<213> ORGANISM: Artificial Sequence
<220> FEATURE:
<223> OTHER INFORMATION: VH-CDR2

<400> SEQUENCE: 7

Ile Thr Thr Gly Gly Ser Thr
1               5

<210> SEQ ID NO 8
<211> LENGTH: 19
<212> TYPE: PRT
<213> ORGANISM: Artificial Sequence
<220> FEATURE:
<223> OTHER INFORMATION: VH-CDR3

<400> SEQUENCE: 8

Asn Ala Val Cys Ser Gly Ser Gly Cys Tyr Glu Val Ser Trp Glu Ser
1               5                   10                  15

Tyr Asp Tyr

<210> SEQ ID NO 9
<211> LENGTH: 125
<212> TYPE: PRT
<213> ORGANISM: Artificial Sequence
<220> FEATURE:
<223> OTHER INFORMATION: 2HCE138

<400> SEQUENCE: 9

Gln Val Gln Leu Gln Glu Ser Gly Gly Gly Leu Val Gln Ala Gly Gly
1               5                   10                  15

Ser Leu Arg Leu Ser Cys Ala Val Ser Gly Phe Thr Thr Asp Asp Tyr
            20                  25                  30

Gly Ile Gly Trp Phe Arg Gln Ala Pro Gly Lys Gln Arg Glu Leu Val
            35                  40                  45

Ala Ile Ile Thr Thr Gly Gly Ser Thr Asn Tyr Ala Asp Ser Val Lys
        50                  55                  60

Gly Arg Phe Lys Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Val Cys Ser Gly Ser Gly Cys Tyr Glu Val Ser Trp Glu Ser Tyr
            100                 105                 110

Asp Tyr Trp Gly Gln Gly Thr Gln Val Thr Val Ser Ser
        115                 120                 125
```

```
<210> SEQ ID NO 10
<211> LENGTH: 8
<212> TYPE: PRT
<213> ORGANISM: Artificial Sequence
<220> FEATURE:
<223> OTHER INFORMATION: VH-CDR1

<400> SEQUENCE: 10

Gly Arg Thr Tyr Ser Asn Tyr Phe
1               5

<210> SEQ ID NO 11
<211> LENGTH: 8
<212> TYPE: PRT
<213> ORGANISM: Artificial Sequence
<220> FEATURE:
<223> OTHER INFORMATION: VH-CDR2

<400> SEQUENCE: 11

Val Ser Trp Ser Gly Asp Arg Thr
1               5

<210> SEQ ID NO 12
<211> LENGTH: 11
<212> TYPE: PRT
<213> ORGANISM: Artificial Sequence
<220> FEATURE:
<223> OTHER INFORMATION: VH-CDR3

<400> SEQUENCE: 12

Ala Ala Gly Pro Leu Ile Asn Arg Ile Asn Tyr
1               5                   10

<210> SEQ ID NO 13
<211> LENGTH: 118
<212> TYPE: PRT
<213> ORGANISM: Artificial Sequence
<220> FEATURE:
<223> OTHER INFORMATION: 3HCE7

<400> SEQUENCE: 13

Gln Val Gln Leu Gln Glu Ser Gly Gly Gly Leu Val Gln Ala Gly Asp
1               5                   10                  15

Ser Leu Arg Leu Ser Cys Ala Gly Ser Gly Arg Thr Tyr Ser Asn Tyr
                20                  25                  30

Phe Ile Asp Trp Phe Arg Gln Ala Pro Gly Lys Glu Arg Glu Phe Val
            35                  40                  45

Ala Ala Val Ser Trp Ser Gly Asp Arg Thr Thr Tyr Ala Asp Ser Val
        50                  55                  60

Lys Gly Arg Phe Thr Val Ser Arg Asp Asn Ala Lys Asn Thr Trp Tyr
65                  70                  75                  80

Leu Gln Met Asn Ser Leu Lys Pro Glu Asp Thr Ala Val Tyr Tyr Cys
                85                  90                  95

Ala Ala Gly Pro Leu Ile Asn Arg Ile Asn Tyr Trp Gly Gln Gly Thr
            100                 105                 110

Gln Val Thr Val Ser Ser
        115

<210> SEQ ID NO 14
<211> LENGTH: 8
<212> TYPE: PRT
<213> ORGANISM: Artificial Sequence
<220> FEATURE:
<223> OTHER INFORMATION: VH-CDR1
```

-continued

<400> SEQUENCE: 14

Gly Phe Thr Phe Ser Ser Tyr Ala
1               5

<210> SEQ ID NO 15
<211> LENGTH: 8
<212> TYPE: PRT
<213> ORGANISM: Artificial Sequence
<220> FEATURE:
<223> OTHER INFORMATION: VH-CDR2

<400> SEQUENCE: 15

Ile Asp Ser Gly Gly Gly Ser Thr
1               5

<210> SEQ ID NO 16
<211> LENGTH: 10
<212> TYPE: PRT
<213> ORGANISM: Artificial Sequence
<220> FEATURE:
<223> OTHER INFORMATION: VH-CDR3

<400> SEQUENCE: 16

Ala Lys Glu Pro Trp Val Val Ala Asp Tyr
1               5                   10

<210> SEQ ID NO 17
<211> LENGTH: 117
<212> TYPE: PRT
<213> ORGANISM: Artificial Sequence
<220> FEATURE:
<223> OTHER INFORMATION: 2HCE151

<400> SEQUENCE: 17

Gln Val Gln Leu Gln Glu Ser Gly Gly Gly Leu Val Gln Pro Gly Gly
1               5                   10                  15

Ser Leu Arg Leu Ser Cys Val Ala Ser Gly Phe Thr Phe Ser Ser Tyr
            20                  25                  30

Ala Met Ser Trp Val Arg Gln Ala Pro Gly Lys Gly Pro Glu Trp Val
        35                  40                  45

Ser Arg Ile Asp Ser Gly Gly Gly Ser Thr Ser Tyr Ala Asp Ser Val
    50                  55                  60

Lys Gly Arg Phe Thr Ile Ser Arg Asp Asn Ala Lys Asn Thr Leu His
65                  70                  75                  80

Leu Gln Met Asn Gly Leu Lys Pro Glu Asp Thr Ala Val Tyr Tyr Cys
                85                  90                  95

Ala Lys Glu Pro Trp Val Val Ala Asp Tyr Trp Gly Gln Gly Thr Gln
            100                 105                 110

Val Thr Val Ser Ser
        115

<210> SEQ ID NO 18
<211> LENGTH: 8
<212> TYPE: PRT
<213> ORGANISM: Artificial Sequence
<220> FEATURE:
<223> OTHER INFORMATION: VH-CDR1

<400> SEQUENCE: 18

Gly Arg Ala Gly Ser Ser Tyr Asp
1               5

-continued

<210> SEQ ID NO 19
<211> LENGTH: 7
<212> TYPE: PRT
<213> ORGANISM: Artificial Sequence
<220> FEATURE:
<223> OTHER INFORMATION: VH-CDR2

<400> SEQUENCE: 19

Ile Thr Trp Ser Gly Asn Thr
1               5

<210> SEQ ID NO 20
<211> LENGTH: 11
<212> TYPE: PRT
<213> ORGANISM: Artificial Sequence
<220> FEATURE:
<223> OTHER INFORMATION: VH-CDR3

<400> SEQUENCE: 20

Ala Ala Ala Leu Ser Glu Lys Lys Tyr Glu Tyr
1               5                   10

<210> SEQ ID NO 21
<211> LENGTH: 117
<212> TYPE: PRT
<213> ORGANISM: Artificial Sequence
<220> FEATURE:
<223> OTHER INFORMATION: 3HCE4

<400> SEQUENCE: 21

Gln Val Gln Leu Gln Glu Ser Gly Gly Gly Leu Val Gln Ala Gly Ala
1               5                   10                  15

Ser Leu Lys Leu Ser Cys Ala Val Ser Gly Arg Ala Gly Ser Ser Tyr
            20                  25                  30

Asp Met Gly Trp Leu Arg Gln Ala Pro Gly Lys Glu Arg Glu Phe Val
        35                  40                  45

Ala Ile Ile Thr Trp Ser Gly Asn Thr Ala Tyr Lys Asp Ser Val Lys
    50                  55                  60

Gly Arg Phe Ile Ile Ser Arg Asp Asn Ala Lys Asn Thr Val Tyr Leu
65                  70                  75                  80

Glu Met Asn Ser Leu Ala Pro Glu Asp Thr Ala Val Tyr Tyr Cys Ala
                85                  90                  95

Ala Ala Leu Ser Glu Lys Lys Tyr Glu Tyr Trp Gly Gln Gly Thr Gln
            100                 105                 110

Val Thr Val Ser Ser
        115

<210> SEQ ID NO 22
<211> LENGTH: 8
<212> TYPE: PRT
<213> ORGANISM: Artificial Sequence
<220> FEATURE:
<223> OTHER INFORMATION: VH-CDR1

<400> SEQUENCE: 22

Gly Ser Ile Ser Ser Ile Ile Ser
1               5

<210> SEQ ID NO 23
<211> LENGTH: 8
<212> TYPE: PRT
<213> ORGANISM: Artificial Sequence
<220> FEATURE:

```
<223> OTHER INFORMATION: VH-CDR2

<400> SEQUENCE: 23

Ala Ile Thr Ser Gly Gly Ser Thr
1               5

<210> SEQ ID NO 24
<211> LENGTH: 13
<212> TYPE: PRT
<213> ORGANISM: Artificial Sequence
<220> FEATURE:
<223> OTHER INFORMATION: VH-CDR3

<400> SEQUENCE: 24

Asn Ala His Val Arg Asp Tyr Ser Gly Ser Ala Tyr Tyr
1               5                   10

<210> SEQ ID NO 25
<211> LENGTH: 120
<212> TYPE: PRT
<213> ORGANISM: Artificial Sequence
<220> FEATURE:
<223> OTHER INFORMATION: 3HCE80

<400> SEQUENCE: 25

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Ser Ser Ile Ile
            20                  25                  30

Ser Met Gly Trp Tyr Arg Gln Ala Pro Gly Lys Gln Arg Gly Glu Leu
        35                  40                  45

Val Ala Ala Ile Thr Ser Gly Gly Ser Thr Ser Tyr Ala Gly Ser Val
    50                  55                  60

Glu Gly Arg Phe Ala Ile Ser Arg Asp Ser Ala Lys Asn Thr Ala Tyr
65                  70                  75                  80

Leu Gln Met Asn Ser Leu Lys Pro Glu Asp Thr Ala Val Tyr Tyr Cys
                85                  90                  95

Asn Ala His Val Arg Asp Tyr Ser Gly Ser Ala Tyr Tyr Thr Gly Gln
            100                 105                 110

Gly Thr Gln Val Thr Val Ser Ser
        115                 120

<210> SEQ ID NO 26
<211> LENGTH: 8
<212> TYPE: PRT
<213> ORGANISM: Artificial Sequence
<220> FEATURE:
<223> OTHER INFORMATION: VH-CDR1

<400> SEQUENCE: 26

Gly Gly Thr Phe Ser Asn Tyr Asp
1               5

<210> SEQ ID NO 27
<211> LENGTH: 8
<212> TYPE: PRT
<213> ORGANISM: Artificial Sequence
<220> FEATURE:
<223> OTHER INFORMATION: VH-CDR2

<400> SEQUENCE: 27

Val Asn Arg Tyr Gly Asp Tyr Ser
1               5
```

```
<210> SEQ ID NO 28
<211> LENGTH: 12
<212> TYPE: PRT
<213> ORGANISM: Artificial Sequence
<220> FEATURE:
<223> OTHER INFORMATION: VH-CDR3

<400> SEQUENCE: 28

Ala Ala Arg Leu Trp Asn Ser Ala Lys Tyr Ala Tyr
1               5                   10

<210> SEQ ID NO 29
<211> LENGTH: 119
<212> TYPE: PRT
<213> ORGANISM: Artificial Sequence
<220> FEATURE:
<223> OTHER INFORMATION: 3HCE86

<400> SEQUENCE: 29

Gln Val Gln Leu Gln Glu Ser Gly Gly Gly Leu Val Gln Pro Gly Gly
1               5                   10                  15

Ser Leu Arg Leu Ser Cys Ala Ala Ser Gly Gly Thr Phe Ser Asn Tyr
            20                  25                  30

Asp Ile Ala Trp Phe Arg Gln Ala Pro Gly Lys Glu Arg Glu Phe Val
        35                  40                  45

Ala Ala Val Asn Arg Tyr Gly Asp Tyr Ser Tyr Tyr Ala Asp Ser Val
    50                  55                  60

Lys Gly Arg Phe Thr Ile Ser Arg Asp Asn Ala Lys Ser Thr Val Ser
65                  70                  75                  80

Leu Gln Met Asn Ser Leu Lys Pro Glu Asp Thr Phe Ser Tyr Tyr Cys
                85                  90                  95

Ala Ala Arg Leu Trp Asn Ser Ala Lys Tyr Ala Tyr Trp Gly Gln Gly
            100                 105                 110

Thr Gln Val Thr Val Ser Ser
        115

<210> SEQ ID NO 30
<211> LENGTH: 8
<212> TYPE: PRT
<213> ORGANISM: Artificial Sequence
<220> FEATURE:
<223> OTHER INFORMATION: VH-CDR1

<400> SEQUENCE: 30

Gly Ser Ile Phe Ser Ile Tyr Ala
1               5

<210> SEQ ID NO 31
<211> LENGTH: 15
<212> TYPE: PRT
<213> ORGANISM: Artificial Sequence
<220> FEATURE:
<223> OTHER INFORMATION: VH-CDR3

<400> SEQUENCE: 31

Tyr Ala Gly Arg Pro Pro Ser Ala Ser Tyr Ser Gly Ala His Tyr
1               5                   10                  15

<210> SEQ ID NO 32
<211> LENGTH: 121
<212> TYPE: PRT
<213> ORGANISM: Artificial Sequence
```

<220> FEATURE:
<223> OTHER INFORMATION: 3DLT81

<400> SEQUENCE: 32

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Ile Tyr
                20                  25                  30

Ala Met Gly Trp Tyr Arg Gln Ala Pro Gly Lys Lys Arg Glu Leu Val
            35                  40                  45

Ala Gly Ile Gly Ser Glu Gly Ser Arg Asp Tyr Ala Asp Ser Val Lys
        50                  55                  60

Gly Arg Phe Thr Ile Ser Arg Asp Asn Ala Lys Arg Thr Val Tyr Leu
65                  70                  75                  80

Gln Met Asn Thr Leu Gln Pro Glu Asp Thr Ala Val Tyr Tyr Cys Tyr
                85                  90                  95

Ala Gly Arg Pro Pro Ser Ala Ser Tyr Ser Gly Ala His Tyr Trp Gly
            100                 105                 110

Gln Gly Thr Gln Val Thr Val Ser Ser
        115                 120

<210> SEQ ID NO 33
<211> LENGTH: 8
<212> TYPE: PRT
<213> ORGANISM: Artificial Sequence
<220> FEATURE:
<223> OTHER INFORMATION: VH-CDR1

<400> SEQUENCE: 33

Gly Phe Thr Phe Asp Asp Val Ala
1               5

<210> SEQ ID NO 34
<211> LENGTH: 12
<212> TYPE: PRT
<213> ORGANISM: Artificial Sequence
<220> FEATURE:
<223> OTHER INFORMATION: VH-CDR3

<400> SEQUENCE: 34

Ala Ala Arg Arg Asp Ser Arg Gly Gln Tyr His Asp
1               5                   10

<210> SEQ ID NO 35
<211> LENGTH: 118
<212> TYPE: PRT
<213> ORGANISM: Artificial Sequence
<220> FEATURE:
<223> OTHER INFORMATION: 3HCE38

<400> SEQUENCE: 35

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Asp Asp Val
                20                  25                  30

Ala Met Ser Trp Val Arg Gln Ala Pro Gly Lys Gln Arg Glu Leu Val
            35                  40                  45

Ala Val Ile Thr Ser Gly Gly Ser Thr Tyr Thr Ala Asp Ser Val Lys
        50                  55                  60

Gly Arg Phe Ala Ile Ser Arg Asp Asn Ala Lys Asn Thr Val Tyr Leu
65                  70                  75                  80

-continued

```
Gln Met Asn Ser Leu Lys Pro Glu Asp Thr Ala Leu Tyr Tyr Cys Ala
                85              90              95

Ala Arg Arg Asp Ser Arg Gly Gln Tyr His Asp Trp Gly Gln Gly Thr
            100             105             110

Gln Val Thr Val Ser Ser
        115
```

```
<210> SEQ ID NO 36
<211> LENGTH: 8
<212> TYPE: PRT
<213> ORGANISM: Artificial Sequence
<220> FEATURE:
<223> OTHER INFORMATION: VH-CDR1

<400> SEQUENCE: 36

Gly Phe Thr Phe Ser Asn Ser Pro
1               5
```

```
<210> SEQ ID NO 37
<211> LENGTH: 12
<212> TYPE: PRT
<213> ORGANISM: Artificial Sequence
<220> FEATURE:
<223> OTHER INFORMATION: VH-CDR3

<400> SEQUENCE: 37

Ala Lys Gly Ala Thr Pro Ser Val Leu Tyr Asp Tyr
1               5                   10
```

```
<210> SEQ ID NO 38
<211> LENGTH: 119
<212> TYPE: PRT
<213> ORGANISM: Artificial Sequence
<220> FEATURE:
<223> OTHER INFORMATION: 2HCE6

<400> SEQUENCE: 38

Gln Val Gln Leu Gln Glu Ser Gly Gly Gly Leu Val Gln Thr Gly Gly
1               5               10              15

Ser Leu Arg Leu Ser Cys Ala Ala Ser Gly Phe Thr Phe Ser Asn Ser
            20              25              30

Pro Met Ser Trp Val Arg Arg Ala Pro Gly Lys Gly Pro Glu Trp Val
        35              40              45

Ser Ala Ile Ser Ser Asn Gly Arg Asn Thr Ser Tyr Ala Asp Ser Val
    50              55              60

Lys Gly Arg Phe Thr Ile Ser Arg Asp Asn Ala Lys Asn Thr Leu Phe
65              70              75              80

Leu Gln Met His Ser Leu Lys Phe Glu Asp Thr Ala Val Tyr Tyr Cys
                85              90              95

Ala Lys Gly Ala Thr Pro Ser Val Leu Tyr Asp Tyr Gly Gly Gln Gly
            100             105             110

Thr Gln Val Thr Val Ser Ser
        115
```

```
<210> SEQ ID NO 39
<211> LENGTH: 8
<212> TYPE: PRT
<213> ORGANISM: Artificial Sequence
<220> FEATURE:
<223> OTHER INFORMATION: VH-CDR1

<400> SEQUENCE: 39
```

-continued

```
Gly Arg Ile Phe Ser Met Phe Pro
1               5

<210> SEQ ID NO 40
<211> LENGTH: 7
<212> TYPE: PRT
<213> ORGANISM: Artificial Sequence
<220> FEATURE:
<223> OTHER INFORMATION: VH-CDR2

<400> SEQUENCE: 40

Ile Thr Thr Gly Gly Arg Pro
1               5

<210> SEQ ID NO 41
<211> LENGTH: 14
<212> TYPE: PRT
<213> ORGANISM: Artificial Sequence
<220> FEATURE:
<223> OTHER INFORMATION: VH-CDR3

<400> SEQUENCE: 41

Asn Ala Val Ser Thr Pro Glu Leu Ala Tyr Pro Tyr Asp Tyr
1               5                   10

<210> SEQ ID NO 42
<211> LENGTH: 120
<212> TYPE: PRT
<213> ORGANISM: Artificial Sequence
<220> FEATURE:
<223> OTHER INFORMATION: 1DLT39

<400> SEQUENCE: 42

Gln Val Gln Leu Gln Glu Ser Gly Gly Gly Leu Val Gln Pro Gly Gly
1               5                   10                  15

Ser Leu Arg Leu Ser Cys Ala Ala Ser Gly Arg Ile Phe Ser Met Phe
            20                  25                  30

Pro Met Gly Trp Tyr Arg Gln Ala Pro Gly Lys Gln Arg Glu Leu Val
            35                  40                  45

Ala Asp Ile Thr Thr Gly Gly Arg Pro Asn Tyr Ala Asp Ser Val Lys
        50                  55                  60

Gly Arg Phe Thr Ile Thr Arg Asp Asn Ala Lys Asn Thr Val Tyr Leu
65                  70                  75                  80

Gln Met Asn Ser Leu Gln Pro Glu Asp Thr Ala Val Tyr Phe Cys Asn
                85                  90                  95

Ala Val Ser Thr Pro Glu Leu Ala Tyr Pro Tyr Asp Tyr Trp Gly Gln
            100                 105                 110

Gly Thr Gln Val Thr Val Ser Ser
        115                 120

<210> SEQ ID NO 43
<211> LENGTH: 8
<212> TYPE: PRT
<213> ORGANISM: Artificial Sequence
<220> FEATURE:
<223> OTHER INFORMATION: VH-CDR2

<400> SEQUENCE: 43

Ile Asn Ser Gly Gly Gly Ser Thr
1               5

<210> SEQ ID NO 44
```

```
<211> LENGTH: 10
<212> TYPE: PRT
<213> ORGANISM: Artificial Sequence
<220> FEATURE:
<223> OTHER INFORMATION: VH-CDR3

<400> SEQUENCE: 44

Ala Lys Glu Pro Trp Val Thr Gln Gly Ser
1               5                   10

<210> SEQ ID NO 45
<211> LENGTH: 117
<212> TYPE: PRT
<213> ORGANISM: Artificial Sequence
<220> FEATURE:
<223> OTHER INFORMATION: 3HCE25

<400> SEQUENCE: 45

Gln Val Gln Leu Gln Glu Ser Gly Gly Gly Leu Val Gln Pro Gly Gly
1               5                   10                  15

Ser Leu Arg Leu Ser Cys Glu Ala Ser Gly Phe Thr Phe Ser Ser Tyr
            20                  25                  30

Ala Met Ser Trp Val Arg Gln Ala Pro Gly Lys Gly Pro Glu Trp Val
        35                  40                  45

Ser Arg Ile Asn Ser Gly Gly Gly Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Glu Pro Trp Val Thr Gln Gly Ser Trp Gly Gln Gly Thr Gln
            100                 105                 110

Val Thr Val Ser Ser
        115

<210> SEQ ID NO 46
<211> LENGTH: 8
<212> TYPE: PRT
<213> ORGANISM: Artificial Sequence
<220> FEATURE:
<223> OTHER INFORMATION: VH-CDR1

<400> SEQUENCE: 46

Gly Arg Thr Phe Arg Ser Tyr Ala
1               5

<210> SEQ ID NO 47
<211> LENGTH: 8
<212> TYPE: PRT
<213> ORGANISM: Artificial Sequence
<220> FEATURE:
<223> OTHER INFORMATION: VH-CDR2

<400> SEQUENCE: 47

Ile Ile Met Ser Asp Gly Ser Thr
1               5

<210> SEQ ID NO 48
<211> LENGTH: 13
<212> TYPE: PRT
<213> ORGANISM: Artificial Sequence
<220> FEATURE:
<223> OTHER INFORMATION: VH-CDR3
```

-continued

<400> SEQUENCE: 48

Ala Ala Arg Arg Asp Tyr Phe Thr Gly Val Tyr Asp Tyr
1               5                   10

<210> SEQ ID NO 49
<211> LENGTH: 120
<212> TYPE: PRT
<213> ORGANISM: Artificial Sequence
<220> FEATURE:
<223> OTHER INFORMATION: 2HCE27

<400> SEQUENCE: 49

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Arg Ser Tyr
            20                  25                  30

Ala Met Gly Trp Phe Arg Gln Ala Pro Gly Lys Glu Arg Glu Phe Ile
            35                  40                  45

Ala Val Ile Ile Met Ser Asp Gly Ser Thr Ser Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Ala Arg Arg Asp Tyr Phe Thr Gly Val Tyr Asp Tyr Trp Gly Gln
            100                 105                 110

Gly Thr Gln Val Thr Val Ser Ser
        115                 120

<210> SEQ ID NO 50
<211> LENGTH: 120
<212> TYPE: PRT
<213> ORGANISM: Artificial Sequence
<220> FEATURE:
<223> OTHER INFORMATION: 2HCE27 14.1

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg Ser Tyr
            20                  25                  30

Ala Met Gly Trp Phe Arg Gln Ala Pro Gly Lys Glu Arg Glu Phe Ile
            35                  40                  45

Ala Val Ile Ile Met Ser Asp Gly Ser Thr Ser Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Ala Arg Arg Asp Tyr Phe Thr Gly Val Tyr Asp Tyr Trp Gly Gln
            100                 105                 110

Gly Thr Leu Val Thr Val Ser Ser
        115                 120

<210> SEQ ID NO 51
<211> LENGTH: 120
<212> TYPE: PRT
<213> ORGANISM: Artificial Sequence
<220> FEATURE:

<223> OTHER INFORMATION: 2HCE27 14.2

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg Ser Tyr
            20                  25                  30

Ala Met Gly Trp Phe Arg Gln Ala Pro Gly Lys Glu Arg Glu Phe Ile
        35                  40                  45

Ala Val Ile Ile Met Ser Asp Gly Ser Thr Ser Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Arg Asp Tyr Phe Thr Gly Val Tyr Asp Tyr Trp Gly Gln
            100                 105                 110

Gly Thr Leu Val Thr Val Ser Ser
        115                 120

<210> SEQ ID NO 52
<211> LENGTH: 8
<212> TYPE: PRT
<213> ORGANISM: Artificial Sequence
<220> FEATURE:
<223> OTHER INFORMATION: VH-CDR1

<400> SEQUENCE: 52

Gly Arg Thr Phe Ser Val Asp Ala
1               5

<210> SEQ ID NO 53
<211> LENGTH: 8
<212> TYPE: PRT
<213> ORGANISM: Artificial Sequence
<220> FEATURE:
<223> OTHER INFORMATION: VH-CDR2

<400> SEQUENCE: 53

Ile Asp Trp Thr Gly Gly Ser Thr
1               5

<210> SEQ ID NO 54
<211> LENGTH: 12
<212> TYPE: PRT
<213> ORGANISM: Artificial Sequence
<220> FEATURE:
<223> OTHER INFORMATION: VH-CDR3

<400> SEQUENCE: 54

Ala Ala Arg Glu Arg Ser Arg Thr Ala Tyr Asp Tyr
1               5                   10

<210> SEQ ID NO 55
<211> LENGTH: 119
<212> TYPE: PRT
<213> ORGANISM: Artificial Sequence
<220> FEATURE:
<223> OTHER INFORMATION: 3HCE56

<400> SEQUENCE: 55

Gln Val Gln Leu Gln Glu Ser Gly Gly Gly Leu Val Gln Ala Gly Gly
1               5                   10                  15

-continued

```
Ser Leu Arg Leu Ser Cys Ala Ala Ser Gly Arg Thr Phe Ser Val Asp
            20                  25                  30

Ala Met Gly Trp Leu Arg Gln Ala Pro Gly Lys Glu Arg Glu Phe Val
            35                  40                  45

Val Val Ile Asp Trp Thr Gly Gly Ser Thr Ala Tyr Ala Asp Ser Val
    50                  55                  60

Lys Gly Arg Phe Thr Ile Ser Arg Asp Asn Ala Arg Asn Thr Val Tyr
65                  70                  75                  80

Leu Gln Met Asn Asn Leu Lys Pro Glu Asp Thr Gly Val Tyr Tyr Cys
                85                  90                  95

Ala Ala Arg Glu Arg Ser Arg Thr Ala Tyr Asp Tyr Trp Gly Gln Gly
            100                 105                 110

Thr Gln Val Thr Val Ser Ser
        115
```

```
<210> SEQ ID NO 56
<211> LENGTH: 119
<212> TYPE: PRT
<213> ORGANISM: Artificial Sequence
<220> FEATURE:
<223> OTHER INFORMATION: 3HCE56 15.1

<400> SEQUENCE: 56
```

```
Glu Val Gln Leu Val Glu Ser Gly Gly Gly Leu Val Gln Pro Gly Gly
1                   5                   10                  15

Ser Leu Arg Leu Ser Cys Ala Ala Ser Gly Arg Thr Phe Ser Val Asp
            20                  25                  30

Ala Met Gly Trp Leu Arg Gln Ala Pro Gly Lys Glu Arg Glu Phe Val
            35                  40                  45

Val Val Ile Asp Trp Thr Gly Gly Ser Thr Ala Tyr Ala Asp Ser Val
    50                  55                  60

Lys Gly Arg Phe Thr Ile Ser Arg Asp Asn Ala Arg Asn Thr Val Tyr
65                  70                  75                  80

Leu Gln Met Asn Asn Leu Lys Pro Glu Asp Thr Gly Val Tyr Tyr Cys
                85                  90                  95

Ala Ala Arg Glu Arg Ser Arg Thr Ala Tyr Asp Tyr Trp Gly Gln Gly
            100                 105                 110

Thr Leu Val Thr Val Ser Ser
        115
```

```
<210> SEQ ID NO 57
<211> LENGTH: 119
<212> TYPE: PRT
<213> ORGANISM: Artificial Sequence
<220> FEATURE:
<223> OTHER INFORMATION: 3HCE56 15.2

<400> SEQUENCE: 57
```

```
Glu Val Gln Leu Val Glu Ser Gly Gly Gly Leu Val Gln Pro Gly Gly
1                   5                   10                  15

Ser Leu Arg Leu Ser Cys Ala Ala Ser Gly Arg Thr Phe Ser Val Asp
            20                  25                  30

Ala Met Gly Trp Leu Arg Gln Ala Pro Gly Lys Glu Arg Glu Phe Val
            35                  40                  45

Val Val Ile Asp Trp Thr Gly Gly Ser Thr Ala Tyr Ala Asp Ser Val
    50                  55                  60

Lys Gly Arg Phe Thr Ile Ser Arg Asp Asn Ala Arg Asn Thr Val Tyr
```

```
65                  70                  75                  80
Leu Gln Met Asn Ser Leu Arg Pro Glu Asp Thr Ala Val Tyr Tyr Cys
                85                  90                  95

Ala Ala Arg Glu Arg Ser Arg Thr Ala Tyr Asp Tyr Trp Gly Gln Gly
            100                 105                 110

Thr Leu Val Thr Val Ser Ser
            115

<210> SEQ ID NO 58
<211> LENGTH: 119
<212> TYPE: PRT
<213> ORGANISM: Artificial Sequence
<220> FEATURE:
<223> OTHER INFORMATION: 3HCE56 15.3

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Val Asp
            20                  25                  30

Ala Met Gly Trp Leu Arg Gln Ala Pro Gly Lys Glu Arg Glu Phe Val
            35                  40                  45

Val Val Ile Asp Trp Thr Gly Gly Ser Thr Ala Tyr Ala Asp Ser Val
            50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Arg Glu Arg Ser Arg Thr Ala Tyr Asp Tyr Trp Gly Gln Gly
            100                 105                 110

Thr Leu Val Thr Val Ser Ser
            115

<210> SEQ ID NO 59
<211> LENGTH: 115
<212> TYPE: PRT
<213> ORGANISM: Artificial Sequence
<220> FEATURE:
<223> OTHER INFORMATION: 2DLT2

<400> SEQUENCE: 59

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Val Gly Asn Tyr
            20                  25                  30

Ala Met Gly Trp Tyr Arg Gln Ala Pro Gly Lys Glu Arg Glu Leu Val
            35                  40                  45

Ala Gly Ile Gly Ser Glu Gly Ser Arg Asp Tyr Ala Asp Ser Val Lys
            50                  55                  60

Gly Arg Phe Thr Ile Ser Arg Asp Thr Ala Lys Arg Thr Val Tyr Leu
65                  70                  75                  80

Gln Met Asn Ser Leu Lys Ser Glu Asp Thr Ala Val Tyr Ile Cys Phe
                85                  90                  95

Leu Tyr Asn Ser Gly Asp Asp Tyr Trp Gly Gln Gly Thr Gln Val Thr
            100                 105                 110

Val Ser Ser
            115
```

<210> SEQ ID NO 60
<211> LENGTH: 8
<212> TYPE: PRT
<213> ORGANISM: Artificial Sequence
<220> FEATURE:
<223> OTHER INFORMATION: VH-CDR1

<400> SEQUENCE: 60

Gly Ser Ile Phe Ser Ile Asn Ser
1               5

<210> SEQ ID NO 61
<211> LENGTH: 7
<212> TYPE: PRT
<213> ORGANISM: Artificial Sequence
<220> FEATURE:
<223> OTHER INFORMATION: VH-CDR2

<400> SEQUENCE: 61

Lys Ala Ser Asp Gly Ser Thr
1               5

<210> SEQ ID NO 62
<211> LENGTH: 9
<212> TYPE: PRT
<213> ORGANISM: Artificial Sequence
<220> FEATURE:
<223> OTHER INFORMATION: VH-CDR3

<400> SEQUENCE: 62

Phe Leu Tyr Ala Asn Asn Ile Pro Tyr
1               5

<210> SEQ ID NO 63
<211> LENGTH: 115
<212> TYPE: PRT
<213> ORGANISM: Artificial Sequence
<220> FEATURE:
<223> OTHER INFORMATION: 3HCE44

<400> SEQUENCE: 63

Gln Val Gln Leu Gln Glu Ser Gly Gly Gly Ser Val Gln Ala Gly Gly
1               5                   10                  15

Ser Leu Arg Leu Ser Cys Ala Ala Ser Gly Ser Ile Phe Ser Ile Asn
            20                  25                  30

Ser Met Gly Trp His Arg His Ala Pro Gly Lys Gln Arg Glu Leu Val
        35                  40                  45

Ala Ala Lys Ala Ser Asp Gly Ser Thr Asn Tyr Ala Gly Pro Val Arg
    50                  55                  60

Gly Arg Phe Thr Ile Thr Ser Asp Asp Ala Lys Asn Thr Val Tyr Leu
65                  70                  75                  80

Gln Met Asn Asn Leu Lys Pro Glu Asp Thr Ala Val Tyr Tyr Cys Phe
            85                  90                  95

Leu Tyr Ala Asn Asn Ile Pro Tyr Trp Ala Lys Gly Thr Gln Val Thr
            100                 105                 110

Val Ser Ser
        115

<210> SEQ ID NO 64
<211> LENGTH: 115
<212> TYPE: PRT
<213> ORGANISM: Artificial Sequence
<220> FEATURE:

-continued

```
<223> OTHER INFORMATION: 2HCE174

<400> SEQUENCE: 64

Gln Val Gln Leu Gln Glu Ser Gly Gly Gly Ser Val Gln Ala Gly Gly
1               5                   10                  15

Ser Leu Arg Leu Ser Cys Ala Ala Ser Gly Ser Ile Phe Ser Ile Asn
            20                  25                  30

Ser Met Gly Trp His Arg His Ala Pro Gly Lys Gln Arg Glu Leu Val
        35                  40                  45

Ala Ala Lys Ala Ser Asp Gly Ser Thr Asn Tyr Ala Gly Pro Val Arg
    50                  55                  60

Gly Arg Phe Thr Ile Thr Ser Asp Asp Ala Lys Asn Thr Val Tyr Leu
65                  70                  75                  80

Gln Met Asn Ser Leu Lys Pro Glu Asp Thr Ala Val Tyr Tyr Cys Phe
                85                  90                  95

Leu Tyr Ala Asn Asn Ile Pro Tyr Trp Ala Lys Gly Thr Gln Val Thr
            100                 105                 110

Val Ser Ser
        115

<210> SEQ ID NO 65
<211> LENGTH: 8
<212> TYPE: PRT
<213> ORGANISM: Artificial Sequence
<220> FEATURE:
<223> OTHER INFORMATION: VH-CDR1

<400> SEQUENCE: 65

Gly Arg Thr Phe Ser Ser Tyr Ala
1               5

<210> SEQ ID NO 66
<211> LENGTH: 8
<212> TYPE: PRT
<213> ORGANISM: Artificial Sequence
<220> FEATURE:
<223> OTHER INFORMATION: VH-CDR2

<400> SEQUENCE: 66

Ile Ser Gly Ser Gly Tyr Ser Ala
1               5

<210> SEQ ID NO 67
<211> LENGTH: 14
<212> TYPE: PRT
<213> ORGANISM: Artificial Sequence
<220> FEATURE:
<223> OTHER INFORMATION: VH-CDR3

<400> SEQUENCE: 67

Ala Ala Arg Asn Glu Arg Gly Ala Ser Ser Ser Tyr Asp Tyr
1               5                   10

<210> SEQ ID NO 68
<211> LENGTH: 121
<212> TYPE: PRT
<213> ORGANISM: Artificial Sequence
<220> FEATURE:
<223> OTHER INFORMATION: 2HCE167

<400> SEQUENCE: 68

Gln Val Gln Leu Gln Glu Ser Gly Gly Gly Leu Val Gln Ala Gly Gly
1               5                   10                  15
```

Ser Leu Arg Leu Ser Cys Ala Ala Ser Gly Arg Thr Phe Ser Ser Tyr
          20                  25                  30

Ala Met Gly Trp Leu Arg Gln Ala Pro Gly Lys Glu Arg Glu Phe Val
          35                  40                  45

Ala Val Ile Ser Gly Ser Gly Tyr Ser Ala Ser Tyr Arg Asp Ser Val
      50                  55                  60

Lys Gly Arg Phe Thr Ile Ser Arg Asp Asn Ser Lys Asn Thr Val Phe
65                  70                  75                  80

Leu Gln Met Asn Ser Leu Lys Pro Glu Asp Thr Ala Val Tyr Tyr Cys
                  85                  90                  95

Ala Ala Arg Asn Glu Arg Gly Ala Ser Ser Ser Tyr Asp Tyr Trp Gly
              100                 105                 110

Gln Gly Thr Gln Val Thr Val Ser Ser
          115                 120

<210> SEQ ID NO 69
<211> LENGTH: 8
<212> TYPE: PRT
<213> ORGANISM: Artificial Sequence
<220> FEATURE:
<223> OTHER INFORMATION: VH-CDR1

<400> SEQUENCE: 69

Gly Ser Ile Phe Ser Ile Ile Thr
1               5

<210> SEQ ID NO 70
<211> LENGTH: 120
<212> TYPE: PRT
<213> ORGANISM: Artificial Sequence
<220> FEATURE:
<223> OTHER INFORMATION: 3HCE18

<400> SEQUENCE: 70

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Ser Ile Ile
          20                  25                  30

Thr Met Gly Trp Tyr Arg Gln Ala Pro Gly Lys Gln Arg Gly Glu Leu
          35                  40                  45

Val Ala Ala Ile Thr Ser Gly Gly Ser Thr Ser Tyr Ala Asp Ser Val
      50                  55                  60

Lys Gly Arg Phe Ala Ile Ser Arg Asp Ser Ala Lys Asn Thr Ala Tyr
65                  70                  75                  80

Leu Gln Met Asn Ser Leu Lys Pro Glu Asp Thr Ala Val Tyr Tyr Cys
                  85                  90                  95

Asn Ala His Val Arg Asp Tyr Ser Gly Ser Ala Tyr Tyr Thr Gly Gln
              100                 105                 110

Gly Thr Gln Val Thr Val Ser Ser
          115                 120

<210> SEQ ID NO 71
<211> LENGTH: 8
<212> TYPE: PRT
<213> ORGANISM: Artificial Sequence
<220> FEATURE:
<223> OTHER INFORMATION: VH-CDR3

<400> SEQUENCE: 71

-continued

```
Ala Thr Pro Phe Glu Ile Gly Ser
1               5

<210> SEQ ID NO 72
<211> LENGTH: 115
<212> TYPE: PRT
<213> ORGANISM: Artificial Sequence
<220> FEATURE:
<223> OTHER INFORMATION: 2HCE117

<400> SEQUENCE: 72

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Asn Ser Gly Gly Gly Ser Thr Tyr Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asp Ser Leu Lys Pro Glu Asp Thr Ala Val Tyr Tyr Cys
                85                  90                  95

Ala Thr Pro Phe Glu Ile Gly Ser Trp Gly Gln Gly Thr Gln Val Thr
                100                 105                 110

Val Ser Ser
        115

<210> SEQ ID NO 73
<211> LENGTH: 8
<212> TYPE: PRT
<213> ORGANISM: Artificial Sequence
<220> FEATURE:
<223> OTHER INFORMATION: VH-CDR1

<400> SEQUENCE: 73

Gly Phe Ile Phe Asp Asp Tyr Ile
1               5

<210> SEQ ID NO 74
<211> LENGTH: 8
<212> TYPE: PRT
<213> ORGANISM: Artificial Sequence
<220> FEATURE:
<223> OTHER INFORMATION: VH-CDR2

<400> SEQUENCE: 74

Ile Ser Trp Ser Gly Ser Ala Thr
1               5

<210> SEQ ID NO 75
<211> LENGTH: 16
<212> TYPE: PRT
<213> ORGANISM: Artificial Sequence
<220> FEATURE:
<223> OTHER INFORMATION: VH-CDR3

<400> SEQUENCE: 75

Ala Ala Ser Ser Arg Gly Pro Tyr Asn Ser Gly Ser Ser Tyr Asp Tyr
1               5                   10                  15

<210> SEQ ID NO 76
<211> LENGTH: 123
```

```
<212> TYPE: PRT
<213> ORGANISM: Artificial Sequence
<220> FEATURE:
<223> OTHER INFORMATION: 3HCE87

<400> SEQUENCE: 76

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Ile Phe Asp Asp Tyr
            20                  25                  30

Ile Ile Gly Trp Phe Arg Gln Ala Pro Gly Lys Glu Arg Glu Phe Val
        35                  40                  45

Ala Ala Ile Ser Trp Ser Gly Ser Ala Thr Ala Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Thr Leu Lys Pro Glu Asp Thr Ala Val Tyr Tyr Cys
                85                  90                  95

Ala Ala Ser Ser Arg Gly Pro Tyr Asn Ser Gly Ser Ser Tyr Asp Tyr
            100                 105                 110

Trp Gly Gln Gly Thr Gln Val Thr Val Ser Ser
        115                 120

<210> SEQ ID NO 77
<211> LENGTH: 8
<212> TYPE: PRT
<213> ORGANISM: Artificial Sequence
<220> FEATURE:
<223> OTHER INFORMATION: VH-CDR1

<400> SEQUENCE: 77

Gly Tyr Thr Phe Thr Asp Tyr Ala
1               5

<210> SEQ ID NO 78
<211> LENGTH: 8
<212> TYPE: PRT
<213> ORGANISM: Artificial Sequence
<220> FEATURE:
<223> OTHER INFORMATION: VH-CDR2

<400> SEQUENCE: 78

Ile Asn Thr Tyr Thr Gly Lys Pro
1               5

<210> SEQ ID NO 79
<211> LENGTH: 13
<212> TYPE: PRT
<213> ORGANISM: Artificial Sequence
<220> FEATURE:
<223> OTHER INFORMATION: VH-CDR3

<400> SEQUENCE: 79

Ser Arg Glu Arg Gly Tyr Tyr Asp Tyr Ser Arg Ser Asp
1               5                   10

<210> SEQ ID NO 80
<211> LENGTH: 120
<212> TYPE: PRT
<213> ORGANISM: Artificial Sequence
<220> FEATURE:
<223> OTHER INFORMATION: Anti-DLL3-1

<400> SEQUENCE: 80
```

```
Gln Ile Gln Leu Val Gln Ser Gly Pro Glu Leu Lys Lys Pro Gly Glu
1               5               10              15

Ser Val Lys Ile Ser Cys Lys Ala Ser Gly Tyr Thr Phe Thr Asp Tyr
            20              25              30

Ala Met His Trp Val Lys Gln Ala Pro Gly Lys Gly Leu Lys Trp Met
        35              40              45

Gly Trp Ile Asn Thr Tyr Thr Gly Lys Pro Thr Tyr Ala Asp Asp Phe
    50              55              60

Lys Gly Arg Phe Val Leu Ser Leu Glu Ala Ser Ala Ser Thr Ser Thr
65              70              75              80

Leu Gln Ile Ser Asp Leu Arg Asn Glu Asp Thr Ala Ile Tyr Phe Cys
                85              90              95

Ser Arg Glu Arg Gly Tyr Tyr Asp Tyr Ser Arg Ser Asp Trp Gly Gln
            100             105             110

Gly Thr Leu Val Thr Val Ser Ser
        115             120
```

```
<210> SEQ ID NO 81
<211> LENGTH: 7
<212> TYPE: PRT
<213> ORGANISM: Artificial Sequence
<220> FEATURE:
<223> OTHER INFORMATION: VH-CDR2

<400> SEQUENCE: 81

Ile Thr Ser Gly Gly Ser Thr
1               5
```

```
<210> SEQ ID NO 82
<211> LENGTH: 8
<212> TYPE: PRT
<213> ORGANISM: Artificial Sequence
<220> FEATURE:
<223> OTHER INFORMATION: VH-CDR2

<400> SEQUENCE: 82

Ile Ser Ser Asn Gly Arg Asn Thr
1               5
```

```
<210> SEQ ID NO 83
<211> LENGTH: 8
<212> TYPE: PRT
<213> ORGANISM: Artificial Sequence
<220> FEATURE:
<223> OTHER INFORMATION: VH-CDR1

<400> SEQUENCE: 83

Gly Ser Ile Val Gly Asn Tyr Ala
1               5
```

```
<210> SEQ ID NO 84
<211> LENGTH: 9
<212> TYPE: PRT
<213> ORGANISM: Artificial Sequence
<220> FEATURE:
<223> OTHER INFORMATION: VH-CDR3

<400> SEQUENCE: 84

Phe Leu Tyr Asn Ser Gly Asp Asp Tyr
1               5
```

```
<210> SEQ ID NO 85
```

```
<211> LENGTH: 20
<212> TYPE: PRT
<213> ORGANISM: Artificial Sequence
<220> FEATURE:
<223> OTHER INFORMATION: STD1

<400> SEQUENCE: 85

Asn Tyr Gly Gly Gly Gly Ser Gly Gly Gly Gly Ser Gly Gly Gly Gly
1               5                   10                  15

Ser Gly Asn Ser
            20

<210> SEQ ID NO 86
<211> LENGTH: 38
<212> TYPE: PRT
<213> ORGANISM: Artificial Sequence
<220> FEATURE:
<223> OTHER INFORMATION: STD2

<400> SEQUENCE: 86

Asn Tyr Gly Gly Gly Gly Ser Gly Gly Gly Gly Ser Gly Gly Gly Gly
1               5                   10                  15

Ser Gly Asn Tyr Gly Gly Gly Gly Ser Gly Gly Gly Gly Ser Gly Gly
            20                  25                  30

Gly Gly Ser Gly Asn Ser
        35

<210> SEQ ID NO 87
<211> LENGTH: 2
<212> TYPE: PRT
<213> ORGANISM: Artificial Sequence
<220> FEATURE:
<223> OTHER INFORMATION: H1

<400> SEQUENCE: 87

Asn Ser
1

<210> SEQ ID NO 88
<211> LENGTH: 8
<212> TYPE: PRT
<213> ORGANISM: Artificial Sequence
<220> FEATURE:
<223> OTHER INFORMATION: H2

<400> SEQUENCE: 88

Gly Gly Gly Gly Ser Gly Asn Ser
1               5

<210> SEQ ID NO 89
<211> LENGTH: 10
<212> TYPE: PRT
<213> ORGANISM: Artificial Sequence
<220> FEATURE:
<223> OTHER INFORMATION: H3

<400> SEQUENCE: 89

Asn Tyr Gly Gly Gly Gly Ser Gly Asn Ser
1               5                   10

<210> SEQ ID NO 90
<211> LENGTH: 13
<212> TYPE: PRT
<213> ORGANISM: Artificial Sequence
<220> FEATURE:
<223> OTHER INFORMATION: H4
```

-continued

```
<400> SEQUENCE: 90

Gly Gly Gly Gly Ser Gly Gly Gly Gly Ser Gly Asn Ser
1               5                   10

<210> SEQ ID NO 91
<211> LENGTH: 15
<212> TYPE: PRT
<213> ORGANISM: Artificial Sequence
<220> FEATURE:
<223> OTHER INFORMATION: H5

<400> SEQUENCE: 91

Asn Tyr Gly Gly Gly Gly Ser Gly Gly Gly Gly Ser Gly Asn Ser
1               5                   10                  15

<210> SEQ ID NO 92
<211> LENGTH: 18
<212> TYPE: PRT
<213> ORGANISM: Artificial Sequence
<220> FEATURE:
<223> OTHER INFORMATION: H6

<400> SEQUENCE: 92

Gly Gly Gly Gly Ser Gly Gly Gly Gly Ser Gly Gly Gly Gly Ser Gly
1               5                   10                  15

Asn Ser

<210> SEQ ID NO 93
<211> LENGTH: 8
<212> TYPE: PRT
<213> ORGANISM: Artificial Sequence
<220> FEATURE:
<223> OTHER INFORMATION: H7

<400> SEQUENCE: 93

Gly Cys Pro Pro Cys Pro Asn Ser
1               5

<210> SEQ ID NO 94
<211> LENGTH: 5
<212> TYPE: PRT
<213> ORGANISM: Artificial Sequence
<220> FEATURE:
<223> OTHER INFORMATION: Gly4Ser

<400> SEQUENCE: 94

Gly Gly Gly Gly Ser
1               5

<210> SEQ ID NO 95
<211> LENGTH: 15
<212> TYPE: PRT
<213> ORGANISM: Artificial Sequence
<220> FEATURE:
<223> OTHER INFORMATION: (G4S)3

<400> SEQUENCE: 95

Gly Gly Gly Gly Ser Gly Gly Gly Gly Ser Gly Gly Gly Gly Ser
1               5                   10                  15

<210> SEQ ID NO 96
<211> LENGTH: 16
<212> TYPE: PRT
<213> ORGANISM: Artificial Sequence
<220> FEATURE:
```

-continued

<223> OTHER INFORMATION: H105

<400> SEQUENCE: 96

Ser Gly Gly Gly Gly Ser Gly Gly Gly Gly Ser Gly Gly Gly Gly Ser
1               5                   10                  15

<210> SEQ ID NO 97
<211> LENGTH: 20
<212> TYPE: PRT
<213> ORGANISM: Artificial Sequence
<220> FEATURE:
<223> OTHER INFORMATION: (G4S)4

<400> SEQUENCE: 97

Gly Gly Gly Gly Ser Gly Gly Gly Gly Ser Gly Gly Gly Gly Ser Gly
1               5                   10                  15

Gly Gly Gly Ser
            20

<210> SEQ ID NO 98
<211> LENGTH: 21
<212> TYPE: PRT
<213> ORGANISM: Artificial Sequence
<220> FEATURE:
<223> OTHER INFORMATION: H75 (NKG2A quadruple mutant)

<400> SEQUENCE: 98

Gln Arg His Asn Asn Ser Ser Leu Asn Thr Gly Thr Gln Met Ala Gly
1               5                   10                  15

His Ser Pro Asn Ser
            20

<210> SEQ ID NO 99
<211> LENGTH: 16
<212> TYPE: PRT
<213> ORGANISM: Artificial Sequence
<220> FEATURE:
<223> OTHER INFORMATION: H83 (NKG2A derived)

<400> SEQUENCE: 99

Ser Ser Leu Asn Thr Gly Thr Gln Met Ala Gly His Ser Pro Asn Ser
1               5                   10                  15

<210> SEQ ID NO 100
<211> LENGTH: 18
<212> TYPE: PRT
<213> ORGANISM: Artificial Sequence
<220> FEATURE:
<223> OTHER INFORMATION: H106 (NKG2A derived)

<400> SEQUENCE: 100

Gln Arg His Asn Asn Ser Ser Leu Asn Thr Gly Thr Gln Met Ala Gly
1               5                   10                  15

His Ser

<210> SEQ ID NO 101
<211> LENGTH: 14
<212> TYPE: PRT
<213> ORGANISM: Artificial Sequence
<220> FEATURE:
<223> OTHER INFORMATION: H81 (NKG2D derived)

<400> SEQUENCE: 101

Glu Val Gln Ile Pro Leu Thr Glu Ser Tyr Ser Pro Asn Ser
1               5                   10

```
<210> SEQ ID NO 102
<211> LENGTH: 20
<212> TYPE: PRT
<213> ORGANISM: Artificial Sequence
<220> FEATURE:
<223> OTHER INFORMATION: H91 (NKG2D derived)

<400> SEQUENCE: 102

Asn Ser Leu Ala Asn Gln Glu Val Gln Ile Pro Leu Thr Glu Ser Tyr
1               5                   10                  15

Ser Pro Asn Ser
            20

<210> SEQ ID NO 103
<211> LENGTH: 19
<212> TYPE: PRT
<213> ORGANISM: Artificial Sequence
<220> FEATURE:
<223> OTHER INFORMATION: H94

<400> SEQUENCE: 103

Ser Gly Gly Gly Gly Ser Gly Gly Gly Gly Ser Gly Gly Gly Gly Ser
1               5                   10                  15

Pro Asn Ser

<210> SEQ ID NO 104
<211> LENGTH: 19
<212> TYPE: PRT
<213> ORGANISM: Artificial Sequence
<220> FEATURE:
<223> OTHER INFORMATION: H111

<400> SEQUENCE: 104

Ser Gly Gly Gly Gly Ser Gly Gly Gly Gly Ser Gly Gly Gly Gly Ser
1               5                   10                  15

Pro Gly Ser

<210> SEQ ID NO 105
<211> LENGTH: 19
<212> TYPE: PRT
<213> ORGANISM: Artificial Sequence
<220> FEATURE:
<223> OTHER INFORMATION: H113

<400> SEQUENCE: 105

Ser Gly Gly Gly Gly Ser Gly Gly Gly Gly Ser Gly Gly Gly Gly Ser
1               5                   10                  15

Pro Ala Ser

<210> SEQ ID NO 106
<211> LENGTH: 18
<212> TYPE: PRT
<213> ORGANISM: Artificial Sequence
<220> FEATURE:
<223> OTHER INFORMATION: H114

<400> SEQUENCE: 106

Ser Gly Gly Gly Gly Ser Gly Gly Gly Gly Ser Gly Gly Gly Gly Ser
1               5                   10                  15

Pro Ser

<210> SEQ ID NO 107
```

```
<211> LENGTH: 19
<212> TYPE: PRT
<213> ORGANISM: Artificial Sequence
<220> FEATURE:
<223> OTHER INFORMATION: H115

<400> SEQUENCE: 107

Ser Gly Gly Gly Gly Ser Gly Gly Gly Ser Gly Gly Gly Gly Ser
1               5                   10                  15

Pro Ser Ser

<210> SEQ ID NO 108
<211> LENGTH: 16
<212> TYPE: PRT
<213> ORGANISM: Artificial Sequence
<220> FEATURE:
<223> OTHER INFORMATION: H116

<400> SEQUENCE: 108

Ser Gly Ser Glu Thr Pro Gly Thr Ser Glu Ser Ala Thr Pro Glu Ser
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: H117

<400> SEQUENCE: 109

Gly Gly Gly Gly Ser Gly Gly Gly Gly Ser Gly Gly Gly Gly Ser
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: H118

<400> SEQUENCE: 110

Ala His His Ser Glu Asp Pro Ser Ser Lys Ala Pro Lys Ala Pro
1               5                   10                  15

<210> SEQ ID NO 111
<211> LENGTH: 16
<212> TYPE: PRT
<213> ORGANISM: Artificial Sequence
<220> FEATURE:
<223> OTHER INFORMATION: H119

<400> SEQUENCE: 111

Ser Pro Ser Thr Pro Pro Thr Pro Ser Pro Ser Thr Pro Pro Ala Ser
1               5                   10                  15

<210> SEQ ID NO 112
<211> LENGTH: 101
<212> TYPE: PRT
<213> ORGANISM: Artificial Sequence
<220> FEATURE:
<223> OTHER INFORMATION: CH3

<400> SEQUENCE: 112

Glu Pro Gln Val Tyr Thr Leu Pro Pro Ser Arg Asp Glu Leu Thr Lys
1               5                   10                  15

Asn Gln Val Ser Leu Thr Cys Leu Val Lys Gly Phe Tyr Pro Ser Asp
```

-continued

```
             20              25              30
Ile Ala Val Glu Trp Glu Ser Asn Gly Gln Pro Glu Asn Asn Tyr Lys
         35              40              45

Thr Thr Pro Pro Val Leu Asp Ser Asp Gly Ser Phe Phe Leu Tyr Ser
     50              55              60

Lys Leu Thr Val Asp Lys Ser Arg Trp Gln Gln Gly Asn Val Phe Ser
65              70              75              80

Cys Ser Val Met His Glu Ala Leu His Asn His Tyr Thr Gln Lys Ser
             85              90              95

Leu Ser Leu Ser Pro
             100

<210> SEQ ID NO 113
<211> LENGTH: 5
<212> TYPE: PRT
<213> ORGANISM: Artificial Sequence
<220> FEATURE:
<223> OTHER INFORMATION: HSA-1-CDR1

<400> SEQUENCE: 113

Ser Phe Gly Met Ser
1               5

<210> SEQ ID NO 114
<211> LENGTH: 17
<212> TYPE: PRT
<213> ORGANISM: Artificial Sequence
<220> FEATURE:
<223> OTHER INFORMATION: HSA-1-CDR2

<400> SEQUENCE: 114

Ser Ile Ser Gly Ser Gly Ser Asp Thr Leu Tyr Ala Asp Ser Val Lys
1               5               10              15

Gly

<210> SEQ ID NO 115
<211> LENGTH: 6
<212> TYPE: PRT
<213> ORGANISM: Artificial Sequence
<220> FEATURE:
<223> OTHER INFORMATION: HSA-1-CDR3

<400> SEQUENCE: 115

Gly Gly Ser Leu Ser Arg
1               5

<210> SEQ ID NO 116
<211> LENGTH: 5
<212> TYPE: PRT
<213> ORGANISM: Artificial Sequence
<220> FEATURE:
<223> OTHER INFORMATION: HSA-2-CDR1

<400> SEQUENCE: 116

Leu Asn Leu Met Gly
1               5

<210> SEQ ID NO 117
<211> LENGTH: 16
<212> TYPE: PRT
<213> ORGANISM: Artificial Sequence
<220> FEATURE:
<223> OTHER INFORMATION: HSA-2-CDR2
```

```
<400> SEQUENCE: 117

Thr Ile Thr Val Gly Asp Ser Thr Asn Tyr Ala Asp Ser Val Lys Gly
1               5                   10                  15

<210> SEQ ID NO 118
<211> LENGTH: 8
<212> TYPE: PRT
<213> ORGANISM: Artificial Sequence
<220> FEATURE:
<223> OTHER INFORMATION: HSA-2-CDR3

<400> SEQUENCE: 118

Arg Arg Thr Trp His Ser Glu Leu
1               5

<210> SEQ ID NO 119
<211> LENGTH: 5
<212> TYPE: PRT
<213> ORGANISM: Artificial Sequence
<220> FEATURE:
<223> OTHER INFORMATION: HSA-3-CDR1

<400> SEQUENCE: 119

Ile Asn Leu Leu Gly
1               5

<210> SEQ ID NO 120
<211> LENGTH: 16
<212> TYPE: PRT
<213> ORGANISM: Artificial Sequence
<220> FEATURE:
<223> OTHER INFORMATION: HSA-3-CDR2

<400> SEQUENCE: 120

Thr Ile Thr Val Gly Asp Ser Thr Ser Tyr Ala Asp Ser Val Lys Gly
1               5                   10                  15

<210> SEQ ID NO 121
<211> LENGTH: 8
<212> TYPE: PRT
<213> ORGANISM: Artificial Sequence
<220> FEATURE:
<223> OTHER INFORMATION: HSA-3-CDR3

<400> SEQUENCE: 121

Arg Arg Thr Trp His Ser Glu Leu
1               5

<210> SEQ ID NO 122
<211> LENGTH: 5
<212> TYPE: PRT
<213> ORGANISM: Artificial Sequence
<220> FEATURE:
<223> OTHER INFORMATION: HSA-4-CDR1

<400> SEQUENCE: 122

Ser Phe Gly Met Ser
1               5

<210> SEQ ID NO 123
<211> LENGTH: 17
<212> TYPE: PRT
<213> ORGANISM: Artificial Sequence
<220> FEATURE:
<223> OTHER INFORMATION: HSA-4-CDR2

<400> SEQUENCE: 123
```

```
Ser Ile Asn Gly Arg Gly Asp Asp Thr Arg Tyr Ala Asp Ser Val Lys
1               5                   10                  15

Gly

<210> SEQ ID NO 124
<211> LENGTH: 7
<212> TYPE: PRT
<213> ORGANISM: Artificial Sequence
<220> FEATURE:
<223> OTHER INFORMATION: HSA-4-CDR3

<400> SEQUENCE: 124

Gly Arg Ser Val Ser Arg Ser
1               5

<210> SEQ ID NO 125
<211> LENGTH: 5
<212> TYPE: PRT
<213> ORGANISM: Artificial Sequence
<220> FEATURE:
<223> OTHER INFORMATION: HSA-5-CDR1

<400> SEQUENCE: 125

Ser Phe Gly Met Ser
1               5

<210> SEQ ID NO 126
<211> LENGTH: 17
<212> TYPE: PRT
<213> ORGANISM: Artificial Sequence
<220> FEATURE:
<223> OTHER INFORMATION: HSA-5-CDR2

<400> SEQUENCE: 126

Ala Ile Ser Ala Asp Ser Ser Asp Lys Arg Tyr Ala Asp Ser Val Lys
1               5                   10                  15

Gly

<210> SEQ ID NO 127
<211> LENGTH: 5
<212> TYPE: PRT
<213> ORGANISM: Artificial Sequence
<220> FEATURE:
<223> OTHER INFORMATION: HSA-5-CDR3

<400> SEQUENCE: 127

Gly Arg Gly Ser Pro
1               5

<210> SEQ ID NO 128
<211> LENGTH: 5
<212> TYPE: PRT
<213> ORGANISM: Artificial Sequence
<220> FEATURE:
<223> OTHER INFORMATION: HSA-6-CDR1

<400> SEQUENCE: 128

Ser Phe Gly Met Ser
1               5

<210> SEQ ID NO 129
<211> LENGTH: 17
<212> TYPE: PRT
<213> ORGANISM: Artificial Sequence
<220> FEATURE:
```

<223> OTHER INFORMATION: HSA-6-CDR2

<400> SEQUENCE: 129

Ala Ile Ser Ala Asp Ser Ser Asp Lys Arg Tyr Ala Asp Ser Val Lys
1               5                   10                  15

Gly

<210> SEQ ID NO 130
<211> LENGTH: 5
<212> TYPE: PRT
<213> ORGANISM: Artificial Sequence
<220> FEATURE:
<223> OTHER INFORMATION: HSA-6-CDR3

<400> SEQUENCE: 130

Gly Arg Gly Ser Pro
1               5

<210> SEQ ID NO 131
<211> LENGTH: 5
<212> TYPE: PRT
<213> ORGANISM: Artificial Sequence
<220> FEATURE:
<223> OTHER INFORMATION: HSA-7-CDR1

<400> SEQUENCE: 131

Asn Tyr Trp Met Tyr
1               5

<210> SEQ ID NO 132
<211> LENGTH: 17
<212> TYPE: PRT
<213> ORGANISM: Artificial Sequence
<220> FEATURE:
<223> OTHER INFORMATION: HSA-7-CDR2

<400> SEQUENCE: 132

Arg Ile Ser Thr Gly Gly Gly Tyr Ser Tyr Tyr Ala Asp Ser Val Lys
1               5                   10                  15

Gly

<210> SEQ ID NO 133
<211> LENGTH: 13
<212> TYPE: PRT
<213> ORGANISM: Artificial Sequence
<220> FEATURE:
<223> OTHER INFORMATION: HSA-7-CDR3

<400> SEQUENCE: 133

Asp Arg Glu Ala Gln Val Asp Thr Leu Asp Phe Asp Tyr
1               5                   10

<210> SEQ ID NO 134
<211> LENGTH: 12
<212> TYPE: PRT
<213> ORGANISM: Artificial Sequence
<220> FEATURE:
<223> OTHER INFORMATION: DLL3-VL-1-CDR1

<400> SEQUENCE: 134

Arg Ala Ser Gln Arg Val Asn Asn Asn Tyr Leu Ala
1               5                   10

<210> SEQ ID NO 135
<211> LENGTH: 7

<212> TYPE: PRT
<213> ORGANISM: Artificial Sequence
<220> FEATURE:
<223> OTHER INFORMATION: DLL3-VL-1-CDR2

<400> SEQUENCE: 135

Gly Ala Ser Ser Arg Ala Thr
1               5

<210> SEQ ID NO 136
<211> LENGTH: 9
<212> TYPE: PRT
<213> ORGANISM: Artificial Sequence
<220> FEATURE:
<223> OTHER INFORMATION: DLL3-VL-1-CDR3

<400> SEQUENCE: 136

Gln Gln Tyr Asp Arg Ser Pro Leu Thr
1               5

<210> SEQ ID NO 137
<211> LENGTH: 12
<212> TYPE: PRT
<213> ORGANISM: Artificial Sequence
<220> FEATURE:
<223> OTHER INFORMATION: DLL3-VL-2-CDR1

<400> SEQUENCE: 137

Arg Ala Ser Gln Ser Val Asn Lys Asn Tyr Leu Ala
1               5                   10

<210> SEQ ID NO 138
<211> LENGTH: 7
<212> TYPE: PRT
<213> ORGANISM: Artificial Sequence
<220> FEATURE:
<223> OTHER INFORMATION: DLL3-VL-2-CDR2

<400> SEQUENCE: 138

Gly Ala Ser Ser Arg Ala Thr
1               5

<210> SEQ ID NO 139
<211> LENGTH: 9
<212> TYPE: PRT
<213> ORGANISM: Artificial Sequence
<220> FEATURE:
<223> OTHER INFORMATION: DLL3-VL-2-CDR3

<400> SEQUENCE: 139

Gln Gln Tyr Asp Arg Ser Pro Leu Thr
1               5

<210> SEQ ID NO 140
<211> LENGTH: 12
<212> TYPE: PRT
<213> ORGANISM: Artificial Sequence
<220> FEATURE:
<223> OTHER INFORMATION: DLL3-VL-3-CDR1

<400> SEQUENCE: 140

Arg Ala Ser Gln Ser Val Ser Arg Gly Tyr Leu Ala
1               5                   10

<210> SEQ ID NO 141
<211> LENGTH: 7
<212> TYPE: PRT

```
<213> ORGANISM: Artificial Sequence
<220> FEATURE:
<223> OTHER INFORMATION: DLL3-VL-3-CDR2

<400> SEQUENCE: 141

Gly Ala Ser Ser Arg Ala Thr
1               5

<210> SEQ ID NO 142
<211> LENGTH: 9
<212> TYPE: PRT
<213> ORGANISM: Artificial Sequence
<220> FEATURE:
<223> OTHER INFORMATION: DLL3-VL-3-CDR3

<400> SEQUENCE: 142

Gln Gln Tyr Asp Thr Ser Pro Ile Thr
1               5

<210> SEQ ID NO 143
<211> LENGTH: 16
<212> TYPE: PRT
<213> ORGANISM: Artificial Sequence
<220> FEATURE:
<223> OTHER INFORMATION: DLL3-VL-4-CDR1

<400> SEQUENCE: 143

Arg Ser Ser Gln Ser Leu Leu His Ser Asn Gly Tyr Asn Tyr Leu Asp
1               5                   10                  15

<210> SEQ ID NO 144
<211> LENGTH: 7
<212> TYPE: PRT
<213> ORGANISM: Artificial Sequence
<220> FEATURE:
<223> OTHER INFORMATION: DLL3-VL-4-CDR2

<400> SEQUENCE: 144

Leu Gly Ser Asn Arg Ala Ser
1               5

<210> SEQ ID NO 145
<211> LENGTH: 9
<212> TYPE: PRT
<213> ORGANISM: Artificial Sequence
<220> FEATURE:
<223> OTHER INFORMATION: DLL3-VL-4-CDR3

<400> SEQUENCE: 145

Met Gln Ala Leu Gln Thr Pro Phe Thr
1               5

<210> SEQ ID NO 146
<211> LENGTH: 11
<212> TYPE: PRT
<213> ORGANISM: Artificial Sequence
<220> FEATURE:
<223> OTHER INFORMATION: DLL3-VL-5-CDR1

<400> SEQUENCE: 146

Arg Ala Ser Gln Ser Ile Ser Ser Tyr Leu Asn
1               5                   10

<210> SEQ ID NO 147
<211> LENGTH: 7
<212> TYPE: PRT
<213> ORGANISM: Artificial Sequence
```

```
<220> FEATURE:
<223> OTHER INFORMATION: DLL3-VL-5-CDR2

<400> SEQUENCE: 147

Ala Ala Ser Ser Leu Gln Ser
1               5

<210> SEQ ID NO 148
<211> LENGTH: 9
<212> TYPE: PRT
<213> ORGANISM: Artificial Sequence
<220> FEATURE:
<223> OTHER INFORMATION: DLL3-VL-5-CDR3

<400> SEQUENCE: 148

Gln Gln Ser Phe Thr Thr Pro Leu Thr
1               5

<210> SEQ ID NO 149
<211> LENGTH: 11
<212> TYPE: PRT
<213> ORGANISM: Artificial Sequence
<220> FEATURE:
<223> OTHER INFORMATION: DLL3-VL-6-CDR1

<400> SEQUENCE: 149

Ser Pro Gly Glu Arg Ala Thr Leu Ser Cys Lys
1               5                   10

<210> SEQ ID NO 150
<211> LENGTH: 6
<212> TYPE: PRT
<213> ORGANISM: Artificial Sequence
<220> FEATURE:
<223> OTHER INFORMATION: DLL3-VL-6-CDR2

<400> SEQUENCE: 150

Tyr Ala Ser Asn Arg Tyr
1               5

<210> SEQ ID NO 151
<211> LENGTH: 9
<212> TYPE: PRT
<213> ORGANISM: Artificial Sequence
<220> FEATURE:
<223> OTHER INFORMATION: DLL3-VL-6-CDR3

<400> SEQUENCE: 151

Gln Gln Asp Tyr Thr Ser Pro Trp Thr
1               5

<210> SEQ ID NO 152
<211> LENGTH: 12
<212> TYPE: PRT
<213> ORGANISM: Artificial Sequence
<220> FEATURE:
<223> OTHER INFORMATION: DLL3-VL-7-CDR1

<400> SEQUENCE: 152

Arg Ala Ser Gln Ser Val Ser Ser Ser Tyr Leu Ala
1               5                   10

<210> SEQ ID NO 153
<211> LENGTH: 7
<212> TYPE: PRT
<213> ORGANISM: Artificial Sequence
<220> FEATURE:
```

-continued

<223> OTHER INFORMATION: DLL3-VL-7-CDR2

<400> SEQUENCE: 153

Gly Ala Ser Thr Arg Ala Thr
1               5

<210> SEQ ID NO 154
<211> LENGTH: 9
<212> TYPE: PRT
<213> ORGANISM: Artificial Sequence
<220> FEATURE:
<223> OTHER INFORMATION: DLL3-VL-7-CDR3

<400> SEQUENCE: 154

Gln Gln Tyr Gly Thr Ser Pro Leu Thr
1               5

<210> SEQ ID NO 155
<211> LENGTH: 11
<212> TYPE: PRT
<213> ORGANISM: Artificial Sequence
<220> FEATURE:
<223> OTHER INFORMATION: DLL3-VL-8-CDR1

<400> SEQUENCE: 155

Gln Ala Ser Gln Asp Ile Arg Asn Tyr Leu Asn
1               5                   10

<210> SEQ ID NO 156
<211> LENGTH: 7
<212> TYPE: PRT
<213> ORGANISM: Artificial Sequence
<220> FEATURE:
<223> OTHER INFORMATION: DLL3-VL-8-CDR2

<400> SEQUENCE: 156

Asp Ala Ser Asn Leu Glu Thr
1               5

<210> SEQ ID NO 157
<211> LENGTH: 10
<212> TYPE: PRT
<213> ORGANISM: Artificial Sequence
<220> FEATURE:
<223> OTHER INFORMATION: DLL3-VL-8-CDR3

<400> SEQUENCE: 157

Gln His Tyr Asp Asn Leu Pro Leu Thr Phe
1               5                   10

<210> SEQ ID NO 158
<211> LENGTH: 11
<212> TYPE: PRT
<213> ORGANISM: Artificial Sequence
<220> FEATURE:
<223> OTHER INFORMATION: DLL3-VL-9-CDR1

<400> SEQUENCE: 158

Arg Ala Ser Gln Gly Ile Arg Asn Tyr Leu Gly
1               5                   10

<210> SEQ ID NO 159
<211> LENGTH: 7
<212> TYPE: PRT
<213> ORGANISM: Artificial Sequence
<220> FEATURE:
<223> OTHER INFORMATION: DLL3-VL-9-CDR2

<400> SEQUENCE: 159

Ala Ala Ser Ser Leu Gln Ser
1               5

<210> SEQ ID NO 160
<211> LENGTH: 10
<212> TYPE: PRT
<213> ORGANISM: Artificial Sequence
<220> FEATURE:
<223> OTHER INFORMATION: DLL3-VL-9-CDR3

<400> SEQUENCE: 160

Leu Gln His Asp Ser Asp Leu Arg Thr Phe
1               5                   10

<210> SEQ ID NO 161
<211> LENGTH: 10
<212> TYPE: PRT
<213> ORGANISM: Artificial Sequence
<220> FEATURE:
<223> OTHER INFORMATION: DLL3-VL-10-CDR1

<400> SEQUENCE: 161

Thr Ala Ser Ser Ser Val Ser Ser Ser Tyr
1               5                   10

<210> SEQ ID NO 162
<211> LENGTH: 7
<212> TYPE: PRT
<213> ORGANISM: Artificial Sequence
<220> FEATURE:
<223> OTHER INFORMATION: DLL3-VL-10-CDR2

<400> SEQUENCE: 162

Ser Thr Ser Asn Leu Ala Ser
1               5

<210> SEQ ID NO 163
<211> LENGTH: 19
<212> TYPE: PRT
<213> ORGANISM: Artificial Sequence
<220> FEATURE:
<223> OTHER INFORMATION: DLL3-VL-10-CDR3

<400> SEQUENCE: 163

His Gln Tyr His Arg Ser Pro Phe Thr Phe Gly Ala Gly Thr Lys Leu
1               5                   10                  15

Lys Ile Arg

<210> SEQ ID NO 164
<211> LENGTH: 9
<212> TYPE: PRT
<213> ORGANISM: Artificial Sequence
<220> FEATURE:
<223> OTHER INFORMATION: DLL3-VL-11-CDR1

<400> SEQUENCE: 164

Arg Ala Ser Gln Asp Ile Ser Asn Tyr
1               5

<210> SEQ ID NO 165
<211> LENGTH: 7
<212> TYPE: PRT
<213> ORGANISM: Artificial Sequence
<220> FEATURE:

<223> OTHER INFORMATION: DLL3-VL-11-CDR2

<400> SEQUENCE: 165

Tyr Thr Ser Arg Leu His Ser
1               5

<210> SEQ ID NO 166
<211> LENGTH: 19
<212> TYPE: PRT
<213> ORGANISM: Artificial Sequence
<220> FEATURE:
<223> OTHER INFORMATION: DLL3-VL-11-CDR3

<400> SEQUENCE: 166

Gln Gln Gly Asp Met Leu Pro Trp Thr Phe Gly Gly Gly Thr Lys Leu
1               5                   10                  15

Glu Ile Lys

<210> SEQ ID NO 167
<211> LENGTH: 8
<212> TYPE: PRT
<213> ORGANISM: Artificial Sequence
<220> FEATURE:
<223> OTHER INFORMATION: DLL3-VL-12-CDR1

<400> SEQUENCE: 167

Ser Ala Ser Ser Ser Val Ser Tyr
1               5

<210> SEQ ID NO 168
<211> LENGTH: 7
<212> TYPE: PRT
<213> ORGANISM: Artificial Sequence
<220> FEATURE:
<223> OTHER INFORMATION: DLL3-VL-12-CDR2

<400> SEQUENCE: 168

Asp Thr Ser Lys Leu Ala Ser
1               5

<210> SEQ ID NO 169
<211> LENGTH: 19
<212> TYPE: PRT
<213> ORGANISM: Artificial Sequence
<220> FEATURE:
<223> OTHER INFORMATION: DLL3-VL-12-CDR3

<400> SEQUENCE: 169

Gln Gln Trp Thr Arg Asn Pro Leu Thr Phe Gly Ala Gly Thr Lys Leu
1               5                   10                  15

Glu Leu Lys

<210> SEQ ID NO 170
<211> LENGTH: 16
<212> TYPE: PRT
<213> ORGANISM: Artificial Sequence
<220> FEATURE:
<223> OTHER INFORMATION: DLL3-VL-13-CDR1

<400> SEQUENCE: 170

Lys Ser Ser Gln Ser Val Leu Val Tyr Ser Ser Asn Gln Lys Asn Tyr
1               5                   10                  15

<210> SEQ ID NO 171
<211> LENGTH: 7

```
<212> TYPE: PRT
<213> ORGANISM: Artificial Sequence
<220> FEATURE:
<223> OTHER INFORMATION: DLL3-VL-13-CDR2

<400> SEQUENCE: 171

Trp Ala Ser Thr Arg Glu Ser
1               5

<210> SEQ ID NO 172
<211> LENGTH: 18
<212> TYPE: PRT
<213> ORGANISM: Artificial Sequence
<220> FEATURE:
<223> OTHER INFORMATION: DLL3-VL-13-CDR3

<400> SEQUENCE: 172

His Gln Tyr Leu Ser Ser Trp Thr Phe Gly Gly Gly Thr Lys Leu Glu
1               5                   10                  15

Ile Lys

<210> SEQ ID NO 173
<211> LENGTH: 9
<212> TYPE: PRT
<213> ORGANISM: Artificial Sequence
<220> FEATURE:
<223> OTHER INFORMATION: DLL3-VL-14-CDR1

<400> SEQUENCE: 173

Gln Ala Thr Gln Asp Ile Val Lys Asn
1               5

<210> SEQ ID NO 174
<211> LENGTH: 7
<212> TYPE: PRT
<213> ORGANISM: Artificial Sequence
<220> FEATURE:
<223> OTHER INFORMATION: DLL3-VL-14-CDR2

<400> SEQUENCE: 174

Tyr Ala Ile Glu Leu Ala Glu
1               5

<210> SEQ ID NO 175
<211> LENGTH: 19
<212> TYPE: PRT
<213> ORGANISM: Artificial Sequence
<220> FEATURE:
<223> OTHER INFORMATION: DLL3-VL-14-CDR3

<400> SEQUENCE: 175

Leu Gln Phe Tyr Glu Phe Pro Phe Thr Phe Gly Ala Gly Thr Lys Leu
1               5                   10                  15

Glu Leu Lys

<210> SEQ ID NO 176
<211> LENGTH: 10
<212> TYPE: PRT
<213> ORGANISM: Artificial Sequence
<220> FEATURE:
<223> OTHER INFORMATION: DLL3-VL-15-CDR1

<400> SEQUENCE: 176

Thr Ala Ser Ser Ser Val Ser Ser Ser Tyr
1               5                   10
```

-continued

<210> SEQ ID NO 177
<211> LENGTH: 14
<212> TYPE: PRT
<213> ORGANISM: Artificial Sequence
<220> FEATURE:
<223> OTHER INFORMATION: DLL3-VL-16-CDR1

<400> SEQUENCE: 177

Lys Ser Ser Gln Ser Leu Ser Asp Ser Asp Gly Lys Thr Tyr
1               5                   10

<210> SEQ ID NO 178
<211> LENGTH: 19
<212> TYPE: PRT
<213> ORGANISM: Artificial Sequence
<220> FEATURE:
<223> OTHER INFORMATION: DLL3-VL-15-CDR3

<400> SEQUENCE: 178

His Gln Tyr His Arg Ser Pro Phe Thr Phe Gly Ser Gly Thr Lys Leu
1               5                   10                  15

Glu Ile Lys

<210> SEQ ID NO 179
<211> LENGTH: 19
<212> TYPE: PRT
<213> ORGANISM: Artificial Sequence
<220> FEATURE:
<223> OTHER INFORMATION: DLL3-VL-16-CDR3

<400> SEQUENCE: 179

Trp Gln Gly Lys His Phe Pro Trp Thr Phe Gly Gly Gly Thr Lys Leu
1               5                   10                  15

Glu Ile Lys

<210> SEQ ID NO 180
<211> LENGTH: 8
<212> TYPE: PRT
<213> ORGANISM: Artificial Sequence
<220> FEATURE:
<223> OTHER INFORMATION: DLL3-VL-17-CDR1

<400> SEQUENCE: 180

Ser Ala Ser Ser Ser Val Ser Tyr
1               5

<210> SEQ ID NO 181
<211> LENGTH: 7
<212> TYPE: PRT
<213> ORGANISM: Artificial Sequence
<220> FEATURE:
<223> OTHER INFORMATION: DLL3-VL-17-CDR2

<400> SEQUENCE: 181

Leu Thr Ser Asn Leu Ala Ser
1               5

<210> SEQ ID NO 182
<211> LENGTH: 19
<212> TYPE: PRT
<213> ORGANISM: Artificial Sequence
<220> FEATURE:
<223> OTHER INFORMATION: DLL3-VL-17-CDR3

<400> SEQUENCE: 182

Gln Gln Trp Arg Ser Asn Pro Phe Thr Phe Gly Ser Gly Thr Lys Leu
1               5                   10                  15

Glu Ile Lys

<210> SEQ ID NO 183
<211> LENGTH: 9
<212> TYPE: PRT
<213> ORGANISM: Artificial Sequence
<220> FEATURE:
<223> OTHER INFORMATION: DLL3-VL-18-CDR1

<400> SEQUENCE: 183

Arg Ala Ser Glu Asn Ile Tyr Tyr Asn
1               5

<210> SEQ ID NO 184
<211> LENGTH: 7
<212> TYPE: PRT
<213> ORGANISM: Artificial Sequence
<220> FEATURE:
<223> OTHER INFORMATION: DLL3-VL-18-CDR2

<400> SEQUENCE: 184

Thr Ala Asn Ser Leu Glu Asp
1               5

<210> SEQ ID NO 185
<211> LENGTH: 19
<212> TYPE: PRT
<213> ORGANISM: Artificial Sequence
<220> FEATURE:
<223> OTHER INFORMATION: DLL3-VL-18-CDR3

<400> SEQUENCE: 185

Lys Gln Ala Tyr Asp Val Pro Pro Thr Phe Gly Gly Gly Thr Lys Leu
1               5                   10                  15

Glu Ile Lys

<210> SEQ ID NO 186
<211> LENGTH: 9
<212> TYPE: PRT
<213> ORGANISM: Artificial Sequence
<220> FEATURE:
<223> OTHER INFORMATION: DLL3-VL-19-CDR1

<400> SEQUENCE: 186

Arg Ala Ser Gln Asn Ile Ile Asn Tyr
1               5

<210> SEQ ID NO 187
<211> LENGTH: 7
<212> TYPE: PRT
<213> ORGANISM: Artificial Sequence
<220> FEATURE:
<223> OTHER INFORMATION: DLL3-VL-19-CDR2

<400> SEQUENCE: 187

Tyr Thr Ser Arg Leu His Ser
1               5

<210> SEQ ID NO 188
<211> LENGTH: 20
<212> TYPE: PRT
<213> ORGANISM: Artificial Sequence
<220> FEATURE:
<223> OTHER INFORMATION: DLL3-VL-19-CDR3

-continued

```
<400> SEQUENCE: 188

Gln Gln Tyr Ser Glu Arg Pro Tyr Thr Phe Gly Gly Gly Thr Lys Leu
1               5                   10                  15

Glu Ile Lys Arg
            20

<210> SEQ ID NO 189
<211> LENGTH: 9
<212> TYPE: PRT
<213> ORGANISM: Artificial Sequence
<220> FEATURE:
<223> OTHER INFORMATION: DLL3-VL-20-CDR1

<400> SEQUENCE: 189

Lys Ala Ser Gln Asp Ile His Lys Tyr
1               5

<210> SEQ ID NO 190
<211> LENGTH: 7
<212> TYPE: PRT
<213> ORGANISM: Artificial Sequence
<220> FEATURE:
<223> OTHER INFORMATION: DLL3-VL-20-CDR2

<400> SEQUENCE: 190

Tyr Thr Ser Thr Leu Gln Pro
1               5

<210> SEQ ID NO 191
<211> LENGTH: 19
<212> TYPE: PRT
<213> ORGANISM: Artificial Sequence
<220> FEATURE:
<223> OTHER INFORMATION: DLL3-VL-20-CDR3

<400> SEQUENCE: 191

Leu Gln Tyr Asn Asn Leu Tyr Thr Phe Gly Gly Gly Thr Lys Leu Glu
1               5                   10                  15

Ile Lys Arg

<210> SEQ ID NO 192
<211> LENGTH: 9
<212> TYPE: PRT
<213> ORGANISM: Artificial Sequence
<220> FEATURE:
<223> OTHER INFORMATION: DLL3-VL-21-CDR1

<400> SEQUENCE: 192

Gln Ala Thr Gln Asp Ile Val Lys Asn
1               5

<210> SEQ ID NO 193
<211> LENGTH: 7
<212> TYPE: PRT
<213> ORGANISM: Artificial Sequence
<220> FEATURE:
<223> OTHER INFORMATION: DLL3-VL-21-CDR2

<400> SEQUENCE: 193

Tyr Ala Thr Glu Leu Ala Glu
1               5

<210> SEQ ID NO 194
<211> LENGTH: 19
```

```
<212> TYPE: PRT
<213> ORGANISM: Artificial Sequence
<220> FEATURE:
<223> OTHER INFORMATION: DLL3-VL-21-CDR3

<400> SEQUENCE: 194

Leu Gln Phe Tyr Glu Phe Pro Phe Thr Phe Gly Ala Gly Thr Lys Leu
1               5                   10                  15

Glu Leu Lys

<210> SEQ ID NO 195
<211> LENGTH: 15
<212> TYPE: PRT
<213> ORGANISM: Artificial Sequence
<220> FEATURE:
<223> OTHER INFORMATION: DLL3-VL-22-CDR1

<400> SEQUENCE: 195

Lys Ser Ser Gln Ser Leu Leu Asn Ser Ser Asn Gln Lys Asn Tyr
1               5                   10                  15

<210> SEQ ID NO 196
<211> LENGTH: 7
<212> TYPE: PRT
<213> ORGANISM: Artificial Sequence
<220> FEATURE:
<223> OTHER INFORMATION: DLL3-VL-22-CDR2

<400> SEQUENCE: 196

Phe Ala Ser Thr Arg Glu Ser
1               5

<210> SEQ ID NO 197
<211> LENGTH: 19
<212> TYPE: PRT
<213> ORGANISM: Artificial Sequence
<220> FEATURE:
<223> OTHER INFORMATION: DLL3-VL-22-CDR3

<400> SEQUENCE: 197

Gln Gln His Tyr Ser Ile Pro Leu Thr Phe Gly Ala Gly Thr Lys Leu
1               5                   10                  15

Glu Leu Lys

<210> SEQ ID NO 198
<211> LENGTH: 9
<212> TYPE: PRT
<213> ORGANISM: Artificial Sequence
<220> FEATURE:
<223> OTHER INFORMATION: DLL3-VL-23-CDR1

<400> SEQUENCE: 198

Arg Ala Ser Gln Asp Ile Lys Asn Tyr
1               5

<210> SEQ ID NO 199
<211> LENGTH: 7
<212> TYPE: PRT
<213> ORGANISM: Artificial Sequence
<220> FEATURE:
<223> OTHER INFORMATION: DLL3-VL-23-CDR2

<400> SEQUENCE: 199

Tyr Thr Ser Arg Val His Ser
1               5
```

-continued

```
<210> SEQ ID NO 200
<211> LENGTH: 17
<212> TYPE: PRT
<213> ORGANISM: Artificial Sequence
<220> FEATURE:
<223> OTHER INFORMATION: DLL3-VL-23-CDR3

<400> SEQUENCE: 200

Gln Gln Gly Tyr Thr Leu Pro Phe Thr Phe Gly Ser Gly Thr Lys Leu
1               5                   10                  15

Glu

<210> SEQ ID NO 201
<211> LENGTH: 10
<212> TYPE: PRT
<213> ORGANISM: Artificial Sequence
<220> FEATURE:
<223> OTHER INFORMATION: DLL3-VL-24-CDR1

<400> SEQUENCE: 201

Ser Ala Ser Ser Ser Val Ser Ser Arg Tyr
1               5                   10

<210> SEQ ID NO 202
<211> LENGTH: 7
<212> TYPE: PRT
<213> ORGANISM: Artificial Sequence
<220> FEATURE:
<223> OTHER INFORMATION: DLL3-VL-24-CDR2

<400> SEQUENCE: 202

Ser Thr Ser Asn Leu Ala Ser
1               5

<210> SEQ ID NO 203
<211> LENGTH: 19
<212> TYPE: PRT
<213> ORGANISM: Artificial Sequence
<220> FEATURE:
<223> OTHER INFORMATION: DLL3-VL-24-CDR3

<400> SEQUENCE: 203

His Gln Trp Ser Asn Tyr Pro Leu Thr Phe Gly Ala Gly Thr Lys Leu
1               5                   10                  15

Glu Leu Lys

<210> SEQ ID NO 204
<211> LENGTH: 8
<212> TYPE: PRT
<213> ORGANISM: Artificial Sequence
<220> FEATURE:
<223> OTHER INFORMATION: DLL3-VL-25-CDR1

<400> SEQUENCE: 204

Ser Ala Ser Ser Ser Val Ser Tyr
1               5

<210> SEQ ID NO 205
<211> LENGTH: 7
<212> TYPE: PRT
<213> ORGANISM: Artificial Sequence
<220> FEATURE:
<223> OTHER INFORMATION: DLL3-VL-25-CDR2

<400> SEQUENCE: 205
```

Asp Ser Ser Lys Leu Ala Ser
1               5

<210> SEQ ID NO 206
<211> LENGTH: 19
<212> TYPE: PRT
<213> ORGANISM: Artificial Sequence
<220> FEATURE:
<223> OTHER INFORMATION: DLL3-VL-25-CDR3

<400> SEQUENCE: 206

Gln Gln Trp Ser Ser Asn Pro Leu Thr Phe Gly Ala Gly Thr Lys Leu
1               5                   10                  15

Glu Leu Lys

<210> SEQ ID NO 207
<211> LENGTH: 14
<212> TYPE: PRT
<213> ORGANISM: Artificial Sequence
<220> FEATURE:
<223> OTHER INFORMATION: DLL3-VL-26-CDR1

<400> SEQUENCE: 207

Lys Ser Ser Gln Ser Leu Ser Asp Ser Asp Gly Lys Thr Tyr
1               5                   10

<210> SEQ ID NO 208
<211> LENGTH: 7
<212> TYPE: PRT
<213> ORGANISM: Artificial Sequence
<220> FEATURE:
<223> OTHER INFORMATION: DLL3-VL-26-CDR2

<400> SEQUENCE: 208

Leu Val Ser Lys Leu Asp Ser
1               5

<210> SEQ ID NO 209
<211> LENGTH: 19
<212> TYPE: PRT
<213> ORGANISM: Artificial Sequence
<220> FEATURE:
<223> OTHER INFORMATION: DLL3-VL-26-CDR3

<400> SEQUENCE: 209

Trp Gln Gly Lys His Phe Pro Trp Thr Phe Gly Gly Gly Thr Lys Leu
1               5                   10                  15

Glu Ile Lys

<210> SEQ ID NO 210
<211> LENGTH: 8
<212> TYPE: PRT
<213> ORGANISM: Artificial Sequence
<220> FEATURE:
<223> OTHER INFORMATION: DLL3-VL-27-CDR1

<400> SEQUENCE: 210

Ser Ala Ser Ser Ser Val Ser Tyr
1               5

<210> SEQ ID NO 211
<211> LENGTH: 7
<212> TYPE: PRT
<213> ORGANISM: Artificial Sequence
<220> FEATURE:
<223> OTHER INFORMATION: DLL3-VL-27-CDR2

<400> SEQUENCE: 211

Thr Thr Ser Asn Leu Ala Ser
1               5

<210> SEQ ID NO 212
<211> LENGTH: 19
<212> TYPE: PRT
<213> ORGANISM: Artificial Sequence
<220> FEATURE:
<223> OTHER INFORMATION: DLL3-VL-27-CDR3

<400> SEQUENCE: 212

Gln Gln Arg Ser Leu Tyr Pro Tyr Thr Phe Gly Gly Gly Thr Lys Val
1               5                   10                  15

Glu Ile Lys

<210> SEQ ID NO 213
<211> LENGTH: 10
<212> TYPE: PRT
<213> ORGANISM: Artificial Sequence
<220> FEATURE:
<223> OTHER INFORMATION: DLL3-VL-28-CDR1

<400> SEQUENCE: 213

Thr Ala Ser Ser Ser Val Thr Ser Ser Tyr
1               5                   10

<210> SEQ ID NO 214
<211> LENGTH: 7
<212> TYPE: PRT
<213> ORGANISM: Artificial Sequence
<220> FEATURE:
<223> OTHER INFORMATION: DLL3-VL-28-CDR2

<400> SEQUENCE: 214

Ser Thr Ser Asn Leu Ala Ser
1               5

<210> SEQ ID NO 215
<211> LENGTH: 19
<212> TYPE: PRT
<213> ORGANISM: Artificial Sequence
<220> FEATURE:
<223> OTHER INFORMATION: DLL3-VL-28-CDR3

<400> SEQUENCE: 215

His Gln Phe His Arg Ser Pro Phe Thr Phe Gly Ser Gly Thr Lys Leu
1               5                   10                  15

Glu Ile Lys

<210> SEQ ID NO 216
<211> LENGTH: 14
<212> TYPE: PRT
<213> ORGANISM: Artificial Sequence
<220> FEATURE:
<223> OTHER INFORMATION: DLL3-VL-29-CDR1

<400> SEQUENCE: 216

Lys Ser Thr Lys Ser Leu Leu Asn Ser Asp Gly Phe Thr Tyr
1               5                   10

<210> SEQ ID NO 217
<211> LENGTH: 7
<212> TYPE: PRT

```
<213> ORGANISM: Artificial Sequence
<220> FEATURE:
<223> OTHER INFORMATION: DLL3-VL-29-CDR2

<400> SEQUENCE: 217

Leu Val Ser Asn Arg Phe Ser
1               5

<210> SEQ ID NO 218
<211> LENGTH: 19
<212> TYPE: PRT
<213> ORGANISM: Artificial Sequence
<220> FEATURE:
<223> OTHER INFORMATION: DLL3-VL-29-CDR3

<400> SEQUENCE: 218

Phe Gln Ser Asn Tyr Leu Pro Leu Thr Phe Gly Ala Gly Thr Lys Leu
1               5                   10                  15

Glu Leu Arg

<210> SEQ ID NO 219
<211> LENGTH: 9
<212> TYPE: PRT
<213> ORGANISM: Artificial Sequence
<220> FEATURE:
<223> OTHER INFORMATION: DLL3-VL-30-CDR1

<400> SEQUENCE: 219

Lys Ala Ser Gln Ser Val Ser Asn Asp
1               5

<210> SEQ ID NO 220
<211> LENGTH: 7
<212> TYPE: PRT
<213> ORGANISM: Artificial Sequence
<220> FEATURE:
<223> OTHER INFORMATION: DLL3-VL-30-CDR2

<400> SEQUENCE: 220

Tyr Ala Ser Asn Arg Tyr Ser
1               5

<210> SEQ ID NO 221
<211> LENGTH: 19
<212> TYPE: PRT
<213> ORGANISM: Artificial Sequence
<220> FEATURE:
<223> OTHER INFORMATION: DLL3-VL-30-CDR3

<400> SEQUENCE: 221

Gln Gln Asp Tyr Ser Ser Pro Trp Thr Phe Gly Gly Gly Thr Lys Leu
1               5                   10                  15

Glu Ile Lys

<210> SEQ ID NO 222
<211> LENGTH: 9
<212> TYPE: PRT
<213> ORGANISM: Artificial Sequence
<220> FEATURE:
<223> OTHER INFORMATION: DLL3-VL-31-CDR1

<400> SEQUENCE: 222

Arg Ala Ser Gln Asp Ile Ser Asn Tyr
1               5
```

-continued

```
<210> SEQ ID NO 223
<211> LENGTH: 7
<212> TYPE: PRT
<213> ORGANISM: Artificial Sequence
<220> FEATURE:
<223> OTHER INFORMATION: DLL3-VL-31-CDR2

<400> SEQUENCE: 223

Tyr Thr Ser Arg Leu His Ser
1               5

<210> SEQ ID NO 224
<211> LENGTH: 19
<212> TYPE: PRT
<213> ORGANISM: Artificial Sequence
<220> FEATURE:
<223> OTHER INFORMATION: DLL3-VL-31-CDR3

<400> SEQUENCE: 224

Gln Gln Gly Asn Thr Leu Pro Tyr Thr Phe Gly Gly Gly Thr Lys Leu
1               5                   10                  15

Glu Ile Lys

<210> SEQ ID NO 225
<211> LENGTH: 9
<212> TYPE: PRT
<213> ORGANISM: Artificial Sequence
<220> FEATURE:
<223> OTHER INFORMATION: DLL3-VL-32-CDR1

<400> SEQUENCE: 225

Ile Thr Thr Pro Asp Ile Asp Asp Asp
1               5

<210> SEQ ID NO 226
<211> LENGTH: 7
<212> TYPE: PRT
<213> ORGANISM: Artificial Sequence
<220> FEATURE:
<223> OTHER INFORMATION: DLL3-VL-32-CDR2

<400> SEQUENCE: 226

Glu Gly Asn Ser Leu Arg Pro
1               5

<210> SEQ ID NO 227
<211> LENGTH: 19
<212> TYPE: PRT
<213> ORGANISM: Artificial Sequence
<220> FEATURE:
<223> OTHER INFORMATION: DLL3-VL-32-CDR3

<400> SEQUENCE: 227

Leu Gln Ser Asp Asn Met Pro Phe Thr Phe Gly Ser Gly Thr Lys Leu
1               5                   10                  15

Glu Ile Lys

<210> SEQ ID NO 228
<211> LENGTH: 8
<212> TYPE: PRT
<213> ORGANISM: Artificial Sequence
<220> FEATURE:
<223> OTHER INFORMATION: DLL3-VL-33-CDR1

<400> SEQUENCE: 228

Ser Ala Ser Ser Ser Ile Asn Tyr
```

1               5

<210> SEQ ID NO 229
<211> LENGTH: 7
<212> TYPE: PRT
<213> ORGANISM: Artificial Sequence
<220> FEATURE:
<223> OTHER INFORMATION: DLL3-VL-33-CDR2

<400> SEQUENCE: 229

Asp Thr Ser Lys Leu Ala Ser
1               5

<210> SEQ ID NO 230
<211> LENGTH: 17
<212> TYPE: PRT
<213> ORGANISM: Artificial Sequence
<220> FEATURE:
<223> OTHER INFORMATION: DLL3-VL-33-CDR3

<400> SEQUENCE: 230

His Gln Arg Ser Thr Trp Thr Phe Gly Gly Gly Thr Lys Leu Glu Ile
1               5                   10                  15

Lys

<210> SEQ ID NO 231
<211> LENGTH: 9
<212> TYPE: PRT
<213> ORGANISM: Artificial Sequence
<220> FEATURE:
<223> OTHER INFORMATION: DLL3-VL-34-CDR1

<400> SEQUENCE: 231

Arg Ala Ser Gln Asp Val Ile Asn Tyr
1               5

<210> SEQ ID NO 232
<211> LENGTH: 7
<212> TYPE: PRT
<213> ORGANISM: Artificial Sequence
<220> FEATURE:
<223> OTHER INFORMATION: DLL3-VL-34-CDR2

<400> SEQUENCE: 232

Tyr Thr Ser Arg Leu His Ser
1               5

<210> SEQ ID NO 233
<211> LENGTH: 20
<212> TYPE: PRT
<213> ORGANISM: Artificial Sequence
<220> FEATURE:
<223> OTHER INFORMATION: DLL3-VL-34-CDR3

<400> SEQUENCE: 233

Gln Gln Tyr Ser Glu Arg Pro Tyr Thr Phe Gly Gly Gly Thr Lys Leu
1               5                   10                  15

Glu Ile Lys Arg
            20

<210> SEQ ID NO 234
<211> LENGTH: 14
<212> TYPE: PRT
<213> ORGANISM: Artificial Sequence
<220> FEATURE:
<223> OTHER INFORMATION: DLL3-VL-35-CDR1

-continued

<400> SEQUENCE: 234

Arg Ser Ser Gln Asn Ile Val His Ser Asp Arg Tyr Thr Tyr
1               5                   10

<210> SEQ ID NO 235
<211> LENGTH: 7
<212> TYPE: PRT
<213> ORGANISM: Artificial Sequence
<220> FEATURE:
<223> OTHER INFORMATION: DLL3-VL-35-CDR2

<400> SEQUENCE: 235

Gly Val Ser Asn Arg Phe Ser
1               5

<210> SEQ ID NO 236
<211> LENGTH: 19
<212> TYPE: PRT
<213> ORGANISM: Artificial Sequence
<220> FEATURE:
<223> OTHER INFORMATION: DLL3-VL-35-CDR3

<400> SEQUENCE: 236

Phe Gln Gly Thr His Val Pro Tyr Thr Phe Gly Gly Gly Thr Lys Leu
1               5                   10                  15

Glu Ile Lys

<210> SEQ ID NO 237
<211> LENGTH: 9
<212> TYPE: PRT
<213> ORGANISM: Artificial Sequence
<220> FEATURE:
<223> OTHER INFORMATION: DLL3-VL-36-CDR1

<400> SEQUENCE: 237

Gln Ala Thr Gln Asp Ile Val Lys Asn
1               5

<210> SEQ ID NO 238
<211> LENGTH: 7
<212> TYPE: PRT
<213> ORGANISM: Artificial Sequence
<220> FEATURE:
<223> OTHER INFORMATION: DLL3-VL-36-CDR2

<400> SEQUENCE: 238

Tyr Ala Thr Glu Leu Ala Glu
1               5

<210> SEQ ID NO 239
<211> LENGTH: 19
<212> TYPE: PRT
<213> ORGANISM: Artificial Sequence
<220> FEATURE:
<223> OTHER INFORMATION: DLL3-VL-36-CDR3

<400> SEQUENCE: 239

Leu Gln Phe Tyr Glu Phe Pro Phe Thr Phe Gly Ala Gly Thr Lys Leu
1               5                   10                  15

Glu Leu Lys

<210> SEQ ID NO 240
<211> LENGTH: 14
<212> TYPE: PRT

```
<213> ORGANISM: Artificial Sequence
<220> FEATURE:
<223> OTHER INFORMATION: DLL3-VL-37-CDR1

<400> SEQUENCE: 240

Lys Ser Thr Lys Ser Leu Leu Asn Ser Asp Gly Phe Thr Tyr
1               5                   10

<210> SEQ ID NO 241
<211> LENGTH: 7
<212> TYPE: PRT
<213> ORGANISM: Artificial Sequence
<220> FEATURE:
<223> OTHER INFORMATION: DLL3-VL-37-CDR2

<400> SEQUENCE: 241

Leu Val Ser Asn Arg Phe Ser
1               5

<210> SEQ ID NO 242
<211> LENGTH: 19
<212> TYPE: PRT
<213> ORGANISM: Artificial Sequence
<220> FEATURE:
<223> OTHER INFORMATION: DLL3-VL-37-CDR3

<400> SEQUENCE: 242

Phe Gln Ser Asn Tyr Leu Pro Leu Thr Phe Gly Ala Gly Thr Lys Leu
1               5                   10                  15

Glu Leu Arg

<210> SEQ ID NO 243
<211> LENGTH: 10
<212> TYPE: PRT
<213> ORGANISM: Artificial Sequence
<220> FEATURE:
<223> OTHER INFORMATION: DLL3-VL-38-CDR1

<400> SEQUENCE: 243

Lys Ala Ser Gln Asp Ile Asn Ser Tyr Leu
1               5                   10

<210> SEQ ID NO 244
<211> LENGTH: 7
<212> TYPE: PRT
<213> ORGANISM: Artificial Sequence
<220> FEATURE:
<223> OTHER INFORMATION: DLL3-VL-38-CDR2

<400> SEQUENCE: 244

Arg Ala Asn Arg Leu Val Asp
1               5

<210> SEQ ID NO 245
<211> LENGTH: 19
<212> TYPE: PRT
<213> ORGANISM: Artificial Sequence
<220> FEATURE:
<223> OTHER INFORMATION: DLL3-VL-38-CDR3

<400> SEQUENCE: 245

Leu Gln Tyr Asp Glu Phe Pro Leu Thr Phe Gly Ala Gly Thr Lys Leu
1               5                   10                  15

Glu Leu Lys
```

```
<210> SEQ ID NO 246
<211> LENGTH: 9
<212> TYPE: PRT
<213> ORGANISM: Artificial Sequence
<220> FEATURE:
<223> OTHER INFORMATION: DLL3-VL-39-CDR1

<400> SEQUENCE: 246

Arg Ala Ser Gln Asp Ile Ser Asn Tyr
1               5

<210> SEQ ID NO 247
<211> LENGTH: 7
<212> TYPE: PRT
<213> ORGANISM: Artificial Sequence
<220> FEATURE:
<223> OTHER INFORMATION: DLL3-VL-39-CDR2

<400> SEQUENCE: 247

Tyr Thr Ser Arg Leu His Ser
1               5

<210> SEQ ID NO 248
<211> LENGTH: 18
<212> TYPE: PRT
<213> ORGANISM: Artificial Sequence
<220> FEATURE:
<223> OTHER INFORMATION: DLL3-VL-39-CDR3

<400> SEQUENCE: 248

Gln Gln Gly Asn Thr Leu Arg Thr Phe Gly Gly Gly Thr Lys Leu Glu
1               5                   10                  15

Ile Lys

<210> SEQ ID NO 249
<211> LENGTH: 9
<212> TYPE: PRT
<213> ORGANISM: Artificial Sequence
<220> FEATURE:
<223> OTHER INFORMATION: DLL3-VL-40-CDR1

<400> SEQUENCE: 249

Arg Ala Ser Gln Gly Ile Arg Gly Thr
1               5

<210> SEQ ID NO 250
<211> LENGTH: 7
<212> TYPE: PRT
<213> ORGANISM: Artificial Sequence
<220> FEATURE:
<223> OTHER INFORMATION: DLL3-VL-40-CDR2

<400> SEQUENCE: 250

Ser Thr Ser Asn Leu Asn Ser
1               5

<210> SEQ ID NO 251
<211> LENGTH: 19
<212> TYPE: PRT
<213> ORGANISM: Artificial Sequence
<220> FEATURE:
<223> OTHER INFORMATION: DLL3-VL-40-CDR3

<400> SEQUENCE: 251

Leu Gln Arg Asn Ala Tyr Pro Leu Thr Phe Gly Ala Gly Thr Lys Leu
1               5                   10                  15
```

Glu Leu Lys

<210> SEQ ID NO 252
<211> LENGTH: 9
<212> TYPE: PRT
<213> ORGANISM: Artificial Sequence
<220> FEATURE:
<223> OTHER INFORMATION: DLL3-VL-41-CDR1

<400> SEQUENCE: 252

Lys Ala Ser Gln Asp Ile Asn Ser Tyr
1               5

<210> SEQ ID NO 253
<211> LENGTH: 7
<212> TYPE: PRT
<213> ORGANISM: Artificial Sequence
<220> FEATURE:
<223> OTHER INFORMATION: DLL3-VL-41-CDR2

<400> SEQUENCE: 253

Arg Ala Asn Arg Leu Val Asp
1               5

<210> SEQ ID NO 254
<211> LENGTH: 20
<212> TYPE: PRT
<213> ORGANISM: Artificial Sequence
<220> FEATURE:
<223> OTHER INFORMATION: DLL3-VL-41-CDR3

<400> SEQUENCE: 254

Leu Gln Tyr Asp Glu Phe Pro Tyr Thr Phe Gly Gly Gly Thr Lys Leu
1               5                   10                  15

Glu Ile Lys Arg
            20

<210> SEQ ID NO 255
<211> LENGTH: 9
<212> TYPE: PRT
<213> ORGANISM: Artificial Sequence
<220> FEATURE:
<223> OTHER INFORMATION: DLL3-VL-42-CDR1

<400> SEQUENCE: 255

Lys Ala Ser Gln Ser Val Ser Asn Asp
1               5

<210> SEQ ID NO 256
<211> LENGTH: 7
<212> TYPE: PRT
<213> ORGANISM: Artificial Sequence
<220> FEATURE:
<223> OTHER INFORMATION: DLL3-VL-42-CDR2

<400> SEQUENCE: 256

Tyr Ala Ser Asn Arg Tyr Thr
1               5

<210> SEQ ID NO 257
<211> LENGTH: 19
<212> TYPE: PRT
<213> ORGANISM: Artificial Sequence
<220> FEATURE:
<223> OTHER INFORMATION: DLL3-VL-42-CDR3

<400> SEQUENCE: 257

Gln Gln Asp Tyr Thr Ser Pro Trp Thr Phe Gly Gly Gly Thr Lys Leu
1               5                   10                  15

Glu Ile Arg

<210> SEQ ID NO 258
<211> LENGTH: 9
<212> TYPE: PRT
<213> ORGANISM: Artificial Sequence
<220> FEATURE:
<223> OTHER INFORMATION: DLL3-VL-43-CDR1

<400> SEQUENCE: 258

Lys Ala Ser Gln Asp Val Ser Ile Phe
1               5

<210> SEQ ID NO 259
<211> LENGTH: 7
<212> TYPE: PRT
<213> ORGANISM: Artificial Sequence
<220> FEATURE:
<223> OTHER INFORMATION: DLL3-VL-43-CDR2

<400> SEQUENCE: 259

Ser Ala Ser Tyr Arg Tyr Thr
1               5

<210> SEQ ID NO 260
<211> LENGTH: 19
<212> TYPE: PRT
<213> ORGANISM: Artificial Sequence
<220> FEATURE:
<223> OTHER INFORMATION: DLL3-VL-43-CDR3

<400> SEQUENCE: 260

Gln Gln His Tyr Gly Thr Pro Phe Thr Phe Gly Ser Gly Thr Lys Leu
1               5                   10                  15

Lys Ile Arg

<210> SEQ ID NO 261
<211> LENGTH: 9
<212> TYPE: PRT
<213> ORGANISM: Artificial Sequence
<220> FEATURE:
<223> OTHER INFORMATION: DLL3-VL-44-CDR1

<400> SEQUENCE: 261

Arg Ala Ser Glu Asn Ile Tyr Ser Tyr
1               5

<210> SEQ ID NO 262
<211> LENGTH: 7
<212> TYPE: PRT
<213> ORGANISM: Artificial Sequence
<220> FEATURE:
<223> OTHER INFORMATION: DLL3-VL-44-CDR2

<400> SEQUENCE: 262

Asn Ala Lys Thr Leu Ala Glu
1               5

<210> SEQ ID NO 263
<211> LENGTH: 19
<212> TYPE: PRT
<213> ORGANISM: Artificial Sequence
<220> FEATURE:

<223> OTHER INFORMATION: DLL3-VL-44-CDR3

<400> SEQUENCE: 263

Gln His His Tyr Asp Ser Pro Leu Thr Phe Gly Ala Gly Thr Lys Leu
1               5                   10                  15

Glu Leu Arg

<210> SEQ ID NO 264
<211> LENGTH: 15
<212> TYPE: PRT
<213> ORGANISM: Artificial Sequence
<220> FEATURE:
<223> OTHER INFORMATION: DLL3-VL-45-CDR1

<400> SEQUENCE: 264

Lys Ser Ser Gln Ser Leu Leu Asn Ser Ser Asn Gln Lys Asn Tyr
1               5                   10                  15

<210> SEQ ID NO 265
<211> LENGTH: 7
<212> TYPE: PRT
<213> ORGANISM: Artificial Sequence
<220> FEATURE:
<223> OTHER INFORMATION: DLL3-VL-45-CDR2

<400> SEQUENCE: 265

Phe Ala Ser Thr Arg Glu Ser
1               5

<210> SEQ ID NO 266
<211> LENGTH: 19
<212> TYPE: PRT
<213> ORGANISM: Artificial Sequence
<220> FEATURE:
<223> OTHER INFORMATION: DLL3-VL-45-CDR3

<400> SEQUENCE: 266

Gln Gln His Tyr Ser Ile Pro Leu Thr Phe Gly Ala Gly Thr Lys Leu
1               5                   10                  15

Glu Leu Lys

<210> SEQ ID NO 267
<211> LENGTH: 9
<212> TYPE: PRT
<213> ORGANISM: Artificial Sequence
<220> FEATURE:
<223> OTHER INFORMATION: DLL3-VL-46-CDR1

<400> SEQUENCE: 267

Lys Ala Ser Gln Asp Ile Asn Ser Phe
1               5

<210> SEQ ID NO 268
<211> LENGTH: 7
<212> TYPE: PRT
<213> ORGANISM: Artificial Sequence
<220> FEATURE:
<223> OTHER INFORMATION: DLL3-VL-46-CDR2

<400> SEQUENCE: 268

Arg Ala Asn Arg Leu Val Asp
1               5

<210> SEQ ID NO 269
<211> LENGTH: 20

```
<212> TYPE: PRT
<213> ORGANISM: Artificial Sequence
<220> FEATURE:
<223> OTHER INFORMATION: DLL3-VL-46-CDR3

<400> SEQUENCE: 269

Leu Gln Tyr Asp Glu Phe Pro Tyr Thr Phe Gly Gly Gly Thr Lys Leu
1               5                   10                  15

Glu Ile Lys Arg
            20

<210> SEQ ID NO 270
<211> LENGTH: 8
<212> TYPE: PRT
<213> ORGANISM: Artificial Sequence
<220> FEATURE:
<223> OTHER INFORMATION: DLL3-VL-47-CDR1

<400> SEQUENCE: 270

Ser Ala Ser Ser Ser Val Ser Tyr
1               5

<210> SEQ ID NO 271
<211> LENGTH: 7
<212> TYPE: PRT
<213> ORGANISM: Artificial Sequence
<220> FEATURE:
<223> OTHER INFORMATION: DLL3-VL-47-CDR2

<400> SEQUENCE: 271

Asp Thr Ser Lys Leu Ala Ser
1               5

<210> SEQ ID NO 272
<211> LENGTH: 19
<212> TYPE: PRT
<213> ORGANISM: Artificial Sequence
<220> FEATURE:
<223> OTHER INFORMATION: DLL3-VL-47-CDR3

<400> SEQUENCE: 272

Gln Gln Trp Ser Ser Asn Pro Tyr Thr Phe Gly Gly Gly Thr Lys Leu
1               5                   10                  15

Glu Ile Lys

<210> SEQ ID NO 273
<211> LENGTH: 8
<212> TYPE: PRT
<213> ORGANISM: Artificial Sequence
<220> FEATURE:
<223> OTHER INFORMATION: DLL3-VL-48-CDR1

<400> SEQUENCE: 273

Ser Val Thr Ser Ser Val Ser Tyr
1               5

<210> SEQ ID NO 274
<211> LENGTH: 7
<212> TYPE: PRT
<213> ORGANISM: Artificial Sequence
<220> FEATURE:
<223> OTHER INFORMATION: DLL3-VL-48-CDR2

<400> SEQUENCE: 274

Leu Thr Ser Asn Leu Ala Ser
1               5
```

-continued

```
<210> SEQ ID NO 275
<211> LENGTH: 19
<212> TYPE: PRT
<213> ORGANISM: Artificial Sequence
<220> FEATURE:
<223> OTHER INFORMATION: DLL3-VL-48-CDR3

<400> SEQUENCE: 275

Gln Gln Trp Arg Asn Asn Pro Phe Thr Phe Gly Ser Gly Thr Lys Val
1               5                   10                  15

Glu Ile Lys

<210> SEQ ID NO 276
<211> LENGTH: 12
<212> TYPE: PRT
<213> ORGANISM: Artificial Sequence
<220> FEATURE:
<223> OTHER INFORMATION: DLL3-VL-49-CDR1

<400> SEQUENCE: 276

Arg Ser Ser Thr Gly Ala Val Thr Thr Ser Asn Tyr
1               5                   10

<210> SEQ ID NO 277
<211> LENGTH: 7
<212> TYPE: PRT
<213> ORGANISM: Artificial Sequence
<220> FEATURE:
<223> OTHER INFORMATION: DLL3-VL-49-CDR2

<400> SEQUENCE: 277

Gly Thr Asn Asn Arg Ala Pro
1               5

<210> SEQ ID NO 278
<211> LENGTH: 19
<212> TYPE: PRT
<213> ORGANISM: Artificial Sequence
<220> FEATURE:
<223> OTHER INFORMATION: DLL3-VL-49-CDR3

<400> SEQUENCE: 278

Gly Leu Trp Tyr Ser Asn His Leu Val Phe Gly Gly Gly Thr Lys Leu
1               5                   10                  15

Thr Val Leu

<210> SEQ ID NO 279
<211> LENGTH: 9
<212> TYPE: PRT
<213> ORGANISM: Artificial Sequence
<220> FEATURE:
<223> OTHER INFORMATION: DLL3-VL-50-CDR1

<400> SEQUENCE: 279

Ile Thr Ser Thr Asp Ile Asp Asp Asp
1               5

<210> SEQ ID NO 280
<211> LENGTH: 7
<212> TYPE: PRT
<213> ORGANISM: Artificial Sequence
<220> FEATURE:
<223> OTHER INFORMATION: DLL3-VL-50-CDR2

<400> SEQUENCE: 280
```

-continued

Glu Gly Asn Thr Leu Arg Pro
1               5

<210> SEQ ID NO 281
<211> LENGTH: 19
<212> TYPE: PRT
<213> ORGANISM: Artificial Sequence
<220> FEATURE:
<223> OTHER INFORMATION: DLL3-VL-50-CDR3

<400> SEQUENCE: 281

Leu Gln Ser Asp Asn Met Pro Leu Thr Phe Gly Ala Gly Thr Lys Leu
1               5                   10                  15

Glu Leu Lys

<210> SEQ ID NO 282
<211> LENGTH: 8
<212> TYPE: PRT
<213> ORGANISM: Artificial Sequence
<220> FEATURE:
<223> OTHER INFORMATION: DLL3-VL-51-CDR1

<400> SEQUENCE: 282

Arg Ala Ser Ser Ser Val Asn Tyr
1               5

<210> SEQ ID NO 283
<211> LENGTH: 7
<212> TYPE: PRT
<213> ORGANISM: Artificial Sequence
<220> FEATURE:
<223> OTHER INFORMATION: DLL3-VL-51-CDR2

<400> SEQUENCE: 283

Tyr Thr Ser Asn Leu Ala Pro
1               5

<210> SEQ ID NO 284
<211> LENGTH: 20
<212> TYPE: PRT
<213> ORGANISM: Artificial Sequence
<220> FEATURE:
<223> OTHER INFORMATION: DLL3-VL-51-CDR3

<400> SEQUENCE: 284

Gln Gln Phe Thr Ser Ser Pro Tyr Thr Phe Gly Gly Gly Thr Lys Leu
1               5                   10                  15

Glu Ile Lys Arg
            20

<210> SEQ ID NO 285
<211> LENGTH: 9
<212> TYPE: PRT
<213> ORGANISM: Artificial Sequence
<220> FEATURE:
<223> OTHER INFORMATION: DLL3-VL-52-CDR1

<400> SEQUENCE: 285

Arg Ala Ser Gln Asp Ile Gly Tyr Ser
1               5

<210> SEQ ID NO 286
<211> LENGTH: 7
<212> TYPE: PRT
<213> ORGANISM: Artificial Sequence

<220> FEATURE:
<223> OTHER INFORMATION: DLL3-VL-52-CDR2

<400> SEQUENCE: 286

Ala Thr Ser Ser Leu Asp Ser
1               5

<210> SEQ ID NO 287
<211> LENGTH: 19
<212> TYPE: PRT
<213> ORGANISM: Artificial Sequence
<220> FEATURE:
<223> OTHER INFORMATION: DLL3-VL-52-CDR3

<400> SEQUENCE: 287

Leu Gln Tyr Ala Ser Ser Pro Trp Thr Phe Gly Gly Gly Thr Lys Leu
1               5                   10                  15

Glu Ile Lys

<210> SEQ ID NO 288
<211> LENGTH: 9
<212> TYPE: PRT
<213> ORGANISM: Artificial Sequence
<220> FEATURE:
<223> OTHER INFORMATION: DLL3-VL-53-CDR1

<400> SEQUENCE: 288

Lys Ala Ser Gln Asp Ile Asn Ser Tyr
1               5

<210> SEQ ID NO 289
<211> LENGTH: 7
<212> TYPE: PRT
<213> ORGANISM: Artificial Sequence
<220> FEATURE:
<223> OTHER INFORMATION: DLL3-VL-53-CDR2

<400> SEQUENCE: 289

Arg Ala Asn Arg Leu Val Asp
1               5

<210> SEQ ID NO 290
<211> LENGTH: 19
<212> TYPE: PRT
<213> ORGANISM: Artificial Sequence
<220> FEATURE:
<223> OTHER INFORMATION: DLL3-VL-53-CDR3

<400> SEQUENCE: 290

Leu Gln Tyr Asp Glu Phe Pro Phe Thr Phe Gly Ser Gly Thr Lys Leu
1               5                   10                  15

Glu Ile Lys

<210> SEQ ID NO 291
<211> LENGTH: 15
<212> TYPE: PRT
<213> ORGANISM: Artificial Sequence
<220> FEATURE:
<223> OTHER INFORMATION: DLL3-VL-54-CDR1

<400> SEQUENCE: 291

Lys Ser Ser Gln Ser Leu Leu Asn Ser Arg Thr Arg Lys Asn Tyr
1               5                   10                  15

<210> SEQ ID NO 292

-continued

```
<211> LENGTH: 7
<212> TYPE: PRT
<213> ORGANISM: Artificial Sequence
<220> FEATURE:
<223> OTHER INFORMATION: DLL3-VL-54-CDR2

<400> SEQUENCE: 292

Trp Ala Ser Thr Arg Glu Ser
1               5

<210> SEQ ID NO 293
<211> LENGTH: 19
<212> TYPE: PRT
<213> ORGANISM: Artificial Sequence
<220> FEATURE:
<223> OTHER INFORMATION: DLL3-VL-54-CDR3

<400> SEQUENCE: 293

Lys Gln Ser Tyr Asn Leu Tyr Thr Phe Gly Gly Gly Thr Lys Leu Lys
1               5                   10                  15

Ile Lys Arg

<210> SEQ ID NO 294
<211> LENGTH: 9
<212> TYPE: PRT
<213> ORGANISM: Artificial Sequence
<220> FEATURE:
<223> OTHER INFORMATION: DLL3-VL-55-CDR1

<400> SEQUENCE: 294

Ile Thr Ser Thr Asp Ile Asp Asp Asp
1               5

<210> SEQ ID NO 295
<211> LENGTH: 7
<212> TYPE: PRT
<213> ORGANISM: Artificial Sequence
<220> FEATURE:
<223> OTHER INFORMATION: DLL3-VL-55-CDR2

<400> SEQUENCE: 295

Glu Gly Asn Thr Leu Arg Pro
1               5

<210> SEQ ID NO 296
<211> LENGTH: 20
<212> TYPE: PRT
<213> ORGANISM: Artificial Sequence
<220> FEATURE:
<223> OTHER INFORMATION: DLL3-VL-55-CDR3

<400> SEQUENCE: 296

Leu Lys Arg Asp Asp Leu Pro Tyr Thr Phe Gly Gly Gly Thr Gln Val
1               5                   10                  15

Glu Ile Lys Arg
            20

<210> SEQ ID NO 297
<211> LENGTH: 10
<212> TYPE: PRT
<213> ORGANISM: Artificial Sequence
<220> FEATURE:
<223> OTHER INFORMATION: DLL3-VL-56-CDR1

<400> SEQUENCE: 297

Thr Ala Ser Ser Ser Val Ser Ser Ser Tyr
```

-continued 1               5                    10

<210> SEQ ID NO 298
<211> LENGTH: 7
<212> TYPE: PRT
<213> ORGANISM: Artificial Sequence
<220> FEATURE:
<223> OTHER INFORMATION: DLL3-VL-56-CDR2

<400> SEQUENCE: 298

Ser Thr Ser Asn Leu Ala Ser
1               5

<210> SEQ ID NO 299
<211> LENGTH: 19
<212> TYPE: PRT
<213> ORGANISM: Artificial Sequence
<220> FEATURE:
<223> OTHER INFORMATION: DLL3-VL-56-CDR3

<400> SEQUENCE: 299

His Gln Tyr Asn Arg Ser Pro Leu Thr Phe Gly Ala Gly Thr Lys Leu
1               5                    10                   15

Glu Leu Lys

<210> SEQ ID NO 300
<211> LENGTH: 9
<212> TYPE: PRT
<213> ORGANISM: Artificial Sequence
<220> FEATURE:
<223> OTHER INFORMATION: DLL3-VL-57-CDR1

<400> SEQUENCE: 300

Lys Ala Ser Gln Asp Ile Lys Lys Tyr
1               5

<210> SEQ ID NO 301
<211> LENGTH: 7
<212> TYPE: PRT
<213> ORGANISM: Artificial Sequence
<220> FEATURE:
<223> OTHER INFORMATION: DLL3-VL-57-CDR2

<400> SEQUENCE: 301

Tyr Thr Ser Thr Leu Glu Pro
1               5

<210> SEQ ID NO 302
<211> LENGTH: 18
<212> TYPE: PRT
<213> ORGANISM: Artificial Sequence
<220> FEATURE:
<223> OTHER INFORMATION: DLL3-VL-57-CDR3

<400> SEQUENCE: 302

Leu Gln Tyr Asp Ile Leu Trp Thr Phe Gly Gly Gly Thr Lys Leu Glu
1               5                    10                   15

Ile Lys

<210> SEQ ID NO 303
<211> LENGTH: 10
<212> TYPE: PRT
<213> ORGANISM: Artificial Sequence
<220> FEATURE:
<223> OTHER INFORMATION: DLL3-VL-58-CDR1

-continued

```
<400> SEQUENCE: 303

Ser Ala Ser Ser Ser Val Ser Ser Ser Tyr
1               5                   10

<210> SEQ ID NO 304
<211> LENGTH: 7
<212> TYPE: PRT
<213> ORGANISM: Artificial Sequence
<220> FEATURE:
<223> OTHER INFORMATION: DLL3-VL-58-CDR2

<400> SEQUENCE: 304

Arg Thr Ser Asn Leu Ala Ser
1               5

<210> SEQ ID NO 305
<211> LENGTH: 19
<212> TYPE: PRT
<213> ORGANISM: Artificial Sequence
<220> FEATURE:
<223> OTHER INFORMATION: DLL3-VL-58-CDR3

<400> SEQUENCE: 305

Arg Gln Trp Ser Gly Tyr Pro Trp Thr Phe Gly Gly Gly Thr Lys Leu
1               5                   10                  15

Glu Ile Lys

<210> SEQ ID NO 306
<211> LENGTH: 10
<212> TYPE: PRT
<213> ORGANISM: Artificial Sequence
<220> FEATURE:
<223> OTHER INFORMATION: DLL3-VL-59-CDR1

<400> SEQUENCE: 306

Thr Ala Ser Ser Ser Val Ser Ser Ser Tyr
1               5                   10

<210> SEQ ID NO 307
<211> LENGTH: 7
<212> TYPE: PRT
<213> ORGANISM: Artificial Sequence
<220> FEATURE:
<223> OTHER INFORMATION: DLL3-VL-59-CDR2

<400> SEQUENCE: 307

Ser Thr Ser Asn Leu Ala Ser
1               5

<210> SEQ ID NO 308
<211> LENGTH: 19
<212> TYPE: PRT
<213> ORGANISM: Artificial Sequence
<220> FEATURE:
<223> OTHER INFORMATION: DLL3-VL-59-CDR3

<400> SEQUENCE: 308

His Gln Tyr His Arg Ser Pro Phe Thr Phe Gly Ser Gly Thr Lys Leu
1               5                   10                  15

Glu Ile Lys

<210> SEQ ID NO 309
<211> LENGTH: 13
<212> TYPE: PRT
<213> ORGANISM: Artificial Sequence
```

-continued

```
<220> FEATURE:
<223> OTHER INFORMATION: DLL3-VL-60-CDR1

<400> SEQUENCE: 309

Arg Ala Ser Lys Ser Val Ser Thr Ser Gly Tyr Ser Tyr
1               5                   10

<210> SEQ ID NO 310
<211> LENGTH: 7
<212> TYPE: PRT
<213> ORGANISM: Artificial Sequence
<220> FEATURE:
<223> OTHER INFORMATION: DLL3-VL-60-CDR2

<400> SEQUENCE: 310

Leu Ala Ser Asn Leu Glu Ser
1               5

<210> SEQ ID NO 311
<211> LENGTH: 19
<212> TYPE: PRT
<213> ORGANISM: Artificial Sequence
<220> FEATURE:
<223> OTHER INFORMATION: DLL3-VL-60-CDR3

<400> SEQUENCE: 311

Gln His Ser Arg Glu Leu Pro Leu Thr Phe Gly Ala Gly Thr Lys Leu
1               5                   10                  15

Glu Leu Lys

<210> SEQ ID NO 312
<211> LENGTH: 8
<212> TYPE: PRT
<213> ORGANISM: Artificial Sequence
<220> FEATURE:
<223> OTHER INFORMATION: DLL3-VL-61-CDR1

<400> SEQUENCE: 312

Arg Ala Ser Ser Ser Val Ser Tyr
1               5

<210> SEQ ID NO 313
<211> LENGTH: 7
<212> TYPE: PRT
<213> ORGANISM: Artificial Sequence
<220> FEATURE:
<223> OTHER INFORMATION: DLL3-VL-61-CDR2

<400> SEQUENCE: 313

Ala Thr Ser Asn Leu Ala Ser
1               5

<210> SEQ ID NO 314
<211> LENGTH: 19
<212> TYPE: PRT
<213> ORGANISM: Artificial Sequence
<220> FEATURE:
<223> OTHER INFORMATION: DLL3-VL-61-CDR3

<400> SEQUENCE: 314

Gln Gln Trp Ser Ser Asn Pro Pro Thr Phe Gly Ala Gly Thr Lys Leu
1               5                   10                  15

Glu Leu Lys

<210> SEQ ID NO 315
```

<211> LENGTH: 9
<212> TYPE: PRT
<213> ORGANISM: Artificial Sequence
<220> FEATURE:
<223> OTHER INFORMATION: DLL3-VL-62-CDR1

<400> SEQUENCE: 315

Lys Ala Ser Gln Asp Val Gly Thr Ala
1               5

<210> SEQ ID NO 316
<211> LENGTH: 7
<212> TYPE: PRT
<213> ORGANISM: Artificial Sequence
<220> FEATURE:
<223> OTHER INFORMATION: DLL3-VL-62-CDR2

<400> SEQUENCE: 316

Trp Ala Ser Ile Arg His Thr
1               5

<210> SEQ ID NO 317
<211> LENGTH: 19
<212> TYPE: PRT
<213> ORGANISM: Artificial Sequence
<220> FEATURE:
<223> OTHER INFORMATION: DLL3-VL-62-CDR3

<400> SEQUENCE: 317

Gln Gln Tyr Ser Ser Tyr Pro Leu Thr Phe Gly Ala Gly Thr Lys Leu
1               5                   10                  15

Glu Leu Lys

<210> SEQ ID NO 318
<211> LENGTH: 9
<212> TYPE: PRT
<213> ORGANISM: Artificial Sequence
<220> FEATURE:
<223> OTHER INFORMATION: DLL3-VL-63-CDR1

<400> SEQUENCE: 318

Lys Ala Ser Gln Asp Ile Asn Ser Tyr
1               5

<210> SEQ ID NO 319
<211> LENGTH: 7
<212> TYPE: PRT
<213> ORGANISM: Artificial Sequence
<220> FEATURE:
<223> OTHER INFORMATION: DLL3-VL-63-CDR2

<400> SEQUENCE: 319

Arg Ala Asn Arg Leu Val Asp
1               5

<210> SEQ ID NO 320
<211> LENGTH: 19
<212> TYPE: PRT
<213> ORGANISM: Artificial Sequence
<220> FEATURE:
<223> OTHER INFORMATION: DLL3-VL-63-CDR3

<400> SEQUENCE: 320

Leu Gln Tyr Asp Glu Phe Pro Phe Thr Phe Gly Ser Gly Thr Lys Leu
1               5                   10                  15

Glu Ile Lys

```
<210> SEQ ID NO 321
<211> LENGTH: 9
<212> TYPE: PRT
<213> ORGANISM: Artificial Sequence
<220> FEATURE:
<223> OTHER INFORMATION: DLL3-VL-64-CDR1

<400> SEQUENCE: 321

Lys Ala Ser Gln Asp Val Asn Thr Ala
1               5

<210> SEQ ID NO 322
<211> LENGTH: 7
<212> TYPE: PRT
<213> ORGANISM: Artificial Sequence
<220> FEATURE:
<223> OTHER INFORMATION: DLL3-VL-64-CDR2

<400> SEQUENCE: 322

Ser Ala Ser Tyr Arg Tyr Thr
1               5

<210> SEQ ID NO 323
<211> LENGTH: 20
<212> TYPE: PRT
<213> ORGANISM: Artificial Sequence
<220> FEATURE:
<223> OTHER INFORMATION: DLL3-VL-64-CDR3

<400> SEQUENCE: 323

Gln Gln His Tyr Ser Ser Pro Tyr Thr Phe Gly Gly Gly Thr Lys Leu
1               5                   10                  15

Glu Ile Lys Arg
            20

<210> SEQ ID NO 324
<211> LENGTH: 9
<212> TYPE: PRT
<213> ORGANISM: Artificial Sequence
<220> FEATURE:
<223> OTHER INFORMATION: DLL3-VL-65-CDR1

<400> SEQUENCE: 324

Arg Ala Ser Glu Asn Ile Tyr Ser Tyr
1               5

<210> SEQ ID NO 325
<211> LENGTH: 7
<212> TYPE: PRT
<213> ORGANISM: Artificial Sequence
<220> FEATURE:
<223> OTHER INFORMATION: DLL3-VL-65-CDR2

<400> SEQUENCE: 325

Asn Ala Lys Thr Leu Ala Glu
1               5

<210> SEQ ID NO 326
<211> LENGTH: 20
<212> TYPE: PRT
<213> ORGANISM: Artificial Sequence
<220> FEATURE:
<223> OTHER INFORMATION: DLL3-VL-65-CDR3

<400> SEQUENCE: 326
```

-continued

```
Gln His His Tyr Gly Thr Pro Tyr Thr Phe Gly Gly Gly Thr Lys Leu
1               5                   10                  15

Glu Ile Lys Arg
            20

<210> SEQ ID NO 327
<211> LENGTH: 8
<212> TYPE: PRT
<213> ORGANISM: Artificial Sequence
<220> FEATURE:
<223> OTHER INFORMATION: DLL3-VL-66-CDR1

<400> SEQUENCE: 327

Ser Ala Ser Ser Ser Val Ser Tyr
1               5

<210> SEQ ID NO 328
<211> LENGTH: 7
<212> TYPE: PRT
<213> ORGANISM: Artificial Sequence
<220> FEATURE:
<223> OTHER INFORMATION: DLL3-VL-66-CDR2

<400> SEQUENCE: 328

Asp Thr Ser Asn Leu Ala Ser
1               5

<210> SEQ ID NO 329
<211> LENGTH: 19
<212> TYPE: PRT
<213> ORGANISM: Artificial Sequence
<220> FEATURE:
<223> OTHER INFORMATION: DLL3-VL-66-CDR3

<400> SEQUENCE: 329

Gln Glu Trp Ser Gly Asn Pro Leu Thr Phe Gly Asp Gly Thr Lys Leu
1               5                   10                  15

Glu Leu Lys

<210> SEQ ID NO 330
<211> LENGTH: 9
<212> TYPE: PRT
<213> ORGANISM: Artificial Sequence
<220> FEATURE:
<223> OTHER INFORMATION: DLL3-VL-67-CDR1

<400> SEQUENCE: 330

Lys Ala Ser Gln Ser Val Ser Asn Asp
1               5

<210> SEQ ID NO 331
<211> LENGTH: 7
<212> TYPE: PRT
<213> ORGANISM: Artificial Sequence
<220> FEATURE:
<223> OTHER INFORMATION: DLL3-VL-67-CDR2

<400> SEQUENCE: 331

Tyr Ala Ser Asn Arg Tyr Thr
1               5

<210> SEQ ID NO 332
<211> LENGTH: 19
<212> TYPE: PRT
<213> ORGANISM: Artificial Sequence
<220> FEATURE:
```

<223> OTHER INFORMATION: DLL3-VL-67-CDR3

<400> SEQUENCE: 332

Gln Gln Asp Tyr Ser Ser Pro Pro Thr Phe Gly Gly Gly Thr Lys Leu
1               5                   10                  15

Glu Ile Lys

<210> SEQ ID NO 333
<211> LENGTH: 9
<212> TYPE: PRT
<213> ORGANISM: Artificial Sequence
<220> FEATURE:
<223> OTHER INFORMATION: DLL3-VL-68-CDR1

<400> SEQUENCE: 333

Arg Ala Ser Glu Asn Ile Tyr Tyr Ser
1               5

<210> SEQ ID NO 334
<211> LENGTH: 7
<212> TYPE: PRT
<213> ORGANISM: Artificial Sequence
<220> FEATURE:
<223> OTHER INFORMATION: DLL3-VL-68-CDR2

<400> SEQUENCE: 334

Asn Ala Asn Ser Leu Glu Asp
1               5

<210> SEQ ID NO 335
<211> LENGTH: 19
<212> TYPE: PRT
<213> ORGANISM: Artificial Sequence
<220> FEATURE:
<223> OTHER INFORMATION: DLL3-VL-68-CDR3

<400> SEQUENCE: 335

Lys Gln Thr Tyr Asp Val Pro Leu Thr Phe Gly Ala Gly Thr Lys Leu
1               5                   10                  15

Glu Leu Lys

<210> SEQ ID NO 336
<211> LENGTH: 14
<212> TYPE: PRT
<213> ORGANISM: Artificial Sequence
<220> FEATURE:
<223> OTHER INFORMATION: DLL3-VL-69-CDR1

<400> SEQUENCE: 336

Lys Ser Ser Gln Ser Leu Leu Asp Ser Asp Gly Thr Thr Tyr
1               5                   10

<210> SEQ ID NO 337
<211> LENGTH: 7
<212> TYPE: PRT
<213> ORGANISM: Artificial Sequence
<220> FEATURE:
<223> OTHER INFORMATION: DLL3-VL-69-CDR2

<400> SEQUENCE: 337

Leu Val Ser Lys Leu Asp Ser
1               5

<210> SEQ ID NO 338
<211> LENGTH: 19

```
<212> TYPE: PRT
<213> ORGANISM: Artificial Sequence
<220> FEATURE:
<223> OTHER INFORMATION: DLL3-VL-69-CDR3

<400> SEQUENCE: 338

Trp Gln Gly Thr His Phe Pro Leu Thr Phe Gly Ala Gly Thr Lys Leu
1               5                   10                  15

Glu Leu Lys

<210> SEQ ID NO 339
<211> LENGTH: 8
<212> TYPE: PRT
<213> ORGANISM: Artificial Sequence
<220> FEATURE:
<223> OTHER INFORMATION: DLL3-VL-70-CDR1

<400> SEQUENCE: 339

Arg Ala Ser Ser Ser Val Ser Tyr
1               5

<210> SEQ ID NO 340
<211> LENGTH: 7
<212> TYPE: PRT
<213> ORGANISM: Artificial Sequence
<220> FEATURE:
<223> OTHER INFORMATION: DLL3-VL-70-CDR2

<400> SEQUENCE: 340

Ala Thr Ser Asn Leu Ala Ser
1               5

<210> SEQ ID NO 341
<211> LENGTH: 20
<212> TYPE: PRT
<213> ORGANISM: Artificial Sequence
<220> FEATURE:
<223> OTHER INFORMATION: DLL3-VL-70-CDR3

<400> SEQUENCE: 341

Gln Gln Trp Ser Ser Asn Pro Tyr Thr Phe Gly Gly Gly Thr Lys Leu
1               5                   10                  15

Glu Ile Lys Arg
            20

<210> SEQ ID NO 342
<211> LENGTH: 14
<212> TYPE: PRT
<213> ORGANISM: Artificial Sequence
<220> FEATURE:
<223> OTHER INFORMATION: DLL3-VL-71-CDR1

<400> SEQUENCE: 342

Lys Ser Ser Gln Ser Leu Leu Asp Ser Asp Gly Thr Thr Tyr
1               5                   10

<210> SEQ ID NO 343
<211> LENGTH: 7
<212> TYPE: PRT
<213> ORGANISM: Artificial Sequence
<220> FEATURE:
<223> OTHER INFORMATION: DLL3-VL-71-CDR2

<400> SEQUENCE: 343

Leu Val Ser Lys Leu Asp Ser
1               5
```

```
<210> SEQ ID NO 344
<211> LENGTH: 19
<212> TYPE: PRT
<213> ORGANISM: Artificial Sequence
<220> FEATURE:
<223> OTHER INFORMATION: DLL3-VL-71-CDR3

<400> SEQUENCE: 344

Trp Gln Gly Thr His Phe Pro Leu Thr Phe Gly Ala Gly Thr Lys Leu
1               5                   10                  15

Glu Leu Lys

<210> SEQ ID NO 345
<211> LENGTH: 15
<212> TYPE: PRT
<213> ORGANISM: Artificial Sequence
<220> FEATURE:
<223> OTHER INFORMATION: DLL3-VL-72-CDR1

<400> SEQUENCE: 345

Thr Ser Ser Gln Ser Leu Leu Thr Ser Gly Asn Gln Lys Asn Tyr
1               5                   10                  15

<210> SEQ ID NO 346
<211> LENGTH: 7
<212> TYPE: PRT
<213> ORGANISM: Artificial Sequence
<220> FEATURE:
<223> OTHER INFORMATION: DLL3-VL-72-CDR2

<400> SEQUENCE: 346

Trp Ala Ser Thr Arg Glu Ser
1               5

<210> SEQ ID NO 347
<211> LENGTH: 17
<212> TYPE: PRT
<213> ORGANISM: Artificial Sequence
<220> FEATURE:
<223> OTHER INFORMATION: DLL3-VL-72-CDR3

<400> SEQUENCE: 347

Gln Asn Asp Tyr Ser Leu Thr Phe Gly Ala Gly Thr Lys Leu Glu Leu
1               5                   10                  15

Lys

<210> SEQ ID NO 348
<211> LENGTH: 9
<212> TYPE: PRT
<213> ORGANISM: Artificial Sequence
<220> FEATURE:
<223> OTHER INFORMATION: DLL3-VL-73-CDR1

<400> SEQUENCE: 348

His Val Ser Gln Asn Ile Asn Val Trp
1               5

<210> SEQ ID NO 349
<211> LENGTH: 7
<212> TYPE: PRT
<213> ORGANISM: Artificial Sequence
<220> FEATURE:
<223> OTHER INFORMATION: DLL3-VL-73-CDR2

<400> SEQUENCE: 349
```

-continued

Lys Ala Ser Asn Leu His Thr
1               5

<210> SEQ ID NO 350
<211> LENGTH: 19
<212> TYPE: PRT
<213> ORGANISM: Artificial Sequence
<220> FEATURE:
<223> OTHER INFORMATION: DLL3-VL-73-CDR3

<400> SEQUENCE: 350

Gln Gln Gly Gln Ser Tyr Pro Phe Thr Phe Gly Ser Gly Thr Lys Leu
1               5                   10                  15

Glu Ile Lys

<210> SEQ ID NO 351
<211> LENGTH: 13
<212> TYPE: PRT
<213> ORGANISM: Artificial Sequence
<220> FEATURE:
<223> OTHER INFORMATION: DLL3-VL-74-CDR1

<400> SEQUENCE: 351

Lys Ala Ser Gln Ser Val Asp Tyr Asp Gly Asp Ser Tyr
1               5                   10

<210> SEQ ID NO 352
<211> LENGTH: 7
<212> TYPE: PRT
<213> ORGANISM: Artificial Sequence
<220> FEATURE:
<223> OTHER INFORMATION: DLL3-VL-74-CDR2

<400> SEQUENCE: 352

Ala Ala Ser Asn Leu Glu Ser
1               5

<210> SEQ ID NO 353
<211> LENGTH: 20
<212> TYPE: PRT
<213> ORGANISM: Artificial Sequence
<220> FEATURE:
<223> OTHER INFORMATION: DLL3-VL-74-CDR3

<400> SEQUENCE: 353

Gln Gln Ser Asn Glu Asp Pro Tyr Thr Phe Gly Gly Gly Thr Lys Leu
1               5                   10                  15

Glu Ile Lys Arg
            20

<210> SEQ ID NO 354
<211> LENGTH: 15
<212> TYPE: PRT
<213> ORGANISM: Artificial Sequence
<220> FEATURE:
<223> OTHER INFORMATION: DLL3-VL-75-CDR1

<400> SEQUENCE: 354

Lys Ser Ser Gln Ser Leu Leu Tyr Ser Ser Thr Gln Lys Asn Tyr
1               5                   10                  15

<210> SEQ ID NO 355
<211> LENGTH: 7
<212> TYPE: PRT
<213> ORGANISM: Artificial Sequence

<220> FEATURE:
<223> OTHER INFORMATION: DLL3-VL-75-CDR2

<400> SEQUENCE: 355

Trp Ala Ser Thr Arg Glu Ser
1               5

<210> SEQ ID NO 356
<211> LENGTH: 20
<212> TYPE: PRT
<213> ORGANISM: Artificial Sequence
<220> FEATURE:
<223> OTHER INFORMATION: DLL3-VL-75-CDR3

<400> SEQUENCE: 356

Gln Gln Tyr Tyr Ser Tyr Pro Tyr Thr Phe Gly Gly Gly Thr Lys Leu
1               5                   10                  15

Glu Ile Lys Arg
            20

<210> SEQ ID NO 357
<211> LENGTH: 8
<212> TYPE: PRT
<213> ORGANISM: Artificial Sequence
<220> FEATURE:
<223> OTHER INFORMATION: DLL3-VL-76-CDR1

<400> SEQUENCE: 357

Ser Ala Ser Ser Ser Val Ser Tyr
1               5

<210> SEQ ID NO 358
<211> LENGTH: 7
<212> TYPE: PRT
<213> ORGANISM: Artificial Sequence
<220> FEATURE:
<223> OTHER INFORMATION: DLL3-VL-76-CDR2

<400> SEQUENCE: 358

Ser Thr Ser Asn Leu Ala Ser
1               5

<210> SEQ ID NO 359
<211> LENGTH: 20
<212> TYPE: PRT
<213> ORGANISM: Artificial Sequence
<220> FEATURE:
<223> OTHER INFORMATION: DLL3-VL-76-CDR3

<400> SEQUENCE: 359

Gln Gln Arg Ser Ser Tyr Pro Pro Thr Phe Gly Gly Gly Thr Lys Leu
1               5                   10                  15

Glu Ile Lys Arg
            20

<210> SEQ ID NO 360
<211> LENGTH: 9
<212> TYPE: PRT
<213> ORGANISM: Artificial Sequence
<220> FEATURE:
<223> OTHER INFORMATION: DLL3-VL-77-CDR1

<400> SEQUENCE: 360

Lys Ala Ser Gln Asn Val Gly Thr Asn
1               5

<210> SEQ ID NO 361
<211> LENGTH: 7
<212> TYPE: PRT
<213> ORGANISM: Artificial Sequence
<220> FEATURE:
<223> OTHER INFORMATION: DLL3-VL-77-CDR2

<400> SEQUENCE: 361

Ser Ala Ser Tyr Arg Tyr Ser
1               5

<210> SEQ ID NO 362
<211> LENGTH: 19
<212> TYPE: PRT
<213> ORGANISM: Artificial Sequence
<220> FEATURE:
<223> OTHER INFORMATION: DLL3-VL-77-CDR3

<400> SEQUENCE: 362

Gln Gln Tyr Asn Ser Tyr Pro Leu Thr Phe Gly Gly Gly Thr Lys Leu
1               5                   10                  15

Glu Ile Lys

<210> SEQ ID NO 363
<211> LENGTH: 10
<212> TYPE: PRT
<213> ORGANISM: Artificial Sequence
<220> FEATURE:
<223> OTHER INFORMATION: DLL3-VL-78-CDR1

<400> SEQUENCE: 363

Thr Ala Ser Ser Ser Val Ser Ser Ser Tyr
1               5                   10

<210> SEQ ID NO 364
<211> LENGTH: 7
<212> TYPE: PRT
<213> ORGANISM: Artificial Sequence
<220> FEATURE:
<223> OTHER INFORMATION: DLL3-VL-78-CDR2

<400> SEQUENCE: 364

Ser Thr Ser Asn Leu Ala Ser
1               5

<210> SEQ ID NO 365
<211> LENGTH: 19
<212> TYPE: PRT
<213> ORGANISM: Artificial Sequence
<220> FEATURE:
<223> OTHER INFORMATION: DLL3-VL-78-CDR3

<400> SEQUENCE: 365

His Gln Tyr His Arg Ser Pro Phe Thr Phe Gly Ser Gly Thr Lys Leu
1               5                   10                  15

Glu Ile Lys

<210> SEQ ID NO 366
<211> LENGTH: 9
<212> TYPE: PRT
<213> ORGANISM: Artificial Sequence
<220> FEATURE:
<223> OTHER INFORMATION: DLL3-VL-79-CDR1

<400> SEQUENCE: 366

-continued

Leu Ala Ser Gln Thr Ile Gly Thr Trp
1               5

<210> SEQ ID NO 367
<211> LENGTH: 7
<212> TYPE: PRT
<213> ORGANISM: Artificial Sequence
<220> FEATURE:
<223> OTHER INFORMATION: DLL3-VL-79-CDR2

<400> SEQUENCE: 367

Ala Ala Thr Ser Leu Ala Asp
1               5

<210> SEQ ID NO 368
<211> LENGTH: 19
<212> TYPE: PRT
<213> ORGANISM: Artificial Sequence
<220> FEATURE:
<223> OTHER INFORMATION: DLL3-VL-79-CDR3

<400> SEQUENCE: 368

Gln Gln Leu Tyr Ser Thr Pro Trp Thr Phe Gly Gly Gly Thr Lys Leu
1               5                   10                  15

Glu Ile Lys

<210> SEQ ID NO 369
<211> LENGTH: 9
<212> TYPE: PRT
<213> ORGANISM: Artificial Sequence
<220> FEATURE:
<223> OTHER INFORMATION: DLL3-VL-80-CDR1

<400> SEQUENCE: 369

His Ala Ser Gln Asn Ile Asn Val Trp
1               5

<210> SEQ ID NO 370
<211> LENGTH: 7
<212> TYPE: PRT
<213> ORGANISM: Artificial Sequence
<220> FEATURE:
<223> OTHER INFORMATION: DLL3-VL-80-CDR2

<400> SEQUENCE: 370

Lys Ala Ser Ile Leu His Thr
1               5

<210> SEQ ID NO 371
<211> LENGTH: 19
<212> TYPE: PRT
<213> ORGANISM: Artificial Sequence
<220> FEATURE:
<223> OTHER INFORMATION: DLL3-VL-80-CDR3

<400> SEQUENCE: 371

Gln Gln Gly Gln Ser Tyr Pro Tyr Thr Phe Gly Gly Gly Thr Lys Leu
1               5                   10                  15

Glu Ile Lys

<210> SEQ ID NO 372
<211> LENGTH: 9
<212> TYPE: PRT
<213> ORGANISM: Artificial Sequence
<220> FEATURE:
<223> OTHER INFORMATION: DLL3-VL-81-CDR1

<400> SEQUENCE: 372

His Ala Ser Gln Asn Ile Asn Val Trp
1               5

<210> SEQ ID NO 373
<211> LENGTH: 7
<212> TYPE: PRT
<213> ORGANISM: Artificial Sequence
<220> FEATURE:
<223> OTHER INFORMATION: DLL3-VL-81-CDR2

<400> SEQUENCE: 373

Lys Ala Ser Asn Leu His Thr
1               5

<210> SEQ ID NO 374
<211> LENGTH: 19
<212> TYPE: PRT
<213> ORGANISM: Artificial Sequence
<220> FEATURE:
<223> OTHER INFORMATION: DLL3-VL-81-CDR3

<400> SEQUENCE: 374

Gln Gln Gly Gln Ser Tyr Pro Phe Thr Phe Gly Ser Gly Thr Lys Leu
1               5                   10                  15

Glu Ile Lys

<210> SEQ ID NO 375
<211> LENGTH: 9
<212> TYPE: PRT
<213> ORGANISM: Artificial Sequence
<220> FEATURE:
<223> OTHER INFORMATION: DLL3-VL-82-CDR1

<400> SEQUENCE: 375

Leu Ala Ser Gln Thr Ile Gly Thr Trp
1               5

<210> SEQ ID NO 376
<211> LENGTH: 7
<212> TYPE: PRT
<213> ORGANISM: Artificial Sequence
<220> FEATURE:
<223> OTHER INFORMATION: DLL3-VL-82-CDR2

<400> SEQUENCE: 376

Ala Ala Thr Ser Leu Ala Asp
1               5

<210> SEQ ID NO 377
<211> LENGTH: 20
<212> TYPE: PRT
<213> ORGANISM: Artificial Sequence
<220> FEATURE:
<223> OTHER INFORMATION: DLL3-VL-82-CDR3

<400> SEQUENCE: 377

Gln Gln Leu Tyr Ser Thr Pro Tyr Thr Phe Gly Gly Gly Thr Lys Leu
1               5                   10                  15

Glu Ile Lys Arg
            20

<210> SEQ ID NO 378
<211> LENGTH: 9

-continued

```
<212> TYPE: PRT
<213> ORGANISM: Artificial Sequence
<220> FEATURE:
<223> OTHER INFORMATION: DLL3-VL-83-CDR1

<400> SEQUENCE: 378

Arg Ala Ser Gly Ser Ile His Asn Tyr
1               5

<210> SEQ ID NO 379
<211> LENGTH: 7
<212> TYPE: PRT
<213> ORGANISM: Artificial Sequence
<220> FEATURE:
<223> OTHER INFORMATION: DLL3-VL-83-CDR2

<400> SEQUENCE: 379

Asn Ala Lys Thr Leu Val Asp
1               5

<210> SEQ ID NO 380
<211> LENGTH: 19
<212> TYPE: PRT
<213> ORGANISM: Artificial Sequence
<220> FEATURE:
<223> OTHER INFORMATION: DLL3-VL-83-CDR3

<400> SEQUENCE: 380

Gln His Phe Trp Thr Thr Pro Trp Thr Phe Gly Gly Gly Thr Lys Leu
1               5                   10                  15

Glu Ile Lys

<210> SEQ ID NO 381
<211> LENGTH: 9
<212> TYPE: PRT
<213> ORGANISM: Artificial Sequence
<220> FEATURE:
<223> OTHER INFORMATION: DLL3-VL-84-CDR1

<400> SEQUENCE: 381

His Val Ser Gln Asn Ile Asn Val Trp
1               5

<210> SEQ ID NO 382
<211> LENGTH: 7
<212> TYPE: PRT
<213> ORGANISM: Artificial Sequence
<220> FEATURE:
<223> OTHER INFORMATION: DLL3-VL-84-CDR2

<400> SEQUENCE: 382

Lys Ala Ser Asn Leu His Thr
1               5

<210> SEQ ID NO 383
<211> LENGTH: 19
<212> TYPE: PRT
<213> ORGANISM: Artificial Sequence
<220> FEATURE:
<223> OTHER INFORMATION: DLL3-VL-84-CDR3

<400> SEQUENCE: 383

Gln Gln Gly Gln Ser Tyr Pro Phe Thr Phe Gly Ser Gly Thr Lys Leu
1               5                   10                  15

Glu Ile Lys
```

```
<210> SEQ ID NO 384
<211> LENGTH: 9
<212> TYPE: PRT
<213> ORGANISM: Artificial Sequence
<220> FEATURE:
<223> OTHER INFORMATION: DLL3-VL-85-CDR1

<400> SEQUENCE: 384

Leu Ala Ser Gln Thr Ile Gly Thr Trp
1               5

<210> SEQ ID NO 385
<211> LENGTH: 7
<212> TYPE: PRT
<213> ORGANISM: Artificial Sequence
<220> FEATURE:
<223> OTHER INFORMATION: DLL3-VL-85-CDR2

<400> SEQUENCE: 385

Ala Ala Thr Ser Leu Ala Asp
1               5

<210> SEQ ID NO 386
<211> LENGTH: 19
<212> TYPE: PRT
<213> ORGANISM: Artificial Sequence
<220> FEATURE:
<223> OTHER INFORMATION: DLL3-VL-85-CDR3

<400> SEQUENCE: 386

Gln Gln Leu Tyr Ser Thr Pro Trp Thr Phe Gly Gly Gly Thr Lys Leu
1               5                   10                  15

Glu Ile Lys

<210> SEQ ID NO 387
<211> LENGTH: 9
<212> TYPE: PRT
<213> ORGANISM: Artificial Sequence
<220> FEATURE:
<223> OTHER INFORMATION: DLL3-VL-86-CDR1

<400> SEQUENCE: 387

Lys Ala Ser Gln Ser Val Ser Asn Asp
1               5

<210> SEQ ID NO 388
<211> LENGTH: 7
<212> TYPE: PRT
<213> ORGANISM: Artificial Sequence
<220> FEATURE:
<223> OTHER INFORMATION: DLL3-VL-86-CDR2

<400> SEQUENCE: 388

Cys Ala Ser Asn Arg Tyr Thr
1               5

<210> SEQ ID NO 389
<211> LENGTH: 19
<212> TYPE: PRT
<213> ORGANISM: Artificial Sequence
<220> FEATURE:
<223> OTHER INFORMATION: DLL3-VL-86-CDR3

<400> SEQUENCE: 389

Gln Gln Asp Tyr Ser Ser Pro Leu Thr Phe Gly Ala Gly Thr Lys Leu
1               5                   10                  15
```

Glu Leu Lys

<210> SEQ ID NO 390
<211> LENGTH: 13
<212> TYPE: PRT
<213> ORGANISM: Artificial Sequence
<220> FEATURE:
<223> OTHER INFORMATION: DLL3-VL-87-CDR1

<400> SEQUENCE: 390

Lys Ala Ser Gln Ser Val Asp His Ala Gly Asp Ser Tyr
1               5                   10

<210> SEQ ID NO 391
<211> LENGTH: 7
<212> TYPE: PRT
<213> ORGANISM: Artificial Sequence
<220> FEATURE:
<223> OTHER INFORMATION: DLL3-VL-87-CDR2

<400> SEQUENCE: 391

Ala Ala Ser Asn Leu Glu Ser
1               5

<210> SEQ ID NO 392
<211> LENGTH: 20
<212> TYPE: PRT
<213> ORGANISM: Artificial Sequence
<220> FEATURE:
<223> OTHER INFORMATION: DLL3-VL-87-CDR3

<400> SEQUENCE: 392

Gln Gln Ser Asn Glu Asp Pro Tyr Thr Phe Gly Gly Gly Thr Lys Leu
1               5                   10                  15

Glu Ile Lys Arg
            20

<210> SEQ ID NO 393
<211> LENGTH: 9
<212> TYPE: PRT
<213> ORGANISM: Artificial Sequence
<220> FEATURE:
<223> OTHER INFORMATION: DLL3-VL-88-CDR1

<400> SEQUENCE: 393

Lys Ala Ser Gln Asp Ile Asn Arg Tyr
1               5

<210> SEQ ID NO 394
<211> LENGTH: 7
<212> TYPE: PRT
<213> ORGANISM: Artificial Sequence
<220> FEATURE:
<223> OTHER INFORMATION: DLL3-VL-88-CDR2

<400> SEQUENCE: 394

Arg Ala Asn Arg Leu Val Asp
1               5

<210> SEQ ID NO 395
<211> LENGTH: 19
<212> TYPE: PRT
<213> ORGANISM: Artificial Sequence
<220> FEATURE:
<223> OTHER INFORMATION: DLL3-VL-88-CDR3

```
<400> SEQUENCE: 395

Leu Gln Tyr Asp Glu Phe Pro Phe Thr Phe Gly Ser Gly Thr Lys Leu
1               5                   10                  15

Glu Ile Lys

<210> SEQ ID NO 396
<211> LENGTH: 9
<212> TYPE: PRT
<213> ORGANISM: Artificial Sequence
<220> FEATURE:
<223> OTHER INFORMATION: DLL3-VL-89-CDR1

<400> SEQUENCE: 396

Arg Ala Ser Gly Asn Ile His Asn Tyr
1               5

<210> SEQ ID NO 397
<211> LENGTH: 7
<212> TYPE: PRT
<213> ORGANISM: Artificial Sequence
<220> FEATURE:
<223> OTHER INFORMATION: DLL3-VL-89-CDR2

<400> SEQUENCE: 397

Asn Ala Lys Thr Leu Ala Asp
1               5

<210> SEQ ID NO 398
<211> LENGTH: 19
<212> TYPE: PRT
<213> ORGANISM: Artificial Sequence
<220> FEATURE:
<223> OTHER INFORMATION: DLL3-VL-89-CDR3

<400> SEQUENCE: 398

Gln His Phe Trp Ser Thr Pro Trp Thr Phe Gly Gly Gly Thr Lys Leu
1               5                   10                  15

Glu Ile Lys

<210> SEQ ID NO 399
<211> LENGTH: 8
<212> TYPE: PRT
<213> ORGANISM: Artificial Sequence
<220> FEATURE:
<223> OTHER INFORMATION: DLL3-VL-90-CDR1

<400> SEQUENCE: 399

Ser Ala Ser Ser Ser Val Ser Tyr
1               5

<210> SEQ ID NO 400
<211> LENGTH: 7
<212> TYPE: PRT
<213> ORGANISM: Artificial Sequence
<220> FEATURE:
<223> OTHER INFORMATION: DLL3-VL-90-CDR2

<400> SEQUENCE: 400

Ser Thr Ser Asn Leu Ala Ser
1               5

<210> SEQ ID NO 401
<211> LENGTH: 19
<212> TYPE: PRT
<213> ORGANISM: Artificial Sequence
```

<220> FEATURE:
<223> OTHER INFORMATION: DLL3-VL-90-CDR3

<400> SEQUENCE: 401

His Gln Trp Ser Ser Tyr His Thr Phe Gly Gly Gly Thr Lys Leu Glu
1               5                   10                  15

Ile Lys Arg

<210> SEQ ID NO 402
<211> LENGTH: 9
<212> TYPE: PRT
<213> ORGANISM: Artificial Sequence
<220> FEATURE:
<223> OTHER INFORMATION: DLL3-VL-91-CDR1

<400> SEQUENCE: 402

Leu Ala Ser Gln Thr Ile Gly Thr Trp
1               5

<210> SEQ ID NO 403
<211> LENGTH: 7
<212> TYPE: PRT
<213> ORGANISM: Artificial Sequence
<220> FEATURE:
<223> OTHER INFORMATION: DLL3-VL-91-CDR2

<400> SEQUENCE: 403

Ser Ala Thr Ser Leu Ala Asp
1               5

<210> SEQ ID NO 404
<211> LENGTH: 19
<212> TYPE: PRT
<213> ORGANISM: Artificial Sequence
<220> FEATURE:
<223> OTHER INFORMATION: DLL3-VL-91-CDR3

<400> SEQUENCE: 404

Gln Gln Leu Tyr Ser Thr Pro Trp Thr Phe Gly Gly Gly Thr Lys Leu
1               5                   10                  15

Glu Ile Lys

<210> SEQ ID NO 405
<211> LENGTH: 9
<212> TYPE: PRT
<213> ORGANISM: Artificial Sequence
<220> FEATURE:
<223> OTHER INFORMATION: DLL3-VL-92-CDR1

<400> SEQUENCE: 405

Lys Ala Ser Gln Asp Val Asn Thr Ala
1               5

<210> SEQ ID NO 406
<211> LENGTH: 7
<212> TYPE: PRT
<213> ORGANISM: Artificial Sequence
<220> FEATURE:
<223> OTHER INFORMATION: DLL3-VL-92-CDR2

<400> SEQUENCE: 406

Ser Ala Ser Tyr Arg Tyr Thr
1               5

<210> SEQ ID NO 407

-continued

```
<211> LENGTH: 19
<212> TYPE: PRT
<213> ORGANISM: Artificial Sequence
<220> FEATURE:
<223> OTHER INFORMATION: DLL3-VL-92-CDR3

<400> SEQUENCE: 407

Gln Gln His Tyr Ser Ser Pro Tyr Thr Phe Gly Gly Gly Thr Lys Leu
1               5                   10                  15

Glu Ile Lys

<210> SEQ ID NO 408
<211> LENGTH: 13
<212> TYPE: PRT
<213> ORGANISM: Artificial Sequence
<220> FEATURE:
<223> OTHER INFORMATION: DLL3-VL-93-CDR1

<400> SEQUENCE: 408

Arg Ala Ser Lys Ser Val Ser Thr Ser Gly Tyr Ser Tyr
1               5                   10

<210> SEQ ID NO 409
<211> LENGTH: 7
<212> TYPE: PRT
<213> ORGANISM: Artificial Sequence
<220> FEATURE:
<223> OTHER INFORMATION: DLL3-VL-93-CDR2

<400> SEQUENCE: 409

Leu Ala Ser Asn Leu Glu Ser
1               5

<210> SEQ ID NO 410
<211> LENGTH: 20
<212> TYPE: PRT
<213> ORGANISM: Artificial Sequence
<220> FEATURE:
<223> OTHER INFORMATION: DLL3-VL-93-CDR3

<400> SEQUENCE: 410

Gln His Ser Arg Glu Leu Pro Phe Thr Phe Gly Gly Gly Thr Lys Leu
1               5                   10                  15

Glu Ile Lys Arg
            20

<210> SEQ ID NO 411
<211> LENGTH: 9
<212> TYPE: PRT
<213> ORGANISM: Artificial Sequence
<220> FEATURE:
<223> OTHER INFORMATION: DLL3-VL-94-CDR1

<400> SEQUENCE: 411

Lys Ala Ser Gln Asp Ile Asn Ser Tyr
1               5

<210> SEQ ID NO 412
<211> LENGTH: 7
<212> TYPE: PRT
<213> ORGANISM: Artificial Sequence
<220> FEATURE:
<223> OTHER INFORMATION: DLL3-VL-94-CDR2

<400> SEQUENCE: 412

Arg Ala Asn Arg Leu Val Asp
```

```
1               5
```

```
<210> SEQ ID NO 413
<211> LENGTH: 19
<212> TYPE: PRT
<213> ORGANISM: Artificial Sequence
<220> FEATURE:
<223> OTHER INFORMATION: DLL3-VL-94-CDR3

<400> SEQUENCE: 413

Leu Gln Tyr Asp Glu Phe Pro Phe Thr Phe Gly Ser Gly Thr Lys Leu
1               5                   10                  15

Glu Ile Lys

<210> SEQ ID NO 414
<211> LENGTH: 9
<212> TYPE: PRT
<213> ORGANISM: Artificial Sequence
<220> FEATURE:
<223> OTHER INFORMATION: DLL3-VL-95-CDR1

<400> SEQUENCE: 414

Lys Ala Ser Gln Asp Ile Asn Asn Tyr
1               5

<210> SEQ ID NO 415
<211> LENGTH: 7
<212> TYPE: PRT
<213> ORGANISM: Artificial Sequence
<220> FEATURE:
<223> OTHER INFORMATION: DLL3-VL-95-CDR2

<400> SEQUENCE: 415

Arg Ala Asn Arg Leu Val Asp
1               5

<210> SEQ ID NO 416
<211> LENGTH: 20
<212> TYPE: PRT
<213> ORGANISM: Artificial Sequence
<220> FEATURE:
<223> OTHER INFORMATION: DLL3-VL-95-CDR3

<400> SEQUENCE: 416

Leu Gln Tyr Asp Glu Phe Pro Tyr Thr Phe Gly Gly Gly Thr Lys Leu
1               5                   10                  15

Glu Ile Lys Arg
            20

<210> SEQ ID NO 417
<211> LENGTH: 14
<212> TYPE: PRT
<213> ORGANISM: Artificial Sequence
<220> FEATURE:
<223> OTHER INFORMATION: DLL3-VL-96-CDR1

<400> SEQUENCE: 417

Arg Ser Ser Gln Ser Ile Val His Ser Asn Gly Asn Thr Tyr
1               5                   10

<210> SEQ ID NO 418
<211> LENGTH: 7
<212> TYPE: PRT
<213> ORGANISM: Artificial Sequence
<220> FEATURE:
<223> OTHER INFORMATION: DLL3-VL-96-CDR2
```

-continued

<400> SEQUENCE: 418

Lys Val Ser Asn Arg Phe Ser
1               5

<210> SEQ ID NO 419
<211> LENGTH: 19
<212> TYPE: PRT
<213> ORGANISM: Artificial Sequence
<220> FEATURE:
<223> OTHER INFORMATION: DLL3-VL-96-CDR3

<400> SEQUENCE: 419

Phe Gln Gly Ser His Val Pro Leu Thr Phe Gly Ala Gly Thr Lys Leu
1               5                   10                  15

Glu Leu Lys

<210> SEQ ID NO 420
<211> LENGTH: 9
<212> TYPE: PRT
<213> ORGANISM: Artificial Sequence
<220> FEATURE:
<223> OTHER INFORMATION: DLL3-VL-97-CDR1

<400> SEQUENCE: 420

Lys Ala Ser Gln Ser Val Ser Asn Asp
1               5

<210> SEQ ID NO 421
<211> LENGTH: 7
<212> TYPE: PRT
<213> ORGANISM: Artificial Sequence
<220> FEATURE:
<223> OTHER INFORMATION: DLL3-VL-97-CDR2

<400> SEQUENCE: 421

Tyr Ala Ser Asn Arg Tyr Asn
1               5

<210> SEQ ID NO 422
<211> LENGTH: 19
<212> TYPE: PRT
<213> ORGANISM: Artificial Sequence
<220> FEATURE:
<223> OTHER INFORMATION: DLL3-VL-97-CDR3

<400> SEQUENCE: 422

Gln Gln Asp Tyr Ser Ser Pro Trp Thr Phe Gly Gly Gly Thr Lys Leu
1               5                   10                  15

Glu Ile Lys

<210> SEQ ID NO 423
<211> LENGTH: 9
<212> TYPE: PRT
<213> ORGANISM: Artificial Sequence
<220> FEATURE:
<223> OTHER INFORMATION: DLL3-VL-98-CDR1

<400> SEQUENCE: 423

Arg Ala Ser Gln Asp Ile Asn Asn Tyr
1               5

<210> SEQ ID NO 424
<211> LENGTH: 7
<212> TYPE: PRT

<213> ORGANISM: Artificial Sequence
<220> FEATURE:
<223> OTHER INFORMATION: DLL3-VL-98-CDR2

<400> SEQUENCE: 424

Tyr Thr Ser Arg Leu His Ser
1               5

<210> SEQ ID NO 425
<211> LENGTH: 19
<212> TYPE: PRT
<213> ORGANISM: Artificial Sequence
<220> FEATURE:
<223> OTHER INFORMATION: DLL3-VL-98-CDR3

<400> SEQUENCE: 425

Gln Gln Gly Asp Thr Leu Pro Trp Thr Phe Gly Gly Gly Thr Lys Leu
1               5                   10                  15

Glu Ile Lys

<210> SEQ ID NO 426
<211> LENGTH: 8
<212> TYPE: PRT
<213> ORGANISM: Artificial Sequence
<220> FEATURE:
<223> OTHER INFORMATION: DLL3-VL-99-CDR1

<400> SEQUENCE: 426

Ser Ala Ser Ser Ser Val Ser Tyr
1               5

<210> SEQ ID NO 427
<211> LENGTH: 7
<212> TYPE: PRT
<213> ORGANISM: Artificial Sequence
<220> FEATURE:
<223> OTHER INFORMATION: DLL3-VL-99-CDR2

<400> SEQUENCE: 427

Asp Thr Ser Asn Leu Ala Ser
1               5

<210> SEQ ID NO 428
<211> LENGTH: 19
<212> TYPE: PRT
<213> ORGANISM: Artificial Sequence
<220> FEATURE:
<223> OTHER INFORMATION: DLL3-VL-99-CDR3

<400> SEQUENCE: 428

Gln Glu Trp Ser Asn Asn Pro Leu Thr Phe Gly Asp Gly Thr Lys Leu
1               5                   10                  15

Glu Leu Lys

<210> SEQ ID NO 429
<211> LENGTH: 9
<212> TYPE: PRT
<213> ORGANISM: Artificial Sequence
<220> FEATURE:
<223> OTHER INFORMATION: DLL3-VL-100-CDR1

<400> SEQUENCE: 429

His Ala Ser Gln Asn Ile Asn Val Trp
1               5

```
<210> SEQ ID NO 430
<211> LENGTH: 7
<212> TYPE: PRT
<213> ORGANISM: Artificial Sequence
<220> FEATURE:
<223> OTHER INFORMATION: DLL3-VL-100-CDR2

<400> SEQUENCE: 430

Lys Ala Ser His Leu His Thr
1               5

<210> SEQ ID NO 431
<211> LENGTH: 19
<212> TYPE: PRT
<213> ORGANISM: Artificial Sequence
<220> FEATURE:
<223> OTHER INFORMATION: DLL3-VL-100-CDR3

<400> SEQUENCE: 431

Gln Gln Gly Gln Ser Tyr Pro Phe Thr Phe Gly Ser Gly Thr Thr Leu
1               5                   10                  15

Glu Ile Lys

<210> SEQ ID NO 432
<211> LENGTH: 15
<212> TYPE: PRT
<213> ORGANISM: Artificial Sequence
<220> FEATURE:
<223> OTHER INFORMATION: DLL3-VL-101-CDR1

<400> SEQUENCE: 432

Met Ser Ser Gln Ser Leu Leu Tyr Ser Ser Thr Gln Lys Asn Tyr
1               5                   10                  15

<210> SEQ ID NO 433
<211> LENGTH: 7
<212> TYPE: PRT
<213> ORGANISM: Artificial Sequence
<220> FEATURE:
<223> OTHER INFORMATION: DLL3-VL-101-CDR2

<400> SEQUENCE: 433

Trp Ala Ser Thr Arg Glu Ser
1               5

<210> SEQ ID NO 434
<211> LENGTH: 20
<212> TYPE: PRT
<213> ORGANISM: Artificial Sequence
<220> FEATURE:
<223> OTHER INFORMATION: DLL3-VL-101-CDR3

<400> SEQUENCE: 434

Gln Gln Tyr Tyr Ser Tyr Pro Tyr Thr Phe Gly Gly Gly Thr Lys Leu
1               5                   10                  15

Glu Ile Lys Arg
            20

<210> SEQ ID NO 435
<211> LENGTH: 8
<212> TYPE: PRT
<213> ORGANISM: Artificial Sequence
<220> FEATURE:
<223> OTHER INFORMATION: DLL3-VL-102-CDR1

<400> SEQUENCE: 435
```

Ser Ala Ser Ser Ser Val Ser Tyr
1               5

<210> SEQ ID NO 436
<211> LENGTH: 7
<212> TYPE: PRT
<213> ORGANISM: Artificial Sequence
<220> FEATURE:
<223> OTHER INFORMATION: DLL3-VL-102-CDR2

<400> SEQUENCE: 436

Leu Thr Ser Asn Leu Ala Ser
1               5

<210> SEQ ID NO 437
<211> LENGTH: 20
<212> TYPE: PRT
<213> ORGANISM: Artificial Sequence
<220> FEATURE:
<223> OTHER INFORMATION: DLL3-VL-102-CDR3

<400> SEQUENCE: 437

Gln Gln Trp Arg Ser Asn Pro Phe Thr Phe Gly Gln Gly Thr Lys Leu
1               5                   10                  15

Glu Ile Lys Arg
            20

<210> SEQ ID NO 438
<211> LENGTH: 9
<212> TYPE: PRT
<213> ORGANISM: Artificial Sequence
<220> FEATURE:
<223> OTHER INFORMATION: DLL3-VL-103-CDR1

<400> SEQUENCE: 438

Arg Ala Ser Glu Asn Ile Tyr Tyr Asn
1               5

<210> SEQ ID NO 439
<211> LENGTH: 7
<212> TYPE: PRT
<213> ORGANISM: Artificial Sequence
<220> FEATURE:
<223> OTHER INFORMATION: DLL3-VL-103-CDR2

<400> SEQUENCE: 439

Thr Ala Asn Ser Leu Glu Asp
1               5

<210> SEQ ID NO 440
<211> LENGTH: 19
<212> TYPE: PRT
<213> ORGANISM: Artificial Sequence
<220> FEATURE:
<223> OTHER INFORMATION: DLL3-VL-103-CDR3

<400> SEQUENCE: 440

Lys Gln Ala Tyr Asp Val Pro Pro Thr Phe Gly Gly Gly Thr Lys Leu
1               5                   10                  15

Glu Ile Lys

<210> SEQ ID NO 441
<211> LENGTH: 8
<212> TYPE: PRT
<213> ORGANISM: Artificial Sequence
<220> FEATURE:

-continued

<223> OTHER INFORMATION: DLL3-VL-104-CDR1

<400> SEQUENCE: 441

Ser Ala Ser Ser Ser Val Ser Tyr
1               5

<210> SEQ ID NO 442
<211> LENGTH: 7
<212> TYPE: PRT
<213> ORGANISM: Artificial Sequence
<220> FEATURE:
<223> OTHER INFORMATION: DLL3-VL-104-CDR2

<400> SEQUENCE: 442

Asp Ser Ser Lys Leu Ala Ser
1               5

<210> SEQ ID NO 443
<211> LENGTH: 19
<212> TYPE: PRT
<213> ORGANISM: Artificial Sequence
<220> FEATURE:
<223> OTHER INFORMATION: DLL3-VL-104-CDR3

<400> SEQUENCE: 443

Gln Gln Trp Ser Ser Asn Pro Leu Thr Phe Gly Gln Gly Thr Lys Leu
1               5                   10                  15

Glu Ile Lys

<210> SEQ ID NO 444
<211> LENGTH: 9
<212> TYPE: PRT
<213> ORGANISM: Artificial Sequence
<220> FEATURE:
<223> OTHER INFORMATION: DLL3-VL-105-CDR1

<400> SEQUENCE: 444

Lys Ala Ser Gln Ser Val Ser Asn Asp
1               5

<210> SEQ ID NO 445
<211> LENGTH: 7
<212> TYPE: PRT
<213> ORGANISM: Artificial Sequence
<220> FEATURE:
<223> OTHER INFORMATION: DLL3-VL-105-CDR2

<400> SEQUENCE: 445

Tyr Ala Ser Asn Arg Tyr Ser
1               5

<210> SEQ ID NO 446
<211> LENGTH: 19
<212> TYPE: PRT
<213> ORGANISM: Artificial Sequence
<220> FEATURE:
<223> OTHER INFORMATION: DLL3-VL-105-CDR3

<400> SEQUENCE: 446

Gln Gln Asp Tyr Ser Ser Pro Trp Thr Phe Gly Gly Gly Thr Lys Val
1               5                   10                  15

Glu Ile Lys

<210> SEQ ID NO 447
<211> LENGTH: 9

```
<212> TYPE: PRT
<213> ORGANISM: Artificial Sequence
<220> FEATURE:
<223> OTHER INFORMATION: DLL3-VL-106-CDR1

<400> SEQUENCE: 447

Lys Ala Ser Gln Ser Val Ser Asn Asp
1               5

<210> SEQ ID NO 448
<211> LENGTH: 7
<212> TYPE: PRT
<213> ORGANISM: Artificial Sequence
<220> FEATURE:
<223> OTHER INFORMATION: DLL3-VL-106-CDR2

<400> SEQUENCE: 448

Tyr Ala Ser Asn Arg Tyr Thr
1               5

<210> SEQ ID NO 449
<211> LENGTH: 20
<212> TYPE: PRT
<213> ORGANISM: Artificial Sequence
<220> FEATURE:
<223> OTHER INFORMATION: DLL3-VL-106-CDR3

<400> SEQUENCE: 449

Gln Gln Asp Tyr Thr Ser Pro Trp Thr Phe Gly Gln Gly Thr Lys Leu
1               5                   10                  15

Glu Ile Lys Arg
            20

<210> SEQ ID NO 450
<211> LENGTH: 6
<212> TYPE: PRT
<213> ORGANISM: Artificial Sequence
<220> FEATURE:
<223> OTHER INFORMATION: CD16-VH-CDR1

<400> SEQUENCE: 450

Thr Ser Tyr Tyr Met His
1               5

<210> SEQ ID NO 451
<211> LENGTH: 17
<212> TYPE: PRT
<213> ORGANISM: Artificial Sequence
<220> FEATURE:
<223> OTHER INFORMATION: CD16-VH-CDR2

<400> SEQUENCE: 451

Ile Ile Asn Pro Ser Gly Gly Ser Thr Ser Tyr Ala Gln Lys Phe Gln
1               5                   10                  15

Gly

<210> SEQ ID NO 452
<211> LENGTH: 11
<212> TYPE: PRT
<213> ORGANISM: Artificial Sequence
<220> FEATURE:
<223> OTHER INFORMATION: CD16-VH-CDR3

<400> SEQUENCE: 452

Gly Ser Ala Tyr Tyr Tyr Asp Phe Ala Asp Tyr
1               5                   10
```

<210> SEQ ID NO 453
<211> LENGTH: 11
<212> TYPE: PRT
<213> ORGANISM: Artificial Sequence
<220> FEATURE:
<223> OTHER INFORMATION: CD16-VL-1-CDR1

<400> SEQUENCE: 453

Ser Gly Asp Lys Leu Glu Glu Lys Tyr Val Ser
1               5                   10

<210> SEQ ID NO 454
<211> LENGTH: 7
<212> TYPE: PRT
<213> ORGANISM: Artificial Sequence
<220> FEATURE:
<223> OTHER INFORMATION: CD16-VL-1-CDR2

<400> SEQUENCE: 454

Gln Asp Asn Lys Arg Pro Ser
1               5

<210> SEQ ID NO 455
<211> LENGTH: 9
<212> TYPE: PRT
<213> ORGANISM: Artificial Sequence
<220> FEATURE:
<223> OTHER INFORMATION: CD16-VL-1-CDR3

<400> SEQUENCE: 455

Gln Val Trp Asp Asn Tyr Ser Val Leu
1               5

<210> SEQ ID NO 456
<211> LENGTH: 11
<212> TYPE: PRT
<213> ORGANISM: Artificial Sequence
<220> FEATURE:
<223> OTHER INFORMATION: CD16-VL-2-CDR1

<400> SEQUENCE: 456

Gly Gly Asn Asn Ile Glu Ser Arg Asn Val His
1               5                   10

<210> SEQ ID NO 457
<211> LENGTH: 7
<212> TYPE: PRT
<213> ORGANISM: Artificial Sequence
<220> FEATURE:
<223> OTHER INFORMATION: CD16-VL-2-CDR2

<400> SEQUENCE: 457

Arg Asp Asn Asn Arg Pro Ser
1               5

<210> SEQ ID NO 458
<211> LENGTH: 9
<212> TYPE: PRT
<213> ORGANISM: Artificial Sequence
<220> FEATURE:
<223> OTHER INFORMATION: CD16-VL-2-CDR3

<400> SEQUENCE: 458

Gln Val Trp Asp Asn Tyr Thr Val Leu
1               5

<210> SEQ ID NO 459
<211> LENGTH: 11
<212> TYPE: PRT
<213> ORGANISM: Artificial Sequence
<220> FEATURE:
<223> OTHER INFORMATION: CD16-VL-3-CDR1

<400> SEQUENCE: 459

Gly Gly Asn Asn Ile Gly Ser Lys Asn Val His
1               5                   10

<210> SEQ ID NO 460
<211> LENGTH: 7
<212> TYPE: PRT
<213> ORGANISM: Artificial Sequence
<220> FEATURE:
<223> OTHER INFORMATION: CD16-VL-3-CDR2

<400> SEQUENCE: 460

Arg Asp Ser Asn Arg Pro Ser
1               5

<210> SEQ ID NO 461
<211> LENGTH: 9
<212> TYPE: PRT
<213> ORGANISM: Artificial Sequence
<220> FEATURE:
<223> OTHER INFORMATION: CD16-VL-3-CDR3

<400> SEQUENCE: 461

Gln Val Trp Asp Asn Tyr Ile Val Leu
1               5

<210> SEQ ID NO 462
<211> LENGTH: 11
<212> TYPE: PRT
<213> ORGANISM: Artificial Sequence
<220> FEATURE:
<223> OTHER INFORMATION: CD16-VL-4-CDR1

<400> SEQUENCE: 462

Glu Gly Asn Asn Ile Gly Ser Lys Asn Val His
1               5                   10

<210> SEQ ID NO 463
<211> LENGTH: 7
<212> TYPE: PRT
<213> ORGANISM: Artificial Sequence
<220> FEATURE:
<223> OTHER INFORMATION: CD16-VL-4-CDR2

<400> SEQUENCE: 463

Asp Asp Ser Asp Arg Pro Ser
1               5

<210> SEQ ID NO 464
<211> LENGTH: 9
<212> TYPE: PRT
<213> ORGANISM: Artificial Sequence
<220> FEATURE:
<223> OTHER INFORMATION: CD16-VL-4-CDR3

<400> SEQUENCE: 464

Gln Val Trp Asp Asn Tyr Ser Val Leu
1               5

-continued

<210> SEQ ID NO 465
<211> LENGTH: 11
<212> TYPE: PRT
<213> ORGANISM: Artificial Sequence
<220> FEATURE:
<223> OTHER INFORMATION: CD16-VL-5-CDR1

<400> SEQUENCE: 465

Gly Gly Asn Asn Ile Gly Ser Lys Asn Val His
1               5                   10

<210> SEQ ID NO 466
<211> LENGTH: 7
<212> TYPE: PRT
<213> ORGANISM: Artificial Sequence
<220> FEATURE:
<223> OTHER INFORMATION: CD16-VL-5-CDR2

<400> SEQUENCE: 466

Arg Asp Ser Ser Arg Pro Ser
1               5

<210> SEQ ID NO 467
<211> LENGTH: 9
<212> TYPE: PRT
<213> ORGANISM: Artificial Sequence
<220> FEATURE:
<223> OTHER INFORMATION: CD16-VL-5-CDR3

<400> SEQUENCE: 467

Gln Val Trp Asp Asp Tyr Ile Val Val
1               5

<210> SEQ ID NO 468
<211> LENGTH: 11
<212> TYPE: PRT
<213> ORGANISM: Artificial Sequence
<220> FEATURE:
<223> OTHER INFORMATION: CD16-VL-6-CDR1

<400> SEQUENCE: 468

Gly Ala Asn Asp Ile Gly Lys Arg Asn Val His
1               5                   10

<210> SEQ ID NO 469
<211> LENGTH: 7
<212> TYPE: PRT
<213> ORGANISM: Artificial Sequence
<220> FEATURE:
<223> OTHER INFORMATION: CD16-VL-6-CDR2

<400> SEQUENCE: 469

Gln Asp Asn Lys Arg Pro Ser
1               5

<210> SEQ ID NO 470
<211> LENGTH: 9
<212> TYPE: PRT
<213> ORGANISM: Artificial Sequence
<220> FEATURE:
<223> OTHER INFORMATION: CD16-VL-6-CDR3

<400> SEQUENCE: 470

Gln Val Trp Asp Asn Tyr Ser Val Leu
1               5

<210> SEQ ID NO 471

-continued

```
<211> LENGTH: 11
<212> TYPE: PRT
<213> ORGANISM: Artificial Sequence
<220> FEATURE:
<223> OTHER INFORMATION: CD16-VL-7-CDR1

<400> SEQUENCE: 471

Gly Gly His Asn Ile Gly Ser Lys Asn Val His
1               5                   10

<210> SEQ ID NO 472
<211> LENGTH: 7
<212> TYPE: PRT
<213> ORGANISM: Artificial Sequence
<220> FEATURE:
<223> OTHER INFORMATION: CD16-VL-7-CDR2

<400> SEQUENCE: 472

Gln Asp Asn Lys Arg Pro Ser
1               5

<210> SEQ ID NO 473
<211> LENGTH: 9
<212> TYPE: PRT
<213> ORGANISM: Artificial Sequence
<220> FEATURE:
<223> OTHER INFORMATION: CD16-VL-7-CDR3

<400> SEQUENCE: 473

Gln Val Trp Asp Asn Tyr Ser Val Leu
1               5

<210> SEQ ID NO 474
<211> LENGTH: 14
<212> TYPE: PRT
<213> ORGANISM: Artificial Sequence
<220> FEATURE:
<223> OTHER INFORMATION: CD3-VL-1-CDR1

<400> SEQUENCE: 474

Gly Ser Ser Thr Gly Ala Val Thr Ser Gly Tyr Tyr Pro Asn
1               5                   10

<210> SEQ ID NO 475
<211> LENGTH: 7
<212> TYPE: PRT
<213> ORGANISM: Artificial Sequence
<220> FEATURE:
<223> OTHER INFORMATION: CD3-VL-1-CDR2

<400> SEQUENCE: 475

Gly Thr Lys Phe Leu Ala Pro
1               5

<210> SEQ ID NO 476
<211> LENGTH: 9
<212> TYPE: PRT
<213> ORGANISM: Artificial Sequence
<220> FEATURE:
<223> OTHER INFORMATION: CD3-VL-1-CDR3

<400> SEQUENCE: 476

Ala Leu Trp Tyr Ser Asn Arg Trp Val
1               5

<210> SEQ ID NO 477
<211> LENGTH: 14
```

```
<212> TYPE: PRT
<213> ORGANISM: Artificial Sequence
<220> FEATURE:
<223> OTHER INFORMATION: CD3-VL-2-CDR1

<400> SEQUENCE: 477

Arg Ser Ser Thr Gly Ala Val Thr Ser Gly Tyr Tyr Pro Asn
1               5                   10

<210> SEQ ID NO 478
<211> LENGTH: 7
<212> TYPE: PRT
<213> ORGANISM: Artificial Sequence
<220> FEATURE:
<223> OTHER INFORMATION: CD3-VL-2-CDR2

<400> SEQUENCE: 478

Ala Thr Asp Met Arg Pro Ser
1               5

<210> SEQ ID NO 479
<211> LENGTH: 9
<212> TYPE: PRT
<213> ORGANISM: Artificial Sequence
<220> FEATURE:
<223> OTHER INFORMATION: CD3-VL-2-CDR3

<400> SEQUENCE: 479

Ala Leu Trp Tyr Ser Asn Arg Trp Val
1               5

<210> SEQ ID NO 480
<211> LENGTH: 14
<212> TYPE: PRT
<213> ORGANISM: Artificial Sequence
<220> FEATURE:
<223> OTHER INFORMATION: CD3-VL-3-CDR1

<400> SEQUENCE: 480

Gly Ser Ser Thr Gly Ala Val Thr Ser Gly Asn Tyr Pro Asn
1               5                   10

<210> SEQ ID NO 481
<211> LENGTH: 7
<212> TYPE: PRT
<213> ORGANISM: Artificial Sequence
<220> FEATURE:
<223> OTHER INFORMATION: CD3-VL-3-CDR2

<400> SEQUENCE: 481

Gly Thr Lys Phe Leu Ala Pro
1               5

<210> SEQ ID NO 482
<211> LENGTH: 9
<212> TYPE: PRT
<213> ORGANISM: Artificial Sequence
<220> FEATURE:
<223> OTHER INFORMATION: CD3-VL-3-CDR3

<400> SEQUENCE: 482

Val Leu Trp Tyr Ser Asn Arg Trp Val
1               5

<210> SEQ ID NO 483
<211> LENGTH: 5
<212> TYPE: PRT
```

<213> ORGANISM: Artificial Sequence
<220> FEATURE:
<223> OTHER INFORMATION: CD3-VH-1-CDR1

<400> SEQUENCE: 483

Ile Tyr Ala Met Asn
1               5

<210> SEQ ID NO 484
<211> LENGTH: 19
<212> TYPE: PRT
<213> ORGANISM: Artificial Sequence
<220> FEATURE:
<223> OTHER INFORMATION: CD3-VH-1-CDR2

<400> SEQUENCE: 484

Arg Ile Arg Ser Lys Tyr Asn Asn Tyr Ala Thr Tyr Tyr Ala Asp Ser
1               5                   10                  15

Val Lys Ser

<210> SEQ ID NO 485
<211> LENGTH: 14
<212> TYPE: PRT
<213> ORGANISM: Artificial Sequence
<220> FEATURE:
<223> OTHER INFORMATION: CD3-VH-1-CDR3

<400> SEQUENCE: 485

His Gly Asn Phe Gly Asn Ser Tyr Val Ser Phe Phe Ala Tyr
1               5                   10

<210> SEQ ID NO 486
<211> LENGTH: 5
<212> TYPE: PRT
<213> ORGANISM: Artificial Sequence
<220> FEATURE:
<223> OTHER INFORMATION: CD3-VH-2-CDR1

<400> SEQUENCE: 486

Lys Tyr Ala Met Asn
1               5

<210> SEQ ID NO 487
<211> LENGTH: 19
<212> TYPE: PRT
<213> ORGANISM: Artificial Sequence
<220> FEATURE:
<223> OTHER INFORMATION: CD3-VH-2-CDR2

<400> SEQUENCE: 487

Arg Ile Arg Ser Lys Tyr Asn Asn Tyr Ala Thr Tyr Tyr Ala Asp Ser
1               5                   10                  15

Val Lys Asp

<210> SEQ ID NO 488
<211> LENGTH: 14
<212> TYPE: PRT
<213> ORGANISM: Artificial Sequence
<220> FEATURE:
<223> OTHER INFORMATION: CD3-VH-2-CDR3

<400> SEQUENCE: 488

His Gly Asn Phe Gly Asn Ser Tyr Ile Ser Tyr Trp Ala Tyr
1               5                   10

-continued

```
<210> SEQ ID NO 489
<211> LENGTH: 5
<212> TYPE: PRT
<213> ORGANISM: Artificial Sequence
<220> FEATURE:
<223> OTHER INFORMATION: CD3-VH-3-CDR1

<400> SEQUENCE: 489

Ser Tyr Ala Met Asn
1               5

<210> SEQ ID NO 490
<211> LENGTH: 19
<212> TYPE: PRT
<213> ORGANISM: Artificial Sequence
<220> FEATURE:
<223> OTHER INFORMATION: CD3-VH-3-CDR2

<400> SEQUENCE: 490

Arg Ile Arg Ser Lys Tyr Asn Asn Tyr Ala Thr Tyr Tyr Ala Asp Ser
1               5                   10                  15

Val Lys Gly

<210> SEQ ID NO 491
<211> LENGTH: 14
<212> TYPE: PRT
<213> ORGANISM: Artificial Sequence
<220> FEATURE:
<223> OTHER INFORMATION: CD3-VH-3-CDR3

<400> SEQUENCE: 491

His Gly Asn Phe Gly Asn Ser Tyr Leu Ser Phe Trp Ala Tyr
1               5                   10

<210> SEQ ID NO 492
<211> LENGTH: 5
<212> TYPE: PRT
<213> ORGANISM: Artificial Sequence
<220> FEATURE:
<223> OTHER INFORMATION: CD3-VH-4-CDR1

<400> SEQUENCE: 492

Arg Tyr Ala Met Asn
1               5

<210> SEQ ID NO 493
<211> LENGTH: 19
<212> TYPE: PRT
<213> ORGANISM: Artificial Sequence
<220> FEATURE:
<223> OTHER INFORMATION: CD3-VH-4-CDR2

<400> SEQUENCE: 493

Arg Ile Arg Ser Lys Tyr Asn Asn Tyr Ala Thr Tyr Tyr Ala Asp Ser
1               5                   10                  15

Val Lys Gly

<210> SEQ ID NO 494
<211> LENGTH: 14
<212> TYPE: PRT
<213> ORGANISM: Artificial Sequence
<220> FEATURE:
<223> OTHER INFORMATION: CD3-VH-4-CDR3

<400> SEQUENCE: 494

His Gly Asn Phe Gly Asn Ser Tyr Leu Ser Tyr Phe Ala Tyr
```

```
1               5              10
```

<210> SEQ ID NO 495
<211> LENGTH: 5
<212> TYPE: PRT
<213> ORGANISM: Artificial Sequence
<220> FEATURE:
<223> OTHER INFORMATION: CD3-VH-5-CDR1

<400> SEQUENCE: 495

Val Tyr Ala Met Asn
1               5

<210> SEQ ID NO 496
<211> LENGTH: 19
<212> TYPE: PRT
<213> ORGANISM: Artificial Sequence
<220> FEATURE:
<223> OTHER INFORMATION: CD3-VH-5-CDR2

<400> SEQUENCE: 496

Arg Ile Arg Ser Lys Tyr Asn Asn Tyr Ala Thr Tyr Tyr Ala Asp Ser
1               5              10              15

Val Lys Lys

<210> SEQ ID NO 497
<211> LENGTH: 14
<212> TYPE: PRT
<213> ORGANISM: Artificial Sequence
<220> FEATURE:
<223> OTHER INFORMATION: CD3-VH-5-CDR3

<400> SEQUENCE: 497

His Gly Asn Phe Gly Asn Ser Tyr Leu Ser Trp Trp Ala Tyr
1               5              10

<210> SEQ ID NO 498
<211> LENGTH: 5
<212> TYPE: PRT
<213> ORGANISM: Artificial Sequence
<220> FEATURE:
<223> OTHER INFORMATION: CD3-VH-6-CDR1

<400> SEQUENCE: 498

Lys Tyr Ala Met Asn
1               5

<210> SEQ ID NO 499
<211> LENGTH: 19
<212> TYPE: PRT
<213> ORGANISM: Artificial Sequence
<220> FEATURE:
<223> OTHER INFORMATION: CD3-VH-6-CDR2

<400> SEQUENCE: 499

Arg Ile Arg Ser Lys Tyr Asn Asn Tyr Ala Thr Tyr Tyr Ala Asp Ser
1               5              10              15

Val Lys Ser

<210> SEQ ID NO 500
<211> LENGTH: 14
<212> TYPE: PRT
<213> ORGANISM: Artificial Sequence
<220> FEATURE:
<223> OTHER INFORMATION: CD3-VH-6-CDR3

```
<400> SEQUENCE: 500

His Gly Asn Phe Gly Asn Ser Tyr Thr Ser Tyr Tyr Ala Tyr
1               5                   10

<210> SEQ ID NO 501
<211> LENGTH: 5
<212> TYPE: PRT
<213> ORGANISM: Artificial Sequence
<220> FEATURE:
<223> OTHER INFORMATION: CD3-VH-7-CDR1

<400> SEQUENCE: 501

Gly Tyr Ala Met Asn
1               5

<210> SEQ ID NO 502
<211> LENGTH: 19
<212> TYPE: PRT
<213> ORGANISM: Artificial Sequence
<220> FEATURE:
<223> OTHER INFORMATION: CD3-VH-7-CDR2

<400> SEQUENCE: 502

Arg Ile Arg Ser Lys Tyr Asn Asn Tyr Ala Thr Tyr Tyr Ala Asp Ser
1               5                   10                  15

Val Lys Glu

<210> SEQ ID NO 503
<211> LENGTH: 14
<212> TYPE: PRT
<213> ORGANISM: Artificial Sequence
<220> FEATURE:
<223> OTHER INFORMATION: CD3-VH-7-CDR3

<400> SEQUENCE: 503

His Arg Asn Phe Gly Asn Ser Tyr Leu Ser Trp Phe Ala Tyr
1               5                   10

<210> SEQ ID NO 504
<211> LENGTH: 5
<212> TYPE: PRT
<213> ORGANISM: Artificial Sequence
<220> FEATURE:
<223> OTHER INFORMATION: CD3-VH-8-CDR1

<400> SEQUENCE: 504

Val Tyr Ala Met Asn
1               5

<210> SEQ ID NO 505
<211> LENGTH: 19
<212> TYPE: PRT
<213> ORGANISM: Artificial Sequence
<220> FEATURE:
<223> OTHER INFORMATION: CD3-VH-8-CDR2

<400> SEQUENCE: 505

Arg Ile Arg Ser Lys Tyr Asn Asn Tyr Ala Thr Tyr Tyr Ala Asp Ser
1               5                   10                  15

Val Lys Lys

<210> SEQ ID NO 506
<211> LENGTH: 14
<212> TYPE: PRT
<213> ORGANISM: Artificial Sequence
```

```
<220> FEATURE:
<223> OTHER INFORMATION: CD3-VH-8-CDR3

<400> SEQUENCE: 506

His Gly Asn Phe Gly Asn Ser Tyr Ile Ser Trp Trp Ala Tyr
1               5                   10

<210> SEQ ID NO 507
<211> LENGTH: 5
<212> TYPE: PRT
<213> ORGANISM: Artificial Sequence
<220> FEATURE:
<223> OTHER INFORMATION: CD3-VH-9-CDR1

<400> SEQUENCE: 507

Ser Tyr Ala Met Asn
1               5

<210> SEQ ID NO 508
<211> LENGTH: 19
<212> TYPE: PRT
<213> ORGANISM: Artificial Sequence
<220> FEATURE:
<223> OTHER INFORMATION: CD3-VH-9-CDR2

<400> SEQUENCE: 508

Arg Ile Arg Ser Lys Tyr Asn Asn Tyr Ala Thr Tyr Tyr Ala Asp Ser
1               5                   10                  15

Val Lys Gly

<210> SEQ ID NO 509
<211> LENGTH: 14
<212> TYPE: PRT
<213> ORGANISM: Artificial Sequence
<220> FEATURE:
<223> OTHER INFORMATION: CD3-VH-9-CDR3

<400> SEQUENCE: 509

His Gly Asn Phe Gly Asn Ser Tyr Val Ser Trp Trp Ala Tyr
1               5                   10

<210> SEQ ID NO 510
<211> LENGTH: 5
<212> TYPE: PRT
<213> ORGANISM: Artificial Sequence
<220> FEATURE:
<223> OTHER INFORMATION: CD3-VH-10-CDR1

<400> SEQUENCE: 510

Lys Tyr Ala Met Asn
1               5

<210> SEQ ID NO 511
<211> LENGTH: 19
<212> TYPE: PRT
<213> ORGANISM: Artificial Sequence
<220> FEATURE:
<223> OTHER INFORMATION: CD3-VH-10-CDR2

<400> SEQUENCE: 511

Arg Ile Arg Ser Lys Tyr Asn Asn Tyr Ala Thr Tyr Tyr Ala Asp Ser
1               5                   10                  15

Val Lys Asp

<210> SEQ ID NO 512
```

```
<211> LENGTH: 14
<212> TYPE: PRT
<213> ORGANISM: Artificial Sequence
<220> FEATURE:
<223> OTHER INFORMATION: CD3-VH-10-CDR3

<400> SEQUENCE: 512

His Gly Asn Phe Gly Asn Ser Tyr Ile Ser Tyr Trp Ala Tyr
1               5                   10

<210> SEQ ID NO 513
<211> LENGTH: 13
<212> TYPE: PRT
<213> ORGANISM: Artificial Sequence
<220> FEATURE:
<223> OTHER INFORMATION: CD3-VL-4-CDR1

<400> SEQUENCE: 513

Ser Ser Thr Gly Ala Val Thr Thr Ser Asn Tyr Ala Asn
1               5                   10

<210> SEQ ID NO 514
<211> LENGTH: 6
<212> TYPE: PRT
<213> ORGANISM: Artificial Sequence
<220> FEATURE:
<223> OTHER INFORMATION: CD3-VL-4-CDR2

<400> SEQUENCE: 514

Gly Thr Asn Lys Arg Ala
1               5

<210> SEQ ID NO 515
<211> LENGTH: 8
<212> TYPE: PRT
<213> ORGANISM: Artificial Sequence
<220> FEATURE:
<223> OTHER INFORMATION: CD3-VL-4-CDR3

<400> SEQUENCE: 515

Leu Trp Tyr Ser Asn Leu Trp Val
1               5

<210> SEQ ID NO 516
<211> LENGTH: 5
<212> TYPE: PRT
<213> ORGANISM: Artificial Sequence
<220> FEATURE:
<223> OTHER INFORMATION: CD3-VH-11-CDR1

<400> SEQUENCE: 516

Thr Tyr Ala Met Asn
1               5

<210> SEQ ID NO 517
<211> LENGTH: 18
<212> TYPE: PRT
<213> ORGANISM: Artificial Sequence
<220> FEATURE:
<223> OTHER INFORMATION: CD3-VH-11-CDR2

<400> SEQUENCE: 517

Ile Arg Ser Lys Tyr Asn Asn Tyr Ala Thr Tyr Tyr Ala Asp Ser Val
1               5                   10                  15

Lys Asp
```

```
<210> SEQ ID NO 518
<211> LENGTH: 14
<212> TYPE: PRT
<213> ORGANISM: Artificial Sequence
<220> FEATURE:
<223> OTHER INFORMATION: CD3-VH-11-CDR3

<400> SEQUENCE: 518

His Gly Asn Phe Gly Asn Ser Tyr Val Ser Trp Phe Ala Tyr
1               5                   10

<210> SEQ ID NO 519
<211> LENGTH: 8
<212> TYPE: PRT
<213> ORGANISM: Artificial Sequence
<220> FEATURE:
<223> OTHER INFORMATION: CD3-VH-12-CDR1

<400> SEQUENCE: 519

Gly Phe Thr Phe Asp Asp Tyr Ser
1               5

<210> SEQ ID NO 520
<211> LENGTH: 8
<212> TYPE: PRT
<213> ORGANISM: Artificial Sequence
<220> FEATURE:
<223> OTHER INFORMATION: CD3-VH-12-CDR2

<400> SEQUENCE: 520

Ile Ser Trp Asn Ser Gly Ser Lys
1               5

<210> SEQ ID NO 521
<211> LENGTH: 17
<212> TYPE: PRT
<213> ORGANISM: Artificial Sequence
<220> FEATURE:
<223> OTHER INFORMATION: CD3-VH-12-CDR3

<400> SEQUENCE: 521

Ala Lys Tyr Gly Ser Gly Tyr Gly Lys Phe Tyr His Tyr Gly Leu Asp
1               5                   10                  15

Val

<210> SEQ ID NO 522
<211> LENGTH: 8
<212> TYPE: PRT
<213> ORGANISM: Artificial Sequence
<220> FEATURE:
<223> OTHER INFORMATION: CD3-VH-13-CDR1

<400> SEQUENCE: 522

Gly Phe Thr Phe Asp Asp Tyr Ala
1               5

<210> SEQ ID NO 523
<211> LENGTH: 8
<212> TYPE: PRT
<213> ORGANISM: Artificial Sequence
<220> FEATURE:
<223> OTHER INFORMATION: CD3-VH-13-CDR2

<400> SEQUENCE: 523

Ile Ser Trp Asn Ser Gly Ser Ile
1               5
```

-continued

```
<210> SEQ ID NO 524
<211> LENGTH: 17
<212> TYPE: PRT
<213> ORGANISM: Artificial Sequence
<220> FEATURE:
<223> OTHER INFORMATION: CD3-VH-13-CDR3

<400> SEQUENCE: 524

Ala Lys Asp Gly Ser Gly Tyr Gly Tyr Phe Tyr Tyr Tyr Gly Met Asp
1               5                   10                  15

Val

<210> SEQ ID NO 525
<211> LENGTH: 8
<212> TYPE: PRT
<213> ORGANISM: Artificial Sequence
<220> FEATURE:
<223> OTHER INFORMATION: CD3-VH-14-CDR1

<400> SEQUENCE: 525

Gly Phe Thr Phe Asp Asp Tyr Ser
1               5

<210> SEQ ID NO 526
<211> LENGTH: 8
<212> TYPE: PRT
<213> ORGANISM: Artificial Sequence
<220> FEATURE:
<223> OTHER INFORMATION: CD3-VH-14-CDR2

<400> SEQUENCE: 526

Ile Ser Trp Asn Ser Gly Ser Ile
1               5

<210> SEQ ID NO 527
<211> LENGTH: 17
<212> TYPE: PRT
<213> ORGANISM: Artificial Sequence
<220> FEATURE:
<223> OTHER INFORMATION: CD3-VH-14-CDR3

<400> SEQUENCE: 527

Ala Lys Asp Gly Ser Gly Tyr Gly Tyr Phe Tyr Tyr Tyr Gly Met Asp
1               5                   10                  15

Val

<210> SEQ ID NO 528
<211> LENGTH: 8
<212> TYPE: PRT
<213> ORGANISM: Artificial Sequence
<220> FEATURE:
<223> OTHER INFORMATION: CD3-VH-15-CDR1

<400> SEQUENCE: 528

Gly Phe Thr Phe Asp Asp Tyr Ala
1               5

<210> SEQ ID NO 529
<211> LENGTH: 8
<212> TYPE: PRT
<213> ORGANISM: Artificial Sequence
<220> FEATURE:
<223> OTHER INFORMATION: CD3-VH-15-CDR2

<400> SEQUENCE: 529
```

Ile Ser Trp Asn Ser Gly Ser Ile
1               5

<210> SEQ ID NO 530
<211> LENGTH: 17
<212> TYPE: PRT
<213> ORGANISM: Artificial Sequence
<220> FEATURE:
<223> OTHER INFORMATION: CD3-VH-15-CDR3

<400> SEQUENCE: 530

Ala Lys Asp Gly Ser Gly Tyr Gly Lys Phe Tyr Tyr Tyr Gly Met Asp
1               5                   10                  15

Val

<210> SEQ ID NO 531
<211> LENGTH: 8
<212> TYPE: PRT
<213> ORGANISM: Artificial Sequence
<220> FEATURE:
<223> OTHER INFORMATION: CD3-VH-16-CDR1

<400> SEQUENCE: 531

Gly Phe Thr Phe Asp Asp Tyr Ser
1               5

<210> SEQ ID NO 532
<211> LENGTH: 8
<212> TYPE: PRT
<213> ORGANISM: Artificial Sequence
<220> FEATURE:
<223> OTHER INFORMATION: CD3-VH-16-CDR2

<400> SEQUENCE: 532

Ile Ser Trp Asn Ser Gly Ser Ile
1               5

<210> SEQ ID NO 533
<211> LENGTH: 17
<212> TYPE: PRT
<213> ORGANISM: Artificial Sequence
<220> FEATURE:
<223> OTHER INFORMATION: CD3-VH-16-CDR3

<400> SEQUENCE: 533

Ala Lys Asp Gly Ser Gly Tyr Gly Lys Phe Tyr Tyr Tyr Gly Met Asp
1               5                   10                  15

Val

<210> SEQ ID NO 534
<211> LENGTH: 8
<212> TYPE: PRT
<213> ORGANISM: Artificial Sequence
<220> FEATURE:
<223> OTHER INFORMATION: CD3-VH-17-CDR1

<400> SEQUENCE: 534

Gly Phe Thr Phe Asp Asp Tyr Ser
1               5

<210> SEQ ID NO 535
<211> LENGTH: 8
<212> TYPE: PRT
<213> ORGANISM: Artificial Sequence
<220> FEATURE:
<223> OTHER INFORMATION: CD3-VH-17-CDR2

<400> SEQUENCE: 535

Ile Ser Trp Asn Ser Gly Ser Ile
1               5

<210> SEQ ID NO 536
<211> LENGTH: 17
<212> TYPE: PRT
<213> ORGANISM: Artificial Sequence
<220> FEATURE:
<223> OTHER INFORMATION: CD3-VH-17-CDR3

<400> SEQUENCE: 536

Ala Lys Tyr Gly Ser Gly Tyr Gly Lys Phe Tyr His Tyr Gly Leu Asp
1               5                   10                  15

Val

<210> SEQ ID NO 537
<211> LENGTH: 8
<212> TYPE: PRT
<213> ORGANISM: Artificial Sequence
<220> FEATURE:
<223> OTHER INFORMATION: CD3-VH-18-CDR1

<400> SEQUENCE: 537

Gly Phe Thr Phe Asp Asp Tyr Ser
1               5

<210> SEQ ID NO 538
<211> LENGTH: 8
<212> TYPE: PRT
<213> ORGANISM: Artificial Sequence
<220> FEATURE:
<223> OTHER INFORMATION: CD3-VH-18-CDR2

<400> SEQUENCE: 538

Ile Ser Trp Asn Ser Gly Ser Lys
1               5

<210> SEQ ID NO 539
<211> LENGTH: 17
<212> TYPE: PRT
<213> ORGANISM: Artificial Sequence
<220> FEATURE:
<223> OTHER INFORMATION: CD3-VH-18-CDR3

<400> SEQUENCE: 539

Ala Lys Asp Gly Ser Gly Tyr Gly Lys Phe Tyr His Tyr Gly Leu Asp
1               5                   10                  15

Val

<210> SEQ ID NO 540
<211> LENGTH: 8
<212> TYPE: PRT
<213> ORGANISM: Artificial Sequence
<220> FEATURE:
<223> OTHER INFORMATION: CD3-VH-19-CDR1

<400> SEQUENCE: 540

Gly Phe Thr Phe Asp Asp Tyr Ser
1               5

<210> SEQ ID NO 541
<211> LENGTH: 8
<212> TYPE: PRT

```
<213> ORGANISM: Artificial Sequence
<220> FEATURE:
<223> OTHER INFORMATION: CD3-VH-19-CDR2

<400> SEQUENCE: 541

Ile Ser Trp Asn Ser Gly Ser Lys
1               5

<210> SEQ ID NO 542
<211> LENGTH: 17
<212> TYPE: PRT
<213> ORGANISM: Artificial Sequence
<220> FEATURE:
<223> OTHER INFORMATION: CD3-VH-19-CDR3

<400> SEQUENCE: 542

Ala Lys Tyr Gly Ser Gly Tyr Gly Lys Phe Tyr Tyr Tyr Gly Leu Asp
1               5                   10                  15

Val

<210> SEQ ID NO 543
<211> LENGTH: 8
<212> TYPE: PRT
<213> ORGANISM: Artificial Sequence
<220> FEATURE:
<223> OTHER INFORMATION: CD3-VH-20-CDR1

<400> SEQUENCE: 543

Gly Phe Thr Phe Asp Asp Tyr Ser
1               5

<210> SEQ ID NO 544
<211> LENGTH: 8
<212> TYPE: PRT
<213> ORGANISM: Artificial Sequence
<220> FEATURE:
<223> OTHER INFORMATION: CD3-VH-20-CDR2

<400> SEQUENCE: 544

Ile Ser Trp Asn Ser Gly Ser Lys
1               5

<210> SEQ ID NO 545
<211> LENGTH: 17
<212> TYPE: PRT
<213> ORGANISM: Artificial Sequence
<220> FEATURE:
<223> OTHER INFORMATION: CD3-VH-20-CDR3

<400> SEQUENCE: 545

Ala Lys Tyr Gly Ser Gly Tyr Gly Lys Phe Tyr His Tyr Gly Met Asp
1               5                   10                  15

Val

<210> SEQ ID NO 546
<211> LENGTH: 8
<212> TYPE: PRT
<213> ORGANISM: Artificial Sequence
<220> FEATURE:
<223> OTHER INFORMATION: CD3-VH-21-CDR1

<400> SEQUENCE: 546

Gly Phe Thr Phe Asp Asp Tyr Ser
1               5
```

```
<210> SEQ ID NO 547
<211> LENGTH: 8
<212> TYPE: PRT
<213> ORGANISM: Artificial Sequence
<220> FEATURE:
<223> OTHER INFORMATION: CD3-VH-21-CDR2

<400> SEQUENCE: 547

Ile Ser Trp Asn Ser Gly Ser Ile
1               5

<210> SEQ ID NO 548
<211> LENGTH: 17
<212> TYPE: PRT
<213> ORGANISM: Artificial Sequence
<220> FEATURE:
<223> OTHER INFORMATION: CD3-VH-21-CDR3

<400> SEQUENCE: 548

Ala Lys Asp Gly Ser Gly Tyr Gly Lys Phe Tyr His Tyr Gly Leu Asp
1               5                   10                  15

Val

<210> SEQ ID NO 549
<211> LENGTH: 8
<212> TYPE: PRT
<213> ORGANISM: Artificial Sequence
<220> FEATURE:
<223> OTHER INFORMATION: CD3-VH-22-CDR1

<400> SEQUENCE: 549

Gly Phe Thr Phe Asp Asp Tyr Ser
1               5

<210> SEQ ID NO 550
<211> LENGTH: 8
<212> TYPE: PRT
<213> ORGANISM: Artificial Sequence
<220> FEATURE:
<223> OTHER INFORMATION: CD3-VH-22-CDR2

<400> SEQUENCE: 550

Ile Ser Trp Asn Ser Gly Ser Ile
1               5

<210> SEQ ID NO 551
<211> LENGTH: 17
<212> TYPE: PRT
<213> ORGANISM: Artificial Sequence
<220> FEATURE:
<223> OTHER INFORMATION: CD3-VH-22-CDR3

<400> SEQUENCE: 551

Ala Lys Tyr Gly Ser Gly Tyr Gly Lys Phe Tyr Tyr Tyr Gly Leu Asp
1               5                   10                  15

Val

<210> SEQ ID NO 552
<211> LENGTH: 8
<212> TYPE: PRT
<213> ORGANISM: Artificial Sequence
<220> FEATURE:
<223> OTHER INFORMATION: CD3-VH-23-CDR1

<400> SEQUENCE: 552

Gly Phe Thr Phe Asp Asp Tyr Ser
```

-continued

```
1               5

<210> SEQ ID NO 553
<211> LENGTH: 8
<212> TYPE: PRT
<213> ORGANISM: Artificial Sequence
<220> FEATURE:
<223> OTHER INFORMATION: CD3-VH-23-CDR2

<400> SEQUENCE: 553

Ile Ser Trp Asn Ser Gly Ser Ile
1               5

<210> SEQ ID NO 554
<211> LENGTH: 17
<212> TYPE: PRT
<213> ORGANISM: Artificial Sequence
<220> FEATURE:
<223> OTHER INFORMATION: CD3-VH-23-CDR3

<400> SEQUENCE: 554

Ala Lys Tyr Gly Ser Gly Tyr Gly Lys Phe Tyr His Tyr Gly Met Asp
1               5                   10                  15

Val

<210> SEQ ID NO 555
<211> LENGTH: 8
<212> TYPE: PRT
<213> ORGANISM: Artificial Sequence
<220> FEATURE:
<223> OTHER INFORMATION: CD3-VH-24-CDR1

<400> SEQUENCE: 555

Gly Phe Thr Phe Asp Asp Tyr Ser
1               5

<210> SEQ ID NO 556
<211> LENGTH: 8
<212> TYPE: PRT
<213> ORGANISM: Artificial Sequence
<220> FEATURE:
<223> OTHER INFORMATION: CD3-VH-24-CDR2

<400> SEQUENCE: 556

Ile Ser Trp Asn Ser Gly Ser Lys
1               5

<210> SEQ ID NO 557
<211> LENGTH: 17
<212> TYPE: PRT
<213> ORGANISM: Artificial Sequence
<220> FEATURE:
<223> OTHER INFORMATION: CD3-VH-24-CDR3

<400> SEQUENCE: 557

Ala Lys Asp Gly Ser Gly Tyr Gly Lys Phe Tyr Tyr Tyr Gly Leu Asp
1               5                   10                  15

Val

<210> SEQ ID NO 558
<211> LENGTH: 8
<212> TYPE: PRT
<213> ORGANISM: Artificial Sequence
<220> FEATURE:
<223> OTHER INFORMATION: CD3-VH-25-CDR1
```

```
<400> SEQUENCE: 558

Gly Phe Thr Phe Asp Asp Tyr Ser
1               5

<210> SEQ ID NO 559
<211> LENGTH: 8
<212> TYPE: PRT
<213> ORGANISM: Artificial Sequence
<220> FEATURE:
<223> OTHER INFORMATION: CD3-VH-25-CDR2

<400> SEQUENCE: 559

Ile Ser Trp Asn Ser Gly Ser Lys
1               5

<210> SEQ ID NO 560
<211> LENGTH: 17
<212> TYPE: PRT
<213> ORGANISM: Artificial Sequence
<220> FEATURE:
<223> OTHER INFORMATION: CD3-VH-25-CDR3

<400> SEQUENCE: 560

Ala Lys Asp Gly Ser Gly Tyr Gly Lys Phe Tyr His Tyr Gly Met Asp
1               5                   10                  15

Val

<210> SEQ ID NO 561
<211> LENGTH: 8
<212> TYPE: PRT
<213> ORGANISM: Artificial Sequence
<220> FEATURE:
<223> OTHER INFORMATION: CD3-VH-26-CDR1

<400> SEQUENCE: 561

Gly Phe Thr Phe Asp Asp Tyr Ser
1               5

<210> SEQ ID NO 562
<211> LENGTH: 8
<212> TYPE: PRT
<213> ORGANISM: Artificial Sequence
<220> FEATURE:
<223> OTHER INFORMATION: CD3-VH-26-CDR2

<400> SEQUENCE: 562

Ile Ser Trp Asn Ser Gly Ser Lys
1               5

<210> SEQ ID NO 563
<211> LENGTH: 17
<212> TYPE: PRT
<213> ORGANISM: Artificial Sequence
<220> FEATURE:
<223> OTHER INFORMATION: CD3-VH-26-CDR3

<400> SEQUENCE: 563

Ala Lys Tyr Gly Ser Gly Tyr Gly Lys Phe Tyr Tyr Tyr Gly Met Asp
1               5                   10                  15

Val

<210> SEQ ID NO 564
<211> LENGTH: 8
<212> TYPE: PRT
<213> ORGANISM: Artificial Sequence
```

```
<220> FEATURE:
<223> OTHER INFORMATION: CD3-VH-27-CDR1

<400> SEQUENCE: 564

Gly Phe Thr Phe Asp Asp Tyr Ser
1               5

<210> SEQ ID NO 565
<211> LENGTH: 8
<212> TYPE: PRT
<213> ORGANISM: Artificial Sequence
<220> FEATURE:
<223> OTHER INFORMATION: CD3-VH-27-CDR2

<400> SEQUENCE: 565

Ile Ser Trp Asn Ser Gly Ser Ile
1               5

<210> SEQ ID NO 566
<211> LENGTH: 17
<212> TYPE: PRT
<213> ORGANISM: Artificial Sequence
<220> FEATURE:
<223> OTHER INFORMATION: CD3-VH-27-CDR3

<400> SEQUENCE: 566

Ala Lys Asp Gly Ser Gly Tyr Gly Lys Phe Tyr Tyr Tyr Gly Leu Asp
1               5                   10                  15

Val

<210> SEQ ID NO 567
<211> LENGTH: 8
<212> TYPE: PRT
<213> ORGANISM: Artificial Sequence
<220> FEATURE:
<223> OTHER INFORMATION: CD3-VH-28-CDR1

<400> SEQUENCE: 567

Gly Phe Thr Phe Asp Asp Tyr Ser
1               5

<210> SEQ ID NO 568
<211> LENGTH: 8
<212> TYPE: PRT
<213> ORGANISM: Artificial Sequence
<220> FEATURE:
<223> OTHER INFORMATION: CD3-VH-28-CDR2

<400> SEQUENCE: 568

Ile Ser Trp Asn Ser Gly Ser Ile
1               5

<210> SEQ ID NO 569
<211> LENGTH: 17
<212> TYPE: PRT
<213> ORGANISM: Artificial Sequence
<220> FEATURE:
<223> OTHER INFORMATION: CD3-VH-28-CDR3

<400> SEQUENCE: 569

Ala Lys Asp Gly Ser Gly Tyr Gly Lys Phe Tyr His Tyr Gly Met Asp
1               5                   10                  15

Val

<210> SEQ ID NO 570
```

-continued

```
<211> LENGTH: 8
<212> TYPE: PRT
<213> ORGANISM: Artificial Sequence
<220> FEATURE:
<223> OTHER INFORMATION: CD3-VH-29-CDR1

<400> SEQUENCE: 570

Gly Phe Thr Phe Asp Asp Tyr Ser
1               5

<210> SEQ ID NO 571
<211> LENGTH: 8
<212> TYPE: PRT
<213> ORGANISM: Artificial Sequence
<220> FEATURE:
<223> OTHER INFORMATION: CD3-VH-29-CDR2

<400> SEQUENCE: 571

Ile Ser Trp Asn Ser Gly Ser Ile
1               5

<210> SEQ ID NO 572
<211> LENGTH: 17
<212> TYPE: PRT
<213> ORGANISM: Artificial Sequence
<220> FEATURE:
<223> OTHER INFORMATION: CD3-VH-29-CDR3

<400> SEQUENCE: 572

Ala Lys Tyr Gly Ser Gly Tyr Gly Lys Phe Tyr Tyr Tyr Gly Met Asp
1               5                   10                  15

Val

<210> SEQ ID NO 573
<211> LENGTH: 8
<212> TYPE: PRT
<213> ORGANISM: Artificial Sequence
<220> FEATURE:
<223> OTHER INFORMATION: CD3-VH-30-CDR1

<400> SEQUENCE: 573

Gly Phe Thr Phe Asp Asp Tyr Ser
1               5

<210> SEQ ID NO 574
<211> LENGTH: 8
<212> TYPE: PRT
<213> ORGANISM: Artificial Sequence
<220> FEATURE:
<223> OTHER INFORMATION: CD3-VH-30-CDR2

<400> SEQUENCE: 574

Ile Ser Trp Asn Ser Gly Ser Lys
1               5

<210> SEQ ID NO 575
<211> LENGTH: 17
<212> TYPE: PRT
<213> ORGANISM: Artificial Sequence
<220> FEATURE:
<223> OTHER INFORMATION: CD3-VH-30-CDR3

<400> SEQUENCE: 575

Ala Lys Asp Gly Ser Gly Tyr Gly Lys Phe Tyr Tyr Tyr Gly Met Asp
1               5                   10                  15

Val
```

```
<210> SEQ ID NO 576
<211> LENGTH: 8
<212> TYPE: PRT
<213> ORGANISM: Artificial Sequence
<220> FEATURE:
<223> OTHER INFORMATION: CD3-VH-31-CDR1

<400> SEQUENCE: 576

Gly Phe Thr Phe Asp Asp Tyr Ser
1               5

<210> SEQ ID NO 577
<211> LENGTH: 8
<212> TYPE: PRT
<213> ORGANISM: Artificial Sequence
<220> FEATURE:
<223> OTHER INFORMATION: CD3-VH-31-CDR2

<400> SEQUENCE: 577

Ile Ser Trp Asn Ser Gly Ser Lys
1               5

<210> SEQ ID NO 578
<211> LENGTH: 17
<212> TYPE: PRT
<213> ORGANISM: Artificial Sequence
<220> FEATURE:
<223> OTHER INFORMATION: CD3-VH-31-CDR3

<400> SEQUENCE: 578

Ala Lys Tyr Gly Ser Gly Tyr Gly Lys Phe Tyr His Tyr Gly Leu Asp
1               5                   10                  15

Val

<210> SEQ ID NO 579
<211> LENGTH: 5
<212> TYPE: PRT
<213> ORGANISM: Artificial Sequence
<220> FEATURE:
<223> OTHER INFORMATION: CD3-VH-32-CDR1

<400> SEQUENCE: 579

Asn Tyr Tyr Ile His
1               5

<210> SEQ ID NO 580
<211> LENGTH: 17
<212> TYPE: PRT
<213> ORGANISM: Artificial Sequence
<220> FEATURE:
<223> OTHER INFORMATION: CD3-VH-32-CDR2

<400> SEQUENCE: 580

Trp Ile Tyr Pro Gly Asp Gly Asn Thr Lys Tyr Asn Glu Lys Phe Lys
1               5                   10                  15

Gly

<210> SEQ ID NO 581
<211> LENGTH: 10
<212> TYPE: PRT
<213> ORGANISM: Artificial Sequence
<220> FEATURE:
<223> OTHER INFORMATION: CD3-VH-32-CDR3

<400> SEQUENCE: 581
```

-continued

```
Asp Ser Tyr Ser Asn Tyr Tyr Phe Asp Tyr
1               5                   10

<210> SEQ ID NO 582
<211> LENGTH: 5
<212> TYPE: PRT
<213> ORGANISM: Artificial Sequence
<220> FEATURE:
<223> OTHER INFORMATION: CD3-VH-n-CDR1

<400> SEQUENCE: 582

Ser Tyr Tyr Ile His
1               5

<210> SEQ ID NO 583
<211> LENGTH: 17
<212> TYPE: PRT
<213> ORGANISM: Artificial Sequence
<220> FEATURE:
<223> OTHER INFORMATION: CD3-VH-n-CDR2

<400> SEQUENCE: 583

Trp Ile Tyr Pro Glu Asn Asp Asn Thr Lys Tyr Asn Glu Lys Phe Lys
1               5                   10                  15

Asp

<210> SEQ ID NO 584
<211> LENGTH: 10
<212> TYPE: PRT
<213> ORGANISM: Artificial Sequence
<220> FEATURE:
<223> OTHER INFORMATION: CD3-VH-n-CDR3

<400> SEQUENCE: 584

Asp Gly Tyr Ser Arg Tyr Tyr Phe Asp Tyr
1               5                   10

<210> SEQ ID NO 585
<211> LENGTH: 5
<212> TYPE: PRT
<213> ORGANISM: Artificial Sequence
<220> FEATURE:
<223> OTHER INFORMATION: CD3-VH-n-CDR1

<400> SEQUENCE: 585

Gly Tyr Thr Met Asn
1               5

<210> SEQ ID NO 586
<211> LENGTH: 17
<212> TYPE: PRT
<213> ORGANISM: Artificial Sequence
<220> FEATURE:
<223> OTHER INFORMATION: CD3-VH-n-CDR2

<400> SEQUENCE: 586

Leu Ile Asn Pro Tyr Lys Gly Val Ser Thr Tyr Asn Gln Lys Phe Lys
1               5                   10                  15

Asp

<210> SEQ ID NO 587
<211> LENGTH: 10
<212> TYPE: PRT
<213> ORGANISM: Artificial Sequence
<220> FEATURE:
```

-continued

<223> OTHER INFORMATION: CD3-VH-n-CDR3

<400> SEQUENCE: 587

Asp Ala Tyr Ser Arg Tyr Tyr Phe Asp Tyr
1               5                   10

<210> SEQ ID NO 588
<211> LENGTH: 5
<212> TYPE: PRT
<213> ORGANISM: Artificial Sequence
<220> FEATURE:
<223> OTHER INFORMATION: CD3-VH-n-CDR1

<400> SEQUENCE: 588

Thr Tyr Ala Met Asn
1               5

<210> SEQ ID NO 589
<211> LENGTH: 17
<212> TYPE: PRT
<213> ORGANISM: Artificial Sequence
<220> FEATURE:
<223> OTHER INFORMATION: CD3-VH-n-CDR2

<400> SEQUENCE: 589

Leu Ile Asn Pro Tyr Lys Gly Val Thr Thr Tyr Ala Asp Ser Val Lys
1               5                   10                  15

Gly

<210> SEQ ID NO 590
<211> LENGTH: 10
<212> TYPE: PRT
<213> ORGANISM: Artificial Sequence
<220> FEATURE:
<223> OTHER INFORMATION: CD3-VH-n-CDR3

<400> SEQUENCE: 590

Thr Gly Tyr Ser Arg Tyr Tyr Phe Asp Tyr
1               5                   10

<210> SEQ ID NO 591
<211> LENGTH: 5
<212> TYPE: PRT
<213> ORGANISM: Artificial Sequence
<220> FEATURE:
<223> OTHER INFORMATION: CD3-VH-n-CDR1

<400> SEQUENCE: 591

Asn Tyr Gly Met Asn
1               5

<210> SEQ ID NO 592
<211> LENGTH: 17
<212> TYPE: PRT
<213> ORGANISM: Artificial Sequence
<220> FEATURE:
<223> OTHER INFORMATION: CD3-VH-n-CDR2

<400> SEQUENCE: 592

Leu Ile Asn Pro Tyr Lys Gly Val Ser Thr Tyr Ala Asp Ser Val Lys
1               5                   10                  15

Gly

<210> SEQ ID NO 593
<211> LENGTH: 10

```
<212> TYPE: PRT
<213> ORGANISM: Artificial Sequence
<220> FEATURE:
<223> OTHER INFORMATION: CD3-VH-n-CDR3

<400> SEQUENCE: 593

Asp Gly Tyr Ser Arg Tyr Ala Phe Asp Tyr
1               5                   10

<210> SEQ ID NO 594
<211> LENGTH: 5
<212> TYPE: PRT
<213> ORGANISM: Artificial Sequence
<220> FEATURE:
<223> OTHER INFORMATION: CD3-VH-n-CDR1

<400> SEQUENCE: 594

Ser Tyr Tyr Ile His
1               5

<210> SEQ ID NO 595
<211> LENGTH: 19
<212> TYPE: PRT
<213> ORGANISM: Artificial Sequence
<220> FEATURE:
<223> OTHER INFORMATION: CD3-VH-n-CDR2

<400> SEQUENCE: 595

Arg Ile Arg Ser Lys Tyr Asn Asn Tyr Ala Thr Tyr Tyr Ala Asp Ser
1               5                   10                  15

Val Lys Asp

<210> SEQ ID NO 596
<211> LENGTH: 10
<212> TYPE: PRT
<213> ORGANISM: Artificial Sequence
<220> FEATURE:
<223> OTHER INFORMATION: CD3-VH-n-CDR3

<400> SEQUENCE: 596

Ser Gly Tyr Ser Arg Tyr Tyr Phe Asp Tyr
1               5                   10

<210> SEQ ID NO 597
<211> LENGTH: 5
<212> TYPE: PRT
<213> ORGANISM: Artificial Sequence
<220> FEATURE:
<223> OTHER INFORMATION: CD3-VH-n-CDR1

<400> SEQUENCE: 597

Asn Tyr Ala Ile His
1               5

<210> SEQ ID NO 598
<211> LENGTH: 17
<212> TYPE: PRT
<213> ORGANISM: Artificial Sequence
<220> FEATURE:
<223> OTHER INFORMATION: CD3-VH-n-CDR2

<400> SEQUENCE: 598

Trp Ile Asn Thr Asn Thr Gly Lys Pro Thr Tyr Ala Glu Glu Phe Lys
1               5                   10                  15

Gly
```

-continued

<210> SEQ ID NO 599
<211> LENGTH: 10
<212> TYPE: PRT
<213> ORGANISM: Artificial Sequence
<220> FEATURE:
<223> OTHER INFORMATION: CD3-VH-n-CDR3

<400> SEQUENCE: 599

Asp Gly Tyr Ser Arg Ala Tyr Phe Asp Tyr
1               5                   10

<210> SEQ ID NO 600
<211> LENGTH: 10
<212> TYPE: PRT
<213> ORGANISM: Artificial Sequence
<220> FEATURE:
<223> OTHER INFORMATION: CD3-VH-n-CDR1

<400> SEQUENCE: 600

Gly Phe Ser Leu Thr Asn Tyr Ala Ile His
1               5                   10

<210> SEQ ID NO 601
<211> LENGTH: 17
<212> TYPE: PRT
<213> ORGANISM: Artificial Sequence
<220> FEATURE:
<223> OTHER INFORMATION: CD3-VH-n-CDR2

<400> SEQUENCE: 601

Trp Ile Tyr Pro Gly Asn Val Asn Thr Lys Tyr Asn Glu Lys Phe Lys
1               5                   10                  15

Gly

<210> SEQ ID NO 602
<211> LENGTH: 10
<212> TYPE: PRT
<213> ORGANISM: Artificial Sequence
<220> FEATURE:
<223> OTHER INFORMATION: CD3-VH-n-CDR3

<400> SEQUENCE: 602

Asp Ser Tyr Ser Asn Tyr Tyr Phe Asp Tyr
1               5                   10

<210> SEQ ID NO 603
<211> LENGTH: 5
<212> TYPE: PRT
<213> ORGANISM: Artificial Sequence
<220> FEATURE:
<223> OTHER INFORMATION: CD3-VH-n-CDR1

<400> SEQUENCE: 603

Gly Ser Ala Met His
1               5

<210> SEQ ID NO 604
<211> LENGTH: 16
<212> TYPE: PRT
<213> ORGANISM: Artificial Sequence
<220> FEATURE:
<223> OTHER INFORMATION: CD3-VH-n-CDR2

<400> SEQUENCE: 604

Val Ile Trp Ala Gly Gly Asn Thr Lys Tyr Asn Ser Ala Leu Met Ser
1               5                   10                  15

```
<210> SEQ ID NO 605
<211> LENGTH: 13
<212> TYPE: PRT
<213> ORGANISM: Artificial Sequence
<220> FEATURE:
<223> OTHER INFORMATION: CD3-VH-n-CDR3

<400> SEQUENCE: 605

Ser Gly Tyr Tyr Gly Asp Ser Asp Trp Tyr Phe Asp Val
1               5                   10

<210> SEQ ID NO 606
<211> LENGTH: 5
<212> TYPE: PRT
<213> ORGANISM: Artificial Sequence
<220> FEATURE:
<223> OTHER INFORMATION: CD3-VH-n-CDR1

<400> SEQUENCE: 606

Ser Asp Tyr Ile His
1               5

<210> SEQ ID NO 607
<211> LENGTH: 17
<212> TYPE: PRT
<213> ORGANISM: Artificial Sequence
<220> FEATURE:
<223> OTHER INFORMATION: CD3-VH-n-CDR2

<400> SEQUENCE: 607

Gly Val Ile Trp Ala Gly Gly Asn Thr Lys Tyr Asn Ser Ala Leu Met
1               5                   10                  15

Ser

<210> SEQ ID NO 608
<211> LENGTH: 14
<212> TYPE: PRT
<213> ORGANISM: Artificial Sequence
<220> FEATURE:
<223> OTHER INFORMATION: CD3-VH-n-CDR3

<400> SEQUENCE: 608

His Gly Asn Phe Gly Asn Ser Tyr Val Ser Trp Phe Ala Tyr
1               5                   10

<210> SEQ ID NO 609
<211> LENGTH: 5
<212> TYPE: PRT
<213> ORGANISM: Artificial Sequence
<220> FEATURE:
<223> OTHER INFORMATION: CD3-VH-n-CDR1

<400> SEQUENCE: 609

Ser His Tyr Leu His
1               5

<210> SEQ ID NO 610
<211> LENGTH: 19
<212> TYPE: PRT
<213> ORGANISM: Artificial Sequence
<220> FEATURE:
<223> OTHER INFORMATION: CD3-VH-n-CDR2

<400> SEQUENCE: 610

Arg Ile Arg Ser Arg Ala Asn Ser Tyr Ala Thr Ala Tyr Ala Ala Ser
```

-continued

```
1               5               10              15

Val Lys Asp

<210> SEQ ID NO 611
<211> LENGTH: 11
<212> TYPE: PRT
<213> ORGANISM: Artificial Sequence
<220> FEATURE:
<223> OTHER INFORMATION: CD3-VH-n-CDR3

<400> SEQUENCE: 611

Arg Gly Asp Tyr Arg Tyr Ala Trp Phe Leu Tyr
1               5               10

<210> SEQ ID NO 612
<211> LENGTH: 5
<212> TYPE: PRT
<213> ORGANISM: Artificial Sequence
<220> FEATURE:
<223> OTHER INFORMATION: CD3-VH-n-CDR1

<400> SEQUENCE: 612

Ser Tyr Tyr Ile His
1               5

<210> SEQ ID NO 613
<211> LENGTH: 17
<212> TYPE: PRT
<213> ORGANISM: Artificial Sequence
<220> FEATURE:
<223> OTHER INFORMATION: CD3-VH-n-CDR2

<400> SEQUENCE: 613

Trp Ile Tyr Phe Gly Asn Val Asn Thr Lys Tyr Asn Glu Lys Phe Lys
1               5               10              15

Gly

<210> SEQ ID NO 614
<211> LENGTH: 8
<212> TYPE: PRT
<213> ORGANISM: Artificial Sequence
<220> FEATURE:
<223> OTHER INFORMATION: CD3-VH-n-CDR3

<400> SEQUENCE: 614

Asn His Asp Tyr Tyr Phe Asp Tyr
1               5

<210> SEQ ID NO 615
<211> LENGTH: 5
<212> TYPE: PRT
<213> ORGANISM: Artificial Sequence
<220> FEATURE:
<223> OTHER INFORMATION: CD3-VH-n-CDR1

<400> SEQUENCE: 615

Ser Tyr Tyr Ile His
1               5

<210> SEQ ID NO 616
<211> LENGTH: 17
<212> TYPE: PRT
<213> ORGANISM: Artificial Sequence
<220> FEATURE:
<223> OTHER INFORMATION: CD3-VH-n-CDR2
```

<400> SEQUENCE: 616

Trp Ile Asn Pro Gly Asp Gly Asn Val Lys Tyr Asn Glu Lys Phe Lys
1               5                   10                  15

Asp

<210> SEQ ID NO 617
<211> LENGTH: 11
<212> TYPE: PRT
<213> ORGANISM: Artificial Sequence
<220> FEATURE:
<223> OTHER INFORMATION: CD3-VH-n-CDR3

<400> SEQUENCE: 617

Glu Asp Ser Ser Gly Tyr Val Ala Leu Asp Tyr
1               5                   10

<210> SEQ ID NO 618
<211> LENGTH: 5
<212> TYPE: PRT
<213> ORGANISM: Artificial Sequence
<220> FEATURE:
<223> OTHER INFORMATION: CD3-VH-n-CDR1

<400> SEQUENCE: 618

Asn Tyr Gly Met Asn
1               5

<210> SEQ ID NO 619
<211> LENGTH: 17
<212> TYPE: PRT
<213> ORGANISM: Artificial Sequence
<220> FEATURE:
<223> OTHER INFORMATION: CD3-VH-n-CDR2

<400> SEQUENCE: 619

Trp Ile Phe Pro Gly Ser Asp Asn Thr Lys Tyr Asn Glu Lys Phe Lys
1               5                   10                  15

Gly

<210> SEQ ID NO 620
<211> LENGTH: 28
<212> TYPE: PRT
<213> ORGANISM: Artificial Sequence
<220> FEATURE:
<223> OTHER INFORMATION: CD3-VH-n-CDR3

<400> SEQUENCE: 620

Gln Met Asn Ser Leu Arg Ala Glu Asp Thr Ala Val Tyr Tyr Cys Ala
1               5                   10                  15

Arg Glu Asp Ser Ser Gly Tyr Val Ala Leu Asp Tyr
            20                  25

<210> SEQ ID NO 621
<211> LENGTH: 5
<212> TYPE: PRT
<213> ORGANISM: Artificial Sequence
<220> FEATURE:
<223> OTHER INFORMATION: CD3-VH-n-CDR1

<400> SEQUENCE: 621

Asn Tyr Tyr Ile His
1               5

<210> SEQ ID NO 622

```
<211> LENGTH: 17
<212> TYPE: PRT
<213> ORGANISM: Artificial Sequence
<220> FEATURE:
<223> OTHER INFORMATION: CD3-VH-n-CDR2

<400> SEQUENCE: 622

Trp Ile Tyr Pro Gly Asn Val Asn Thr Lys Tyr Asn Glu Lys Phe Lys
1               5                   10                  15

Gly

<210> SEQ ID NO 623
<211> LENGTH: 9
<212> TYPE: PRT
<213> ORGANISM: Artificial Sequence
<220> FEATURE:
<223> OTHER INFORMATION: CD3-VH-n-CDR3

<400> SEQUENCE: 623

Asp Thr Met Val Arg Gly Ile Asp Tyr
1               5

<210> SEQ ID NO 624
<211> LENGTH: 5
<212> TYPE: PRT
<213> ORGANISM: Artificial Sequence
<220> FEATURE:
<223> OTHER INFORMATION: CD3-VH-n-CDR1

<400> SEQUENCE: 624

Ser Tyr Trp Met His
1               5

<210> SEQ ID NO 625
<211> LENGTH: 17
<212> TYPE: PRT
<213> ORGANISM: Artificial Sequence
<220> FEATURE:
<223> OTHER INFORMATION: CD3-VH-n-CDR2

<400> SEQUENCE: 625

Trp Ile Asn Thr Asn Thr Gly Lys Pro Thr Tyr Ala Glu Asp Phe Lys
1               5                   10                  15

Gly

<210> SEQ ID NO 626
<211> LENGTH: 8
<212> TYPE: PRT
<213> ORGANISM: Artificial Sequence
<220> FEATURE:
<223> OTHER INFORMATION: CD3-VH-n-CDR3

<400> SEQUENCE: 626

Asp Gly Gly Tyr Tyr Phe Asp Tyr
1               5

<210> SEQ ID NO 627
<211> LENGTH: 5
<212> TYPE: PRT
<213> ORGANISM: Artificial Sequence
<220> FEATURE:
<223> OTHER INFORMATION: CD3-VH-n-CDR1

<400> SEQUENCE: 627

Asn Tyr Tyr Met His
1               5
```

<210> SEQ ID NO 628
<211> LENGTH: 17
<212> TYPE: PRT
<213> ORGANISM: Artificial Sequence
<220> FEATURE:
<223> OTHER INFORMATION: CD3-VH-n-CDR2

<400> SEQUENCE: 628

Trp Ile Tyr Pro Gly Ser Asp Asn Thr Lys Phe Asn Asp Lys Phe Lys
1               5                   10                  15

Gly

<210> SEQ ID NO 629
<211> LENGTH: 8
<212> TYPE: PRT
<213> ORGANISM: Artificial Sequence
<220> FEATURE:
<223> OTHER INFORMATION: CD3-VH-n-CDR3

<400> SEQUENCE: 629

Asp Gly Ala Tyr Tyr Phe Asp Tyr
1               5

<210> SEQ ID NO 630
<211> LENGTH: 5
<212> TYPE: PRT
<213> ORGANISM: Artificial Sequence
<220> FEATURE:
<223> OTHER INFORMATION: CD3-VH-n-CDR1

<400> SEQUENCE: 630

Asn Tyr Tyr Thr His
1               5

<210> SEQ ID NO 631
<211> LENGTH: 17
<212> TYPE: PRT
<213> ORGANISM: Artificial Sequence
<220> FEATURE:
<223> OTHER INFORMATION: CD3-VH-n-CDR2

<400> SEQUENCE: 631

Asn Phe Tyr Pro Gly Asp Leu Thr Val Asn Tyr Asp Glu Lys Phe Lys
1               5                   10                  15

Asn

<210> SEQ ID NO 632
<211> LENGTH: 8
<212> TYPE: PRT
<213> ORGANISM: Artificial Sequence
<220> FEATURE:
<223> OTHER INFORMATION: CD3-VH-n-CDR3

<400> SEQUENCE: 632

Asn Gly Asn Tyr Ala Met Asp Tyr
1               5

<210> SEQ ID NO 633
<211> LENGTH: 5
<212> TYPE: PRT
<213> ORGANISM: Artificial Sequence
<220> FEATURE:
<223> OTHER INFORMATION: CD3-VH-n-CDR1

<400> SEQUENCE: 633

-continued

```
Asn Tyr Tyr Thr His
1               5

<210> SEQ ID NO 634
<211> LENGTH: 17
<212> TYPE: PRT
<213> ORGANISM: Artificial Sequence
<220> FEATURE:
<223> OTHER INFORMATION: CD3-VH-n-CDR2

<400> SEQUENCE: 634

Trp Ile Ser Pro Gly Ser Gly Ser Ile Lys Tyr Asn Glu Lys Phe Lys
1               5                   10                  15

Gly

<210> SEQ ID NO 635
<211> LENGTH: 8
<212> TYPE: PRT
<213> ORGANISM: Artificial Sequence
<220> FEATURE:
<223> OTHER INFORMATION: CD3-VH-n-CDR3

<400> SEQUENCE: 635

Asn His Asp Tyr Tyr Phe Asp Tyr
1               5

<210> SEQ ID NO 636
<211> LENGTH: 5
<212> TYPE: PRT
<213> ORGANISM: Artificial Sequence
<220> FEATURE:
<223> OTHER INFORMATION: CD3-VH-n-CDR1

<400> SEQUENCE: 636

Asn Tyr Tyr Thr His
1               5

<210> SEQ ID NO 637
<211> LENGTH: 17
<212> TYPE: PRT
<213> ORGANISM: Artificial Sequence
<220> FEATURE:
<223> OTHER INFORMATION: CD3-VH-n-CDR2

<400> SEQUENCE: 637

Trp Ile Tyr Pro Gly Asn Gly Asn Ile Lys Tyr Asn Glu Lys Phe Met
1               5                   10                  15

Gly

<210> SEQ ID NO 638
<211> LENGTH: 11
<212> TYPE: PRT
<213> ORGANISM: Artificial Sequence
<220> FEATURE:
<223> OTHER INFORMATION: CD3-VH-n-CDR3

<400> SEQUENCE: 638

Arg Gly Asp Tyr Arg Tyr Ala Trp Phe Thr Tyr
1               5                   10

<210> SEQ ID NO 639
<211> LENGTH: 5
<212> TYPE: PRT
<213> ORGANISM: Artificial Sequence
<220> FEATURE:
```

```
<223> OTHER INFORMATION: CD3-VH-n-CDR1

<400> SEQUENCE: 639

Ser Tyr Trp Met His
1               5

<210> SEQ ID NO 640
<211> LENGTH: 17
<212> TYPE: PRT
<213> ORGANISM: Artificial Sequence
<220> FEATURE:
<223> OTHER INFORMATION: CD3-VH-n-CDR2

<400> SEQUENCE: 640

Trp Ile Tyr Pro Gly Asn Gly Asn Ile Lys Tyr Asn Glu Lys Phe Met
1               5                   10                  15

Gly

<210> SEQ ID NO 641
<211> LENGTH: 10
<212> TYPE: PRT
<213> ORGANISM: Artificial Sequence
<220> FEATURE:
<223> OTHER INFORMATION: CD3-VH-n-CDR3

<400> SEQUENCE: 641

Asp Ser Ile Thr Asn Tyr Tyr Phe Asp Tyr
1               5                   10

<210> SEQ ID NO 642
<211> LENGTH: 5
<212> TYPE: PRT
<213> ORGANISM: Artificial Sequence
<220> FEATURE:
<223> OTHER INFORMATION: CD3-VH-n-CDR1

<400> SEQUENCE: 642

Ser Tyr Tyr Ile His
1               5

<210> SEQ ID NO 643
<211> LENGTH: 17
<212> TYPE: PRT
<213> ORGANISM: Artificial Sequence
<220> FEATURE:
<223> OTHER INFORMATION: CD3-VH-n-CDR2

<400> SEQUENCE: 643

Trp Leu Tyr Pro Gly Asn Gly Asp Thr Arg Tyr Asn Glu Lys Phe Lys
1               5                   10                  15

Asp

<210> SEQ ID NO 644
<211> LENGTH: 10
<212> TYPE: PRT
<213> ORGANISM: Artificial Sequence
<220> FEATURE:
<223> OTHER INFORMATION: CD3-VH-n-CDR3

<400> SEQUENCE: 644

Asp Ala Tyr Ser Arg Tyr Phe Phe Asp Tyr
1               5                   10

<210> SEQ ID NO 645
<211> LENGTH: 5
```

-continued

```
<212> TYPE: PRT
<213> ORGANISM: Artificial Sequence
<220> FEATURE:
<223> OTHER INFORMATION: CD3-VH-n-CDR1

<400> SEQUENCE: 645

Ser Tyr Trp Met His
1               5

<210> SEQ ID NO 646
<211> LENGTH: 17
<212> TYPE: PRT
<213> ORGANISM: Artificial Sequence
<220> FEATURE:
<223> OTHER INFORMATION: CD3-VH-n-CDR2

<400> SEQUENCE: 646

Asn Ser Tyr Pro Gly Asp Leu Asn Val Asn Tyr Asp Glu Lys Phe Lys
1               5                   10                  15

Asn

<210> SEQ ID NO 647
<211> LENGTH: 10
<212> TYPE: PRT
<213> ORGANISM: Artificial Sequence
<220> FEATURE:
<223> OTHER INFORMATION: CD3-VH-n-CDR3

<400> SEQUENCE: 647

Asp Gly Tyr Ser Leu Tyr Phe Phe Asp Phe
1               5                   10

<210> SEQ ID NO 648
<211> LENGTH: 5
<212> TYPE: PRT
<213> ORGANISM: Artificial Sequence
<220> FEATURE:
<223> OTHER INFORMATION: CD3-VH-n-CDR1

<400> SEQUENCE: 648

Ser Cys Ala Ile Ser
1               5

<210> SEQ ID NO 649
<211> LENGTH: 17
<212> TYPE: PRT
<213> ORGANISM: Artificial Sequence
<220> FEATURE:
<223> OTHER INFORMATION: CD3-VH-n-CDR2

<400> SEQUENCE: 649

Trp Leu Tyr Pro Gly Asp Val Ser Thr Arg Tyr Asn Glu Lys Phe Arg
1               5                   10                  15

Asp

<210> SEQ ID NO 650
<211> LENGTH: 10
<212> TYPE: PRT
<213> ORGANISM: Artificial Sequence
<220> FEATURE:
<223> OTHER INFORMATION: CD3-VH-n-CDR3

<400> SEQUENCE: 650

Asp Ser Tyr Gly Ser Tyr Tyr Phe Asp Tyr
1               5                   10
```

```
<210> SEQ ID NO 651
<211> LENGTH: 5
<212> TYPE: PRT
<213> ORGANISM: Artificial Sequence
<220> FEATURE:
<223> OTHER INFORMATION: CD3-VH-n-CDR1

<400> SEQUENCE: 651

Asp Tyr Tyr Ile His
1               5

<210> SEQ ID NO 652
<211> LENGTH: 17
<212> TYPE: PRT
<213> ORGANISM: Artificial Sequence
<220> FEATURE:
<223> OTHER INFORMATION: CD3-VH-n-CDR2

<400> SEQUENCE: 652

Asn Ile Tyr Pro Gly Gly Glu Ile Ile Asn Tyr Ala Glu Lys Phe Lys
1               5                   10                  15

Thr

<210> SEQ ID NO 653
<211> LENGTH: 10
<212> TYPE: PRT
<213> ORGANISM: Artificial Sequence
<220> FEATURE:
<223> OTHER INFORMATION: CD3-VH-n-CDR3

<400> SEQUENCE: 653

Asp Ser Tyr Gly Ser Tyr Tyr Phe Asp Tyr
1               5                   10

<210> SEQ ID NO 654
<211> LENGTH: 16
<212> TYPE: PRT
<213> ORGANISM: Artificial Sequence
<220> FEATURE:
<223> OTHER INFORMATION: CD3-VH-n-CDR2

<400> SEQUENCE: 654

Phe Met Ser Val Thr Gly Ser Ala Tyr Tyr Ala Asn Trp Ala Lys Ser
1               5                   10                  15

<210> SEQ ID NO 655
<211> LENGTH: 10
<212> TYPE: PRT
<213> ORGANISM: Artificial Sequence
<220> FEATURE:
<223> OTHER INFORMATION: CD3-VH-n-CDR3

<400> SEQUENCE: 655

Asp Ser Tyr Gly Asn Tyr Phe Phe Asp Tyr
1               5                   10

<210> SEQ ID NO 656
<211> LENGTH: 17
<212> TYPE: PRT
<213> ORGANISM: Artificial Sequence
<220> FEATURE:
<223> OTHER INFORMATION: CD3-VH-n-CDR2
<220> FEATURE:
<221> NAME/KEY: MISC_FEATURE
<222> LOCATION: (9)..(9)
<223> OTHER INFORMATION: Xaa is any amino acid
<220> FEATURE:
```

-continued

```
<221> NAME/KEY: MISC_FEATURE
<222> LOCATION: (12)..(15)
<223> OTHER INFORMATION: Xaa is any amino acid
<220> FEATURE:
<221> NAME/KEY: MISC_FEATURE
<222> LOCATION: (17)..(17)
<223> OTHER INFORMATION: Xaa is any amino acid

<400> SEQUENCE: 656

Leu Ile Asn Pro Tyr Lys Gly Val Xaa Thr Tyr Xaa Xaa Xaa Xaa Lys
1               5                   10                  15

Xaa

<210> SEQ ID NO 657
<211> LENGTH: 10
<212> TYPE: PRT
<213> ORGANISM: Artificial Sequence
<220> FEATURE:
<223> OTHER INFORMATION: CD3-VH-n-CDR3

<400> SEQUENCE: 657

Asp Ala Tyr Ser Arg Tyr Phe Phe Asp Tyr
1               5                   10

<210> SEQ ID NO 658
<211> LENGTH: 17
<212> TYPE: PRT
<213> ORGANISM: Artificial Sequence
<220> FEATURE:
<223> OTHER INFORMATION: CD3-VH-n-CDR2

<400> SEQUENCE: 658

Trp Ile Tyr Pro Gly Asp Val Ser Thr Arg Phe Asn Glu Lys Phe Lys
1               5                   10                  15

Gly

<210> SEQ ID NO 659
<211> LENGTH: 10
<212> TYPE: PRT
<213> ORGANISM: Artificial Sequence
<220> FEATURE:
<223> OTHER INFORMATION: CD3-VH-n-CDR3

<400> SEQUENCE: 659

Asp Ser Ser Ala Ser Tyr Tyr Phe Asp Phe
1               5                   10

<210> SEQ ID NO 660
<211> LENGTH: 10
<212> TYPE: PRT
<213> ORGANISM: Artificial Sequence
<220> FEATURE:
<223> OTHER INFORMATION: CD3-VH-n-CDR3

<400> SEQUENCE: 660

Asp Thr Thr Gly Asn Tyr Phe Phe Asp Tyr
1               5                   10

<210> SEQ ID NO 661
<211> LENGTH: 9
<212> TYPE: PRT
<213> ORGANISM: Artificial Sequence
<220> FEATURE:
<223> OTHER INFORMATION: CD3-VH-n-CDR3

<400> SEQUENCE: 661
```

```
Val Gly Ile Gly Ser Gly Leu Asn Ile
1               5

<210> SEQ ID NO 662
<211> LENGTH: 10
<212> TYPE: PRT
<213> ORGANISM: Artificial Sequence
<220> FEATURE:
<223> OTHER INFORMATION: CD3-VH-n-CDR3
<220> FEATURE:
<221> NAME/KEY: MISC_FEATURE
<222> LOCATION: (1)..(2)
<223> OTHER INFORMATION: Xaa is any amino acid
<220> FEATURE:
<221> NAME/KEY: MISC_FEATURE
<222> LOCATION: (5)..(7)
<223> OTHER INFORMATION: Xaa is any amino acid

<400> SEQUENCE: 662

Xaa Xaa Tyr Ser Xaa Xaa Xaa Phe Asp Tyr
1               5                   10

<210> SEQ ID NO 663
<211> LENGTH: 10
<212> TYPE: PRT
<213> ORGANISM: Artificial Sequence
<220> FEATURE:
<223> OTHER INFORMATION: CD3-VH-n-CDR3

<400> SEQUENCE: 663

Asp Ser Tyr Gly Asn Tyr Phe Phe Asp Tyr
1               5                   10

<210> SEQ ID NO 664
<211> LENGTH: 17
<212> TYPE: PRT
<213> ORGANISM: Artificial Sequence
<220> FEATURE:
<223> OTHER INFORMATION: CD3-VL-n-CDR1

<400> SEQUENCE: 664

Lys Ser Ser Gln Ser Leu Leu Asn Ser Arg Thr Arg Lys Asn Tyr Leu
1               5                   10                  15

Ala

<210> SEQ ID NO 665
<211> LENGTH: 7
<212> TYPE: PRT
<213> ORGANISM: Artificial Sequence
<220> FEATURE:
<223> OTHER INFORMATION: CD3-VL-n-CDR2

<400> SEQUENCE: 665

Trp Ala Ser Thr Arg Glu Ser
1               5

<210> SEQ ID NO 666
<211> LENGTH: 8
<212> TYPE: PRT
<213> ORGANISM: Artificial Sequence
<220> FEATURE:
<223> OTHER INFORMATION: CD3-VL-n-CDR3

<400> SEQUENCE: 666

Thr Gln Ser Phe Ile Leu Arg Thr
1               5
```

<210> SEQ ID NO 667
<211> LENGTH: 17
<212> TYPE: PRT
<213> ORGANISM: Artificial Sequence
<220> FEATURE:
<223> OTHER INFORMATION: CD3-VL-n-CDR1

<400> SEQUENCE: 667

Lys Ser Ser Gln Ser Leu Leu Asn Ser Arg Thr Arg Lys Asn Tyr Leu
1               5                   10                  15

Ala

<210> SEQ ID NO 668
<211> LENGTH: 7
<212> TYPE: PRT
<213> ORGANISM: Artificial Sequence
<220> FEATURE:
<223> OTHER INFORMATION: CD3-VL-n-CDR2

<400> SEQUENCE: 668

Trp Thr Ser Thr Arg Lys Ser
1               5

<210> SEQ ID NO 669
<211> LENGTH: 8
<212> TYPE: PRT
<213> ORGANISM: Artificial Sequence
<220> FEATURE:
<223> OTHER INFORMATION: CD3-VL-n-CDR3

<400> SEQUENCE: 669

Lys Gln Ser Phe Ile Leu Arg Thr
1               5

<210> SEQ ID NO 670
<211> LENGTH: 11
<212> TYPE: PRT
<213> ORGANISM: Artificial Sequence
<220> FEATURE:
<223> OTHER INFORMATION: CD3-VL-n-CDR1

<400> SEQUENCE: 670

Arg Ala Ser Gln Asp Ile Arg Asn Tyr Leu Asn
1               5                   10

<210> SEQ ID NO 671
<211> LENGTH: 7
<212> TYPE: PRT
<213> ORGANISM: Artificial Sequence
<220> FEATURE:
<223> OTHER INFORMATION: CD3-VL-n-CDR2

<400> SEQUENCE: 671

Tyr Thr Ser Arg Leu Glu Ser
1               5

<210> SEQ ID NO 672
<211> LENGTH: 8
<212> TYPE: PRT
<213> ORGANISM: Artificial Sequence
<220> FEATURE:
<223> OTHER INFORMATION: CD3-VL-n-CDR3

<400> SEQUENCE: 672

Lys Gln Ser Phe Ala Leu Arg Thr
1               5

```
<210> SEQ ID NO 673
<211> LENGTH: 14
<212> TYPE: PRT
<213> ORGANISM: Artificial Sequence
<220> FEATURE:
<223> OTHER INFORMATION: CD3-VL-n-CDR1

<400> SEQUENCE: 673

Arg Ser Ser Thr Gly Ala Val Thr Thr Ser Asn Tyr Ala Asn
1               5                   10

<210> SEQ ID NO 674
<211> LENGTH: 7
<212> TYPE: PRT
<213> ORGANISM: Artificial Sequence
<220> FEATURE:
<223> OTHER INFORMATION: CD3-VL-n-CDR2

<400> SEQUENCE: 674

Gly Thr Asn Lys Arg Ala Pro
1               5

<210> SEQ ID NO 675
<211> LENGTH: 8
<212> TYPE: PRT
<213> ORGANISM: Artificial Sequence
<220> FEATURE:
<223> OTHER INFORMATION: CD3-VL-n-CDR3

<400> SEQUENCE: 675

Lys Ala Ser Phe Ile Leu Arg Thr
1               5

<210> SEQ ID NO 676
<211> LENGTH: 14
<212> TYPE: PRT
<213> ORGANISM: Artificial Sequence
<220> FEATURE:
<223> OTHER INFORMATION: CD3-VL-n-CDR1

<400> SEQUENCE: 676

Arg Ser Ser Thr Gly Ala Val Thr Thr Ser Asn Tyr Ala Asn
1               5                   10

<210> SEQ ID NO 677
<211> LENGTH: 7
<212> TYPE: PRT
<213> ORGANISM: Artificial Sequence
<220> FEATURE:
<223> OTHER INFORMATION: CD3-VL-n-CDR2

<400> SEQUENCE: 677

Gly Thr Ser Asn Arg Ala Pro
1               5

<210> SEQ ID NO 678
<211> LENGTH: 8
<212> TYPE: PRT
<213> ORGANISM: Artificial Sequence
<220> FEATURE:
<223> OTHER INFORMATION: CD3-VL-n-CDR3

<400> SEQUENCE: 678

Lys Gln Ser Ala Ile Leu Arg Thr
1               5
```

-continued

```
<210> SEQ ID NO 679
<211> LENGTH: 17
<212> TYPE: PRT
<213> ORGANISM: Artificial Sequence
<220> FEATURE:
<223> OTHER INFORMATION: CD3-VL-n-CDR1

<400> SEQUENCE: 679

Lys Ser Ser Gln Ser Leu Leu Asn Ser Arg Thr Arg Lys Asn Tyr Leu
1               5                   10                  15

Ala

<210> SEQ ID NO 680
<211> LENGTH: 7
<212> TYPE: PRT
<213> ORGANISM: Artificial Sequence
<220> FEATURE:
<223> OTHER INFORMATION: CD3-VL-n-CDR2

<400> SEQUENCE: 680

Trp Ala Ser Thr Arg Glu Ser
1               5

<210> SEQ ID NO 681
<211> LENGTH: 8
<212> TYPE: PRT
<213> ORGANISM: Artificial Sequence
<220> FEATURE:
<223> OTHER INFORMATION: CD3-VL-n-CDR3

<400> SEQUENCE: 681

Thr Gln Ser Phe Ile Leu Arg Thr
1               5

<210> SEQ ID NO 682
<211> LENGTH: 17
<212> TYPE: PRT
<213> ORGANISM: Artificial Sequence
<220> FEATURE:
<223> OTHER INFORMATION: CD3-VL-n-CDR1

<400> SEQUENCE: 682

Lys Ser Ser Gln Ser Leu Leu Ser Gly Arg Thr Arg Lys Asn Tyr Leu
1               5                   10                  15

Ala

<210> SEQ ID NO 683
<211> LENGTH: 7
<212> TYPE: PRT
<213> ORGANISM: Artificial Sequence
<220> FEATURE:
<223> OTHER INFORMATION: CD3-VL-n-CDR2

<400> SEQUENCE: 683

Trp Ala Ser Thr Arg Glu Ser
1               5

<210> SEQ ID NO 684
<211> LENGTH: 9
<212> TYPE: PRT
<213> ORGANISM: Artificial Sequence
<220> FEATURE:
<223> OTHER INFORMATION: CD3-VL-n-CDR3

<400> SEQUENCE: 684

Gln Gln Gly Asn Thr Leu Pro Trp Thr
```

```
1                 5

<210> SEQ ID NO 685
<211> LENGTH: 17
<212> TYPE: PRT
<213> ORGANISM: Artificial Sequence
<220> FEATURE:
<223> OTHER INFORMATION: CD3-VL-n-CDR1

<400> SEQUENCE: 685

Lys Ser Ser Gln Ser Leu Leu Ser Gly Arg Thr Arg Lys Asn Tyr Leu
1                 5                 10                 15

Ala

<210> SEQ ID NO 686
<211> LENGTH: 7
<212> TYPE: PRT
<213> ORGANISM: Artificial Sequence
<220> FEATURE:
<223> OTHER INFORMATION: CD3-VL-n-CDR2

<400> SEQUENCE: 686

Trp Ala Ser Thr Arg Glu Ser
1                 5

<210> SEQ ID NO 687
<211> LENGTH: 9
<212> TYPE: PRT
<213> ORGANISM: Artificial Sequence
<220> FEATURE:
<223> OTHER INFORMATION: CD3-VL-n-CDR3

<400> SEQUENCE: 687

Ala Leu Trp Tyr Ser Asn Leu Trp Val
1                 5

<210> SEQ ID NO 688
<211> LENGTH: 17
<212> TYPE: PRT
<213> ORGANISM: Artificial Sequence
<220> FEATURE:
<223> OTHER INFORMATION: CD3-VL-n-CDR1

<400> SEQUENCE: 688

Lys Ser Ser Gln Ser Val Leu Tyr Ser Ser Asn Asn Lys Asn Tyr Leu
1                 5                 10                 15

Val

<210> SEQ ID NO 689
<211> LENGTH: 7
<212> TYPE: PRT
<213> ORGANISM: Artificial Sequence
<220> FEATURE:
<223> OTHER INFORMATION: CD3-VL-n-CDR2

<400> SEQUENCE: 689

Arg Ala Ser Thr Arg Glu Ser
1                 5

<210> SEQ ID NO 690
<211> LENGTH: 9
<212> TYPE: PRT
<213> ORGANISM: Artificial Sequence
<220> FEATURE:
<223> OTHER INFORMATION: CD3-VL-n-CDR3
```

<400> SEQUENCE: 690

Ala Leu Trp Tyr Ser Thr His Phe Val
1               5

<210> SEQ ID NO 691
<211> LENGTH: 17
<212> TYPE: PRT
<213> ORGANISM: Artificial Sequence
<220> FEATURE:
<223> OTHER INFORMATION: CD3-VL-n-CDR1

<400> SEQUENCE: 691

Lys Ser Ser Gln Ser Leu Leu Asn Ser Arg Thr Arg Lys Asn Tyr Leu
1               5                   10                  15

Ala

<210> SEQ ID NO 692
<211> LENGTH: 7
<212> TYPE: PRT
<213> ORGANISM: Artificial Sequence
<220> FEATURE:
<223> OTHER INFORMATION: CD3-VL-n-CDR2

<400> SEQUENCE: 692

Trp Ala Ser Thr Arg Glu Ser
1               5

<210> SEQ ID NO 693
<211> LENGTH: 8
<212> TYPE: PRT
<213> ORGANISM: Artificial Sequence
<220> FEATURE:
<223> OTHER INFORMATION: CD3-VL-n-CDR3

<400> SEQUENCE: 693

Lys Gln Ser Tyr Ile Leu Arg Thr
1               5

<210> SEQ ID NO 694
<211> LENGTH: 17
<212> TYPE: PRT
<213> ORGANISM: Artificial Sequence
<220> FEATURE:
<223> OTHER INFORMATION: CD3-VL-n-CDR1

<400> SEQUENCE: 694

Lys Ser Ser Gln Ser Leu Leu Asn Ser Arg Thr Arg Lys Asn Tyr Leu
1               5                   10                  15

Ala

<210> SEQ ID NO 695
<211> LENGTH: 7
<212> TYPE: PRT
<213> ORGANISM: Artificial Sequence
<220> FEATURE:
<223> OTHER INFORMATION: CD3-VL-n-CDR2

<400> SEQUENCE: 695

Trp Ala Ser Thr Arg Glu Ser
1               5

<210> SEQ ID NO 696
<211> LENGTH: 8
<212> TYPE: PRT
<213> ORGANISM: Artificial Sequence -continued

```
<220> FEATURE:
<223> OTHER INFORMATION: CD3-VL-n-CDR3

<400> SEQUENCE: 696

Lys Gln Ser Tyr Tyr Leu Leu Thr
1               5

<210> SEQ ID NO 697
<211> LENGTH: 17
<212> TYPE: PRT
<213> ORGANISM: Artificial Sequence
<220> FEATURE:
<223> OTHER INFORMATION: CD3-VL-n-CDR1

<400> SEQUENCE: 697

Lys Ser Ser Gln Ser Leu Leu Asn Ser Arg Thr Arg Lys Asn Tyr Leu
1               5                   10                  15

Ala

<210> SEQ ID NO 698
<211> LENGTH: 7
<212> TYPE: PRT
<213> ORGANISM: Artificial Sequence
<220> FEATURE:
<223> OTHER INFORMATION: CD3-VL-n-CDR2

<400> SEQUENCE: 698

Trp Ala Ser Thr Arg Glu Ser
1               5

<210> SEQ ID NO 699
<211> LENGTH: 8
<212> TYPE: PRT
<213> ORGANISM: Artificial Sequence
<220> FEATURE:
<223> OTHER INFORMATION: CD3-VL-n-CDR3

<400> SEQUENCE: 699

Lys Gln Ser Tyr Tyr Leu Leu Thr
1               5

<210> SEQ ID NO 700
<211> LENGTH: 17
<212> TYPE: PRT
<213> ORGANISM: Artificial Sequence
<220> FEATURE:
<223> OTHER INFORMATION: CD3-VL-n-CDR1

<400> SEQUENCE: 700

Lys Ser Ser Gln Ser Leu Leu Asn Ser Arg Thr Arg Lys Asn Tyr Leu
1               5                   10                  15

Ala

<210> SEQ ID NO 701
<211> LENGTH: 7
<212> TYPE: PRT
<213> ORGANISM: Artificial Sequence
<220> FEATURE:
<223> OTHER INFORMATION: CD3-VL-n-CDR2

<400> SEQUENCE: 701

Trp Ala Ser Thr Arg Glu Ser
1               5

<210> SEQ ID NO 702
```

-continued

```
<211> LENGTH: 9
<212> TYPE: PRT
<213> ORGANISM: Artificial Sequence
<220> FEATURE:
<223> OTHER INFORMATION: CD3-VL-n-CDR3

<400> SEQUENCE: 702

Gln Gln Tyr Tyr Ser Val Pro Trp Thr
1               5

<210> SEQ ID NO 703
<211> LENGTH: 14
<212> TYPE: PRT
<213> ORGANISM: Artificial Sequence
<220> FEATURE:
<223> OTHER INFORMATION: CD3-VL-n-CDR1

<400> SEQUENCE: 703

Arg Ser Ser Thr Gly Ala Val Thr Thr Ser Asn Tyr Ala Asn
1               5                   10

<210> SEQ ID NO 704
<211> LENGTH: 7
<212> TYPE: PRT
<213> ORGANISM: Artificial Sequence
<220> FEATURE:
<223> OTHER INFORMATION: CD3-VL-n-CDR2

<400> SEQUENCE: 704

Gly Thr Ser Asn Arg Ala Pro
1               5

<210> SEQ ID NO 705
<211> LENGTH: 8
<212> TYPE: PRT
<213> ORGANISM: Artificial Sequence
<220> FEATURE:
<223> OTHER INFORMATION: CD3-VL-n-CDR3

<400> SEQUENCE: 705

Lys Gln Ser Phe Thr Leu Arg Thr
1               5

<210> SEQ ID NO 706
<211> LENGTH: 17
<212> TYPE: PRT
<213> ORGANISM: Artificial Sequence
<220> FEATURE:
<223> OTHER INFORMATION: CD3-VL-n-CDR1

<400> SEQUENCE: 706

Lys Ser Ser Gln Ser Leu Leu Asn Ile Arg Thr Arg Lys Asn Cys Leu
1               5                   10                  15

Ala

<210> SEQ ID NO 707
<211> LENGTH: 7
<212> TYPE: PRT
<213> ORGANISM: Artificial Sequence
<220> FEATURE:
<223> OTHER INFORMATION: CD3-VL-n-CDR2

<400> SEQUENCE: 707

Trp Ala Ser Thr Arg Tyr Ser
1               5
```

<210> SEQ ID NO 708
<211> LENGTH: 8
<212> TYPE: PRT
<213> ORGANISM: Artificial Sequence
<220> FEATURE:
<223> OTHER INFORMATION: CD3-VL-n-CDR3

<400> SEQUENCE: 708

Lys Gln Ser Tyr Thr Leu Arg Thr
1               5

<210> SEQ ID NO 709
<211> LENGTH: 17
<212> TYPE: PRT
<213> ORGANISM: Artificial Sequence
<220> FEATURE:
<223> OTHER INFORMATION: CD3-VL-n-CDR1

<400> SEQUENCE: 709

Lys Ser Ser Gln Ser Leu Leu Asn Ser Arg Thr Arg Lys Asn Tyr Leu
1               5                   10                  15

Ala

<210> SEQ ID NO 710
<211> LENGTH: 7
<212> TYPE: PRT
<213> ORGANISM: Artificial Sequence
<220> FEATURE:
<223> OTHER INFORMATION: CD3-VL-n-CDR2

<400> SEQUENCE: 710

Trp Ala Ser Thr Arg Glu Ser
1               5

<210> SEQ ID NO 711
<211> LENGTH: 8
<212> TYPE: PRT
<213> ORGANISM: Artificial Sequence
<220> FEATURE:
<223> OTHER INFORMATION: CD3-VL-n-CDR3

<400> SEQUENCE: 711

Lys Gln Ser Tyr Thr Leu Arg Thr
1               5

<210> SEQ ID NO 712
<211> LENGTH: 17
<212> TYPE: PRT
<213> ORGANISM: Artificial Sequence
<220> FEATURE:
<223> OTHER INFORMATION: CD3-VL-n-CDR1

<400> SEQUENCE: 712

Lys Ser Ser Gln Ser Leu Leu Asn Ser Arg Thr Arg Lys Asn Tyr Leu
1               5                   10                  15

Ala

<210> SEQ ID NO 713
<211> LENGTH: 7
<212> TYPE: PRT
<213> ORGANISM: Artificial Sequence
<220> FEATURE:
<223> OTHER INFORMATION: CD3-VL-n-CDR2

<400> SEQUENCE: 713

Trp Ala Ser Thr Arg Glu Ser

-continued

```
1               5

<210> SEQ ID NO 714
<211> LENGTH: 8
<212> TYPE: PRT
<213> ORGANISM: Artificial Sequence
<220> FEATURE:
<223> OTHER INFORMATION: CD3-VL-n-CDR3

<400> SEQUENCE: 714

Lys Gln Ser Tyr Ile Leu Arg Thr
1               5

<210> SEQ ID NO 715
<211> LENGTH: 17
<212> TYPE: PRT
<213> ORGANISM: Artificial Sequence
<220> FEATURE:
<223> OTHER INFORMATION: CD3-VL-n-CDR1

<400> SEQUENCE: 715

Lys Ser Ser Gln Ser Leu Leu Asn Ser Arg Thr Arg Lys Asn Tyr Leu
1               5                   10                  15

Ala

<210> SEQ ID NO 716
<211> LENGTH: 7
<212> TYPE: PRT
<213> ORGANISM: Artificial Sequence
<220> FEATURE:
<223> OTHER INFORMATION: CD3-VL-n-CDR2

<400> SEQUENCE: 716

Trp Ala Ser Thr Arg Glu Ser
1               5

<210> SEQ ID NO 717
<211> LENGTH: 9
<212> TYPE: PRT
<213> ORGANISM: Artificial Sequence
<220> FEATURE:
<223> OTHER INFORMATION: CD3-VL-n-CDR3

<400> SEQUENCE: 717

Ala Leu Trp Tyr Ser Thr His Phe Val
1               5

<210> SEQ ID NO 718
<211> LENGTH: 17
<212> TYPE: PRT
<213> ORGANISM: Artificial Sequence
<220> FEATURE:
<223> OTHER INFORMATION: CD3-VL-n-CDR1

<400> SEQUENCE: 718

Lys Ser Ser Gln Ser Leu Leu Asn Ser Arg Thr Arg Lys Asn Tyr Leu
1               5                   10                  15

Ala

<210> SEQ ID NO 719
<211> LENGTH: 7
<212> TYPE: PRT
<213> ORGANISM: Artificial Sequence
<220> FEATURE:
<223> OTHER INFORMATION: CD3-VL-n-CDR2
```

```
<400> SEQUENCE: 719

Trp Ala Ser Thr Arg Glu Ser
1               5

<210> SEQ ID NO 720
<211> LENGTH: 8
<212> TYPE: PRT
<213> ORGANISM: Artificial Sequence
<220> FEATURE:
<223> OTHER INFORMATION: CD3-VL-n-CDR3

<400> SEQUENCE: 720

Thr Gln Ser Tyr Thr Leu Arg Thr
1               5

<210> SEQ ID NO 721
<211> LENGTH: 17
<212> TYPE: PRT
<213> ORGANISM: Artificial Sequence
<220> FEATURE:
<223> OTHER INFORMATION: CD3-VL-n-CDR1

<400> SEQUENCE: 721

Lys Ser Ser Gln Ser Leu Leu Asn Ser Arg Thr Arg Lys Asn Tyr Leu
1               5                   10                  15

Ala

<210> SEQ ID NO 722
<211> LENGTH: 7
<212> TYPE: PRT
<213> ORGANISM: Artificial Sequence
<220> FEATURE:
<223> OTHER INFORMATION: CD3-VL-n-CDR2

<400> SEQUENCE: 722

Trp Ala Ser Thr Arg Glu Ser
1               5

<210> SEQ ID NO 723
<211> LENGTH: 8
<212> TYPE: PRT
<213> ORGANISM: Artificial Sequence
<220> FEATURE:
<223> OTHER INFORMATION: CD3-VL-n-CDR3

<400> SEQUENCE: 723

Cys Gln Ser Phe Ile Leu Arg Thr
1               5

<210> SEQ ID NO 724
<211> LENGTH: 17
<212> TYPE: PRT
<213> ORGANISM: Artificial Sequence
<220> FEATURE:
<223> OTHER INFORMATION: CD3-VL-n-CDR1

<400> SEQUENCE: 724

Lys Ser Ser Gln Ser Leu Leu Asn Ser Arg Thr Arg Lys Asn Tyr Leu
1               5                   10                  15

Ala

<210> SEQ ID NO 725
<211> LENGTH: 7
<212> TYPE: PRT
<213> ORGANISM: Artificial Sequence
```

-continued

```
<220> FEATURE:
<223> OTHER INFORMATION: CD3-VL-n-CDR2

<400> SEQUENCE: 725

Trp Ala Ser Thr Arg Glu Ser
1               5

<210> SEQ ID NO 726
<211> LENGTH: 8
<212> TYPE: PRT
<213> ORGANISM: Artificial Sequence
<220> FEATURE:
<223> OTHER INFORMATION: CD3-VL-n-CDR3

<400> SEQUENCE: 726

Lys Gln Ser Phe Ile Leu Arg Thr
1               5

<210> SEQ ID NO 727
<211> LENGTH: 17
<212> TYPE: PRT
<213> ORGANISM: Artificial Sequence
<220> FEATURE:
<223> OTHER INFORMATION: CD3-VL-n-CDR1

<400> SEQUENCE: 727

Lys Ser Ser Gln Ser Leu Leu Asn Ile Arg Thr Arg Lys Asn Tyr Leu
1               5                   10                  15

Ala

<210> SEQ ID NO 728
<211> LENGTH: 7
<212> TYPE: PRT
<213> ORGANISM: Artificial Sequence
<220> FEATURE:
<223> OTHER INFORMATION: CD3-VL-n-CDR2

<400> SEQUENCE: 728

Trp Ala Ser Thr Arg Ala Ser
1               5

<210> SEQ ID NO 729
<211> LENGTH: 8
<212> TYPE: PRT
<213> ORGANISM: Artificial Sequence
<220> FEATURE:
<223> OTHER INFORMATION: CD3-VL-n-CDR3

<400> SEQUENCE: 729

Thr Gln Ser Phe Ile Leu Arg Thr
1               5

<210> SEQ ID NO 730
<211> LENGTH: 17
<212> TYPE: PRT
<213> ORGANISM: Artificial Sequence
<220> FEATURE:
<223> OTHER INFORMATION: CD3-VL-n-CDR1

<400> SEQUENCE: 730

Lys Ser Ser Gln Ser Leu Leu Asn Ser Arg Thr Arg Lys Asn Tyr Leu
1               5                   10                  15

Ala

<210> SEQ ID NO 731
```

```
<211> LENGTH: 7
<212> TYPE: PRT
<213> ORGANISM: Artificial Sequence
<220> FEATURE:
<223> OTHER INFORMATION: CD3-VL-n-CDR2

<400> SEQUENCE: 731

Trp Ala Ser Thr Arg Glu Ser
1               5

<210> SEQ ID NO 732
<211> LENGTH: 8
<212> TYPE: PRT
<213> ORGANISM: Artificial Sequence
<220> FEATURE:
<223> OTHER INFORMATION: CD3-VL-n-CDR3

<400> SEQUENCE: 732

Lys Gln Ser Phe Ile Leu Arg Thr
1               5

<210> SEQ ID NO 733
<211> LENGTH: 13
<212> TYPE: PRT
<213> ORGANISM: Artificial Sequence
<220> FEATURE:
<223> OTHER INFORMATION: CD3-VL-n-CDR1

<400> SEQUENCE: 733

Gln Ala Ser Glu Thr Val Tyr Ser Asn Asn Tyr Leu Ala
1               5                   10

<210> SEQ ID NO 734
<211> LENGTH: 7
<212> TYPE: PRT
<213> ORGANISM: Artificial Sequence
<220> FEATURE:
<223> OTHER INFORMATION: CD3-VL-n-CDR2

<400> SEQUENCE: 734

Gly Val Ser Thr Leu Asp Ser
1               5

<210> SEQ ID NO 735
<211> LENGTH: 8
<212> TYPE: PRT
<213> ORGANISM: Artificial Sequence
<220> FEATURE:
<223> OTHER INFORMATION: CD3-VL-n-CDR3

<400> SEQUENCE: 735

Lys Gln Ser Phe Ile Leu Arg Thr
1               5

<210> SEQ ID NO 736
<211> LENGTH: 17
<212> TYPE: PRT
<213> ORGANISM: Artificial Sequence
<220> FEATURE:
<223> OTHER INFORMATION: CD3-VL-n-CDR1

<400> SEQUENCE: 736

Lys Ser Ser Gln Ser Leu Leu Asn Ser Arg Thr Arg Lys Asn Tyr Leu
1               5                   10                  15

Ala
```

```
<210> SEQ ID NO 737
<211> LENGTH: 7
<212> TYPE: PRT
<213> ORGANISM: Artificial Sequence
<220> FEATURE:
<223> OTHER INFORMATION: CD3-VL-n-CDR2

<400> SEQUENCE: 737

Trp Ala Ser Thr Arg Glu Ser
1               5

<210> SEQ ID NO 738
<211> LENGTH: 8
<212> TYPE: PRT
<213> ORGANISM: Artificial Sequence
<220> FEATURE:
<223> OTHER INFORMATION: CD3-VL-n-CDR3

<400> SEQUENCE: 738

Cys Gln Ser Phe Ile Leu Arg Thr
1               5

<210> SEQ ID NO 739
<211> LENGTH: 8
<212> TYPE: PRT
<213> ORGANISM: Artificial Sequence
<220> FEATURE:
<223> OTHER INFORMATION: CD3-VL-n-CDR3

<400> SEQUENCE: 739

Thr Gln Ser Phe Ile Leu Arg Thr
1               5

<210> SEQ ID NO 740
<211> LENGTH: 8
<212> TYPE: PRT
<213> ORGANISM: Artificial Sequence
<220> FEATURE:
<223> OTHER INFORMATION: CD3-VL-n-CDR3

<400> SEQUENCE: 740

Thr Gln Ser Phe Ile Leu Arg Thr
1               5

<210> SEQ ID NO 741
<211> LENGTH: 12
<212> TYPE: PRT
<213> ORGANISM: Artificial Sequence
<220> FEATURE:
<223> OTHER INFORMATION: CD3-VL-n-CDR3

<400> SEQUENCE: 741

Ala Gly Tyr Lys Thr Ser Ser Ser Tyr Ala Ile Ala
1               5                   10

<210> SEQ ID NO 742
<211> LENGTH: 8
<212> TYPE: PRT
<213> ORGANISM: Artificial Sequence
<220> FEATURE:
<223> OTHER INFORMATION: CD3-VL-n-CDR3
<220> FEATURE:
<221> NAME/KEY: MISC_FEATURE
<222> LOCATION: (1)..(2)
<223> OTHER INFORMATION: Xaa is any amino acid
<220> FEATURE:
<221> NAME/KEY: MISC_FEATURE
<222> LOCATION: (4)..(5)
<223> OTHER INFORMATION: Xaa is any amino acid
```

<400> SEQUENCE: 742

Xaa Xaa Ser Xaa Xaa Leu Arg Thr
1               5

<210> SEQ ID NO 743
<211> LENGTH: 9
<212> TYPE: PRT
<213> ORGANISM: Artificial Sequence
<220> FEATURE:
<223> OTHER INFORMATION: CD3-VL-n-CDR3

<400> SEQUENCE: 743

Cys Thr Gln Ser Phe Ile Leu Arg Thr
1               5

<210> SEQ ID NO 744
<211> LENGTH: 245
<212> TYPE: PRT
<213> ORGANISM: Artificial Sequence
<220> FEATURE:
<223> OTHER INFORMATION: NKp46

<400> SEQUENCE: 744

Ser Thr Gly Ser Glu Val Gln Leu Gln Gln Ser Gly Pro Glu Leu Val
1               5                   10                  15

Lys Pro Gly Ala Ser Val Lys Ile Ser Cys Lys Thr Ser Gly Tyr Thr
            20                  25                  30

Phe Thr Glu Tyr Thr Met His Trp Val Lys Gln Ser His Gly Lys Ser
        35                  40                  45

Leu Glu Trp Ile Gly Gly Ile Ser Pro Asn Ile Gly Gly Thr Ser Tyr
    50                  55                  60

Asn Gln Lys Phe Lys Gly Lys Ala Thr Leu Thr Val Asp Lys Ser Ser
65                  70                  75                  80

Ser Thr Ala Tyr Met Glu Leu Arg Ser Leu Thr Ser Glu Asp Ser Ala
                85                  90                  95

Val Tyr Tyr Cys Ala Arg Arg Gly Gly Ser Phe Asp Tyr Trp Gly Gln
                100                 105                 110

Gly Thr Thr Leu Thr Val Ser Ser Val Glu Gly Gly Ser Gly Gly Ser
            115                 120                 125

Gly Gly Ser Gly Gly Ser Gly Gly Val Asp Asp Ile Val Met Thr Gln
    130                 135                 140

Ser Pro Ala Thr Leu Ser Val Thr Pro Gly Asp Arg Val Ser Leu Ser
145                 150                 155                 160

Cys Arg Ala Ser Gln Ser Ile Ser Asp Tyr Leu His Trp Tyr Gln Gln
                165                 170                 175

Lys Ser His Glu Ser Pro Arg Leu Leu Ile Lys Tyr Ala Ser Gln Ser
                180                 185                 190

Ile Ser Gly Ile Pro Ser Arg Phe Ser Gly Ser Gly Ser Gly Ser Asp
            195                 200                 205

Phe Thr Leu Ser Ile Asn Ser Val Glu Pro Glu Asp Val Gly Val Tyr
        210                 215                 220

Tyr Cys Gln Asn Gly His Ser Phe Pro Leu Thr Phe Gly Ala Gly Thr
225                 230                 235                 240

Lys Leu Glu Leu Lys
                245

<210> SEQ ID NO 745

```
<211> LENGTH: 25
<212> TYPE: PRT
<213> ORGANISM: Artificial Sequence
<220> FEATURE:
<223> OTHER INFORMATION: FR1

<400> SEQUENCE: 745

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 746
<211> LENGTH: 18
<212> TYPE: PRT
<213> ORGANISM: Artificial Sequence
<220> FEATURE:
<223> OTHER INFORMATION: FR2

<400> SEQUENCE: 746

Met Gly Trp Leu Arg Gln Ala Pro Gly Lys Glu Arg Glu Phe Val Val
1               5                   10                  15

Val Ile

<210> SEQ ID NO 747
<211> LENGTH: 18
<212> TYPE: PRT
<213> ORGANISM: Artificial Sequence
<220> FEATURE:
<223> OTHER INFORMATION: FR2

<400> SEQUENCE: 747

Met Gly Trp Phe Arg Gln Ala Pro Gly Lys Glu Arg Glu Phe Ile Ala
1               5                   10                  15

Val Ile

<210> SEQ ID NO 748
<211> LENGTH: 38
<212> TYPE: PRT
<213> ORGANISM: Artificial Sequence
<220> FEATURE:
<223> OTHER INFORMATION: FR3

<400> SEQUENCE: 748

Ala Tyr Ala Asp Ser Val Lys Gly Arg Phe Thr Ile Ser Arg Asp Asn
1               5                   10                  15

Ala Arg Asn Thr Val Tyr Leu Gln Met Asn Asn Leu Lys Pro Glu Asp
            20                  25                  30

Thr Gly Val Tyr Tyr Cys
        35

<210> SEQ ID NO 749
<211> LENGTH: 38
<212> TYPE: PRT
<213> ORGANISM: Artificial Sequence
<220> FEATURE:
<223> OTHER INFORMATION: FR3

<400> SEQUENCE: 749

Ala Tyr Ala Asp Ser Val Lys Gly Arg Phe Thr Ile Ser Arg Asp Asn
1               5                   10                  15

Ala Arg Asn Thr Val Tyr Leu Gln Met Asn Ser Leu Arg Pro Glu Asp
            20                  25                  30
```

Thr Ala Val Tyr Tyr Cys
          35

<210> SEQ ID NO 750
<211> LENGTH: 38
<212> TYPE: PRT
<213> ORGANISM: Artificial Sequence
<220> FEATURE:
<223> OTHER INFORMATION: FR3

<400> SEQUENCE: 750

Ala Tyr Ala Asp Ser Val Lys Gly Arg Phe Thr Ile Ser Arg Asp Asn
1               5                   10                  15

Ala Lys Asn Thr Val Tyr Leu Gln Met Asn Ser Leu Arg Pro Glu Asp
            20                  25                  30

Thr Ala Val Tyr Tyr Cys
          35

<210> SEQ ID NO 751
<211> LENGTH: 38
<212> TYPE: PRT
<213> ORGANISM: Artificial Sequence
<220> FEATURE:
<223> OTHER INFORMATION: FR3

<400> SEQUENCE: 751

Ser Tyr Ala Asp Ser Val Lys Gly Arg Phe Thr Ile Ser Arg Asp Asn
1               5                   10                  15

Ala Lys Asn Thr Leu Tyr Leu Gln Met Asn Ser Leu Lys Pro Glu Asp
            20                  25                  30

Thr Ala Val Tyr Tyr Cys
          35

<210> SEQ ID NO 752
<211> LENGTH: 38
<212> TYPE: PRT
<213> ORGANISM: Artificial Sequence
<220> FEATURE:
<223> OTHER INFORMATION: FR3

<400> SEQUENCE: 752

Ser Tyr Ala Asp Ser Val Lys Gly Arg Phe Thr Ile Ser Arg Asp Asn
1               5                   10                  15

Ala Lys Asn Thr Leu Tyr Leu Gln Met Asn Ser Leu Arg Pro Glu Asp
            20                  25                  30

Thr Ala Val Tyr Tyr Cys
          35

<210> SEQ ID NO 753
<211> LENGTH: 11
<212> TYPE: PRT
<213> ORGANISM: Artificial Sequence
<220> FEATURE:
<223> OTHER INFORMATION: FR4

<400> SEQUENCE: 753

Trp Gly Gln Gly Thr Leu Val Thr Val Ser Ser
1               5                   10

<210> SEQ ID NO 754
<211> LENGTH: 7282
<212> TYPE: RNA
<213> ORGANISM: Artificial Sequence
<220> FEATURE:

<223> OTHER INFORMATION: SVV

<400> SEQUENCE: 754

```
uuugaaaugg ggggcugggc ccugaugccc aguccuuccu uuccccuucc ggggggguuaa      60 ccggcugugu uugcuagagg cacagaggag caacauccaa ccugcuuuug uggggaacgg     120
ugcggcucca auuccugcgu cgccaaaggu guuagcgcac ccaaacggcg caucuaccaa     180
ugcuauuggu guggucugcg aguucuagcc uacucguuuc uccccuauuc auucacucac     240
gcacaaaaag uguguuguaa cuacaagauu uagcccucac acgggaugug ugauaaccgc     300
aagacugacu caagcgcgga aagcgcugua accgcaugcu guuagucccu uuauggcugc     360
gagauggcua uccaccucgg aucacugaac uggagcucga cccuccuuag uaagggaacc     420
gagaggccuu cuugcaacaa gcuccgacac agaguccacg ugauugcuac caccaugagu     480
acaugguucu ccccucucga cccaggacuu cuuuuugaau auccacggcu cgauccagag     540 ggugggggcau gaucccccua gcauagcgag cuacagcggg aacuguagcu aggccuuagc     600
gugccuugga uacugccuga uagggcgacg gccuagucgu gucgguucua uagguagcac     660
auacaaauau gcagaacucu cauuuuucuu ucgauacagc cucuggcacc uuugaagaug     720
uaaccggaac aaaagucaag aucguugaau accccagauc ggugaacaau gguguuuacg     780
auucgucuac ucauuuggag auacugaacc uacaggguga aauugaaauu uuaaggucuu     840
ucaaugaaua ccaaauucgc gccgccaaac aacaacucgg acuggacauc guguacgaac     900
uacaggguaa uguucagaca cgucaaaga augauuuuga uucccguggc aauaaugggua    960 acaugaccuu caauuacuac gcaaacacuu aucagaauuc aguagacuuc ucgaccuccu    1020
cgucggcguc aggcgccgga ccugggaacu cucggggcgg auuagcgggu cuccucacaa    1080
auuucagugg aaucuugaac ccucuuggcu accucaaaga ucacaacacc gaagaaaugg    1140
aaaacucugc ugaucgaguc acaacgcaaa cggcgggcaa cacugccaua aacacgcaau    1200
caucauuggg uguguugugu gccuacguug aagacccgac caaaucugau ccuccgucca    1260
gcagcacaga ucaaccccacc accacuuuca cugccaucga caggugguac acuggacguc    1320
ucaauucuug gacaaaagcu guaaaaaccu ucucuuuuca ggccgucccg cuucccgguug    1380 ccuuucuguc uaggcaggga ggccucaacg gaggggccuu cacagcuacc cuacauagac    1440
acuuuuugau gaagugcggg uggcaggugc agguccaaug uaauuugaca caauuccacc    1500
aaggcgcucu ccuuguugcc augguuccug aaaccacccu ugaugucaag cccgacgguua    1560 aggcaaagag cuuacaggag cugaaugaag aacaguggu ggaaaugucu gacgauuacc    1620
ggaccgggaa aaacaugccu uuucaggcgc uuggcacaua cuaucggccc ccuaacugga    1680
cuuggggucc caauuucauc aaccccuauc aaguaacggu uuuccacac caaauucuga    1740 acgcgagaac cucuaccucg guagacauaa acgucccaua caucggggag accccccacgc    1800 aauccucaga gacacagaac uccuggaccc uccucguuau gguggcucguu ccccuagacu    1860 auaaggaagg agccacaacu gacccagaaa uuacauuuuc uguaaggccu acaagucccu    1920
acuucaaugg gcuucgcaac cgcuacacgg ccgggacgga cgaagaacag gggcccauuc    1980
cuacggcacc cagagaaaau ucgcuuaugu uucucucaac ccucccugac gacacugucc    2040
cugcuuacgg gaaugugcgu accccuccug ucaauuaccu cccuggugaa auaaccgacc    2100
uuuugcaacu ggcccgcaua cccacucuca uggcauuuga gcgggugccu gaacccgugc    2160
cugccucaga cacauaugug cccuacguug ccguuccccac ccaguucgau gacaggccuc    2220
ucaucuccuu cccgaucacc cuuucagauc ccgucuauca gaacacccug guuggcgcca    2280
```

```
ucaguucaaa uuucgccaau uaccgugggu guauccaaau cacucugaca uuuuguggac   2340
ccaugauggc gagagggaaa uuccugcucu cguauucucc cccaaaugga acgcaaccac   2400
agacucuuuc cgaagcuaug cagugcacau acucuauuug ggacauaggc uugaacucua   2460
guuggaccuu cgucgucccc uacaucucgc ccagugacua ccgugaaacu cgagccauua   2520
ccaacucggu uuacuccgcu gaugguuggu uuagccugca caaguugacc aaaauuacuc   2580
uaccaccuga cguccgcaa aguccccugca uucucuuuuu cgcuucugcu ggugaggauu   2640
acacucuccg ucuccccguu gauuguaauc cuuccuaugu guuccacucc accgacaacg   2700
ccgagaccgg gguuauugag gcggguaaca cugacaccga uuucucuggu gaacuggcgg   2760
cuccuggcuc uaaccacacu aaugucaagu uccuguuuga ucgaucucga uuauugaaug   2820
uaaucaaggu acuggagaag gacgccguuu uccccccgccc uuucccuaca caagaaggug   2880
cgcagcagga ugaugguuac uuuugucuuc ugaccccccg cccaacaguc gcuucccgac   2940
ccgccacucg uuucggccug uacgccaauc cguccggcag uggguguucu gcuaacacuu   3000
cacuggacuu caauuuuuau agcuuggccu guuucacuua cuuuagaucg gaccuugagg   3060
uuacgguggu cucacuagag ccggaucugg aauuugcugu aggguggyuu ccuucuggca   3120
gugaauacca ggcuuccagc uuugucuacg accagcugca ugugcccuuc cacuuuacug   3180
ggcgcacucc ccgcgcuuuc gcuagcaagg gugggaaggu aucuuucgug cucccuugga   3240
acucugucuc gucgugcuc cccgugcgcu ggggggggggc uuccaagcuc ucuucugcua   3300
cgcggggucu accggcgcau gcugauuggg ggacuauuua cgccuuuguc ccccguccua   3360
augagaagaa aagcaccgcu guaaaacacg uggccgugua cauucgguac aagaacgcac   3420
gugccuggug ccccagcaug cuucccuuuc gcagcuacaa gcagaagaug cugaugcaau   3480
cuggcgauau cgagaccaau cccgggccug cuucugacaa cccaauuuug gaguuucuug   3540
aagcagaaaa ugaucuaguc acucuggccu cucucuggaa gauggugcac ucuguucaac   3600
agaccuggag aaaguaugug aagaacgaug auuuuuggcc caauuuacuc agcgagcuag   3660 uggggggaagg cucugucgcc uuggccgcca cgcuauccaa ccaagcuuca guaaaggcuc   3720
uuuugggccu gcacuuucuc ucucgggggc ucaauuacac ugacuuuuac ucuuuacuga   3780
uagagaaaug cucuaguuuc uuuaccguag aaccaccucc uccaccagcu gaaaaccuga   3840
ugaccaagcc cucagugaag ucgaaauucc gaaaacuguu uaagaugcaa ggacccaugg   3900
acaaagucaa agacuggaac caaauagcug ccggcuugaa gaauuuucaa uuuguucgug   3960
accuagucaa agaggugguc gauuggcugc aggccuggau caacaaagag aaagccagcc   4020
cuguccucca guaccaguug gagaugaaga agcucgggcc uguggccuug gcucaugacg   4080
cuuucauggc ugguuccggg cccccucuua gcgacgacca gauugaauac cuccagaacc   4140
ucaaaucucu ugcccuaaca cuggggaaga cuaauuuggc ccaaagucuc accacuauga   4200
ucaaugccaa acaaaguuca gcccaacgag uugaacccgu uguggugguc cuuagaggca   4260
agccgggaug cggcaagagc uuggccucua cguugauugc ccaggcugug uccaagcgcc   4320
ucuauggcuc ccaaagugua uauucucuuc ccccagaucc agauuucuuc gauggauaca   4380
aaggacaguu cgugaccuug auggaugauu ugggacaaaa cccggaugga caagauuucu   4440
ccaccuuuug ucagauggug ucgaccgccc aauuucuccc caacauggcg gaccuugcag   4500
agaaagggcg ucccuuuacc uccaaucuca ucauugcaac uacaaaucuc ccccacuuca   4560
guccugucac cauugcugau ccuucugcag ucucucgccg uaucaacuac gaucugacuc   4620
```

357
358

```
uagaaguauc ugaggccuac aagaaacaca cacggcugaa uuuugacuug gcuuucaggc   4680
gcacagacgc cccccccauu uauccuuuug cugcccaugu gcccuuugug gacguagcug   4740
ugcgcuucaa aaauggucac cagaauuuua aucuccuaga guuggucgau uccauuugua   4800
cagacauucg agccaagcaa caaggugccc gaaacaugca gacucugguu cuacagagcc   4860
ccaacgagaa ugaugacacc cccgucgacg aggcguuggg uagaguucuc ucccccgcug   4920
cggucgauga ggcgcuuguc gaccucacuc cagaggccga cccgguuggc cguuuggcua   4980
uucuugccaa gcuaggucuu gcccuagcug cggucacccc uggucugaua aucuuggcag   5040
ugggacucua cagguacuuc ucuggcucug augcagacca agaagaaaca gaaagugagg   5100
gaucugucaa ggcacccagg agcgaaaaug cuuaugacgg cccgaagaaa aacucuaagc   5160
ccccuggagc acucucucuc auggaaaugc aacagcccaa cguggacaug ggcuuugagg   5220
cugcggucgc uaagaaagug gucguccca uuaccuucau gguucccaac agaccuucug   5280
ggcuuacaca guccgcucuc cugguugaccg gccggaccuu ccuaaucaau gaacauacau   5340
gguccaaucc cuccuggacc agcuucacaa uccgcgguga gguacacacu cgugaugagc   5400
ccuuccaaac gguucauuuc acucaccacg guauucccac agaucugaug augguacguc   5460
ucggaccggg caauucuuuc ccuaacaauc uagacaaguu uggacuugac cagaugccgg   5520
cacgcaacuc ccgugugguu ggcguuucgu ccaguuacgg aaacuucuuc uucucuggaa   5580
auuuccucgg auuuguugau uccaucaccu cugaacaagg aacuuacgca agacucuuua   5640
gguacagggu gacgaccuac aaaggauggu gcggcucggc ccuggucugu gaggccggug   5700
gcguccgacg caucauuggc cugcauucug cuggcgccgc cgguaucggc gccgggaccu   5760
auaucucaaa auuaggacua aucaaagccc ugaaacaccu cggugaaccu uuggccacaa   5820
ugcaaggacu gaugacugaa uuagagccug gaaucaccgu acauguaccc cggaaaucca   5880
aauugagaaa gacgaccgca cacgcggugu acaaaccgga guuugagccu gcuguguugu   5940
caaaauuuga ucccagacug aacaaggaug uugacuugga ugaaguaauu uggcuaaaac   6000
acacugccaa ugucccuuac caaccuccuu uguucuacac auacauguca gaguacgcuc   6060
aucgagucuu cuccuucuug gggaaagaca augacauucu gaccgucaaa gaagcaauuc   6120
ugggcauccc cggacuagac cccauggauc cccacacagc uccgggucug ccuuacgcca   6180
ucaacggccu ucgacguacu gaucucgucg auuuugugaa cgguacagua gaugcggcgc   6240
uggcuguaca aauccagaaa uucuuagacg gugacuacuc ugaccauguc uuccaaacuu   6300
uucugaaaga ugagaucaga ccccagagaa aaguccgagc gggaaaaacc cgcauuguug   6360
augugcccuc ccuggcgcau ugcauugugg gcagaaugu gcuugggcgc uuugcugcca   6420
aguuucaauc ccauccuggc uuucuccucg gcucugcuau cgggcugac ccugauguuu   6480 ucuggaccgu cauaggggcu caacucgagg ggagaaagaa cacguaugac guggacuaca   6540
gugccuuuga cucuucacac ggcacuggcu ccuucgaggc ucucaucucu cacuuuuuca   6600
ccguggacaa ugguuuuagc ccugcgcugg gaccguaucu cagaucccug gcugucucgg   6660
ugcacgcuua cggcgagcgu cgcaucaaga uuaccggugg ccucccucc gguugugccg   6720 cgaccagccu gcugaacaca gugcucaaca augugaucau caggacugcu cuggcauuga   6780
cuuacaagga auuugaauau gacaugguug auaucaucgc cuacggugac gaccuucugg   6840
uuggcacgga uuacgaucug gacuucaaug aggugggcacg acgcgcugcc aaguggggu   6900 auaagaugac uccugccaac aaggguucug ucuucccucc gacuuccucu cuuuccgaug   6960
cuguuuuucu aaagcgcaaa uucguccaaa acaacgacgg cuuauacaaa ccaguuuaugg   7020
```

```
auuuaaagaa uuuggaagcc augcucuccu acuucaaacc aggaacacua cucgagaagc      7080
ugcaaucugu uucuauguug gcucaacauu cuggaaaaga agaauaugau agauugaugc      7140
accccuucgc ugacuacggu gccguaccga gucacgagua ccugcaggca agauggaggg      7200
ccuuguucga cugacccaga uagcccaagg cgcuucggug cugccggcga uucugggaga      7260
acucagucgg aacagaaaag gg                                               7282
```

<210> SEQ ID NO 755
<211> LENGTH: 7405
<212> TYPE: RNA
<213> ORGANISM: Artificial Sequence
<220> FEATURE:
<223> OTHER INFORMATION: CVA

<400> SEQUENCE: 755

```
uuaaaacagc ucuggggmug uucccacccc agaggcccac guggcggcua guacucuggu       60
auuacgguac cuuuguacgc cuguuuugua ucccuucccc cguaacuuua gaagcuuauc      120
aaaaguucaa uagcaggggu acaaaccagu acccuacga acaagcacuu cuguuucccc      180
ggugauauca cauagacugu acccacgguc aaaagugauu gauccguuau ccgcuugagu      240
acuucgagaa gccuaguauc accuuggaau cuucgaugcg uugcgcucaa cacucugccc      300
cgaguguagc uuaggcugau gagucugggc acucccacc ggcgacggug gcccaggcug       360
cguuggcggc cuacccaugg cugaugccgu gggacgcuag uuguugaacaa ggugugaaga     420 gccuauugag cuacucaaga guccuccggc cccugaaugc ggcuaauccu aaccacggag      480
caaccgcuca caacccagug aguagguugu cguaaugcgu aagucugugg cggaaccgac      540
uacuuugggu guccgguguu cccuuuauau ucauacuggc ugcuuauggu gacaauuuac      600
aaauuguuac cauauagcua uuggauuggc cacccaguau ugugcaauau auuugagugu      660
uucuuucaua agccuuauua acaucacauu uuuaaucaca auaaacagug caaauggggg      720
cucaaguuuc aacgcaaaag accggugcgc acgagaauca aaacguggca gccaauggau      780
ccaccauuaa uuacacuacu aucaacuauu acaaagacag ugcgaguaau uccgcuacua      840
gacaagaccu cucccaagau ccaucaaaau ucacagaacc gguuaaggac uuaauguuga      900
aaacagcacc agcucuaaac ucgccuaacg uggaagcaug ugggguacagu gaccguguga     960 ggcaaaucac uuuaggcaac ucgacuauua cuacacaaga agcagccaau gcuauuguug    1020
cuuacgguga auggcccacu uacauaaaug auucagaagc uaauccggua gaugcaccca    1080
cugagccaga cguuaguagc aaccgguuuu acacccuaga aucgguugucu uggaagacca    1140 cuucaagggg auggugguugg aaguuaccag auuguuugaa ggacaugggua auguuugguc    1200 agaauaugua cuaucacuac uuggggcgcu cugguuacac cauucauguc cagugcaacg    1260
cuucaaaauu ucaccaaggg gcguuaggag uuuuucugau accagaguuu gucauggcuu    1320
gcaacacuga gaguaaaacg ucauacguuu cauacaucaa ugcaaauccu ggugagagag    1380
gcggugaguu uacgaacacc uacaauccgu caaauacaga cgccagugag ggcagaaagu    1440
uugcagcauu ggauuauuug cuggguucug uguuucuagc aggaaacgcc uuuguguacc    1500
cgcaccagau caucaaccua cguaccaaca acagugcaac aauugugguug ccauacguaa    1560 acucacuugu gauugauugu auggcaaaac acaauaacug gggcauuguc auauuaccac    1620
uggcacccuu ggccuuugcc gcaacaucgu caccacaggu gccauuaca gugaccauug     1680 cacccaugug uacagaauuc aaugggguuga gaaacaucac cgucccagua caucaagggu    1740
```

```
ugccgacaau gaacacaccu gguuccaauc aauuccuuac aucugaugac uuccagucgc   1800
ccugugccuu accuaauuuu gauguuacuc caccaauaca cauacccggg gaaguaaaga   1860
auaugaugga acuagcugaa auugacacau ugaucccaau gaacgcagug gacgggaagg   1920
ugaacacaau ggagauguau caaauaccau ugaaugacaa uuugagcaag gcaccuauau   1980
ucuguuuauc ccuaucaccu gcuucugaua aacgacugag ccgcaccaug uugggugaaa   2040
uccuaaauua uuacacccau uggacggggu ccaucagguu caccuuucua uuuuguggua   2100
guaugauggc cacugguaaa cugcuccuca gcuauucccc accgggagcu aaaccaccaa   2160
ccaaucgcaa ggaugcaaug cuaggcacac acaucaucug ggaccuaggg uuacaaucca   2220
guuguuccau gguugcaccg uggaucucca acacagugua cagacggugu gcacgugaug   2280
acuucacuga gggcggauuu auaacuugcu ucuaucaaac uagaauugug guaccugcuu   2340 caacccuac caguauguuc auguuaggcu uuguuagugc guguccagac uucaguguca   2400
gacugcuuag ggacacuccc cauauuaguc aaucgaaacu aauaggacgu acacaaggca   2460
uugaagaccu cauugacaca gcgauaaaga augccuuaag agugucccaa ccacccucga   2520
cccagucaac ugaagcaacu aguggaguga auagccagga ggugccagcu cuaacugcug   2580
uggaaacagg agcaucuggu caagcaaucc ccagugaugu gguggaaacu aggcacgugg   2640
uaaauuacaa aaccaggucu gaaucguguc uugagucauu cuuugggaga gcugcgugug   2700
ucacaauccu auccuugacc aacuccucca agagcggaga ggagaaaaag cauuucaaca   2760
uauggaauau uacauacacc gacacugucc aguuacgcag aaaauuagag uuuuucacgu   2820
auuccagguu ugaucuugaa augacuuuug uauucacaga gaacuauccu aguacagcca   2880
guggagaagu gcgaaaccag guguaccaga ucauguauau uccaccaggg gcaccccgcc   2940
caucauccug ggaugacuac acauggcaau ccucuucaaa cccuuccauc uucuacaugu   3000
auggaaaugc accuccacgg augucaauuc cuuacguagg gauugccaau gccuauucac   3060
acuucuacga uggcuuugca cgggugccac uugaggguga gaacaccgau gcuggcgaca   3120
cguuuuacgg uuuagugucc auaaaugauu uuggaguuuu agcaguuaga gcaguaaacc   3180
gcaguaaucc acauacaaua cacacaucug ugagagugua caugaaacca aaacacauuc   3240
ggguuuggug ccccagaccu ccucgagcug uauuauacag gggagaggga guggacauga   3300
uauccagugc aauucuaccu cugaccaagg uagacucaau uaccacuuuu ggguuugguc   3360
aucagaacaa agcaguguac guugccgguu acaagauuug caacuaccac cuagcaaccc   3420
caagugauca cuugaaugca auuaguaugu uaugggacag ggauuuaaug gugguggaau   3480
cuagagccca gggaacugau accaucgcca gauguaguug caggugugga guuuacuauu   3540
gugaaucuag gaggaaguac uacccuguca cuuuuacugg cccaacguuu cgauucaugg   3600
aagcaaacga cuacuaucca gcaagauacc agucucacau gcugauaggg ugcggauuug   3660
cagaacccgg ggacugcggu gggauacuga ggugcacuca uggggUaauu gguaucauua   3720
cugcaggagg ugaaggggua guagccuuug cugacauuag agaccucugg guguaugaag   3780
aggaggccau ggaacaggga auaacaagcu acaucgaauc ucucggcaca gccuuuggcg   3840
caggguucac ccacacaauc agugagaaag ugacugaauu gacaacaaug guuaccagca   3900
cuaucacaga aaaacuacug aaaaacuugg ugaaauagu gucggcucua gugauuguug   3960
ugagaaauua ugaggacacu accacgaucc uugcaacacu agcacuacuc ggguguguaa   4020
uaucuccuug gcaaugguug aagaagaagg caugugacua acuagagauu ccuuaugUga   4080
ugcgccaagg ugaugggugg augaagaaau ucacagaggc gugcaaugca gcuaaaggcu   4140
```

-continued

```
uagaguggau uagcaacaaa auuuccaagu uuauagauug guugaagugu aaaauuaucc   4200
cagacgcuaa ggacaaggug gaauuucuca ccaaguugaa acagcuagac auguuggaaa   4260
aucaaauugc aaccauccac caaucuugcc ccagccaaga acaacaagag auucuuuuca   4320
acaaugugag auggcuagca guccaguccc gucgguuugc accauuauac gcuguggagg   4380
cacgccgaau uaacaaaaug gagagcacaa uaaacaauua uauacaguuc aagagcaaac   4440
accguauuga accaguaugu augcucauuc augggucacc agggacgggu aaaucuauag   4500
cuacuucauu aauagguaga gcaauagcag agaaggaaag cacaucaguc uauucaaugc   4560
caccugaccc aucucacuuu gauggcuaua aacaacaagg gguagugauu auggacgacc   4620
uaaaccaaaa ccccgauggu auggacauga aacuguuuug ccaaauggua ucaacagugg   4680
aguuuauucc uccaauggcc ucauuagagg agaagggcau uuuguuuaca ucugauuaug   4740
uccuggcuuc uaccaacucu cauucaauug uaccacccac aguggcucac agugaugccu   4800
uaaccagacg auuugcauuu gauguggagg uuuacacgau gucugaacau ucagucaaag   4860
gcaaacugaa uauggccacg gccacucaau uguguaagga uuguccaaca ccugcaaauu   4920
uuaaaaagug uugcccucuc guuuguggaa aggccuugca auuaauggac agguacacca   4980
gacaaagguu cacuguagau gagauuacca cauuaaucau gaaugagaaa aacagaaggg   5040
ccaauaucgg caauugcaug gaagccuugu uucaaggacc auuaagguau aaagauuuga   5100
agaucgaugu gaagacaguu ccccccccug agugcaucag ugauuuguua caagcagugg   5160
auucucaaga gguuagggau uacugugaga agaaaggcug gaucguuaac guuacuagcc   5220
agauucaacu agaaaggaac aucaauaggg ccaugacuau acuccaagcu guuaccacau   5280
ucgcagcagu cgcaggagua guguauguaa uguacaaacu cuucgccggu caacagggug   5340
cauacacugg cuugccaaac aaaaaaccca augucccuac uaucagaguc gcuaaagucc   5400
aggggccagg auuugacuac gcaguggcaa uggcaaaaag aaacauaguu acugcaacca   5460
ccaccaaggg ugaauuuacc augcuagggg ugcaugauaa uguagcaaua uugccaaccc   5520
augccgcucc aggagaaacc auuauuauug augggaaaga aguagagauc cuagaugcca   5580
gagccuuaga agaucaagcg ggaaccaauc uugagaucac cauuauuacu cuaaaaagaa   5640
augagaaguu uagagacauc agaucacaua uucccaccca aauuacugaa acuaacgaug   5700
gaguguugau cgugaacacu agcaaguacc ccaauaugua uguccccguu ggugcuguga   5760
ccgaacaggg auaucuuaau cucaguggac gucaaacugc ucgcacuuua auguacaacu   5820
uuccaacaag ggcaggccag ugcggaggaa ucaucacuug uacuggcaaa gucauuggga   5880
ugcauguugg cgggaacggu ucacauggu uugcagcagc ccucaagcga ucauacuuca   5940
cucaaaauca gggcgaaauc cagugggauga ggucaucaaa agaaguggggg uaccccauua   6000 uaaaugcccc auccaagaca aaguuagaac ccagugcuuu ccacuauguu uuugaaggug   6060
uuaaggaacc agcuguacuc acuaagaaug accccagacu aaaaacagau uuugaagaag   6120
ccaucuuuuc uaaauaugug gggaacaaaa uuacugaagu ggacgaguac augaaagaag   6180
caguggauca cuaugcagga caguuaaugu cacuggauau caacacagaa cagaugugcc   6240
uggaggaugc cauguacggc accgaugguc uugaggcccu ggaucuuagc acuagugcug   6300
gauauccuua uguugcaaug gggaaaaaga aaagagacau ucuagauaaa cagaccagag   6360
auacuaagga gaugcagaga cuuuuagaua ccuauggaau caaucuacca uuagucacgu   6420
acgugaaaga ugaacucagg ucaaagacua aaguggaaca aggaaaguca agauugauug   6480
```

-continued

```
aagcuuccag ccuuaaugau ucaguugcaa ugagaauggc cuuuggcaau cuuuacgcag      6540
cuuuccacaa gaauccaggu gguggugacag gaucagcagu ugguugugac ccagauuugu      6600
uuuggaguaa gauaccagug cuaauggaag aaaaacucuu cgcuuuugac uacacagggu      6660
augaugccuc acucagcccu gcuugguuug aagcucuuaa aauggguguua gaaaaaauug      6720 gauuuggcag uagaguagac uauauagacu accugaacca cucucaccac cuuuacaaaa      6780
acaagacuua uugugucaaa ggcggcaugc cauccggcug cucuggcacc ucaauuuuca      6840
acucaaugau uaacaaccug aucauuagga cgcuuuuacu gagaaccuac aagggcauag      6900
acuuggacca uuuaaaaaug auugccuaug gugaugacgu gauagcuucc uacccccaug      6960
agguugacgc uagucuccua gcccaaucag gaaaagacua uggacuaacc augacuccag      7020
cagauaaauc aguaaccuuu gaaacaguca caugggagaa uguaacauuu cugaaaagau      7080
uuuucagagc agaugagaag uauccauucc uggugcaucc agugaugcca augaaagaaa      7140
uucacgaauc aaucagaugg accaaggacc cuagaaacac acaggaucac guacgcucgu      7200
ugugccuauu agcuuggcac aacggugaag aagaauacaa uaaauuuuua gcuaaaauca      7260
gaagugugcc aaucggaaga gcuuuauugc ucccagagua cucuacauug uaccgccgau      7320
ggcucgacuc auuuuaguaa cccuaccuca gucggauugg auuggguuau acguuguag      7380 ggguaaauuu uucuuuaauu cggag                                            7405
```

<210> SEQ ID NO 756
<211> LENGTH: 241
<212> TYPE: PRT
<213> ORGANISM: Artificial Sequence
<220> FEATURE:
<223> OTHER INFORMATION: human DLL3 BiTE

<400> SEQUENCE: 756

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Val Tyr Tyr Ser Gly Thr Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Ser Ile Ala Val Thr Gly Phe Tyr Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Glu Ile Val Leu Thr Gln Ser Pro Gly Thr Leu
    130                 135                 140

Ser Leu Ser Pro Gly Glu Arg Val Thr Leu Ser Cys Arg Ala Ser Gln
145                 150                 155                 160

Arg Val Asn Asn Asn Tyr Leu Ala Trp Tyr Gln Gln Arg Pro Gly Gln
                165                 170                 175

Ala Pro Arg Leu Leu Ile Tyr Gly Ala Ser Ser Arg Ala Thr Gly Ile
            180                 185                 190

Pro Asp Arg Phe Ser Gly Ser Gly Ser Gly Thr Asp Phe Thr Leu Thr
```

```
                195                    200                    205

Ile Ser Arg Leu Glu Pro Glu Asp Phe Ala Val Tyr Tyr Cys Gln Gln
    210                    215                    220

Tyr Asp Arg Ser Pro Leu Thr Phe Gly Gly Gly Thr Lys Leu Glu Ile
225                    230                    235                    240

Lys

<210> SEQ ID NO 757
<211> LENGTH: 17
<212> TYPE: PRT
<213> ORGANISM: Artificial Sequence
<220> FEATURE:
<223> OTHER INFORMATION: VL-CDR1

<400> SEQUENCE: 757

Lys Ser Ser Gln Ser Leu Leu Asp Ser Glu Asp Gln Lys Asp Tyr Leu
1               5                   10                  15

Gly

<210> SEQ ID NO 758
<211> LENGTH: 7
<212> TYPE: PRT
<213> ORGANISM: Artificial Sequence
<220> FEATURE:
<223> OTHER INFORMATION: VL-CDR2

<400> SEQUENCE: 758

Trp Ala Thr Asn Arg His Thr
1               5

<210> SEQ ID NO 759
<211> LENGTH: 9
<212> TYPE: PRT
<213> ORGANISM: Artificial Sequence
<220> FEATURE:
<223> OTHER INFORMATION: VL-CDR3

<400> SEQUENCE: 759

Glu Gln Tyr Phe Ala Tyr Pro Tyr Thr
1               5

<210> SEQ ID NO 760
<211> LENGTH: 113
<212> TYPE: PRT
<213> ORGANISM: Artificial Sequence
<220> FEATURE:
<223> OTHER INFORMATION: VL

<400> SEQUENCE: 760

Asp Ile Ala Ile Ile Gln Ser Pro Ser Ser Val Ala Val Ser Val Gly
1               5                   10                  15

Glu Thr Val Thr Leu Ser Cys Lys Ser Ser Gln Ser Leu Leu Asp Ser
                20                  25                  30

Glu Asp Gln Lys Asp Tyr Leu Gly Trp Tyr Gln Gln Lys Pro Gly Gln
        35                  40                  45

Thr Pro Arg Pro Leu Ile Tyr Trp Ala Thr Asn Arg His Thr Gly Val
    50                  55                  60

Pro Asp Arg Phe Thr Gly Ser Gly Ser Gly Thr Asp Phe Thr Leu Ile
65                  70                  75                  80

Ile Ser Ser Val Gln Ala Glu Asp Leu Ala Asp Tyr Tyr Cys Glu Gln
                85                  90                  95
```

-continued

```
Tyr Phe Ala Tyr Pro Tyr Thr Phe Gly Ala Gly Thr Lys Leu Glu Leu
            100                 105                 110

Lys

<210> SEQ ID NO 761
<211> LENGTH: 4
<212> TYPE: PRT
<213> ORGANISM: Artificial Sequence
<220> FEATURE:
<223> OTHER INFORMATION: IgG core hinge region
<220> FEATURE:
<221> NAME/KEY: MISC_FEATURE
<222> LOCATION: (2)..(3)
<223> OTHER INFORMATION: Xaa is any amino acid

<400> SEQUENCE: 761

Cys Xaa Xaa Cys
1
```

ANTI-DLL3 ANTIBODIES AND METHODS OF USE

CROSS-REFERENCE TO RELATED APPLICATIONS

This application is a U.S. National Phase Application, filed under 35 U.S.C. § 371, of International Application No. PCT/US2021/030836, filed on May 5, 2021, which claims priority to U.S. Provisional Application No. 63/020,444, filed May 5, 2020, the contents of each of which is incorporated herein by reference in their entireties.

INCORPORATION OF THE ELECTRONIC SEQUENCE LISTING FILED HEREWITH

The sequence listing associated with this application is provided in text format in lieu of a paper copy and is hereby incorporated by reference into the specification. The name of the text file containing the sequence listing is ONCR_020_01US_SeqList_ST25.txt. The text file is 213,560 bytes in size, was created on Nov. 3, 2022 and is being submitted electronically via EFS-Web.

FIELD

The present disclosure relates generally to the field of antibodies and single domain antibodies binding to DLL3.

BACKGROUND

Delta-like ligand 3 (DLL3, NCBI Gene ID: 10683, Uni-Prot Ref: M0R177) is an inhibitory Notch pathway ligand that is highly upregulated and aberrantly expressed on the cell surface in SCLC and other high-grade neuroendocrine tumors (Saban et al., Nat Rev Clin Oncol. 2017; 14(9):549-561; Saunders et al., Sci Transl Med. 2015; 7(302): 302ra136). There is a need in the art for DLL3-specific antibodies and antigen-binding fragments thereof for use in the treatment of these and other cancers.

SUMMARY

The present disclosure provides single domain antibodies (sdAb) comprising a complementarity determining region (CDR) 1, a CDR2, and a CDR3, wherein: the CDR1 comprises an amino acid sequence selected from SEQ ID NOs: 1, 6, 10, 14, 18, 22, 26, 30, 33, 36, 39, 46, 52, 60, 65, 69, 73, 77, and 83; the CDR2 comprises an amino acid sequence selected from SEQ ID NOs: 2, 7, 11, 15, 19, 23, 27, 40, 43, 47, 53, 61, 66, 74, 78, 81, and 82; and the CDR3 comprises an amino acid sequence selected from SEQ ID NOs: 3, 8, 12, 16, 20, 24, 28, 31, 34, 37, 41, 44, 48, 54, 62, 67, 71, 75, 79, and 84.

In some embodiments of the disclosure, the sdAb comprises a CDR1, a CDR2, and a CDR3, wherein: the CDR1 comprises an amino acid sequence of SEQ ID NO: 46; the CDR2 comprises an amino acid sequence of SEQ ID NO: 47; and the CDR3 comprises an amino acid sequence of SEQ ID NO: 48.

In some embodiments of the disclosure, the sdAb comprises a CDR1, a CDR2, and a CDR3, wherein: the CDR1 comprises an amino acid sequence of SEQ ID NO: 52; the CDR2 comprises an amino acid sequence of SEQ ID NO: 53; and the CDR3 comprises an amino acid sequence of SEQ ID NO: 54.

In some embodiments of the disclosure, the sdAb comprises a CDR1, a CDR2, and a CDR3, wherein: the CDR1 comprises an amino acid sequence of SEQ ID NO: 18; the CDR2 comprises an amino acid sequence of SEQ ID NO: 19; and the CDR3 comprises an amino acid sequence of SEQ ID NO: 20.

In some embodiments of the disclosure, the sdAb comprises a CDR1, a CDR2, and a CDR3, wherein: the CDR1 comprises an amino acid sequence of SEQ ID NO: 83; the CDR2 comprises an amino acid sequence of SEQ ID NO: 2; and the CDR3 comprises an amino acid sequence of SEQ ID NO: 84.

In some embodiments of the disclosure, the sdAb comprises a CDR1, a CDR2, and a CDR3, wherein: the CDR1 comprises an amino acid sequence of SEQ ID NO: 60; the CDR2 comprises an amino acid sequence of SEQ ID NO: 61; and the CDR3 comprises an amino acid sequence of SEQ ID NO: 62.

In some embodiments of the disclosure, the sdAb comprises a CDR1, a CDR2, and a CDR3, wherein: the CDR1 comprises an amino acid sequence of SEQ ID NO: 65; the CDR2 comprises an amino acid sequence of SEQ ID NO: 66; and the CDR3 comprises an amino acid sequence of SEQ ID NO: 67.

In some embodiments of the disclosure, the sdAb comprises a CDR1, a CDR2, and a CDR3, wherein: the CDR1 comprises an amino acid sequence of SEQ ID NO: 69; the CDR2 comprises an amino acid sequence of SEQ ID NO: 23; and the CDR3 comprises an amino acid sequence of SEQ ID NO: 24.

In some embodiments of the disclosure, the sdAb comprises a CDR1, a CDR2, and a CDR3, wherein: the CDR1 comprises an amino acid sequence of SEQ ID NO: 14; the CDR2 comprises an amino acid sequence of SEQ ID NO: 43; and the CDR3 comprises an amino acid sequence of SEQ ID NO: 71.

In some embodiments of the disclosure, the sdAb comprises a CDR1, a CDR2, and a CDR3, wherein: the CDR1 comprises an amino acid sequence of SEQ ID NO: 73; the CDR2 comprises an amino acid sequence of SEQ ID NO: 74; and the CDR3 comprises an amino acid sequence of SEQ ID NO: 75.

In some embodiments of the disclosure, the sdAb comprises an amino acid sequence that is at least 95%, at least 96%, at least 97%, at least 98%, or at least 99% identical to an amino acid sequence selected from SEQ ID NOs: 4, 5, 9, 13, 17, 21, 25, 29, 32, 35, 38, 42, 45, 49, 55, 59, 63, 64, 68, 70, 72, and 76. In some embodiments, the sdAb comprises or consists of an amino acid sequence selected from SEQ ID NOs: 4, 5, 9, 13, 17, 21, 25, 29, 32, 35, 38, 42, 45, 49, 55, 59, 63, 64, 68, 70, 72, and 76.

The present disclosure provides single domain antibodies (sdAb) comprising (a) a human framework region sequence and (b) a complementarity determining region (CDR) 1, a CDR2, and a CDR3, wherein: (i) the CDR1 comprises an amino acid sequence selected from SEQ ID NOs: 1, 6, 10, 14, 18, 22, 26, 30, 33, 36, 39, 46, 52, 60, 65, 69, 73, 77, and 83; (ii) the CDR2 comprises an amino acid sequence selected from SEQ ID NOs: 2, 7, 11, 15, 19, 23, 27, 40, 43, 47, 53, 61, 66, 74, 78, 81, and 82; and (iii) the CDR3 comprises an amino acid sequence selected from SEQ ID NOs: 3, 8, 12, 16, 20, 24, 28, 31, 34, 37, 41, 44, 48, 54, 62, 67, 71, 75, 79, and 84.

In some embodiments of the disclosure, the sdAb comprises a human framework region sequence, a CDR1, a CDR2 and a CDR3, wherein: the CDR1 comprises an amino acid sequence of SEQ ID NO: 46; the CDR2 comprises an amino acid sequence of SEQ ID NO: 47; and the CDR3 comprises an amino acid sequence of SEQ ID NO: 48.

In some embodiments of the disclosure, the sdAb comprises a human framework region sequence, a CDR1, a CDR2 and a CDR3, wherein: the CDR1 comprises an amino acid sequence of SEQ ID NO: 52; the CDR2 comprises an amino acid sequence of SEQ ID NO: 53; and the CDR3 comprises an amino acid sequence of SEQ ID NO: 54.

In some embodiments of the disclosure, the sdAb comprises a human framework region sequence, a CDR1, a CDR2 and a CDR3, wherein: the CDR1 comprises an amino acid sequence of SEQ ID NO: 18; the CDR2 comprises an amino acid sequence of SEQ ID NO: 19; and the CDR3 comprises an amino acid sequence of SEQ ID NO: 20.

In some embodiments of the disclosure, the sdAb comprises a human framework region sequence, a CDR1, a CDR2 and a CDR3, wherein: the CDR1 comprises an amino acid sequence of SEQ ID NO: 83; the CDR2 comprises an amino acid sequence of SEQ ID NO: 2; and the CDR3 comprises an amino acid sequence of SEQ ID NO: 84.

In some embodiments of the disclosure, the sdAb comprises a human framework region sequence, a CDR1, a CDR2 and a CDR3, wherein: the CDR1 comprises an amino acid sequence of SEQ ID NO: 60; the CDR2 comprises an amino acid sequence of SEQ ID NO: 61; and the CDR3 comprises an amino acid sequence of SEQ ID NO: 62.

In some embodiments of the disclosure, the sdAb comprises a human framework region sequence, a CDR1, a CDR2 and a CDR3, wherein: the CDR1 comprises an amino acid sequence of SEQ ID NO: 65; the CDR2 comprises an amino acid sequence of SEQ ID NO: 66; and the CDR3 comprises an amino acid sequence of SEQ ID NO: 67.

In some embodiments of the disclosure, the sdAb comprises a human framework region sequence, a CDR1, a CDR2 and a CDR3, wherein: the CDR1 comprises an amino acid sequence of SEQ ID NO: 69; the CDR2 comprises an amino acid sequence of SEQ ID NO: 23; and the CDR3 comprises an amino acid sequence of SEQ ID NO: 24.

In some embodiments of the disclosure, the sdAb comprises a human framework region sequence, a CDR1, a CDR2 and a CDR3, wherein: the HCDR1 comprises an amino acid sequence of SEQ ID NO: 14; the HCDR2 comprises an amino acid sequence of SEQ ID NO: 43; and the HCDR3 comprises an amino acid sequence of SEQ ID NO: 71.

In some embodiments of the disclosure, the sdAb comprises a human framework region sequence, a CDR1, a CDR2 and a CDR3, wherein: the CDR1 comprises an amino acid sequence of SEQ ID NO: 73; the CDR2 comprises an amino acid sequence of SEQ ID NO: 74; and the CDR3 comprises an amino acid sequence of SEQ ID NO: 75.

In some embodiments of the disclosure, the sdAb comprising a human framework region sequence comprises an amino acid sequence that is at least 95%, at least 96%, at least 97%, at least 98%, or at least 99% identical to an amino acid sequence selected from SEQ ID NOs: 50, 51, 56, 57 and 58. In some embodiments, the sdAb comprising a human framework region sequence comprises or consists of an amino acid sequence selected from SEQ ID NOs: 50, 51, 56, 57 and 58.

In some embodiments of the disclosure, the sdAb of the disclosure specifically binds to a Delta-like ligand 3 (DLL3) protein. In some embodiments, the DLL3 protein is a human DLL3 protein.

The disclosure provides chimeric antigen receptors (CARs) comprising an extracellular antigen binding domain, a hinge, a transmembrane domain, and a cytoplasmic domain wherein the extracellular antigen binding domain is the sdAb of the disclosure.

The disclosure provides biomolecules comprising the sdAb of the disclosure.

The disclosure provides polynucleotides encoding the single domain antibodies of the disclosure, the CARs of the disclosure, or the biomolecules of the disclosure. In some embodiments, the polynucleotide is an mRNA molecule.

The disclosure provides vectors comprising the polynucleotide of the disclosure.

The disclosure provides binding construct comprising the sdAb of the disclosure. The disclosure provides binding construct comprising the sdAb of the disclosure and an Fc domain.

The disclosure provides bispecific binding constructs comprising a first binding domain and a second binding domain, wherein the first binding domain comprises the sdAb of the disclosure; and the second binding domain is selected from an antigen binding domain that specifically binds to CD3, CD16 or NKp46, or human serum albumin (HSA), or an Fc domain.

The disclosure provides trispecific binding constructs comprising a first binding domain, a second binding domain and a third binding domain, wherein the first binding domain comprises the sdAb of the disclosure; the second binding domain comprises an Fc domain or an antigen binding domain that specifically binds to human serum albumin (HSA); and the third binding domain is an antigen binding domain that specifically binds to CD3, CD16 or NKp46. In some embodiments, the second binding domain is an antigen binding domain that specifically binds to HSA, and the third binding domain is an antigen binding domain that specifically binds to CD3.

The disclosure provides polynucleotides encoding the binding construct of the disclosure, the bispecific binding constructs of the disclosure, or the trispecific binding constructs of the disclosure. In some embodiments, the polynucleotide is an mRNA molecule.

The disclosure provides vectors comprising the polynucleotide of the disclosure.

The disclosure provides methods of treating cancer in a subject in need thereof, comprising administering the sdAb, the CAR, the biomolecule, the binding construct, the bispecific binding construct, or the trispecific binding construct of the disclosure.

The disclosure provides uses of the sdAb, the CAR, the biomolecule, the binding construct, the bispecific binding construct, or the trispecific binding construct of the disclosure, for treating cancer in a subject in need thereof.

The disclosure provides uses of the sdAb, the CAR, the biomolecule, the binding construct, the bispecific binding construct, or the trispecific binding construct of the disclosure in the manufacture of a medicament for treating cancer in a subject in need thereof.

In some embodiments of the disclosure, the cancer is selected from non-small cell lung cancer (NSCLC), small cell lung cancer (SCLC), small cell bladder cancer, large cell neuroendocrine carcinoma (LCNEC), castration-resistant small cell neuroendocrine prostate cancer (CRPC-NE), carcinoid (e.g., pulmonary carcinoid), glioblastoma multiforme-IDH mutant (GBM-IDH mutant), Merkel cell carcinoma, and Gastric neuroendocrine cancer.

In some embodiments, the sdAb or the binding construct of the disclosure is administered in combination with an oncolytic virus or a polynucleotide encoding the oncolytic virus. In some embodiments, the sdAb or the binding construct, and the oncolytic virus or the polynucleotide encoding the oncolytic virus, are administered concurrently. In some embodiments, the sdAb or the binding construct, and the oncolytic virus or the polynucleotide encoding the oncolytic virus, are administered sequentially. In some embodiments, the oncolytic virus is a picornavirus. In some embodiments, the picornavirus is a Coxsackievirus. In some embodiments, the picornavirus is a Seneca Valley virus. In some embodiments, the polynucleotide encoding the oncolytic virus is encapsulated in a lipid nanoparticle.

The disclosure provides oncolytic viruses expressing one or more payload molecules, wherein the one or more payload molecules comprise the sdAb, the binding construct, the bispecific binding construct, or the trispecific binding construct of the disclosure. In some embodiments, the oncolytic virus is selected from herpes simplex virus, an adenovirus, a polio virus, a vaccinia virus, a measles virus, a vesicular stomatitis virus, an orthomyxovirus, a parvovirus, a maraba virus, a picornavirus, a togaviriadae virus, a semliki forest virus, a sindbis virus, a paramyxoviridae virus, and a sendai virus. In some embodiments, the picornavirus is a coxsackievirus or a seneca valley virus.

The disclosure provides methods of treating cancer in a subject in need thereof, comprising administering the oncolytic virus of the disclosure to the subject.

The disclosure provides uses of the oncolytic virus of the disclosure for treating cancer in a subject in need thereof.

The disclosure provides uses of the oncolytic virus of the disclosure in the manufacture of a medicament for treating cancer in a subject in need thereof.

The disclosure provides messenger RNA (mRNA) polynucleotides encoding the sdAb, the binding construct, the bispecific binding construct or the trispecific binding construct of the disclosure.

The disclosure provides methods of treating cancer in a subject in need thereof, comprising administering the mRNA polynucleotide of the disclosure to the subject.

The disclosure provides uses of the mRNA polynucleotide of the disclosure for treating cancer in a subject in need thereof.

The disclosure provides uses of the mRNA polynucleotide of the disclosure in the manufacture of a medicament for treating cancer in a subject in need thereof. In some embodiments of the disclosure, the mRNA polynucleotide is administered in combination with an oncolytic virus. In some embodiments, the mRNA polynucleotide is administered in combination with a polynucleotide encoding an oncolytic virus.

BRIEF DESCRIPTION OF THE DRAWINGS

FIG. 3 shows the binding properties of DLL3 binding constructs determined by binding assay, ELISA, and cell studies.

FIG. 8A illustrates the in vivo efficacy of the anti-DLL3/anti-CD3/anti-HSA trispecific binding construct and/or LNP containing synthetic SVV RNA viral genome in an NCI-H82 tumor model using humanized-NSG mice.

DETAILED DESCRIPTION

Figure 1:
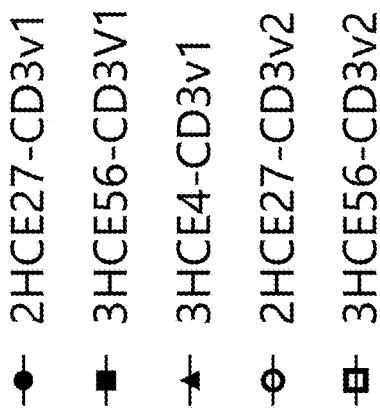
FIG. 1 illustrates the cytotoxicity of multiple anti-DLL3/anti-CD3 bispecific binding constructs.
Figure 1:
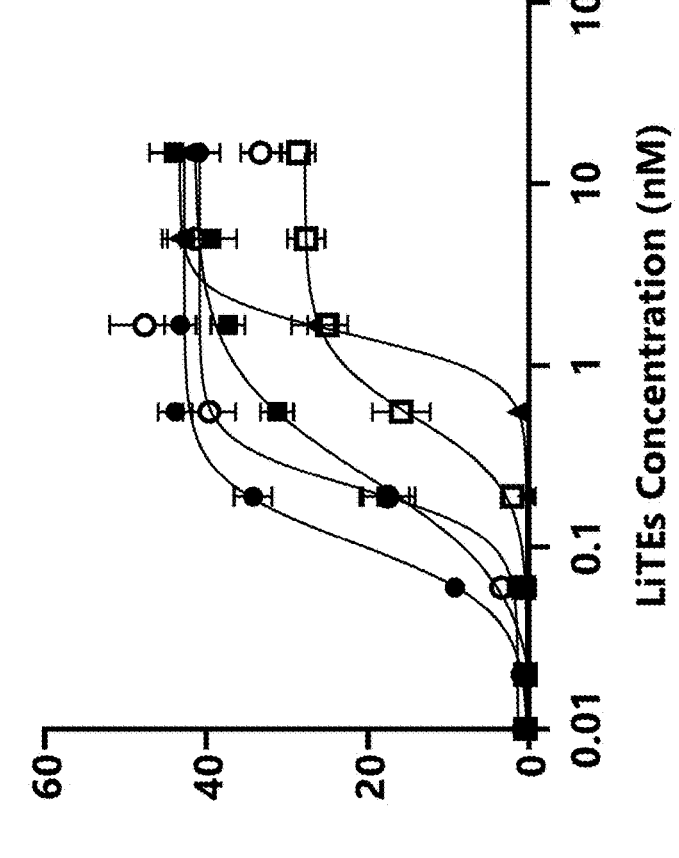

The details of the disclosure are set forth in the accompanying description below. Although methods and materials similar or equivalent to those described herein can be used in the practice or testing of the present disclosure, illustrative methods, and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Definitions

The term "antibody" refers to an immunoglobulin (Ig) molecule capable of binding to a specific target, such as a carbohydrate, polynucleotide, lipid, or polypeptide, through at least one epitope recognition site located in the variable region of the Ig molecule. As used herein, the term encompasses intact polyclonal or monoclonal antibodies and antigen-binding fragments thereof. For example, a native immunoglobulin molecule is comprised of two heavy chain polypeptides and two light chain polypeptides. Each of the heavy chain polypeptides associate with a light chain polypeptide by virtue of interchain disulfide bonds between the heavy and light chain polypeptides to form two heterodimeric proteins or polypeptides (i.e., a protein comprised of two heterologous polypeptide chains). The two heterodimeric proteins then associate by virtue of additional interchain disulfide bonds between the heavy chain polypeptides to form an immunoglobulin protein or polypeptide.

The term "binding construct" refers to a molecule comprising at least one binding domain. A "binding domain" is a domain of a polypeptide that binds to a cognate antigen (e.g., an antigen binding domain such as an antibody or antigen binding fragment thereof), receptor (e.g., an Fc receptor), or other ligand. In some embodiments, the binding constructs described herein comprise at least one, two, or three binding domains. In some embodiments, at least one of the binding domains is an antigen binding domain. Optionally, a binding construct may comprise a non-polypeptide moiety (a non-limiting example is an antibody-drug conjugate).

The terms "DLL3 binding construct" or "anti-DLL3 construct" are used interchangeably and refer to a binding construct comprising a DLL3 binding domain.

The term "bispecific binding construct" refers to a binding construct that comprises two binding domains that each bind to different antigens or targets.

"DVD-Ig" is a dual variable domain immunoglobulin protein, which contains an Fc region and constant regions in a configuration similar to a conventional IgG, while each arm of the molecule comprises two heavy chain variable domains and two light chain variable domains (unlike conventional IgG which only contains one heavy chain variable domain and one light chain variable domain in each arm). The two heavy chain variable domains within an arm are linked in tandem and may possess different binding specificities, and so is the two light chain variable domains.

"mAb2" is a full-length antibody having an overall structure similar to those of regular IgG, except that the Fc region comprises a second distinct antigen binding site which allows mAb2 to bind to two different antigens at the same time.

Fabs-in-tandem immunoglobulins (FIT-Ig) contains an Fc region in a configuration similar to a conventional IgG but each arm of the molecule comprises two or more different Fab domains linked in tandem and each Fab specifically binds to a distinct antigen. In some embodiments, the C-terminus of the constant domain of the light chain of the first Fab domain is linked to the N-terminus of the variable domain of the heavy chain of the second Fab domain.

The term "knobs-in-holes" or "KIH" refers to a format of antibody structure comprising amino acid mutations in the CH3 domain of the heavy chain that result in preferential formation of heterodimeric heavy chains. In some embodiments, the knob is a tyrosine residue and the hole is a threonine residue. In some embodiments, the CH3 domain of the first heavy chain comprises a mutation equivalent to T22Y of SEQ ID NO: 112, and the CH3 domain of the second heavy chain comprises a mutation equivalent to Y63T of SEQ ID NO: 112. Here, the polypeptide sequence of the reference CH3 domain comprises EPQVYTLPPSRDELTKNQVS LTCLVKGFYPSDIA-VEWESNGQPENNYKTTPPVLDSDGSFFLYSK-LTVDKSRWQQGNVF SCSVMHEALHN-HYTQKSLSLSP (SEQ ID NO: 112). As a result, the first heavy chain and the second heavy chain preferentially pair with each other during the formation of antibodies.

The term "BiTE", when referring to a class of antibody or antibody-like molecules, refers to bispecific T-cell engagers. Such molecules have a first binding domain that is specific for an antigen associated with a diseased state (e.g., an antigen expressed on cancerous cells) and second binding domain that is specific for an antigen associated with T cells. In some embodiments, BiTEs are fusion proteins comprising two single-chain variable fragments (scFvs) of different antibodies on a single peptide chain of about 55 kilodaltons. One of the scFvs binds to T-cells via the CD3 receptor, and the other to a tumor cell via a tumor specific molecule. In some embodiments, one or more of the scFv is replaced by VHH. In some embodiments, one of the scFv or VHH specifically binds DLL3.

The term "trispecific binding construct" refers to binding constructs that comprise three binding domains each of which specifically bind to a different antigen or target. In some embodiments, a trispecific binding construct of the disclosure may be a trispecific antibody of the disclosure. In some embodiments, a trispecific binding construct of the disclosure may comprise a first antigen binding domain, a second antigen binding domain, and a third antigen binding domain. In some embodiments, the first antigen, the second antigen and the third antigen are all different.

The term "antigen-binding fragment" as used herein refers to a polypeptide fragment that contains at least one Complementarity-determining region (CDR) of an immunoglobulin heavy and/or light chain that specifically binds to at least one epitope of the antigen of interest. In this regard, an antigen-binding fragment may comprise 1, 2, 3, 4, 5, or all 6 CDRs of a variable heavy chain (VH) and variable light chain (VL) sequence. Antigen-binding fragments include proteins that comprise a portion of a full length antibody, generally the antigen binding or variable region thereof, such as Fab, F(ab')2, Fab', Fv fragments, minibodies, diabodies, single domain antibody (sdAb), single-chain variable fragments (scFv), multispecific antibodies formed from antibody fragments, and any other modified configuration of the immunoglobulin molecule that comprises an antigen-binding site or fragment of the required specificity. In certain embodiments of the disclosure, an antigen-binding fragment, rather than an intact antibody, is used to increase tissue penetration or tumor penetration. In other embodiments, antigen-binding fragments are further modified to increase serum half-life.

The term "half-life", when referring to an antibody and antigen-binding fragment thereof in vivo, refers to a pharmacokinetic property of a molecule that is a measure of the mean survival time of the molecules in vivo following their administration. Half-life can be expressed as the time required to eliminate fifty percent (50%) of a known quantity of the molecule from the subject's body (e.g., human patient or other mammal) or a specific compartment thereof, for example, as measured in serum, i.e., circulating half-life, or in other tissues. In general, an increase in half-life results in an increase in mean residence time (MRT) in circulation for the molecule administered.

The term "F(ab)" refers to two of the protein fragments resulting from proteolytic cleavage of IgG molecules by the enzyme papain. Each F(ab) comprises a covalent heterodimer of the VH chain and VL chain and includes an intact antigen-binding site. Each F(ab) is a monovalent antigen-binding fragment. The term "Fab'" refers to a fragment derived from F(ab')2 and may contain a small portion of Fc. Each Fab' fragment is a monovalent antigen-binding fragment.

The term "F(ab')2" refers to a protein fragment of IgG generated by proteolytic cleavage by the enzyme pepsin. Each F(ab')2 fragment comprises two F(ab') fragments and is therefore a bivalent antigen-binding fragment.

An "Fv fragment" refers to a non-covalent VH::VL heterodimer which includes an antigen-binding site that retains much of the antigen recognition and binding capabilities of the native antibody molecule, but lacks the CH1 and CL domains contained within a Fab. Inbar et al. (1972) Proc. Nat. Acad. Sci. USA 69:2659-2662; Hochman et al. (1976) Biochem 15:2706-2710; and Ehrlich et al. (1980) Biochem 19:4091-4096. In some embodiments, the Fv fragment can be produced by preferential proteolytic cleavage of an IgM, and on rare occasions of an IgG or IgA immunoglobulin molecule. Fv fragments are, however, more commonly derived using recombinant techniques known in the art.

Minibodies comprising a scFv joined to a CH3 domain are also included herein (S. Hu et al., Cancer Res., 56, 3055-3061, 1996). See e.g., Ward, E. S. et al., Nature 341, 544-546 (1989); Bird et al., Science, 242, 423-426, 1988; Huston et al., PNAS USA, 85, 5879-5883, 1988); PCT/US92/09965; WO94/13804; P. Holliger et al., Proc. Natl. Acad. Sci. USA 90 6444-6448, 1993; Y. Reiter et al., Nature Biotech, 14, 1239-1245, 1996; S. Hu et al., Cancer Res., 56, 3055-3061, 1996.

The term "diabody" refers to a bispecific antibody in which VH and VL domains are expressed in a single polypeptide chain using a linker that is too short to allow for pairing between the two domains on the same chain, thereby forcing the domains to pair with complementary domains of another chain and creating two antigen-binding sites (see, e.g., Holliger et al., Proc. Natl. Acad. Sci. USA 90:6444-48 (1993) and Poljak et al., Structure 2:1121-23 (1994)).

The term "nanobody" or a "single domain antibody" refers to an antigen-binding fragment consisting of a single monomeric variable antibody domain. The Nanoclone method is a method for generating Nanobodies against a desired target based on automated high-throughput selection of B-cells. (See, WO 2006/079372)

The term "variable new antigen receptor" (VNAR) refers to the variable domain of immunoglobulin new antigen receptor (IgNAR), which contains only two complementarity-determining regions (CDRs)—CDR1 and CDR3 (see Cheong et al., *Int J Biol Macromol*. 2020 Mar. 15; 147:369-375).

The term "monoclonal antibody" as used herein refers to an antibody obtained from a population of substantially homogeneous antibodies, i.e., the individual antibodies comprising the population are identical except for possible naturally occurring mutations that may be present in minor amounts.

In some embodiments, the term "chimeric antibody" as used herein refers to a monoclonal antibody in which a portion of the heavy and/or light chain is identical or homologous to corresponding sequences in antibodies derived from a particular species or belonging to a particular antibody class or subclass, while the remainder of the chain(s) is identical or homologous to corresponding sequences in antibodies derived from another species or belonging to another antibody class or subclass, as well as fragments of such antibodies, so long as they exhibit the desired biological activity.

The term "single chain variable fragment" or "scFv" refers to a fusion protein of the variable regions of the heavy (VH) and light chains (VL) of immunoglobulins, connected with a short linker peptide of ten to about 25 amino acids. Huston et al. (1988) Proc. Natl. Acad. Sci. USA 85(16):5879-

10

5883. The linker can connect the N-terminus of the VH with the C-terminus of the VL, or vice versa. A number of methods have been described to discern chemical structures for converting the naturally aggregated—but chemically separated—light and heavy polypeptide chains from an antibody V region into an scFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

The term "antigen" refers to a molecule or a portion of a molecule capable of being bound by an antibody or an antigen-binding fragment thereof and additionally capable of being used in an animal to produce antibodies capable of binding to an epitope of that antigen. An antigen may have one or more epitopes. Embodiments herein contemplate the use of a DLL3 protein, or a DLL3 protein conjugated to a hapten, as an antigen.

The term "epitope" refers to a region of an antigen that is bound by an antibody. Epitope determinants can include chemically active surface groupings of molecules such as amino acids, sugar side chains, phosphoryl, or sulfonyl and may have specific three-dimensional structural characteristics, and/or specific charge characteristics.

Herein, the term "specifically binds" refers to the ability of an antibody or antigen-binding fragment thereof to bind a target antigen with a binding affinity (Ka) of at least 105 M-1 while not significantly binding other components or antigens present in a mixture. Reference to an anti-DLL3 antibody herein refers to an antibody or antigen-binding fragment thereof that specifically binds to DLL3.

Binding affinity (Ka) refers to an equilibrium association of a particular interaction expressed in the units of 1/M or M-1. Antibodies or antigen-binding fragments thereof can be classified as "high affinity" antibodies or antigen-binding fragments thereof and "low affinity" antibodies or antigen-binding fragments thereof. "High affinity" antibodies or antigen-binding fragments thereof refer to those antibodies or antigen-binding fragments thereof with a Ka of at least 107 M-1, at least 108 M-1, at least 109 M-1, at least 1010 M-1, at least 1011 M-1, at least 1012 M-1, or at least 1013 M-1. "Low affinity" antibodies or antigen-binding fragments thereof refer to those antibodies or antigen-binding fragments thereof with a Ka of up to 107 M-1, up to 106 M-1, or up to 105 M-1. Alternatively, affinity can be defined as an equilibrium dissociation constant (KD) of a particular binding interaction with units of M (e.g., 10-5 M to 10-13, or about 500 nM, about 300 nM, about 250 nM, about 200 nM, about 150 nM, about 100 nM, about 50 nM, about 25 nM, about 10 nM, about 5 nM, about 2 nM, about 1 nM, about 500 pM, about 200 pM, about 100 pM, about 50 pM, about 20 pM, about 10 pM, about 5 pM, about 2 pM, about 1 pM, about 0.5 pM, about 0.2 pM, or about 0.1 pM, including all ranges and subranges therebetween). Affinities of binding domain polypeptides and single chain polypeptides according to the present disclosure can be readily determined using conventional techniques (see, e.g., Scatchard et al. (1949) Ann. N.Y. Acad. Sci. 51:660; and U.S. Pat. Nos. 5,283,173, 5,468,614, or the equivalent).

A "conservative substitution" is recognized in the art as a substitution of one amino acid for another amino acid that has similar properties. Exemplary conservative substitutions are well-known in the art (see, e.g., PCT Application Publication No. WO 97/09433, page 10, published Mar. 13, 1997; Lehninger, Biochemistry, Second Edition; Worth Publishers, Inc. NY:NY (1975), pp.71-77; Lewin, Genes IV, Oxford University Press, NY and Cell Press, Cambridge, MA (1990), p. 8).

As used herein, the term "derivative" refers to a modification of one or more amino acid residues of a peptide by chemical or biological means, either with or without an enzyme, e.g., by glycosylation, alkylation, acylation, ester formation, or amide formation.

As used herein, a polypeptide or polynucleotide from which another polypeptide or polynucleotide is derived from is referred to as the "parental" or "reference" polynucleotide or polypeptide. For example, a humanized antibody can be derived from a parental murine antibody.

The term "variant" or "variants" as used herein refers to a polynucleotide or polypeptide with a sequence differing from that of a reference polynucleotide or polypeptide but retaining essential properties of the parental polynucleotide or polypeptide. Generally, variant polynucleotide or polypeptide sequences are overall closely similar, and, in many regions, identical to the parental polynucleotide or polypeptide. For instance, a variant polynucleotide or polypeptide may exhibit at least 70%, at least 80%, at least 90%, at least 91%, at least 92%, at least 93%, at least 94%, at least 95%, at least 96%, at least 97%, at least 98% at least 99%, or at least 99.5% sequence identity compared to the parental polynucleotide or polypeptide.

As used herein, the term "sequence identity" refers to a relationship between two or more polynucleotide sequences or between two or more polypeptide sequences. When a position in one sequence is occupied by the same nucleic acid base or amino acid residue in the corresponding position of the comparator sequence, the sequences are said to be "identical" at that position. The percentage sequence identity is calculated by determining the number of positions at which the identical nucleic acid base or amino acid residue occurs in both sequences to yield the number of identical positions. The number of identical positions is then divided by the total number of positions in the comparison window and multiplied by 100 to yield the percentage of sequence identity. Percentage of sequence identity is determined by comparing two optimally aligned sequences over a comparison window. The comparison window for polynucleotide sequences can be, for instance, at least 20, 30, 40, 50, 60, 70, 80, 90, 100, 110, 120, 130, 140, 150, 160, 170, 180, 190, 200, 300, 400, 500, 600, 700, 800, 900 or 1000 or more nucleic acids in length. The comparison window for polypeptide sequences can be, for instance, at least 20, 30, 40, 50, 60, 70, 80, 90, 100, 110, 120, 130, 140, 150, 160, 170, 180, 190, 200, 300 or more amino acids in length. In order to optimally align sequences for comparison, the portion of a polynucleotide or polypeptide sequence in the comparison window can comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using the version of the program "BLAST 2 Sequences" which was available from the National Center for Biotechnology Information as of Sep. 1, 2004, which program incorporates the programs BLASTN (for nucleotide sequence comparison) and BLASTP (for polypeptide sequence comparison), which programs are based on the algorithm of Karlin and Altschul (Proc. Natl. Acad. Sci. USA 90(12):5873-5877, 1993). When utilizing "BLAST 2 Sequences," parameters that were default parameters as of Sep. 1, 2004, can be used for word size (3), open gap penalty (11), extension gap penalty (1), gap dropoff (50), expect value (10) and any other required parameter including but not limited to matrix option. Two nucleotide or amino acid sequences are considered to have "substantially similar sequence identity" or "substantial sequence identity" if the two sequences have at least 80%, at least 85%, at least 90%, at least 95%, at least 96%, at least 97%, at least 98%, or at least 99% sequence identity relative to each other.

The term "substantially identical" refers to a polypeptide sequence that contains a sufficient number of identical amino acids to a second polypeptide sequence such that the first and second polypeptide sequence have similar activity. Polypeptides that are substantially identical are at least 80%, at least 85%, at least 90%, at least 95%, at least 96%, at least 97%, at least 98%, at least 99%, or 100% identical in amino acid sequence.

"Fc region" or "Fc domain" refers to a polypeptide sequence corresponding to or derived from the portion of an antibody that is capable of binding to Fc receptors on cells and/or the C1q component of complement, thereby mediating the effector function of an antibody. Fc stands for "fragment crystalline," the fragment of an antibody that will readily form a protein crystal. Distinct protein fragments, which were originally described by proteolytic digestion, can define the overall general structure of an immunoglobulin protein. As originally defined in the literature, the Fc region is a homodimeric protein comprising two polypeptides that are associated by disulfide bonds, and each comprising a hinge region, a CH2 domain, and a CH3 domain. However, more recently the term has been applied to the single chain monomer component consisting of CH3, CH2, and at least a portion of the hinge sufficient to form a disulfide-linked dimer with a second such chain. As such, and depending on the context, use of the terms "Fc region" or "Fc domain" will refer herein to either the dimeric form or the individual monomers that associate to form the dimeric protein. For a review of immunoglobulin structure and function, see Putnam, The Plasma Proteins, Vol. V (Academic Press, Inc., 1987), pp. 49-140; and Padlan, Mol. Immunol. 31:169-217, 1994. As used herein, the term Fc domain includes variants of naturally occurring sequences.

The term "immunoglobulin constant region" or "constant region" refers to a peptide or polypeptide sequence that corresponds to or is derived from part or all of one or more constant domains of an immunoglobulin (e.g., CH1, CH2, CH3). In certain embodiments, the constant region does not comprise a CH1 domain. In certain embodiments, the constant domains making up the constant region are human The terms "light chain variable region" (also referred to as "light chain variable domain" or "VL") and "heavy chain variable region" (also referred to as "heavy chain variable domain" or "VH") refer to the variable binding region from an antibody light and heavy chain, respectively. The variable binding regions are made up of discrete, well-defined subregions known as "complementarity determining regions" (CDRs) and "framework regions" (FRs).

The term "immunoglobulin light chain constant region" (also referred to as "light chain constant region" or "CL") is a constant region from an antibody light chain.

The term "immunoglobulin heavy chain constant region" (also referred to as "heavy chain constant region" or "CH") refers to the constant region from the antibody heavy chain. The CH is further divisible, depending on the antibody isotype into CH1, CH2, and CH3 (IgA, IgD, IgG), or CH1, CH2, CH3, and CH4 domains (IgE, IgM).

As used herein, the term "complementarity determining region" or "CDR" refer to an immunoglobulin (antibody)

molecule. There are three CDRs per variable domain: CDR1, CDR2 and CDR3 in the variable domain of the light chain and CDR1, CDR2 and CDR3 in the variable domain of the heavy chain.

In some embodiments, a "hinge" or a "hinge region" refers to a polypeptide derived from an immunoglobulin hinge region and located between an antigen-binding domain (e.g., a DLL3 binding domain) and an immuno-globulin constant region in a polypeptide described herein. A "wild-type immunoglobulin hinge region" refers to a naturally occurring upper and middle hinge amino acid sequences interposed between and connecting the CH1 and CH2 domains (for IgG, IgA, and IgD) or interposed between and connecting the CH1 and CH3 domains (for IgE and IgM) found in the heavy chain of an antibody. In certain embodiments, a wild type immunoglobulin hinge region sequence is human, and can comprise a human IgG hinge region (e.g., and IgG1, IgG2, IgG3, or IgG4 hinge region).

An "altered immunoglobulin hinge region" or "variant immunoglobulin hinge region" refers to a hinge region polypeptide with one or more mutations, substitutions, inser-tions, or deletions compared to a corresponding parental wild-type immunoglobulin hinge region. Typically, an altered immunoglobulin hinge region that is a fragment of a wild type immunoglobulin hinge region comprises an IgG core hinge region (e.g., a polypeptide comprising the sequence C-X-X-C (SEQ ID NO: 761), wherein X is any amino acid) as disclosed in U.S. Patent Application Publi-cation Nos. 2013/0129723 and 2013/0095097.

As used herein, the term "humanized" refers to an anti-body or antigen-binding fragment thereof derived from a non-human species that retains the antigen-binding proper-ties of the original non-human antibody. In some embodi-ments, the binding fragments of an antibody (e.g., light and heavy chain variable regions, Fab, scFv) are humanized. Non-human antigen-binding fragments can be humanized using techniques known as CDR grafting (Jones et al., Nature 321:522 (1986)) and variants thereof, including "reshaping" (Verhoeyen, et al., 1988 Science 239:1534-1536; Riechmann, et al., 1988 Nature 332:323-337; Tem-pest, et al., Bio/Technol 1991 9:266-271), "hyperchimeriza-tion" (Queen, et al., 1989 Proc Natl Acad Sci USA 86:10029-10033; Co, et al., 1991 Proc Natl Acad Sci USA 88:2869-2873; Co, et al., 1992 J Immunol 148:1149-1154), and "veneering" (Mark, et al., "Derivation of therapeutically active humanized and veneered anti-CD18 antibodies." In: Metcalf B W, Dalton B J, eds. Cellular adhesion: molecular definition to therapeutic potential. New York: Plenum Press, 1994: 291-312). If derived from a non-human source, other regions of the antibody, such as the hinge region and constant region domains, can also be humanized.

The term "human framework region sequence" refers to the amino acid sequence of all the framework regions (i.e., non-CDR regions) of a variable domain that is derived from a human germline sequence. Typically, a human framework region sequence comprises four framework regions (FRs): FR1, FR2, FR3 and FR4, which are separated by CDRs. The organization of these regions is, from N-terminus to C-ter-minus, N'-FR1-CDR1-FR2-CDR2-FR3-CDR3-FR4-C'. The human framework region sequence may comprise one or more amino acid substitutions, insertions and/or deletions in the framework of the variable domain as compared to the corresponding human germline sequence. The substitution may be a conservative substitution. Such mutations can be readily ascertained by comparing the amino acid sequences disclosed herein to germline sequences available from, for example, public antibody sequence databases. For example, the human framework region sequence may comprises 10 or fewer, 9 or fewer, 8 or fewer, 7 or fewer, 6 or fewer, 5 or fewer, 4 or fewer, 3 or fewer, 2 or fewer, or 1 mutation as compared to the closest germline sequence found in public antibody sequence databases.

As used herein, the term "pharmaceutically acceptable" refers to molecular entities and compositions that do not generally produce allergic or other serious adverse reactions when administered using routes well known in the art. Molecular entities and compositions approved by a regula-tory agency of the Federal or a state government or listed in the U.S. Pharmacopeia or other generally recognized phar-macopeia for use in animals, and more particularly in humans are considered to be "pharmaceutically acceptable."

The term "polynucleotide" as referred to herein means single-stranded or double-stranded nucleic acid polymers. In certain embodiments, the nucleotides comprising the poly-nucleotide can be RNA or DNA or a modified form of either type of nucleotide, such as a modified messenger RNA. Said modifications may include, but are not limited to, base modifications such as bromouridine, ribose modifications such as arabinoside and 2',3'-dideoxyribose and internucle-otide linkage modifications such as phosphorothioate, phos-phorodithioate, phosphoroselenoate, phosphorodiselenoate, phosphoroanilothioate, phoshoraniladate and phosphoro-amidate. The term "polynucleotide" specifically includes single and double stranded forms of DNA.

As used herein, a "polypeptide" or "protein" refers to a single, linear, and contiguous arrangement of covalently linked amino acids. Polypeptides can form one or more intrachain disulfide bonds. The terms polypeptide and pro-tein also encompass embodiments where two polypeptide chains link together in a non-linear fashion, such as via an interchain disulfide bond. Herein, a protein or polypeptide may be an antibody or an antigen-binding fragment of an antibody.

As used herein, the terms "treatment," "treating," or "ameliorating" refers to either a therapeutic treatment or prophylactic/preventative treatment. A treatment is thera-peutic if at least one symptom of disease in an individual receiving treatment improves or a treatment can delay worsening of a progressive disease in an individual or prevent onset of additional associated diseases.

As used in this specification and the appended claims, the singular forms "a," "an" and "the" include plural references unless the content clearly dictates otherwise.

As used in this specification, the term "and/or" is used in this disclosure to either "and" or "or" unless indicated otherwise.

Throughout this specification, unless the context requires otherwise, the word "comprise", or variations such as "com-prises" or "comprising", will be understood to imply the inclusion of a stated element or integer or group of elements or integers but not the exclusion of any other element or integer or group of elements or integers.

Anti-DLL3 Binding Constructs

The present disclosure provides binding constructs and biomolecules that specifically bind to Delta-like ligand 3 (DLL3). In some embodiments, the binding construct is a single domain antibody (sdAb). In some embodiments, the sdAb is a variable domain heavy chain (VHH) sdAb. In some embodiments, the sdAb is a variable new antigen receptor (VNAR) sdAb. VNAR sdAbs are described in Cheong et al., *Int J Biol Macromol.* 2020 Mar. 15; 147:369-375, the content of which is incorporated by reference in its entirety.

The term "biomolecule" refers to a biological molecule (e.g., a small molecule, a protein, a nucleic acid, and the like). In some embodiments, the present disclosure provides biomolecules comprising a DLL3 binding domain. Such biomolecules include DLL3 binding constructs (antibodies, sdAbs, bispecific, and trispecific binding constructs), antibody-drug conjugates comprising a DLL3 binding domain, and engineered antigen receptors (e.g., chimeric antigen receptors and engineered TCRs) that specifically bind to DLL3.

In some embodiments, the binding constructs of the disclosure comprises at least one antigen binding domain that specifically or selectively binds an epitope, an antigen or a target comprised of or derived from a DLL3 polypeptide. In some embodiments, the DLL3 polypeptide is a mammalian DLL3 polypeptide. In some embodiments, the DLL3 polypeptide is a murine DLL3 polypeptide (See e.g., UniProt Ref #O88516). In some embodiments, the DLL3 polypeptide is a primate DLL3 polypeptide. In some embodiments, the DLL3 polypeptide is a human DLL3 polypeptide (See e.g., UniProt Ref #Q9NYJ7).

Delta-like ligand 3 (DLL3, NCBI Gene ID: 10683, Uni-Prot Ref: Q9NYJ7) is an inhibitory Notch pathway ligand that is highly upregulated and aberrantly expressed on the cell surface in SCLC and other high-grade neuroendocrine tumors (Saban et al., Nat Rev Clin Oncol. 2017; 14(9):549-561; Saunders et al., Sci Transl Med. 2015; 7(302):302ra136). Notch signaling is downregulated during neuroendocrine tumor growth and is inhibited by DLL3 expression (Kunnimalaiyaan et al., Oncologist. 2007; 12(5):535-542. doi: 10.1634/theoncologist.12-5-535; Lehman et al., Curr Oncol Rep. 2017; 19(7):49). DLL3 expression is regulated by achaete-scute homolog 1 (ASCL1), a transcription factor that is required for proper development of pulmonary neuroendocrine cells and is an oncogenic driver in SCLC (Augustyn et al., Proc Natl Acad Sci USA. 2014; 111(41):14788-14793; Borromeo et al., Cell Rep. 2016; 16(5):1259-1272). In preclinical models, DLL3 expression promotes SCLC migration and invasion through a mechanism that involves control of the epithelial-mesenchymal transition protein Snail (Furuta et al., Cancer Sci. 2019; 110(5):1599-1608).

In some embodiments, the present disclosure provides an anti-DLL3 antibody comprising a heavy chain variable region (VH) and light chain variable region (VL), wherein the VH comprises a heavy chain complementarity determining region (CDR) 1 (HCDR1), an HCDR2, and an HCDR3 selected from those listed in Table 1, and wherein the VL comprises a light chain CDR1 (LCDR1), an LCDR2, and an LCDR3.

In some embodiments, the present disclosure provides an anti-DLL3 antibody comprising a heavy chain variable region (VH) and light chain variable region (VL), wherein the VH comprises an HCDR1 of SEQ ID NO: 77 (GYTFTDYA), an HCDR2 of SEQ ID NO: 78 (IN-TYTGKP), and an HCDR3 of SEQ ID NO: 79 (SR-ERGYYDYSRSD), and wherein the VL comprises an LCDR1 of SEQ ID NO: 757 (KSSQSLLDSEDQKDYLG), an LCDR2 of SEQ ID NO: 758 (WATNRHT), and an LCDR3 of SEQ ID NO: 759 (EQYFAYPYT). In some embodiments, the anti-DLL3 antibody comprises a heavy chain variable region (VH) that is at least 95%, 96%, 97%, 98%, 99%, or 100% identical to SEQ ID NO: 80 and a light chain variable region (VL) that is at least 95%, 96%, 97%, 98%, 99%, or 100% identical to SEQ ID NO: 760 (DI-AIIQSPSSVAVSVGETVTLSCKSSQSLLD-SEDQKDYLGWYQQKPGQTPRPLIYWATN

RHTGVPDRFTGSGSGTDFTLIISSVQAEDLA-DYYCEQYFAYPYTFGAGTKLELK).

In some embodiments, the present disclosure provides single-domain antibodies (sdAbs) that specifically bind to DLL3 (anti-DLL3 sdAbs). In some embodiments, the anti-DLL3 sdAbs described herein are VHH sdAbs or VNAR sdAbs. In some embodiments, the anti-DLL3 sdAbs described herein are VHH sdAbs. In some embodiments, the present disclosure provides a VHH sdAbs that specifically binds to DLL3 and comprises a CDR1, a CDR2, and a CDR3, wherein the CDR1 comprises an amino acid sequence selected from SEQ ID NOs: 1, 6, 10, 14, 18, 22, 26, 30, 33, 36, 39, 46, 52, 60, 65, 69, 73, 77, and 83, the CDR2 comprises an amino acid sequence selected from SEQ ID NOs: 2, 7, 11, 15, 19, 23, 27, 40, 43, 47, 53, 61, 66, 74, 78, 81, and 82, and the CDR3 comprises an amino acid sequence selected from SEQ ID NOs: 3, 8, 12, 16, 20, 24, 28, 31, 34, 37, 41, 44, 48, 54, 62, 67, 71, 75, 79, and 84. CDRs of exemplary anti-DLL3 VHH sdAbs are shown in Table 1 below.

TABLE 1

Exemplary anti-DLL3 CDR sequences

| Construct ID | Fragment | Sequence | SEQ ID |
|---|---|---|---|
| 2DLT10 | VH-CDR1 | GSIVGDYA | 1 |
| | VH-CDR2 | IGSEGSR | 2 |
| | VH-CDR3 | FLYNSGEDY | 3 |
| 1DLT176 | VH-CDR1 | GSIVGDYA | 1 |
| | VH-CDR2 | IGSEGSR | 2 |
| | VH-CDR3 | FLYNSGEDY | 3 |
| 2HCE138 | VH-CDR1 | GFTTDDYG | 6 |
| | VH-CDR2 | ITTGGST | 7 |
| | VH-CDR3 | NAVCSGSGCYEVSWESYDY | 8 |
| 3HCE7 | VH-CDR1 | GRTYSNYF | 10 |
| | VH-CDR2 | VSWSGDRT | 11 |
| | VH-CDR3 | AAGPLINRINY | 12 |
| 2HCE151 | VH-CDR1 | GFTFSSYA | 14 |
| | VH-CDR2 | IDSGGGST | 15 |
| | VH-CDR3 | AKEPWWADY | 16 |
| 3HCE4 | VH-CDR1 | GRAGSSYD | 18 |
| | VH-CDR2 | ITWSGNT | 19 |
| | VH-CDR3 | AAALSEKKYEY | 20 |
| 3HCE80 | VH-CDR1 | GSISSIIS | 22 |
| | VH-CDR2 | AITSGGST | 23 |
| | VH-CDR3 | NAHVRDYSGSAYY | 24 |
| 3HCE86 | VH-CDR1 | GGTFSNYD | 26 |
| | VH-CDR2 | VNRYGDYS | 27 |
| | VH-CDR3 | AARLWNSAKYAY | 28 |
| 3DLT81 | VH-CDR1 | GSIFSIYA | 30 |
| | VH-CDR2 | IGSEGSR | 2 |
| | VH-CDR3 | YAGRPPSASYSGAHY | 31 |
| 3HCE38 | VH-CDR1 | GFTFDDVA | 33 |
| | VH-CDR2 | ITSGGST | 81 |
| | VH-CDR3 | AARRDSRGQYHD | 34 |
| 2HCE6 | VH-CDR1 | GFTFSNSP | 36 |
| | VH-CDR2 | ISSNGRNT | 82 |
| | VH-CDR3 | AKGATPSVLYDY | 37 |
| 1DLT39 | VH-CDR1 | GRIFSMFP | 39 |
| | VH-CDR2 | ITTGGRP | 40 |
| | VH-CDR3 | NAVSTPELAYPYDY | 41 |

TABLE 1-continued

Exemplary anti-DLL3 CDR sequences

| Construct ID | Fragment | Sequence | SEQ ID |
|---|---|---|---|
| 3HCE25 | VH-CDR1 | GFTFSSYA | 14 |
| | VH-CDR2 | INSGGGST | 43 |
| | VH-CDR3 | AKEPWVTQGS | 44 |
| 2HCE27 | VH-CDR1 | GRTFRSYA | 46 |
| | VH-CDR2 | IIMSDGST | 47 |
| | VH-CDR3 | AARRDYFTGVYDY | 48 |
| 3HCE56 | VH-CDR1 | GRTFSVDA | 52 |
| | VH-CDR2 | IDWTGGST | 53 |
| | VH-CDR3 | AARERSRTAYDY | 54 |
| 2DLT2 | VH-CDR1 | GSIVGNYA | 83 |
| | VH-CDR2 | IGSEGSR | 2 |
| | VH-CDR3 | FLYNSGDDY | 84 |
| 3HCE44 | VH-CDR1 | GSIFSINS | 60 |
| | VH-CDR2 | KASDGST | 61 |
| | VH-CDR3 | FLYANNIPY | 62 |
| 2HCE174 | VH-CDR1 | GSIFSINS | 60 |
| | VH-CDR2 | KASDGST | 61 |
| | VH-CDR3 | FLYANNIPY | 62 |
| 2HCE167 | VH-CDR1 | GRTFSSYA | 65 |
| | VH-CDR2 | ISGSGYSA | 66 |
| | VH-CDR3 | AARNERGASSSYDY | 67 |
| 3HCE18 | VH-CDR1 | GSIFSIIT | 69 |
| | VH-CDR2 | AITSGGST | 23 |
| | VH-CDR3 | NAHVRDYSGSAYY | 24 |
| 2HCE117 | VH-CDR1 | GFTFSSYA | 14 |
| | VH-CDR2 | INSGGGST | 43 |
| | VH-CDR3 | ATPFEIGS | 71 |
| 3HCE87 | VH-CDR1 | GFIFDDYI | 73 |
| | VH-CDR2 | ISWSGSAT | 74 |
| | VH-CDR3 | AASSRGPYNSGSSYDY | 75 |
| Anti-DLL3-1 | VH-CDR1 | GYTFTDYA | 77 |
| | VH-CDR2 | INTYTGKP | 78 |
| | VH-CDR3 | SRERGYYDYSRSD | 79 |

In some embodiments, the present disclosure provides a VHH sdAb that specifically binds to DLL3 and comprises a CDR1 of SEQ ID NO: 1, a CDR2 of SEQ ID NO: 2, and a CDR3 of SEQ ID NO: 3. In some embodiments, the present disclosure provides a VHH sdAb that specifically binds to DLL3 and comprises a CDR1 of SEQ ID NO: 6, a CDR2 of SEQ ID NO: 7, and a CDR3 of SEQ ID NO: 8. In some embodiments, the present disclosure provides a VHH sdAb that specifically binds to DLL3 and comprises a CDR1 of SEQ ID NO: 10, a CDR2 of SEQ ID NO: 11, and a CDR3 of SEQ ID NO: 12. In some embodiments, the present disclosure provides a VHH sdAb that specifically binds to DLL3 and comprises a CDR1 of SEQ ID NO: 14, a CDR2 of SEQ ID NO: 15, and a CDR3 of SEQ ID NO: 16.

In some embodiments, the present disclosure provides a VHH sdAb that specifically binds to DLL3 and comprises a CDR1 of SEQ ID NO: 22, a CDR2 of SEQ ID NO: 23, and a CDR3 of SEQ ID NO: 24. In some embodiments, the present disclosure provides a VHH sdAb that specifically binds to DLL3 and comprises a CDR1 of SEQ ID NO: 26, a CDR2 of SEQ ID NO: 27, and a CDR3 of SEQ ID NO: 28. In some embodiments, the present disclosure provides a VHH sdAb that specifically binds to DLL3 and comprises a CDR1 of SEQ ID NO: 30, a CDR2 of SEQ ID NO: 2, and a CDR3 of SEQ ID NO: 31. In some embodiments, the present disclosure provides a VHH sdAb that specifically binds to DLL3 and comprises a CDR1 of SEQ ID NO: 33, a CDR2 of SEQ ID NO: 81, and a CDR3 of SEQ ID NO: 34.

In some embodiments, the present disclosure provides a VHH sdAb that specifically binds to DLL3 and comprises a CDR1 of SEQ ID NO: 36, a CDR2 of SEQ ID NO: 82, and a CDR3 of SEQ ID NO: 37. In some embodiments, the present disclosure provides a VHH sdAb that specifically binds to DLL3 and comprises a CDR1 of SEQ ID NO: 39, a CDR2 of SEQ ID NO: 40, and a CDR3 of SEQ ID NO: 41. In some embodiments, the present disclosure provides a VHH sdAb that specifically binds to DLL3 and comprises a CDR1 of SEQ ID NO: 14, a CDR2 of SEQ ID NO: 43, and a CDR3 of SEQ ID NO: 44. In some embodiments, the present disclosure provides a VHH sdAb that specifically binds to DLL3 and comprises a CDR1 of SEQ ID NO: 83, a CDR2 of SEQ ID NO: 2, and a CDR3 of SEQ ID NO: 84.

In some embodiments, the present disclosure provides a VHH sdAb that specifically binds to DLL3 and comprises a CDR1 of SEQ ID NO: 18, a CDR2 of SEQ ID NO: 19, and a CDR3 of SEQ ID NO: 20. In some embodiments, the present disclosure provides a VHH sdAb that specifically binds to DLL3 and comprises a CDR1 of SEQ ID NO: 60, a CDR2 of SEQ ID NO: 61, and a CDR3 of SEQ ID NO: 62. In some embodiments, the present disclosure provides a VHH sdAb that specifically binds to DLL3 and comprises a CDR1 of SEQ ID NO: 65, a CDR2 of SEQ ID NO: 66, and a CDR3 of SEQ ID NO: 67. In some embodiments, the present disclosure provides a VHH sdAb that specifically binds to DLL3 and comprises a CDR1 of SEQ ID NO: 69, a CDR2 of SEQ ID NO: 23, and a CDR3 of SEQ ID NO: 24.

In some embodiments, the present disclosure provides a VHH sdAb that specifically binds to DLL3 and comprises a CDR1 of SEQ ID NO: 14, a CDR2 of SEQ ID NO: 43, and a CDR3 of SEQ ID NO: 71. In some embodiments, the present disclosure provides a VHH sdAb that specifically binds to DLL3 and comprises a CDR1 of SEQ ID NO: 73, a CDR2 of SEQ ID NO: 74, and a CDR3 of SEQ ID NO: 75. In some embodiments, the present disclosure provides a VHH sdAb that specifically binds to DLL3 and comprises a CDR1 of SEQ ID NO: 77, a CDR2 of SEQ ID NO: 78, and a CDR3 of SEQ ID NO: 79.

In some embodiments, the present disclosure provides a VHH sdAb that specifically binds to DLL3 and comprises a CDR1 of SEQ ID NO: 46, a CDR2 of SEQ ID NO: 47, and a CDR3 of SEQ ID NO: 48. In some embodiments, the present disclosure provides a VHH sdAb that specifically binds to DLL3 and comprises a CDR1 of SEQ ID NO: 52, a CDR2 of SEQ ID NO: 53, and a CDR3 of SEQ ID NO: 54.

In some embodiments, the present disclosure provides a VHH sdAb that specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to an amino acid sequence selected from the group consisting of SEQ ID NOs: 4, 5, 9, 13, 17, 21, 25, 29, 32, 35, 38, 42, 45, 49, 55, 59, 63, 64, 68, 70, 72, and 76. In some embodiments, the present disclosure provides a VHH sdAb that specifically binds to DLL3 and comprises or consists of an amino acid sequence selected from the group consisting of SEQ ID NOs: 4, 5, 9, 13, 17, 21, 25, 29, 32, 35, 38, 42, 45, 49, 55, 59, 63, 64, 68, 70, 72, and 76. Exemplary VHH sdAb amino acid sequence are shown in Table 2.

In some embodiments, the present disclosure provides a heavy chain variable domain that specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 80. In some embodiments, the present disclosure provides a heavy chain variable domain that specifically binds to DLL3 and comprises or consists of an amino acid sequence according to SEQ ID NO: 80. In some embodiments, the present disclosure provides an antibody that specifically binds to DLL3 and comprises a heavy chain variable domain and a light chain variable domain, wherein the heavy chain variable domain comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 80.

TABLE 2

| Exemplary anti-DLL3 VHH amino acid sequences | | |
|---|---|---|
| Construct ID | Sequence | SEQ ID |
| 2DLT10 | QVQLQESGGGLVQPGESLRLSCAASGSIVGDYAMGWYRQAPGKKRELVAGIGSEGSRDYAD SVKGRFTISRDNAKRTLYLQMNSLKSEDTAVYICFLYNSGEDYWGQGTQVTVSS | 4 |
| 1DLT176 | QVQLQESGGGLVQPGGSLRLACAASGSIVGDYAMGWYRQAPGKKRELVAGIGSEGSRDYAD SVKGRFTISRDNAKRTLYLQMNSLKSEDTAVYICFLYNSGEDYWGQGTQVTVSS | 5 |
| 2HCE138 | QVQLQESGGGLVQAGGSLRLSCAVSGFTTDDYGIGWFRQAPGKQRELVAIITTGGSTNYAD SVKGRFKISRDNAKNTVYLQMNSLKPEDTAVYYCNAVCSGSGCYEVSWESYDYWGQGTQVT VSS | 9 |
| 3HCE7 | QVQLQESGGGLVQAGDSLRLSCAGSGRTYSNYFIDWFRQAPGKEREFVAAVSWSGDRTTYA DSVKGRFTVSRDNAKNTWYLQMNSLKPEDTAVYYCAAGPLINRINYWGQGTQVTVSS | 13 |
| 2HCE151 | QVQLQESGGGLVQPGGSLRLSCVASGFTFSSYAMSWVRQAPGKGPEWVSRIDSGGGSTSYA DSVKGRFTISRDNAKNTLHLQMNGLKPEDTAVYYCAKEPWVVADYWGQGTQVTVSS | 17 |
| 3HCE4 | QVQLQESGGGLVQAGASLKLSCAVSGRAGSSYDMGWLRQAPGKEREFVAIITWSGNTAYKD SVKGRFIISRDNAKNTVYLEMNSLAPEDTAVYYCAAALSEKKYEYWGQGTQVTVSS | 21 |
| 3HCE80 | QVQLQESGGGLVQPGGSLRLSCAASGSISSIISMGWYRQAPGKQRGELVAAITSGGSTSYA GSVEGRFAISRDSAKNTAYLQMNSLKPEDTAVYYCNAHVRDYSGSAYYTGQGTQVTVSS | 25 |
| 3HCE86 | QVQLQESGGGLVQPGGSLRLSCAASGGTFSNYDIAWFRQAPGKEREFVAAVNRYGDYSYYA DSVKGRFTISRDNAKSTVSLQMNSLKPEDTFSYYCAARLWNSAKYAYWGQGTQVTVSS | 29 |
| 3DLT81 | QVQLQESGGGLVQPGGSLRLSCAASGSIFSIYAMGWYRQAPGKKRELVAGIGSEGSRDYAD SVKGRFTISRDNAKRTVYLQMNTLQPEDTAVYYCYAGRPPSASYSGAHYWGQGTQVTVSS | 32 |
| 3HCE38 | QVQLQESGGGLVQPGGSLRLSCAASGFTFDDVAMSWVRQAPGKQRELVAVITSGGSTYTAD SVKGRFAISRDNAKNTVYLQMNSLKPEDTALYYCAARRDSRGQYHDWGQGTQVTVSS | 35 |
| 2HCE6 | QVQLQESGGGLVQTGGSLRLSCAASGFTFSNSPMSWVRRAPGKGPEWVSAISSNGRNTSYA DSVKGRFTISRDNAKNTLFLQMHSLKPEDTAVYYCAKGATPSVLYDYGGQGTQVTVSS | 38 |
| 1DLT39 | QVQLQESGGGLVQPGGSLRLSCAASGRIFSMFPMGWYRQAPGKQRELVADITTGGRPNYAD SVKGRFTITRDNAKNTVYLQMNSLQPEDTAVYFCNAVSTPELAYPYDYWGQGTQVTVSS | 42 |
| 3HCE25 | QVQLQESGGGLVQPGGSLRLSCEASGFTFSSYAMSWVRQAPGKGPEWVSRINSGGGSTSYA DSVKGRFTISRDNAKNTLYLQMNSLKPEDTAVYYCAKEPWVTQGSWGQGTQVTVSS | 45 |
| 2HCE27 | QVQLQESGGGLVQAGGSLRLSCAASGRTFRSYAMGWFRQAPGKEREFIAVIIMSDGSTSYA DSVKGRFTISRDNAKNTLYLQMNSLKPEDTAVYYCAARRDYFTGVYDYWGQGTQVTVSS | 49 |
| 3HCE56 | QVQLQESGGGLVQAGGSLRLSCAASGRTFSVDAMGWLRQAPGKEREFVVVIDWTGGSTAYA DSVKGRFTISRDNARNTVYLQMNNLKPEDTGVYYCAARERSRTAYDYWGQGTQVTVSS | 55 |
| 2DLT2 | QVQLQESGGGLVQPGGSLRLSCAASGSIVGNYAMGWYRQAPGKERELVAGIGSEGSRDYAD SVKGRFTISRDTAKRTVYLQMNSLKSEDTAVYICFLYNSGDDYWGQGTQVTVSS | 59 |
| 3HCE44 | QVQLQESGGGSVQAGGSLRLSCAASGSIFSINSMGWHRHAPGKQRELVAAKASDGSTNYAG PVRGRFTITSDDAKNTVYLQMNNLKPEDTAVYYCFLYANNIPYWAKGTQVTVSS | 63 |
| 2HCE174 | QVQLQESGGGSVQAGGSLRLSCAASGSIFSINSMGWHRHAPGKQRELVAAKASDGSTNYAG PVRGRFTITSDDAKNTVYLQMNSLKPEDTAVYYCFLYANNIPYWAKGTQVTVSS | 64 |
| 2HCE167 | QVQLQESGGGLVQAGGSLRLSCAASGRTFSSYAMGWLRQAPGKEREFVAVISGSGYSASYR DSVKGRFTISRDNSKNTVFLQMNSLKPEDTAVYYCAARNERGASSSYDYWGQGTQVTVSS | 68 |
| 3HCE18 | QVQLQESGGGLVQAGGSLRLSCAASGSIFSIITMGWYRQAPGKQRGELVAAITSGGSTSYA DSVKGRFAISRDSAKNTAYLQMNSLKPEDTAVYYCNAHVRDYSGSAYYTGQGTQVTVSS | 70 |
| 2HCE117 | QVQLQESGGGLVQPGGSLRLSCAASGFTFSSYAMSWVRQAPGKGLEWVSDINSGGGSTYYA DSVKGRFTISRDNAKNTLYLQMDSLKPEDTAVYYCATPFEIGSWGQGTQVTVSS | 72 |

TABLE 2-continued

Exemplary anti-DLL3 VHH amino acid sequences

| Construct ID | Sequence | SEQ ID |
|---|---|---|
| 3HCE87 | QVQLQESGGGLVQAGGSLRLSCAASGFIFDDYIIGWFRQAPGKEREFVAAISWSGSATAYA DSVKGRFTISRDNAKNTLYLQMNTLKPEDTAVYYCAASSRGPYNSGSSYDYWGQGTQVTVS S | 76 |
| Anti-DLL3-1 | QIQLVQSGPELKKPGESVKISCKASGYTFTDYAMHWVKQAPGKGLKWMGWINTYTGKPTYA DDFKGRFVLSLEASASTSTLQISDLRNEDTAIYFCSRERGYYDYSRSDWGQGTLVTVSS | 80 |

In some embodiments, the present disclosure provides a VHH sdAb that specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 4. In some embodiments, the present disclosure provides a VHH sdAb that specifically binds to DLL3 and comprises or consists of SEQ ID NO: 4.

In some embodiments, the present disclosure provides a VHH sdAb that specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 5. In some embodiments, the present disclosure provides a VHH sdAb that specifically binds to DLL3 and comprises or consists of SEQ ID NO: 5.

In some embodiments, the present disclosure provides a VHH sdAb that specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 9. In some embodiments, the present disclosure provides a VHH sdAb that specifically binds to DLL3 and comprises or consists of SEQ ID NO: 9.

In some embodiments, the present disclosure provides a VHH sdAb that specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 13. In some embodiments, the present disclosure provides a VHH sdAb that specifically binds to DLL3 and comprises or consists of SEQ ID NO: 13.

In some embodiments, the present disclosure provides a VHH sdAb that specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 17. In some embodiments, the present disclosure provides a VHH sdAb that specifically binds to DLL3 and comprises or consists of SEQ ID NO: 17.

In some embodiments, the present disclosure provides a VHH sdAb that specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 21. In some embodiments, the present disclosure provides a VHH sdAb that specifically binds to DLL3 and comprises or consists of SEQ ID NO: 21.

In some embodiments, the present disclosure provides a VHH sdAb that specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 25. In some embodiments, the present disclosure provides a VHH sdAb that specifically binds to DLL3 and comprises or consists of SEQ ID NO: 25.

In some embodiments, the present disclosure provides a VHH sdAb that specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 29. In some embodiments, the present disclosure provides a VHH sdAb that specifically binds to DLL3 and comprises or consists of SEQ ID NO: 29.

In some embodiments, the present disclosure provides a VHH sdAb that specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 32. In some embodiments, the present disclosure provides a VHH sdAb that specifically binds to DLL3 and comprises or consists of SEQ ID NO: 32.

In some embodiments, the present disclosure provides a VHH sdAb that specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 35. In some embodiments, the present disclosure provides a VHH sdAb that specifically binds to DLL3 and comprises or consists of SEQ ID NO: 35.

In some embodiments, the present disclosure provides a VHH sdAb that specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 38. In some embodiments, the present disclosure provides a VHH sdAb that specifically binds to DLL3 and comprises or consists of SEQ ID NO: 38.

In some embodiments, the present disclosure provides a VHH sdAb that specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 42. In some embodiments, the present disclosure provides a VHH sdAb that specifically binds to DLL3 and comprises or consists of SEQ ID NO: 42.

In some embodiments, the present disclosure provides a VHH sdAb that specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 45. In some embodiments, the present disclosure provides a VHH sdAb that specifically binds to DLL3 and comprises or consists of SEQ ID NO: 45.

In some embodiments, the present disclosure provides a VHH sdAb that specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 49. In some embodiments, the present disclosure provides a VHH sdAb that specifically binds to DLL3 and comprises or consists of SEQ ID NO: 49.

In some embodiments, the present disclosure provides a VHH sdAb that specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 55. In some embodiments, the present disclosure provides a VHH sdAb that specifically binds to DLL3 and comprises or consists of SEQ ID NO: 55.

In some embodiments, the present disclosure provides a VHH sdAb that specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 59. In some embodiments, the present disclosure provides a VHH sdAb that specifically binds to DLL3 and comprises or consists of SEQ ID NO: 59.

In some embodiments, the present disclosure provides a VHH sdAb that specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 63. In some embodiments, the present disclosure provides a VHH sdAb that specifically binds to DLL3 and comprises or consists of SEQ ID NO: 63.

In some embodiments, the present disclosure provides a VHH sdAb that specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 64. In some embodiments, the present disclosure provides a VHH sdAb that specifically binds to DLL3 and comprises or consists of SEQ ID NO: 64.

In some embodiments, the present disclosure provides a VHH sdAb that specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 68. In some embodiments, the present disclosure provides a VHH sdAb that specifically binds to DLL3 and comprises or consists of SEQ ID NO: 68.

In some embodiments, the present disclosure provides a VHH sdAb that specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 70. In some embodiments, the present disclosure provides a VHH sdAb that specifically binds to DLL3 and comprises or consists of SEQ ID NO: 70.

In some embodiments, the present disclosure provides a VHH sdAb that specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 72. In some embodiments, the present disclosure provides a VHH sdAb that specifically binds to DLL3 and comprises or consists of SEQ ID NO: 72.

In some embodiments, the present disclosure provides a VHH sdAb that specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 76. In some embodiments, the present disclosure provides a VHH sdAb that specifically binds to DLL3 and comprises or consists of SEQ ID NO: 76.

In some embodiments, the VHH sdAb described herein are humanized. Humanized antibodies and antigen-binding fragments thereof (e.g., VHHs) have the same or similar binding specificity and affinity as a mouse or other nonhuman antibody that provides the starting material for construction of the humanized binding construct. In some embodiments, the humanized antibodies and antigen-binding fragments thereof comprise a human framework region sequence. In some embodiments, the human framework region sequence comprises or consists of an FR1 sequence according to SEQ ID NO: 745, an FR2 sequence according to any one of SEQ ID NO: 746-747, an FR3 sequence according to any one of SEQ ID NO: 748-752, and an FR4 sequence according to SEQ ID NO: 753, or a polypeptide sequence having at least 80%, at least 85%, at least 90%, at least 95%, at least 97%, at least 98%, or at least 99% identity to any one of the FR1/FR2/FR3/FR4 combinations described herein.

In some embodiments, the VHH sdAbs described herein comprise a human framework region sequence and a CDR1, a CDR2, and a CDR3, wherein the CDR1 comprises an amino acid sequence selected from SEQ ID NOs: 1, 6, 10, 14, 18, 22, 26, 30, 33, 36, 39, 46, 52, 60, 65, 69, 73, 77, and 83, the CDR2 comprises an amino acid sequence selected from SEQ ID NOs: 2, 7, 11, 15, 19, 23, 27, 40, 43, 47, 53, 61, 66, 74, 78, 81, and 82, and the CDR3 comprises an amino acid sequence selected from SEQ ID NOs: 3, 8, 12, 16, 20, 24, 28, 31, 34, 37, 41, 44, 48, 54, 62, 67, 71, 75, 79, and 84. Exemplary humanized VHH sdAb amino acid sequences are provided in Table 3 below.

TABLE 3

Humanized Anti-DLL3 VHH Sequences

| Construct ID | Sequence | SEQ ID |
|---|---|---|
| 2HCE27 14.1 | EVQLVESGGGLVQPGGSLRLSCAASGRTFRSYAMGWFRQAPGKEREFIAVIIMSDGSTSYA DSVKGRFTISRDNAKNTLYLQMNSLKPEDTAVYYCAARRDYFTGVYDYWGQGTLVTVSS | 50 |
| 2HCE27 14.2 | EVQLVESGGGLVQPGGSLRLSCAASGRTFRSYAMGWFRQAPGKEREFIAVIIMSDGSTSYA DSVKGRFTISRDNAKNTLYLQMNSLRPEDTAVYYCAARRDYFTGVYDYWGQGTLVTVSS | 51 |
| 3HCE56 15.1 | EVQLVESGGGLVQPGGSLRLSCAASGRTFSVDAMGWLRQAPGKEREFVVVIDWTGGSTAYA DSVKGRFTISRDNARNTVYLQMNNLKPEDTGVYYCAARERSRTAYDYWGQGTLVTVSS | 56 |
| 3HCE56 15.2 | EVQLVESGGGLVQPGGSLRLSCAASGRTFSVDAMGWLRQAPGKEREFVVVIDWTGGSTAYA DSVKGRFTISRDNARNTVYLQMNSLRPEDTAVYYCAARERSRTAYDYWGQGTLVTVSS | 57 |
| 3HCE56 15.3 | EVQLVESGGGLVQPGGSLRLSCAASGRTFSVDAMGWLRQAPGKEREFVVVIDWTGGSTAYA DSVKGRFTISRDNAKNTVYLQMNSLRPEDTAVYYCAARERSRTAYDYWGQGTLVTVSS | 58 |

In some embodiments, the humanized VHH sdAb specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 50. In some embodiments, the present disclosure provides a VHH sdAb that specifically binds to DLL3 and comprises or consists of SEQ ID NO: 50.

In some embodiments, the humanized VHH sdAb specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 51. In some embodiments, the present disclosure provides a VHH sdAb that specifically binds to DLL3 and comprises or consists of SEQ ID NO: 51.

In some embodiments, the humanized VHH sdAb specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 56. In some embodiments, the present disclosure provides a VHH sdAb that specifically binds to DLL3 and comprises or consists of SEQ ID NO: 56.

In some embodiments, the humanized VHH sdAb specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 57. In some embodiments, the present disclosure provides a VHH sdAb that specifically binds to DLL3 and comprises or consists of SEQ ID NO: 57.

In some embodiments, the humanized VHH sdAb specifically binds to DLL3 and comprises an amino acid sequence that is at least 85%, at least 90%, at least 91%, at least 92%, at least 93%, at least 94%, at least 95%, at least 96%, at least 97%, at least 98%, at least 99%, at least 99.5%, or 100% identical to SEQ ID NO: 58. In some embodiments, the present disclosure provides a VHH sdAb that specifically binds to DLL3 and comprises or consists of SEQ ID NO: 58.

In some embodiments, the present disclosure provides bispecific binding constructs comprising at least a first binding domain and a second binding domain, wherein the first binding domain binds to a first antigen or target (e.g., DLL3), and the second binding domain binds to a second antigen or target. In some embodiments, a bispecific binding construct of the disclosure may be a bispecific antibody of the disclosure.

Bispecific binding constructs of the disclosure may include, but are not limited to, formats such as DVD-Ig, mAb2, FIT-Ig, mAb-dAb, dock and lock, Fab-arm exchange, SEEDbody, Triomab, LUZ-Y, Fcab, κλ-body, orthogonal Fab, scDiabody-Fc, diabody-Fc, tandem scFv-Fc, Fab-scFv-Fc, Fab-scFv, intrabody, BITE, diabody, DART, TandAb, scDiabody, scDiabody-CH3, Diabody-CH3, Triple body, Miniantibody, minibody, TriBi minibody, scFv-CH3 KIH, scFv-CH-CL-scFv, F(ab')2-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, Duta-Mab, IgG(H)-scFv, scFv-(H)IgG, IgG(L)-scFv, scFv-(L) IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig and zybody. In some embodiments, at least one Fab or scFv in any one of the bispecific formats as described in this paragraph is replaced by a VHH (e.g., an anti-DLL3 VHH of the present disclosure).

In some embodiments, the anti-DLL3 sdAbs described herein are linked or directly fused to a second domain to form a bispecific binding construct. In some embodiments, such binding constructs comprise, from N- to C-terminus, anti-DLL3 sdAb—second domain, second domain—anti-DLL3 sdAb, anti-DLL3 sdAb—linker—second domain, or second domain—linker—anti-DLL3 sdAb.

As used herein, the term "linker" generally refers to a short polypeptide sequence connecting two sub-domains of a polypeptide. Non-limiting examples of linkers include flexible linkers comprising glycine-serine repeats, and linkers derived from (a) an interdomain region of a transmembrane protein (e.g., a type I transmembrane protein); (b) a stalk region of a type II C-lectin; or (c) an immunoglobulin hinge. In some embodiments, a linker provides a spacer function compatible with interaction of the two sub-binding domains so that the resulting polypeptide retains a specific binding affinity to the same target molecule as an antibody that comprises the same light and heavy chain variable regions. In certain embodiments, a linker is comprised of five to about 35 amino acids, for instance, about 15 to about 25 amino acids. Exemplary linkers are shown in Table 4.

TABLE 4

Exemplary Linker Sequences

| Linker | Amino Acid Sequence | SEQ ID |
|---|---|---|
| STD1 | NYGGGGSGGGGSGGGGSGNS | 85 |
| STD2 | NYGGGGSGGGGSGGGGSGNYGGGGSGGGGSGGGGSGNS | 86 |
| H1 | NS | 87 |
| H2 | GGGGSGNS | 88 |
| H3 | NYGGGGSGNS | 89 |
| H4 | GGGGSGGGGSGNS | 90 |
| H5 | NYGGGGSGGGGSGNS | 91 |
| H6 | GGGGSGGGGSGGGGSGNS | 92 |
| H7 | GCPPCPNS | 93 |
| Gly₄Ser | GGGGS | 94 |
| (G₄S)₃ | GGGGSGGGGSGGGGS | 95 |
| H105 | SGGGGSGGGGSGGGGS | 96 |
| (G₄S)₄ | GGGGSGGGGSGGGGSGGGGS | 97 |
| H75 (NKG2A quadruple mutant) | QRHNNSSLNTGTQMAGHSPNS | 98 |
| H83 (NKG2A derived) | SSLNTGTQMAGHSPNS | 99 |
| H106 (NKG2A derived) | QRHNNSSLNTGTQMAGHS | 100 |
| H81 (NKG2D derived) | EVQIPLTESYSPNS | 101 |
| H91 (NKG2D derived) | NSLANQEVQIPLTESYSPNS | 102 |
| H94 | SGGGGSGGGGSGGGGSPNS | 103 |
| H111 | SGGGGSGGGGSGGGGSPGS | 104 |
| H113 | SGGGGSGGGGSGGGGSPAS | 105 |
| H114 | SGGGGSGGGGSGGGGSPS | 106 |
| H115 | SGGGGSGGGGSGGGGSPSS | 107 |
| H116 | SGSETPGTSESATPES | 108 |
| H117 | GGGGSGGGGSGGGGS | 109 |
| H118 | AHHSEDPSSKAPKAP | 110 |
| H119 | SPSTPPTPSPSTPPAS | 111 |

In some embodiments, the VHH sdAbs described herein are linked or directly fused to a second binding domain. Therefore, in some embodiments, the present disclosure provides bispecific binding constructs comprising an anti-DLL3 sdAb described herein and a second binding domain. In some embodiments, the second binding domain is an antigen binding domain. In some embodiments, the antigen binding domain is selected from an antigen binding domain that specifically binds to CD3, an antigen binding domain that specifically binds to human serum albumin (HSA). In some embodiments, the second binding domain is an Fc domain. In some embodiments, the bispecific binding constructs specifically bind to DLL3 and CD3. In some embodiments, the bispecific binding constructs comprise a VHH that specifically binds to DLL3 and an scFv that specifically binds to CD3. In some embodiments, the bispecific binding constructs comprise a VHH that specifically binds to DLL3 and a VH-VL pairing that specifically binds to CD3. In some embodiments, the bispecific binding constructs comprise an Fc domain. In some embodiments, the bispecific binding constructs comprise an Fc domain having a knobs-in-holes (KIH) format. In some embodiments, the Fc KIH format comprise an amino acid substitution when compared to a wild type Fc amino acid sequence. In some embodiments, the CD3 antigen binding domain comprises one or more CDRs selected from those in Table 6.

In some embodiments, the bispecific binding constructs described herein comprise an anti-DLL3 sdAb linked or directly fused to a second antigen binding domain. In some embodiments, the second antigen binding domain specifically binds to human serum albumin (HSA) or CD3. In some embodiments, the anti-DLL3 single domain antibody is a VHH antibody domain and the second antigen-binding domain is an scFv. Such embodiments are also referred to as light T-cell engagers (LiTEs) (See e.g., Molgaard et al., Cancer Immunol Immunother. 2018 August; 67(8):1251-1260). In some embodiments, the HSA antigen binding domain comprises one or more CDRs selected from those in Table 5. In some embodiments, the CD3 antigen binding domain comprises one or more CDRs selected from those in Table 6

In some embodiments, the bispecific binding constructs described herein comprise an anti-DLL3 sdAb linked or directly fused to a second antigen-specific binding domain that specifically binds to a cell surface protein found on natural killer (NK) cells (e.g., CD16 or NKp46). In some embodiments, the anti-DLL3 single domain antibody is a VHH antibody domain and the second antigen-binding domain is an scFv. NKp46, also known as CD335, belongs to the natural cytotoxicity receptor (NCR) family and is a glycoprotein with 2 Ig-like domains and a short cytoplasmic tail. CD16, also known as FcγRIII, is a cluster of differentiation molecule found on the surface of natural killer cells, neutrophils, monocytes, and macrophages. In some embodiments, the CD16 antigen binding domain comprises one or more CDRs selected from those in Table 7.

In some embodiments, the present disclosure provides trispecific binding constructs that specifically bind DLL3. Trispecific binding constructs comprise at least a first binding domain, a second binding domain, and a third binding domain, wherein at least one of the binding domains is an antigen binding domain that specifically binds to DLL3. In some embodiments, the first, second, and third binding domains are antigen binding domains, wherein the first antigen binding domain specifically binds to DLL3 the second binding domain binds to a second antigen or target, and the third binding domain binds to a third antigen or target. Each antigen binding domain may be a VHH, an scFv, an Fab, or other antigen binding domain format, and the three binding domains may be of different format (e.g., VHH or scFv or Fab). In some embodiments, the trispecific binding construct comprises two arms with each arm comprising two different VHH/scFv/Fab linked in tandem and each VHH/scFv/Fab specifically binds to a distinct antigen, an IgG constant region that links to the arms at one end, and a third VHH/scFv/Fab specifically binding to a third antigen linked to the other end of the IgG constant domain. In some embodiments, the trispecific binding construct comprises two arms and an IgG constant region that links to the arms, one of the arm comprises two different VHH/scFv/Fab linked in tandem and each VHH/scFv/Fab specifically binds to a distinct antigen, and the other arm comprises a third VHH/scFv/Fab that specifically binds to a third antigen. In some embodiments, three different VHH/scFv/Fab are linked in tandem, and each VHH/scFv/Fab specifically binds a distinct antigen. In some embodiments, one of the VHH/scFv/Fab of the trispecific binding construct is replaced by an Fc domain. Exemplary formats of trispecific antibodies include those disclosed in Runcie et al., Mol Med. 2018 September s24; 24(1):50; Wu et al., Nature Cancer 2020, volume 1, p86-98; Wu and Demarest, Methods. 2019 Feb. 1; 154:3-9. In some embodiments, at least one binding domain of the trispecific binding construct is an anti-DLL3 VHH of the present disclosure.

In some embodiments, the trispecific binding constructs comprise a first antigen binding domain comprising an anti-DLL3 sdAb, a second binding domain, and a third binding domain. In some embodiments, the second binding domain and/or the third binding domain of the trispecific binding construct are antigen binding domains comprising a VHH or an scFv. In some embodiments, the second binding domain of the trispecific binding construct is an antigen binding domain that specifically binds to human serum albumin (HSA). In some embodiments, the third binding domain is an antigen binding domain that specifically binds to CD3, CD16, or NKp46. In some embodiments, the second binding domain of the trispecific binding construct comprises an Fc domain that binds to Fc receptors. In some embodiments, the trispecific binding constructs comprise three antigen binding domains specifically binding, individually, to DLL3, HSA and CD3. In some embodiments, the trispecific binding construct comprises a VHH that specifically binds to DLL3, a VHH that specifically binds to HSA and an scFv that specifically binds to CD3. In some embodiments, the trispecific binding constructs comprise a first antigen binding domain that specifically binds to DLL3, a second antigen binding domain that specifically binds to CD3, and a third binding domain comprising an Fc domain. In some embodiments, the trispecific binding construct comprises a VHH that specifically binds to DLL3, an Fc domain, and an scFv or a VH-VL pairing that specifically binds to CD3. In some embodiments, the Fc domain comprises a knobs-in-holes (KIH) format or at least one amino acid substitution compared to a wild type Fc that confers a KIH format.

In some embodiments, the trispecific binding construct comprises a VHH that specifically binds to DLL3, a second binding domain that specifically binds to HSA, and a third binding domain that specifically binds to CD3.

Exemplary HSA antigen binding domains suitable for use according to the present disclosure include, but are not limited to, those comprising CDR1, CDR2 and CDR3 sequences as shown in Table 5 or described in U.S. Pat. No. 8,188,223. In some embodiments, the HSA binding domain of the disclosure comprises a CDR1, a CDR2, and a CDR3 according to Table 5.

TABLE 5

| | | | Exemplary anti-HSA CDR sequences | | | |
|---|---|---|---|---|---|---|
| | CDR1 | SEQ ID: | CDR2 | SEQ ID: | CDR3 | SEQ ID: |
| HSA-1 | SFGMS | 113 | SISGSGSDTLYADSVKG | 114 | GGSLSR | 115 |
| HSA-2 | LNLMG | 116 | TITVGDSTNYADSVKG | 117 | RRTWHSEL | 118 |
| HSA-3 | INLLG | 119 | TITVGDSTSYADSVKG | 120 | RRTWHSEL | 121 |

TABLE 5-continued

Exemplary anti-HSA CDR sequences

| | CDR1 | SEQ ID: | CDR2 | SEQ ID: | CDR3 | SEQ ID: |
|---|---|---|---|---|---|---|
| HSA-4 | SFGMS | 122 | SINGRGDDTRYADSVKG | 123 | GRSVSRS | 124 |
| HSA-5 | SFGMS | 125 | AISADSSDKRYADSVKG | 126 | GRGSP | 127 |
| HSA-6 | SFGMS | 128 | AISADSSDKRYADSVKG | 129 | GRGSP | 130 |
| HSA-7 | NYWMY | 131 | RISTGGGYSYYADSVKG | 132 | DREAQVDTLDFDY | 133 |

Exemplary CD3 antigen binding domain suitable for use according to the present disclosure include, but are not limited to, those described in WO 2008/119567, U.S. Pat. Pub. Nos: US2016/0176973, US2013/0156770, US2020/0071405, US2019/0040135, US2018/0355038, U.S. Pat. No. 10,174,124. Exemplary heavy chain variable domain (CD3-VH) and light chain variable domain (CD3-VL)

CDRs that specifically bind to CD3 are shown in Table 6. In some embodiments, the CD3 binding domain of the disclosure comprises a heavy chain variable domain (CD3-VH) comprising a CDR1, a CDR2, and a CDR3 according to Table 6, and/or a light chain variable domain (CD3-VL) comprising a CDR1, a CDR2, and a CDR3 according to Table 6.

TABLE 6

Exemplary anti-CD3 CDR sequences

| | CDR1 | SEQ ID: | CDR2 | SEQ ID: | CDR3 | SEQ ID: |
|---|---|---|---|---|---|---|
| CD3-VL-1 | GSSTGAVTSGYYPN | 474 | GTKFLAP | 475 | ALWYSNRWV | 476 |
| CD3-VL-2 | RSSTGAVTSGYYPN | 477 | ATDMRPS | 478 | ALWYSNRWV | 479 |
| CD3-VL-3 | GSSTGAVTSGNYPN | 480 | GTKFLAP | 481 | VLWYSNRWV | 482 |
| CD3-VH-1 | IYAMN | 483 | RIRSKYNNYATYYADSVKS | 484 | HGNFGNSYVSFFAY | 485 |
| CD3-VH-2 | KYAMN | 486 | RIRSKYNNYATYYADSVKD | 487 | HGNFGNSYISYWAY | 488 |
| CD3-VH-3 | SYAMN | 489 | RIRSKYNNYATYYADSVKG | 490 | HGNFGNSYLSFWAY | 491 |
| CD3-VH-4 | RYAMN | 492 | RIRSKYNNYATYYADSVKG | 493 | HGNFGNSYLSYFAY | 494 |
| CD3-VH-5 | VYAMN | 495 | RIRSKYNNYATYYADSVKK | 496 | HGNFGNSYLSWWA | 497 |
| CD3-VH-6 | KYAMN | 498 | RIRSKYNNYATYYADSVKS | 499 | HGNFGNSYTSYYAY | 500 |
| CD3-VH-7 | GYAMN | 501 | RIRSKYNNYATYYADSVKE | 502 | HRNFGNSYLSWFAY | 503 |
| CD3-VH-8 | VYAMN | 504 | RIRSKYNNYATYYADSVKK | 505 | HGNFGNSYISWWAY | 506 |
| CD3-VH-9 | SYAMN | 507 | RIRSKYNNYATYYADSVKG | 508 | HGNFGNSYVSWWA | 509 |
| CD3-VH-10 | KYAMN | 510 | RIRSKYNNYATYYADSVKD | 511 | HGNFGNSYISYWAY | 512 |
| CD3-VL-4 | SSTGAVTTSNYAN | 513 | GTNKRA | 514 | LWYSNLWV | 515 |
| CD3-VH-11 | TYAMN | 516 | IRSKYNNYATYYADSVKD | 517 | HGNFGNSYVSWFAY | 518 |
| CD3-VH-12 | GFTFDDYS | 519 | ISWNSGSK | 520 | AKYGSGYGKFYHYGLDV | 521 |

TABLE 6-continued

Exemplary anti-CD3 CDR sequences

| | CDR1 | SEQ ID: | CDR2 | SEQ ID: | CDR3 | SEQ ID: |
|---|---|---|---|---|---|---|
| CD3-VH-13 | GFTFDDYA | 522 | ISWNSGSI | 523 | AKDGSGYGYFYYY GMDV | 524 |
| CD3-VH-14 | GFTFDDYS | 525 | ISWNSGSI | 526 | AKDGSGYGYFYYY GMDV | 527 |
| CD3-VH-15 | GFTFDDYA | 528 | ISWNSGSI | 529 | AKDGSGYGKFYYY GMDV | 530 |
| CD3-VH-16 | GFTFDDYS | 531 | ISWNSGSI | 532 | AKDGSGYGKFYYY GMDV | 533 |
| CD3-VH-17 | GFTFDDYS | 534 | ISWNSGSI | 535 | AKYGSGYGKFYHY GLDV | 536 |
| CD3-VH-18 | GFTFDDYS | 537 | ISWNSGSK | 538 | AKDGSGYGKFYHY GLDV | 539 |
| CD3-VH-19 | GFTFDDYS | 540 | ISWNSGSK | 541 | AKYGSGYGKFYYY GLDV | 542 |
| CD3-VH-20 | GFTFDDYS | 543 | ISWNSGSK | 544 | AKYGSGYGKFYHY GMDV | 545 |
| CD3-VH-21 | GFTFDDYS | 546 | ISWNSGSI | 547 | AKDGSGYGKFYHY GLDV | 548 |
| CD3-VH-22 | GFTFDDYS | 549 | ISWNSGSI | 550 | AKYGSGYGKFYYY GLDV | 551 |
| CD3-VH-23 | GFTFDDYS | 552 | ISWNSGSI | 553 | AKYGSGYGKFYHY GMDV | 554 |
| CD3-VH-24 | GFTFDDYS | 555 | ISWNSGSK | 556 | AKDGSGYGKFYYY GLDV | 557 |
| CD3-VH-25 | GFTFDDYS | 558 | ISWNSGSK | 559 | AKDGSGYGKFYHY GMDV | 560 |
| CD3-VH-26 | GFTFDDYS | 561 | ISWNSGSK | 562 | AKYGSGYGKFYYY GMDV | 563 |
| CD3-VH-27 | GFTFDDYS | 564 | ISWNSGSI | 565 | AKDGSGYGKFYYY GLDV | 566 |
| CD3-VH-28 | GFTFDDYS | 567 | ISWNSGSI | 568 | AKDGSGYGKFYHY GMDV | 569 |
| CD3-VH-29 | GFTFDDYS | 570 | ISWNSGSI | 571 | AKYGSGYGKFYYY GMDV | 572 |
| CD3-VH-30 | GFTFDDYS | 573 | ISWNSGSK | 574 | AKDGSGYGKFYYY GMDV | 575 |
| CD3-VH-31 | GFTFDDYS | 576 | ISWNSGSK | 577 | AKYGSGYGKFYHY GLDV | 578 |
| CD3-VH-32 | NYYIH | 579 | WIYPGDGNTKYNEKFK G | 580 | DSYSNYYFDY | 581 |
| CD3-VH-n | NYYIH | 579 | WIYPGDGNTKYNEKFK G | 580 | DSYSNYYFDY | 581 |
| | SYYIH | 582 | WIYPENDNTKYNEKFK D | 583 | DGYSRYYFDY | 584 |
| | GYTMN | 585 | LINPYKGVSTYNQKFK D | 586 | DAYSRYYFDY | 587 |
| | TYAMN | 588 | LINPYKGVTTYADSVK G | 589 | TGYSRYYFDY | 590 |
| | NYGMN | 591 | LINPYKGVSTYADSVK G | 592 | DGYSRYAFDY | 593 |
| | SYYIH | 594 | RIRSKYNNYATYYADS VKD | 595 | SGYSRYYFDY | 596 |
| | NYAIH | 597 | WINTNTGKPTYAEEFK G | 598 | DGYSRAYFDY | 599 |

TABLE 6-continued

Exemplary anti-CD3 CDR sequences

| | CDR1 | SEQ ID: | CDR2 | SEQ ID: | CDR3 | SEQ ID: |
|---|---|---|---|---|---|---|
| | GFSLTNYAIH | 600 | WIYPGNVNTKYNEKFKG | 601 | DSYSNYYFDY | 602 |
| | GSAMH | 603 | VIWAGGNTKYNSALMS | 604 | SGYYGDSDWYFDV | 605 |
| | SDYIH | 606 | GVIWAGGNTKYNSALMS | 607 | HGNFGNSYVSWFAY | 608 |
| | SHYLH | 609 | RIRSRANSYATAYAASVKD | 610 | RGDYRYAWFLY | 611 |
| | SYYIH | 612 | WIYFGNVNTKYNEKFKG | 613 | NHDYYFDY | 614 |
| | SYYIH | 615 | WINPGDGNVKYNEKFKD | 616 | EDSSGYVALDY | 617 |
| | NYGMN | 618 | WIFPGSDNTKYNEKFKG | 619 | QMNSLRAEDTAVYYCAREDSSGYVALD | 620 |
| | NYYIH | 621 | WIYPGNVNTKYNEKFKG | 622 | DTMVRGIDY | 623 |
| | SYWMH | 624 | WINTNTGKPTYAEDFKG | 625 | DGGYYFDY | 626 |
| | NYYMH | 627 | WIYPGSDNTKFNDKFKG | 628 | DGAYYFDY | 629 |
| | NYYTH | 630 | NFYPGDLTVNYDEKFKN | 631 | NGNYAMDY | 632 |
| | NYYTH | 633 | WISPGSGSIKYNEKFKG | 634 | NHDYYFDY | 635 |
| | NYYTH | 636 | WIYPGNGNIKYNEKFMG | 637 | RGDYRYAWFTY | 638 |
| | SYWMH | 639 | WIYPGNGNIKYNEKFMG | 640 | DSITNYYFDY | 641 |
| | SYYIH | 642 | WLYPGNGDTRYNEKFKD | 643 | DAYSRYFFDY | 644 |
| | SYWMH | 645 | NSYPGDLNVNYDEKFKN | 646 | DGYSLYFFDF | 647 |
| | SCAIS | 648 | WLYPGDVSTRYNEKFRD | 649 | DSYGSYYFDY | 650 |
| | DYYIH | 651 | NIYPGGEIINYAEKFKT | 652 | DSYGSYYFDY | 653 |
| | | | FMSVTGSAYYANWAKS | 654 | DSYGNYFFDY | 655 |
| | | | LINPYKGVXTYXXXXKX ** | 656 | DAYSRYFFDY | 657 |
| | | | WIYPGDVSTRFNEKFKG | 658 | DSSASYYFDF | 659 |
| | | | | | DTTGNYFFDY | 660 |
| | | | | | VGIGSGLNI | 661 |
| | | | | | XXYSXXXFDY | 662 |
| | | | | | DSYGNYFFDY | 663 |
| CD3-VL-5 | KSSQSLLNSRTRKNYLA | 664 | WASTRES | 665 | TQSFILRT | 666 |
| CD3-VL-n | KSSQSLLNSRTRKNYLA | 664 | WASTRES | 665 | TQSFILRT | 666 |
| | KSSQSLLNSRTRKNYLA | 667 | WTSTRKS | 668 | KQSFILRT | 669 |
| | RASQDIRNYLN | 670 | YTSRLES | 671 | KQSFALRT | 672 |
| | RSSTGAVTTSNYAN | 673 | GTNKRAP | 674 | KASFILRT | 675 |
| | RSSTGAVTTSNYAN | 676 | GTSNRAP | 677 | KQSAILRT | 678 |
| | KSSQSLLNSRTRKNYLA | 679 | WASTRES | 680 | TQSFILRT | 681 |
| | KSSQSLLSGRTRKNYLA | 682 | WASTRES | 683 | QQGNTLPWT | 684 |
| | KSSQSLLSGRTRKNYLA | 685 | WASTRES | 686 | ALWYSNLWV | 687 |
| | KSSQSVLYSSNNKNYLV | 688 | RASTRES | 689 | ALWYSTHFV | 690 |
| | KSSQSLLNSRTRKNYLA | 691 | WASTRES | 692 | KQSYILRT | 693 |
| | KSSQSLLNSRTRKNYLA | 694 | WASTRES | 695 | KQSYYLLT | 696 |
| | KSSQSLLNSRTRKNYLA | 697 | WASTRES | 698 | KQSYYLLT | 699 |
| | KSSQSLLNSRTRKNYLA | 700 | WASTRES | 701 | QQYYSVPWT | 702 |

TABLE 6-continued

Exemplary anti-CD3 CDR sequences

| CDR1 | SEQ ID: | CDR2 | SEQ ID: | CDR3 | SEQ ID: |
|---|---|---|---|---|---|
| RSSTGAVTTSNY AN | 703 | GTSNRAP | 704 | KQSFTLRT | 705 |
| KSSQSLLNIRTR KNCLA | 706 | WASTRYS | 707 | KQSYTLRT | 708 |
| KSSQSLLNSRTR KNYLA | 709 | WASTRES | 710 | KQSYTLRT | 711 |
| KSSQSLLNSRTR KNYLA | 712 | WASTRES | 713 | KQSYILRT | 714 |
| KSSQSLLNSRTR KNYLA | 715 | WASTRES | 716 | ALWYSTHFV | 717 |
| KSSQSLLNSRTR KNYLA | 718 | WASTRES | 719 | TQSYTLRT | 720 |
| KSSQSLLNSRTR KNYLA | 721 | WASTRES | 722 | CQSFILRT | 723 |
| KSSQSLLNSRTR KNYLA | 724 | WASTRES | 725 | KQSFILRT | 726 |
| KSSQSLLNIRTR KNYLA | 727 | WASTRAS | 728 | TQSFILRT | 729 |
| KSSQSLLNSRTR KNYLA | 730 | WASTRES | 731 | KQSFILRT | 732 |
| QASETVYSNNY LA | 733 | GVSTLDS | 734 | KQSFILRT | 735 |
| KSSQSLLNSRTR KNYLA | 736 | WASTRES | 737 | CQSFILRT | 738 |
| | | | | TQSFILRT | 739 |
| | | | | TQSFILRT | 740 |
| | | | | AGYKTSSSYAIA | 741 |
| | | | | XXSXXLRT | 742 |
| | | | | CTQSFILRT | 743 |

** "X" indicates any amino acid can occur in that position.

Exemplary CD16 antigen binding domains suitable for use according to the present disclosure include, but are not limited to, those described in U.S. Pat. No. 9,701,750, U.S. Pat. Pub. No. 2020/0010547, 2008/0145362. Exemplary heavy chain variable domain (CD16-VH) and light chain variable domain (CD16-VL) CDRs that specifically bind to CD16 are shown in Table 7. In some embodiments, the CD16 antigen binding domain of the disclosure comprises a heavy chain variable domain (CD16-VH) comprising a CDR1, a CDR2, and a CDR3 according to Table 7, and/or a light chain variable domain (CD16-VL) comprising a CDR1, a CDR2, and a CDR3 according to Table 7.

TABLE 7

Exemplary anti-CD16 CDR sequences

| | CDR1 | SEQ ID: | CDR2 | SEQ ID: | CDR3 | SEQ ID: |
|---|---|---|---|---|---|---|
| CD16-VH | TSYYMH | 450 | IINPSGGSTSY AQKFQG | 451 | GSAYYYDFADY | 452 |
| CD16-VL-1 | SGDKLEEKYVS | 453 | QDNKRPS | 454 | QVWDNYSVL | 455 |
| CD16-VL-2 | GGNNIESRNVH | 456 | RDNNRPS | 457 | QVWDNYTVL | 458 |
| CD16-VL-3 | GGNNIGSKNVH | 459 | RDSNRPS | 460 | QVWDNYIVL | 461 |
| CD16-VL-4 | EGNNIGSKNVH | 462 | DDSDRPS | 463 | QVWDNYSVL | 464 |
| CD16-VL-5 | GGNNIGSKNVH | 465 | RDSSRPS | 466 | QVWDDYIVV | 467 |
| CD16-VL-6 | GANDIGKRNVH | 468 | QDNKRPS | 469 | QVWDNYSVL | 470 |
| CD16-VL-7 | GGHNIGSKNVH | 471 | QDNKRPS | 472 | QVWDNYSVL | 473 |

Exemplary NKp46 antigen binding domains suitable for use according to the present disclosure include, but are not limited to, Bab281, mIgG1, available commercially from Beckman Coulter, Inc. (Brea, Calif., USA) (see Pessino et al., J Exp Med, 1998, 188(5):953-960 and Sivori et al., Eur J Immunol, 1999, 29:1656-1666, describing chromium release cytotoxicity assays). Another NKp46 binding antibody is 9E2, mIgG1, available commercially from Becton Dickinson (Franklin Lakes, N.J., USA) and Miltenyi Biotec (Bergisch Gladback, Germany) (see Brando et al. (2005) J Leukoc Biol 78:359-371 and El-Sherbiny et al. (2007) Cancer Research 67(18):8444-9). Another anti-NKp46 binding antibody is 195314, mIgG2b, available commercially from R&D Systems, Inc. (Minneapolis, USA) (see Nolte-'t Hoen et al. (2007) Blood 109:670-673). The NKp46 antigen binding domain may comprise variable region or CDR sequences from such Bab281, 9E2 or 195314 antibodies. In some embodiments, the NKp46 antigen binding domain comprises a sequence having at least 85%, at least 90%, at least 95%, at least 98%, at least 99%, or 100% identity to STGSEVQLQQSGPELVKPGASVKISCK-TSGYTFTEYTMHWVKQSHGKSLEWIGGIS-PNIGGTSY NQKFKGKATLTVDKSSSTAYMELRSLT-SEDSAVYYCARRGGSFDYWGQGTTLTV SSVEGGSGGS GGSGGSGGVDDI-VMTQSPATLSVTPGDRVSLSCRASQSIS-DYLHWYQQKSHESPRLLIKYASQS ISGIPSRFSGSGSGSDFTLSINSVE-PEDVGVYYCQNGHSFPLTFGAGTKLELK (SEQ ID NO: 744). In some embodiments, the NKp46 antigen binding domain comprises CDR1, CDR2 and CDR3 sequences that are identical to those in SEQ ID NO: 744. See, U.S. Pat. No. 10,344,087 and U.S. Pat Appl. No. 2017/0210802.

In some embodiments, the bispecific or trispecific binding constructs of the disclosure comprise an anti-DLL3 sdAb linked or directly fused to an antibody Fc domain. In some embodiments, the Fc domain is an IgG isotype (e.g. IgG1, IgG2, IgG3, IgG4). In some embodiments, the Fc domain comprises a wild-type IgG amino acid sequence. Such sequences are known in the art, see e.g. Shields et al., J Biol Chem, (2001) 276:9; 6591-6604. In some embodiments, the CH2 or CH3 domain of the Fc domain comprises one or more amino acid mutations that alter the function and/or stability of the antibody. For example, in some embodiments, the Fc domain of an anti-DLL3 antibody described herein lacks or has minimal effector functions while retaining the ability to bind some Fc receptors such as the neonatal Fc receptor (FcRn) and retaining a relatively long half-life in vivo. In some embodiments, the Fc domain is engineered to increase binding to Fcγ receptors. In some embodiments, the Fc domain has enhanced engagement of effector immune cells (e.g., Natural Killer cells, macrophages) and/or increased Fc-mediated effector functions (e.g., ADCC). In some embodiments, the Fc domain is afucosylated. In some embodiments, afucosylation of Fc domain can be achieved by engineering of the expression cell line (e.g., CHO DG44) with strategies including, but not limited to, inactivation of the FUT8 gene, loss-of-function mutations in the Golgi GDP-fucose transporter (GFT) gene (Slc35c1), and overexpression of 4-b-N-acetylglucosaminyltransferase (GnT-III). In some embodiments, afucosylation of Fc domain can be achieved by amino acid mutation in the Fc domain. For IgG1, such mutations include, but are not limited to, one or more mutations selected from T256A, K290A, S298A, E333A, and K334A. In some embodiments, the Fc variant comprises a single S239D or I332E mutation, a double S239D/I332E mutations, or a triple S239D/I332E/A330L mutations. In some embodiments, the engineered Fc domain is an Fc variant with S239D/I332E mutations. See for example Pereira et al., MAbs. 2018 July; 10(5): 693-711; Horton et al., Cancer Res. 2008 Oct. 1; 68(19):8049-57. In some embodiments, such binding constructs with afucosylated Fc domain display enhanced ADCC activity. In some embodiments, the Fc variant of the bispecific or trispecific binding construct does not result in, or substantially reduces the induction of, antibody-dependent cell-mediated cytotoxicity (ADCC), antibody-dependent cell-mediated phagocytosis (ADCP), complement activation, and/or complement-dependent cytotoxicity (CDC). Such mutations are well known in the art, see for example Shields et al., J Biol Chem, (2001) 276:9; 6591-6604; Arduin et al., Mol Immunol (2015) 63:2; 456-463; Vafa et al., Methods (2014) 65:1; 114-126. Unless otherwise noted, the numbering of the residues in an IgG heavy chain is that of the EU index as in Kabat et al., Sequences of Proteins of Immunological Interest, 5th Ed. Public Health Service, National Institutes of Health, Bethesda, MD (1991), expressly incorporated herein by references. The "EU index as in Kabat" refers to the numbering of the human IgG1 EU antibody.

In some embodiments, the present disclosure provides an anti-DLL3 antibody comprising a heavy chain variable region (VH) and light chain variable region (VL), wherein the VH comprises a comprises a heavy chain complementarity determining region (CDR) 1 (HCDR1), an HCDR2, and an HCDR3 selected from those listed in Table 1, and wherein the VL comprises a light chain complementarity determining region (CDR) 1 (LCDR1), an LCDR2, and an LCDR3 selected from those known in the art. Light chain CDRs that specifically bind to DLL3 are known in the art, for example, see WO 2019/222283, WO 2019/222282, WO 2019/222278, U.S. Pat. Pub. Nos. 2019/0046656, 2019/0263907, 2019/0270817, and U.S. Pat. No. 10,308,721. Exemplary light chain variable domain (DLL3-VL) LCDRs that specifically bind to DLL3 are shown in Table 8. In some embodiments, the DLL3 binding domain of the disclosure comprises a light chain variable domain (DLL3-VL) comprising an LCDR1, an LCDR2, and an LCDR3 according to Table 8.

TABLE 8

| | | | | | | |
|---|---|---|---|---|---|---|
| Exemplary anti-DLL3 light chain CDR sequences | | | | | | |
| | LCDR1 | SEQ ID NO: | LCDR2 | SEQ ID NO: | LCDR3 | SEQ ID NO: |
| DLL3-VL-1 | RASQRVNNNYLA | 134 | GASSRAT | 135 | QQYDRSPLT | 136 |
| DLL3-VL-2 | RASQSVNKNYLA | 137 | GASSRAT | 138 | QQYDRSPLT | 139 |

TABLE 8-continued

Exemplary anti-DLL3 light chain CDR sequences

| | LCDR1 | SEQ ID NO: | LCDR2 | SEQ ID NO: | LCDR3 | SEQ ID NO: |
|---|---|---|---|---|---|---|
| DLL3-VL-3 | RASQSVSRGYLA | 140 | GASSRAT | 141 | QQYDTSPIT | 142 |
| DLL3-VL-4 | RSSQSLLHSNGYNYLD | 143 | LGSNRAS | 144 | MQALQTPFT | 145 |
| DLL3-VL-5 | RASQSISSYLN | 146 | AASSLQS | 147 | QQSFTTPLT | 148 |
| DLL3-VL-6 | SPGERATLSCK | 149 | YASNRY | 150 | QQDYTSPWT | 151 |
| DLL3-VL-7 | RASQSVSSSYLA | 152 | GASTRAT | 153 | QQYGTSPLT | 154 |
| DLL3-VL-8 | QASQDIRNYLN | 155 | DASNLET | 156 | QHYDNLPLTF | 157 |
| DLL3-VL-9 | RASQGIRNYLG | 158 | AASSLQS | 159 | LQHDSDLRTF | 160 |
| DLL3-VL-10 | TASSSVSSSY | 161 | STSNLAS | 162 | HQYHRSPFTFGAGTKLKIR | 163 |
| DLL3-VL-11 | RASQDISNY | 164 | YTSRLHS | 165 | QQGDMLPWTFGGGTKLEIK | 166 |
| DLL3-VL-12 | SASSSVSY | 167 | DTSKLAS | 168 | QQWTRNPLTFGAGTKLELK | 169 |
| DLL3-VL-13 | KSSQSVLVYSSNQKNY | 170 | WASTRES | 171 | HQYLSSWTFGGGTKLEIK | 172 |
| DLL3-VL-14 | QATQDIVKN | 173 | YAIELAE | 174 | LQFYEFPFTFGAGTKLELK | 175 |
| DLL3-VL-15 | TASSSVSSSY | 176 | STSNLAS | 162 | HQYHRSPFTFGSGTKLEIK | 178 |
| DLL3-VL-16 | KSSQSLSDSDGKTY | 177 | LVSKLDS | 208 | WQGKHFPWTFGGGTKLEIK | 179 |
| DLL3-VL-17 | SASSSVSY | 180 | LTSNLAS | 181 | QQWRSNPFTFGSGTKLEIK | 182 |
| DLL3-VL-18 | RASENIYYN | 183 | TANSLED | 184 | KQAYDVPPTFGGGTKLEIK | 185 |
| DLL3-VL-19 | RASQNIINY | 186 | YTSRLHS | 187 | QQYSERPYTFGGGTKLEIKR | 188 |
| DLL3-VL-20 | KASQDIHKY | 189 | YTSTLQP | 190 | LQYNNLYTFGGGTKLEIKR | 191 |
| DLL3-VL-21 | QATQDIVKN | 192 | YATELAE | 193 | LQFYEFPFTFGAGTKLELK | 194 |
| DLL3-VL-22 | KSSQSLLNSSNQKNY | 195 | FASTRES | 196 | QQHYSIPLTFGAGTKLELK | 197 |
| DLL3-VL-23 | RASQDIKNY | 198 | YTSRVHS | 199 | QQGYTLPFTFGSGTKLE | 200 |
| DLL3-VL-24 | SASSSVSSRY | 201 | STSNLAS | 202 | HQWSNYPLTFGAGTKLELK | 203 |
| DLL3-VL-25 | SASSSVSY | 204 | DSSKLAS | 205 | QQWSSNPLTFGAGTKLELK | 206 |
| DLL3-VL-26 | KSSQSLSDSDGKTY | 207 | LVSKLDS | 208 | WQGKHFPWTFGGGTKLEIK | 209 |
| DLL3-VL-27 | SASSSVSY | 210 | TTSNLAS | 211 | QQRSLYPYTFGGGTKVEIK | 212 |

TABLE 8-continued

Exemplary anti-DLL3 light chain CDR sequences

| | LCDR1 | SEQ ID NO: | LCDR2 | SEQ ID NO: | LCDR3 | SEQ ID NO: |
|---|---|---|---|---|---|---|
| DLL3-VL-28 | TASSSVTSSY | 213 | STSNLAS | 214 | HQFHRSPFTFGSGTKLEIK | 215 |
| DLL3-VL-29 | KSTKSLLNSDGFTY | 216 | LVSNRFS | 217 | FQSNYLPLTFGAGTKLELR | 218 |
| DLL3-VL-30 | KASQSVSND | 219 | YASNRYS | 220 | QQDYSSPWTFGGGTKLEIK | 221 |
| DLL3-VL-31 | RASQDISNY | 222 | YTSRLHS | 223 | QQGNTLPYTFGGGTKLEIK | 224 |
| DLL3-VL-32 | ITTPDIDDD | 225 | EGNSLRP | 226 | LQSDNMPFTFGSGTKLEIK | 227 |
| DLL3-VL-33 | SASSSINY | 228 | DTSKLAS | 229 | HQRSTWTFGGGTKLEIK | 230 |
| DLL3-VL-34 | RASQDVINY | 231 | YTSRLHS | 232 | QQYSERPYTFGGGTKLEIKR | 233 |
| DLL3-VL-35 | RSSQNIVHSDRYTY | 234 | GVSNRFS | 235 | FQGTHVPYTFGGGTKLEIK | 236 |
| DLL3-VL-36 | QATQDIVKN | 237 | YATELAE | 238 | LQFYEFPFTFGAGTKLELK | 239 |
| DLL3-VL-37 | KSTKSLLNSDGFTY | 240 | LVSNRFS | 241 | FQSNYLPLTFGAGTKLELR | 242 |
| DLL3-VL-38 | KASQDINSYL | 243 | RANRLVD | 244 | LQYDEFPLTFGAGTKLELK | 245 |
| DLL3-VL-39 | RASQDISNY | 246 | YTSRLHS | 247 | QQGNTLRTFGGGTKLEIK | 248 |
| DLL3-VL-40 | RASQGIRGT | 249 | STSNLNS | 250 | LQRNAYPLTFGAGTKLELK | 251 |
| DLL3-VL-41 | KASQDINSY | 252 | RANRLVD | 253 | LQYDEFPYTFGGGTKLEIKR | 254 |
| DLL3-VL-42 | KASQSVSND | 255 | YASNRYT | 256 | QQDYTSPWTFGGGTKLEIR | 257 |
| DLL3-VL-43 | KASQDVSIF | 258 | SASYRYT | 259 | QQHYGTPFTFGSGTKLIR | 260 |
| DLL3-VL-44 | RASENIYSY | 261 | NAKTLAE | 262 | QHHYDSPLTFGAGTKLELR | 263 |
| DLL3-VL-45 | KSSQSLLNSSNQKNY | 264 | FASTRES | 265 | QQHYSIPLTFGAGTKLELK | 266 |
| DLL3-VL-46 | KASQDINSF | 267 | RANRLVD | 268 | LQYDEFPYTFGGGTKLEIKR | 269 |
| DLL3-VL-47 | SASSSVSY | 270 | DTSKLAS | 271 | QQWSSNPYTFGGGTKLEIK | 272 |
| DLL3-VL-48 | SVTSSVSY | 273 | LTSNLAS | 274 | QQWRNNPFTFGSGTKVEIK | 275 |
| DLL3-VL-49 | RSSTGAVTTSNY | 276 | GTNNRAP | 277 | GLWYSNHLVFGGGTKLTVL | 278 |
| DLL3-VL-50 | ITSTDIDDD | 279 | EGNTLRP | 280 | LQSDNMPLTFGAGTKLELK | 281 |
| DLL3-VL-51 | RASSSVNY | 282 | YTSNLAP | 283 | QQFTSSPYTFGGGTKLEIKR | 284 |

TABLE 8-continued

Exemplary anti-DLL3 light chain CDR sequences

|  | LCDR1 | SEQ ID NO: | LCDR2 | SEQ ID NO: | LCDR3 | SEQ ID NO: |
|---|---|---|---|---|---|---|
| DLL3-VL-52 | RASQDIGYS | 285 | ATSSLDS | 286 | LQYASSPWTFGGGTKLEIK | 287 |
| DLL3-VL-53 | KASQDINSY | 288 | RANRLVD | 289 | LQYDEFPFTFGSGTKLEIK | 290 |
| DLL3-VL-54 | KSSQSLLNSRTRKNY | 291 | WASTRES | 292 | KQSYNLYTFGGGTKLKIKR | 293 |
| DLL3-VL-55 | ITSTDIDDD | 294 | EGNTLRP | 295 | LKRDDLPYTFGGGTQVEIKR | 296 |
| DLL3-VL-56 | TASSSVSSSY | 297 | STSNLAS | 298 | HQYNRSPLTFGAGTKLELK | 299 |
| DLL3-VL-57 | KASQDIKKY | 300 | YTSTLEP | 301 | LQYDILWTFGGGTKLEIK | 302 |
| DLL3-VL-58 | SASSSVSSSY | 303 | RTSNLAS | 304 | RQWSGYPWTFGGGTKLEIK | 305 |
| DLL3-VL-59 | TASSSVSSSY | 306 | STSNLAS | 307 | HQYHRSPFTFGSGTKLEIK | 308 |
| DLL3-VL-60 | RASKSVSTSGYSY | 309 | LASNLES | 310 | QHSRELPLTFGAGTKLELK | 311 |
| DLL3-VL-61 | RASSSVSY | 312 | ATSNLAS | 313 | QQWSSNPPTFGAGTKLELK | 314 |
| DLL3-VL-62 | KASQDVGTA | 315 | WASIRHT | 316 | QQYSSYPLTFGAGTKLELK | 317 |
| DLL3-VL-63 | KASQDINSY | 318 | RANRLVD | 319 | LQYDEFPFTFGSGTKLEIK | 320 |
| DLL3-VL-64 | KASQDVNTA | 321 | SASYRYT | 322 | QQHYSSPYTFGGGTKLEIKR | 323 |
| DLL3-VL-65 | RASENIYSY | 324 | NAKTLAE | 325 | QHHYGTPYTFGGGTKLEIKR | 326 |
| DLL3-VL-66 | SASSSVSY | 327 | DTSNLAS | 328 | QEWSGNPLTFGDGTKLELK | 329 |
| DLL3-VL-67 | KASQSVSND | 330 | YASNRYT | 331 | QQDYSSPPTFGGGTKLEIK | 332 |
| DLL3-VL-68 | RASENIYYS | 333 | NANSLED | 334 | KQTYDVPLTFGAGTKLELK | 335 |
| DLL3-VL-69 | KSSQSLLDSDGTTY | 336 | LVSKLDS | 337 | WQGTHFPLTFGAGTKLELK | 338 |
| DLL3-VL-70 | RASSSVSY | 339 | ATSNLAS | 340 | QQWSSNPYTFGGGTKLEIKR | 341 |
| DLL3-VL-71 | KSSQSLLDSDGTTY | 342 | LVSKLDS | 343 | WQGTHFPLTFGAGTKLELK | 344 |
| DLL3-VL-72 | TSSQSLLTSGNQKNY | 345 | WASTRES | 346 | QNDYSLTFGAGTKLELK | 347 |
| DLL3-VL-73 | HVSQNINVW | 348 | KASNLHT | 349 | QQGQSYPFTFGSGTKLEIK | 350 |
| DLL3-VL-74 | KASQSVDYDGDSY | 351 | AASNLES | 352 | QQSNEDPYTFGGGTKLEIKR | 353 |
| DLL3-VL-75 | KSSQSLLYSSTQOKNY | 354 | WASTRES | 355 | QQYYSYPYTFGGGTKLEIKR | 356 |
| DLL3-VL-76 | SASSSVSY | 357 | STSNLAS | 358 | QQRSSYPPTFGGGTKLEIKR | 359 |

TABLE 8-continued

Exemplary anti-DLL3 light chain CDR sequences

| | LCDR1 | SEQ ID NO: | LCDR2 | SEQ ID NO: | LCDR3 | SEQ ID NO: |
|---|---|---|---|---|---|---|
| DLL3-VL-77 | KASQNVGTN | 360 | SASYRYS | 361 | QQYNSYPLTFGGGTKLEIK | 362 |
| DLL3-VL-78 | TASSSVSSSY | 363 | STSNLAS | 364 | HQYHRSPFTFGSGTKLEIK | 365 |
| DLL3-VL-79 | LASQTIGTW | 366 | AATSLAD | 367 | QQLYSTPWTFGGGTKLEIK | 368 |
| DLL3-VL-80 | HASQNINVW | 369 | KASILHT | 370 | QQGQSYPYTFGGGTKLEIK | 371 |
| DLL3-VL-81 | HASQNINVW | 372 | KASNLHT | 373 | QQGQSYPFTFGSGTKLEIK | 374 |
| DLL3-VL-82 | LASQTIGTW | 375 | AATSLAD | 376 | QQLYSTPYTFGGGTKLEIKR | 377 |
| DLL3-VL-83 | RASGSIHNY | 378 | NAKTLVD | 379 | QHFWTTPWTFGGGTKLEIK | 380 |
| DLL3-VL-84 | HVSQNINVW | 381 | KASNLHT | 382 | QQGQSYPFTFGSGTKLEIK | 383 |
| DLL3-VL-85 | LASQTIGTW | 384 | AATSLAD | 385 | QQLYSTPWTFGGGTKLEIK | 386 |
| DLL3-VL-86 | KASQSVSND | 387 | CASNRYT | 388 | QQDYSSPLTFGAGTKLELK | 389 |
| DLL3-VL-87 | KASQSVDHAGDSY | 390 | AASNLES | 391 | QQSNEDPYTFGGGTKLEIKR | 392 |
| DLL3-VL-88 | KASQDINRY | 393 | RANRLVD | 394 | LQYDEFPFTFGSGTKLEIK | 395 |
| DLL3-VL-89 | RASGNIHNY | 396 | NAKTLAD | 397 | QHFWSTPWTFGGGTKLEIK | 398 |
| DLL3-VL-90 | SASSSVSY | 399 | STSNLAS | 400 | HQWSSYHTFGGGTKLEIKR | 401 |
| DLL3-VL-91 | LASQTIGTW | 402 | SATSLAD | 403 | QQLYSTPWTFGGGTKLEIK | 404 |
| DLL3-VL-92 | KASQDVNTA | 405 | SASYRYT | 406 | QQHYSSPYTFGGGTKLEIK | 407 |
| DLL3-VL-93 | RASKSVSTSGYSY | 408 | LASNLES | 409 | QHSRELPFTFGGGTKLEIKR | 410 |
| DLL3-VL-94 | KASQDINSY | 411 | RANRLVD | 412 | LQYDEFPFTFGSGTKLEIK | 413 |
| DLL3-VL-95 | KASQDINNY | 414 | RANRLVD | 415 | LQYDEFPYTFGGGTKLEIKR | 416 |
| DLL3-VL-96 | RSSQSIVHSNGNTY | 417 | KVSNRFS | 418 | FQGSHVPLTFGAGTKLELK | 419 |
| DLL3-VL-97 | KASQSVSND | 420 | YASNRYN | 421 | QQDYSSPWTFGGGTKLEIK | 422 |
| DLL3-VL-98 | RASQDINNY | 423 | YTSRLHS | 424 | QQGDTLPWTFGGGTKLEIK | 425 |
| DLL3-VL-99 | SASSSVSY | 426 | DTSNLAS | 427 | QEWSNNPLTFGDGTKLELK | 428 |
| DLL3-VL-100 | HASQNINVW | 429 | KASHLHT | 430 | QQGQSYPFTFGSGTTLEIK | 431 |

TABLE 8-continued

Exemplary anti-DLL3 light chain CDR sequences

| | LCDR1 | SEQ ID NO: | LCDR2 | SEQ ID NO: | LCDR3 | SEQ ID NO: |
|---|---|---|---|---|---|---|
| DLL3-VL-101 | MSSQSLLYSSTQKNY | 432 | WASTRES | 433 | QQYYSYPYTFGGGTKLEIKR | 434 |
| DLL3-VL-102 | SASSSVSY | 435 | LTSNLAS | 436 | QQWRSNPFTFGQGTKLEIKR | 437 |
| DLL3-VL-103 | RASENIYYN | 438 | TANSLED | 439 | KQAYDVPPTFGGGTKLEIK | 440 |
| DLL3-VL-104 | SASSSVSY | 441 | DSSKLAS | 442 | QQWSSNPLTFGQGTKLEIK | 443 |
| DLL3-VL-105 | KASQSVSND | 444 | YASNRYS | 445 | QQDYSSPWTFGGGTKVEIK | 446 |
| DLL3-VL-106 | KASQSVSND | 447 | YASNRYT | 448 | QQDYTSPWTFGQGTKLEIKR | 449 |

In certain embodiments, the anti-DLL3 binding constructs described herein may be prepared using standard molecular biology techniques with regard to selecting antibodies that have a desired specificity. In some embodiments, the anti-DLL3 binding constructs described herein are produced using recombinant DNA technologies. Procedures for the expression and purification of recombinant proteins are well established in the art.

In some embodiments, the anti-DLL3 binding constructs described herein demonstrate superior functional characteristics compared to other DLL3 binding constructs known in the art. For example, in some embodiments, the anti-DLL3 binding constructs described herein demonstrate superior binding affinity and/or specificity for DLL3, demonstrate a faster on-rate ($k_{on}$) and/or a slower off-rate ($k_{off}$) for DLL3, demonstrate binding to a different or novel epitope of DLL3, demonstrate a longer half-life in vitro and/or in vivo, demonstrate species cross-reactivity with DLL3 from non-human species (e.g., mouse and/or cynomolgus), and/or demonstrate enhanced cytotoxicity of DLL3-expressing cells compared to other DLL3 binding constructs known in the art. In some embodiments, the anti-DLL3 binding constructs described herein demonstrate superior tumor penetration and/or enhanced tumor biodistribution, for example, due to their small sizes and/or binding to human serum albumin (HSA). In some embodiments, the anti-DLL3 binding constructs described herein demonstrate superior manufacturing characteristics compared to other anti-DLL3 constructs known in the art, for example increased protein titer, decreased protein aggregation, and/or increase protein stability.

In some embodiments, the anti-DLL3 binding constructs described herein demonstrate superior binding affinity and/or specificity for human DLL3, as compared to a reference anti-DLL3 construct. In some embodiments, the anti-DLL3 binding constructs described herein bind to human DLL3 with a dissociation constant (KD, M) of less than 1.0E-07, 7.0 E-08, 5.0 E-08, 3.0 E-08, 2.0 E-08, 1.0 E-08, 7.0 E-09, 5.0 E-09, 3.0 E-09, 2.0 E-09, 1.0 E-09, 7.0 E-10, 5.0E-10, 3.0 E-10, 2.0 E-10, or 1.0 E-10, including all ranges and subranges therebetween. In some embodiments, the anti-DLL3 binding constructs described herein have a KD of less than 1.0 E-08 M (i.e., less than 10 nM). In some embodiments, the anti-DLL3 binding constructs described herein have a KD of less than 7.0 E-09 M (i.e., less than 7 nM).

In some embodiments, the anti-DLL3 binding constructs described herein demonstrate a faster on-rate (kon) and/or a slower off-rate (koff) for human DLL3, as compared to a reference anti-DLL3 construct. In some embodiments, the anti-DLL3 binding constructs described herein bind to human DLL3 with an on-rate (kon, 1/Ms) of at least 5.0 E+03, 7.0 E+03, 1.0 E+04, 2.0 E+04, 3.0 E+04, 5.0 E+04, 7.0 E+04, 1.0 E+05, 2.0 E+05, 3.0 E+05, 5.0 E+05, 7.0 E+05, 1.0 E+06, 2.0 E+06, 3.0 E+06, 5.0 E+06, 7.0 E+06, or 1.0 E+07, including all ranges and subranges therebetween. In some embodiments, the anti-DLL3 binding constructs described herein have an on-rate (kon 1/Ms) of at least 5.0 E+04. In some embodiments, the anti-DLL3 binding constructs described herein have an on-rate (kon 1/Ms) of at least 7.0 E+04. In some embodiments, the anti-DLL3 binding constructs described herein have an on-rate (kon 1/Ms) of at least 2.0 E+05. In some embodiments, the anti-DLL3 binding constructs described herein bind to human DLL3 with an off-rate (koff, 1/s) of less than 5.0 E-03, 3.0 E-03, 2.0 E-03, 1.0 E-03, 7.0 E-04, 5.0 E-04, 3.0 E-04, 2.0 E-04, 1.0 E-04, 7.0 E-05, 5.0 E-05, 3.0 E-05, 2.0 E-05, 1.0 E-05, 7.0 E-06, or 5.0 E-06, including all ranges and subranges therebetween. In some embodiments, the anti-DLL3 binding constructs described herein have an off-rate (koff, 1/s) of less than 2.0 E-03. In some embodiments, the anti-DLL3 binding constructs described herein have an off-rate (koff, 1/s) of less than 1.0 E-03. In some embodiments, the anti-DLL3 binding constructs described herein have an off-rate (koff, 1/s) of less than 7.0 E-04.

In some embodiments, the anti-DLL3 binding constructs described herein bind to human DLL3 and demonstrate species cross-reactivity with DLL3 from non-human species (e.g., mouse and/or cynomolgus). In some embodiments, the anti-DLL3 binding constructs described herein demonstrate species cross-reactivity with one or more of mouse, rat, guinea pig, hamster, gerbil, pig, cat, dog, rabbit, goat, sheep, cow, horse, camel, cynomolgus, marmoset, rhesus and chimpanzee DLL3. In some embodiments, the anti-DLL3 binding constructs described herein demonstrate species cross-reactivity with both human and mouse DLL3. In some embodiments, the anti-DLL3 binding constructs described herein demonstrate species cross-reactivity with both human and cynomolgus DLL3. In some embodiments, the anti-DLL3 binding constructs described herein demonstrate species cross-reactivity with human, mouse and cynomolgus DLL3. In some embodiments, species cross-reactivity refers to having similar dissociation constant (KD) values for binding to DLL3 proteins from the two or more species. In some embodiments, the dissociation constant (KD) values are considered "similar" when they are within a 10-fold range, for example, within a 7-fold, 5-fold, 3-fold, or 2-fold range, with one another. In some embodiments, species cross-reactivity refers to having similar EC50 values in the cytotoxicity assay for DLL3 proteins from the two or more species. In some embodiments, the EC50 values in the cytotoxicity assay are considered "similar" when they are within a 10-fold range, for example, within a 7-fold, 5-fold, 3-fold, or 2-fold range, with one another.

In some embodiments, the anti-DLL3 binding constructs described herein demonstrate enhanced cytotoxicity of human DLL3-expressing cells, as compared to a reference anti-DLL3 construct. In some embodiments, the cytotoxicity is mediated at least in part by T cells. In some embodiments, the anti-DLL3 binding constructs described herein have an cytotoxicity EC50 of less than 20 nM, 10 nM, 7 nM, 5 nM, 3 nM, 2 nM, 1 nM, 0.7 nM, 0.5 nM, 0.3 nM, 0.2 nM, 0.1 nM, 0.07 nM, 0.05 nM, 0.03 nM, 0.02 nM, or 0.01 nM, including all ranges and subranges therebetween. In some embodiments, the anti-DLL3 binding constructs described herein have an cytotoxicity EC50 of less than 1 nM. In some embodiments, the anti-DLL3 binding constructs described herein have a cytotoxicity EC50 of less than 0.5 nM.

The binding properties of the anti-DLL3 binding constructs described herein can be characterized using assays known in the art. Non-limiting, exemplary in vitro assays for measuring binding properties are illustrated in Examples herein. For example, the binding affinities and kinetic constants can be determined by a Biacore/SPR instrument using the assay format as defined in Example 4 herein; difference of binding epitopes can be determined by an antibody binning experiment using the assay format as defined in Example 3 herein; the EC50 of cytotoxicity can be determined by a cellular assay according to Example 5 herein.

In some embodiments, the anti-DLL3 binding constructs of the disclosure demonstrate a longer half-life in vitro and/or in vivo. In some embodiments, the anti-DLL3 binding construct comprises a human serum albumin (HSA) binding domain or Fc fusion, and the in vivo half-life of the anti-DLL3 binding construct comprising the HSA binding domain or Fc fusion is extended by about 1-fold, about 2-fold, about 3-fold, about 4-fold, about 5-fold, about 7-fold, about 10-fold, about 15-fold, about 20-fold, about 30-fold, about-40 fold, or about 50-fold compared to the antibody or antigen-binding fragment thereof that does not comprise an HSA binding domain or Fc fusion. In some embodiments, the in vivo half-life of the anti-DLL3 binding construct comprising the HSA binding domain or Fc fusion is extended by 1-fold, 2-fold, 3-fold, 4-fold, 5-fold, 7-fold, 10-fold, 15-fold, 20-fold, 30-fold, about-40 fold, 50-fold, or any value in between, compared to the antibody or antigen-binding fragment thereof that does not comprise an HSA binding domain or Fc fusion. In some embodiments, the in vivo half-life of the anti-DLL3 binding construct comprising the HSA binding domain or Fc fusion is extended by at least 1-fold, at least 2-fold, at least 3-fold, at least 4-fold, at least 5-fold, at least 7-fold, at least 10-fold, at least 15-fold, at least 20-fold, at least 30-fold, about-40 fold, or at least 50-fold compared to the antibody or antigen-binding fragment thereof that does not comprise an HSA binding domain or Fc fusion.

Polynucleotides and Methods of Protein Expression

The disclosure also includes polynucleotides (e.g., DNA or RNA) encoding the anti-DLL3 binding constructs of the present disclosure. In some embodiments, the polynucleotides encode a polypeptide that is substantially identical to a polypeptide listed in Tables 1, 2, and 3. In some embodiments, the polynucleotides encode a polypeptide that is at least 80%, at least 90%, at least 95%, at least 96%, at least 97%, at least 98%, at least 99%, or 100% identical to a polypeptide listed in Tables 1, 2, and 3. Polynucleotides of the disclosure also include complementary nucleic acids. In some instances, the sequences will be fully complementary (no mismatches) when aligned. In other instances, there can be up to about a 20% mismatch in the sequences. The polynucleotide sequences provided herein can be exploited using codon optimization, degenerate sequence, silent mutations, and other DNA techniques to optimize expression in a particular host, and the present disclosure encompasses such sequence modifications.

In some embodiments, the present disclosure provides an mRNA polynucleotide encoding the anti-DLL3 binding constructs described herein. In some embodiments, the mRNA polynucleotides encode a polypeptide that is substantially identical to a polypeptide listed in Tables 1, 2, and 3. In some embodiments, the mRNA polynucleotides encode a polypeptide that is at least 80%, at least 90%, at least 95%, at least 96%, at least 97%, at least 98%, at least 99%, or 100% identical to a polypeptide listed in Tables 1, 2, and 3.

In some embodiments, the polynucleotides of the present disclosure are inserted into a nucleic acid vector. The nucleic acid vector may be a viral vector or a non-viral vector, e.g. a plasmid. Vectors include, without limitation, plasmids, phagemids, cosmids, transposons, artificial chromosomes such as yeast artificial chromosome (YAC), bacterial artificial chromosome (BAC), or P1-derived artificial chromosome (PAC), bacteriophages such as lambda phage or M13 phage, and animal viruses. In some embodiments, the vector is a plasmid selected from pXT1, pSG5 (Stratagene), pSVK3, pBPV, pMSG, and pSVLSV40 (Pharmacia). In some embodiments, the vector is a viral vector selected from viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., U.S. Pat. No. 7,078,387; Ali et al., Hum Gene Ther 9:81 86, 1998, Flannery et al, PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al, Virol. (1988) 166: 154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. Examples of vectors are pClneo vectors (Promega) for expression in mammalian cells; pLenti4/V5-DEST™, pLenti6N5-DEST™, and pLenti6.2/V5-GW/lacZ (Invitrogen) for lentivirus-mediated gene transfer and expression in mammalian cells.

In some embodiments, the polynucleotide is inserted into a nucleic acid vector and is operably linked to one or more regulatory sequences that control transcription, such as promoters, enhancers, terminators, inducers, or repressors. Exemplary promoters include Non-limiting examples of suitable eukaryotic promoters (promoters functional in a eukaryotic cell) include those from cytomegalovirus (CMV) immediate early, herpes simplex virus (HSV) thymidine kinase, a viral simian virus 40 (SV40) (e.g., early and late SV40), a spleen focus forming virus (SFFV) promoter, long terminal repeats (LTRs) from retrovirus (e.g., a Moloney murine leukemia virus (MoMLV) LTR promoter or a Rous sarcoma virus (RSV) LTR), a herpes simplex virus (HSV) (thymidine kinase) promoter, H5, P7.5, and P11 promoters from vaccinia virus, an elongation factor 1-alpha (EF1α) promoter, early growth response 1 (EGR1) promoter, a ferritin H (FerH) promoter, a ferritin L (FerL) promoter, a Glyceraldehyde 3-phosphate dehydrogenase (GAPDH) promoter, a eukaryotic translation initiation factor 4A1 (EIF4A1) promoter, a heat shock 70 kDa protein 5 (HSPA5) promoter, a heat shock protein 90 kDa beta, member 1 (HSP90B1) promoter, a heat shock protein 70 kDa (HSP70) promoter, a β-kinesin (β-KIN) promoter, the human ROSA 26 locus (Irions et al., Nature Biotechnology 25, 1477-1482 (2007)), a Ubiquitin C (UBC) promoter, a phosphoglycerate kinase-1 (PGK) promoter, a cytomegalovirus enhancer/ chicken β-actin (CAG) promoter, a β-actin promoter and a myeloproliferative sarcoma virus enhancer, negative control region deleted, d1587rev primer-binding site substituted (MND) promoter, and mouse metallothionein-1.

In some embodiments, the vector is introduced into a host cell for expression of the anti-DLL3 binding construct. Accordingly, proteins for use within the present disclosure can be produced in genetically engineered host cells according to conventional techniques. Suitable host cells are those cell types that can be transformed or transfected with exogenous DNA and grown in culture, and include bacteria, fungal cells, and cultured higher eukaryotic cells (including cultured cells of multicellular organisms), particularly cultured mammalian cells. Techniques for manipulating cloned DNA molecules and introducing exogenous DNA into a variety of host cells are disclosed by Sambrook and Russell, Molecular Cloning: A Laboratory Manual (3rd ed., Cold Spring Harbor Laboratory Press, Cold Spring Harbor, NY, 2001), and Ausubel et al., Short Protocols in Molecular Biology (4th ed., John Wiley & Sons, 1999).

The gene product encoded by a polynucleotide of the disclosure is expressed in any convenient expression system, including, for example, bacterial, yeast, insect, amphibian, and mammalian systems. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44; CHO DXB11 (Hyclone, Logan, UT); see also, e.g., Chasin et al., Som. Cell. Molec. Genet. 12:555, 1986)), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658). Additional suitable cell lines are known in the art and available from public depositories such as the American Type Culture Collection, Manassas, Virginia. Introduction of the DNA construct can use any convenient method, including, e.g. conjugation, bacterial transformation, calcium-precipitated DNA, electroporation, fusion, transfection, infection with viral vectors, biolistics, and the like.

For example, for recombinant expression of an anti-DLL3 binding construct as described herein, an expression vector will generally include a nucleic acid segment encoding one or more of the amino acid sequences provided in Tables 1, 2, and 3 operably linked to a promoter. The expression vector is introduced to a host cell by conventional techniques, and the host cells are then cultured by conventional techniques to produce the encoded polypeptide(s) to produce the corresponding anti-DLL3 binding constructs.

To direct a recombinant protein into the secretory pathway of a host cell, a secretory signal sequence (also known as a leader sequence) is provided in the expression vector. The secretory signal sequence can be that of the native form of the recombinant protein or can be derived from another secreted protein or synthesized de novo. The secretory signal sequence is operably linked to the polypeptide-encoding DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain signal sequences can be positioned elsewhere in the DNA sequence of interest (see, e.g., U.S. Pat. Nos. 5,037,743 and 5,143,830).

Cultured mammalian cells are suitable hosts for production of recombinant polypeptides and proteins of the present disclosure (e.g., anti-DLL3 binding constructs). Methods for introducing exogenous DNA into mammalian host cells include calcium phosphate-mediated transfection (Wigler et al., Cell 14:725, 1978; Corsaro and Pearson, Somatic Cell Genetics 7:603, 1981: Graham and Van der Eb, Virology 52:456, 1973), electroporation (Neumann et al., EMBO J. 1:841-845, 1982), DEAE-dextran mediated transfection (Ausubel et al., supra), and liposome-mediated transfection (Hawley-Nelson et al., Focus 15:73, 1993; Ciccarone et al., Focus 15:80, 1993). The production of recombinant polypeptides in cultured mammalian cells is disclosed by, for example, U.S. Pat. Nos. 4,713,339; 4,784,950; 4,579,821; and 4,656,134.

Transformed or transfected host cells to produce the polypeptides and proteins of the present disclosure are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins, and minerals. Media can also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

The anti-DLL3 binding constructs of the present disclosure may be purified by conventional protein purification methods, typically by a combination of chromatographic techniques. See generally Affinity Chromatography: Principles & Methods (Pharmacia LKB Biotechnology, Uppsala, Sweden, 1988); Scopes, Protein Purification: Principles and Practice (Springer-Verlag, New York 1994). Proteins comprising an immunoglobulin Fc region can be purified by affinity chromatography on immobilized protein A or protein G. Additional purification steps, such as gel filtration, can be used to obtain the desired level of purity or to provide for desalting, buffer exchange, and the like.

Oncolytic Viruses

In some embodiments, the polynucleotides encoding the anti-DLL3 binding constructs are incorporated into an oncolytic virus. Examples of oncolytic viruses are known in the art including, but not limited to, herpes simplex virus (HSV), an adenovirus, a polio virus, a vaccinia virus, a measles virus, a vesicular stomatitis virus, an orthomyxovirus, a parvovirus, a maraba virus, or a picornavirus (e.g., a coxsackievirus or a Seneca Valley virus). In some embodiments, the oncolytic viruses described herein are referred to as oncolytic vectors.

In some embodiments, the anti-DLL3 binding constructs are administered to a subject in combination with an oncolytic virus. In some embodiments, an anti-DLL3 binding construct or a polynucleotide encoding the same is administered to a subject in combination with an oncolytic virus. In some embodiments, the polynucleotide is an mRNA polynucleotide.

Compositions and Methods of Use

In some embodiments, the present disclosure provides of treating cancer in a subject in need thereof, comprising administering to the subject a therapeutically effective amount of an anti-DLL3 binding construct of the present disclosure. In some embodiments, the methods comprise administering a polynucleotide encoding an anti-DLL3 binding construct a subject in need thereof. In some embodiments, the present disclosure provides of treating cancer in a subject in need thereof, comprising administering to the subject a therapeutically effective amount of an oncolytic virus encoding an anti-DLL3 binding construct. In some embodiments, the present disclosure provides of treating cancer in a subject in need thereof, comprising administering to the subject a therapeutically effective amount of an oncolytic virus or polynucleotide encoding the same in combination with an anti-DLL3 binding construct or polynucleotide encoding the same.

The disclosure also encompasses anti-DLL3 binding constructs, as well as polynucleotides encoding the same, for the manufacture of a medicament for treatment of a cancer in a subject.

In some embodiments, for treatment methods and uses described herein, the anti-DLL3 binding construct is delivered in a manner consistent with conventional methodologies associated with management of the disease or disorder for which treatment is sought. In accordance with the disclosure herein, a therapeutically effective amount of the protein or polypeptide is administered to a subject in need of such treatment for a time and under conditions sufficient to prevent or treat the disease or disorder.

A "subject," as used herein, includes any animal that exhibits a symptom of a disease, disorder, or condition that can be treated with the recombinant viral vectors, compositions, and methods disclosed herein. Suitable subjects (e.g., subjects) include laboratory animals (such as mouse, rat, rabbit, or guinea pig), farm animals (such as horse or cow), and domestic animals or pets (such as cat or dog). Non-human primates and, preferably, human subjects, are included.

The term "treating" and "treatment" as used herein refers to administering to a subject a therapeutically effective amount of a recombinant virus or composition thereof as described herein so that the subject has an improvement in a disease or condition, or a symptom of the disease or condition. The improvement is any improvement or remediation of the disease or condition, or symptom of the disease or condition. The improvement is an observable or measurable improvement or may be an improvement in the general feeling of well-being of the subject. Thus, one of skill in the art realizes that a treatment may improve the disease condition but may not be a complete cure for the disease. A "prophylactically effective amount" refers to an amount of a virus, a viral stock, or a composition effective to achieve the desired prophylactic result. As used herein, "prophylaxis" can mean complete prevention of the symptoms of a disease, a delay in onset of the symptoms of a disease, or a lessening in the severity of subsequently developed disease symptoms. Typically, but not necessarily, since a prophylactic dose is used in subjects prior to or at an earlier stage of disease, the prophylactically effective amount is less than the therapeutically effective amount.

In prophylactic applications, pharmaceutical compositions or medicants comprising the anti-DLL3 binding construct are administered to a subject susceptible to, or otherwise at risk of, a particular disorder in an amount sufficient to eliminate or reduce the risk or delay the onset of the disorder. In therapeutic applications, compositions or medicants comprising a protein of the present disclosure are administered to a subject suspected of, or already suffering from such a disorder in an amount sufficient to cure, or at least partially arrest, the symptoms of the disorder and its complications. An amount adequate to accomplish this is referred to as a therapeutically effective dose or amount. In both prophylactic and therapeutic regimes, agents are usually administered in several dosages until a sufficient response (e.g., inhibition of inappropriate angiogenesis activity) has been achieved. Typically, the response is monitored and repeated dosages are given if the desired response starts to fade.

"Cancer" herein refers to or describes the physiological condition in mammals that is typically characterized by unregulated cell growth. Examples of cancer include but are not limited to carcinoma, lymphoma, blastoma, sarcoma (including liposarcoma, osteogenic sarcoma, angiosarcoma, endotheliosarcoma, leiomyosarcoma, chordoma, lymphangiosarcoma, lymphangioendotheliosarcoma, rhabdomyosarcoma, fibrosarcoma, myxosarcoma, chondrosarcoma), neuroendocrine tumors, mesothelioma, synovioma, schwannoma, meningioma, adenocarcinoma, melanoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, small cell lung carcinoma, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulvar cancer, thyroid cancer, hepatic carcinoma, anal carcinoma, penile carcinoma, testicular cancer, esophageal cancer, tumors of the biliary tract, Ewing's tumor, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, testicular tumor, lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, multiple myeloma, Waldenstrom's macroglobulinemia, myelodysplastic disease, heavy chain disease, neuroendocrine tumors, Schwannoma, and other carcinomas, as well as head and neck cancer. In some embodiments, the cancer is selected from non-small cell lung cancer (NSCLC), small cell lung cancer (SCLC), small cell bladder cancer, large cell neuroendocrine carcinoma (LCNEC), castration-resistant small cell neuroendocrine prostate cancer (CRPC-NE), carcinoid (e.g., pulmonary carcinoid), glioblastoma multiforme-IDH mutant (GBM-IDH mutant), Merkel cell carcinoma, and gastric neuroendocrine tumors.

For administration, the anti-DLL3 binding construct, or the oncolytic virus or the polynucleotide encoding the same, may be formulated as a pharmaceutical composition. A pharmaceutical composition may comprise: (i) a DLL3 binding construct; and (ii) a pharmaceutically acceptable carrier, diluent or excipient. A pharmaceutical composition comprising a DLL3 binding construct can be formulated according to known methods to prepare pharmaceutically useful compositions, whereby the therapeutic molecule is combined in a mixture with a pharmaceutically acceptable carrier, diluent, or excipient. A carrier is said to be a "pharmaceutically acceptable carrier" if its administration can be tolerated by a recipient subject. Sterile phosphate-buffered saline is one example of a pharmaceutically acceptable carrier. Other suitable carriers, diluents, or excipients are well-known to those in the art. (See, e.g., Gennaro (ed.), Remington's Pharmaceutical Sciences (Mack Publishing Company, 19th ed. 1995).) Formulations can further include one or more excipients, preservatives, solubilizers, buffering agents, albumin to prevent protein loss on vial surfaces, etc.

A pharmaceutical composition comprising a polypeptide or protein described herein may be formulated in a dosage form selected from the group consisting of: an oral unit dosage form, an intravenous unit dosage form, an intranasal unit dosage form, a suppository unit dosage form, an intradermal unit dosage form, an intramuscular unit dosage form, an intraperitoneal unit dosage form, a subcutaneous unit dosage form, an epidural unit dosage form, a sublingual unit dosage form, and an intracerebral unit dosage form. The oral unit dosage form may be selected from the group consisting of: tablets, pills, pellets, capsules, powders, lozenges, granules, solutions, suspensions, emulsions, syrups, elixirs, sustained-release formulations, aerosols, and sprays.

A pharmaceutical composition comprising the anti-DLL3 binding construct, or the oncolytic virus or the polynucleotide encoding the same, may be administered to a subject in a therapeutically effective amount. According to the methods of the present disclosure, the anti-DLL3 binding construct, or the oncolytic virus or the polynucleotide encoding the same, can be administered to subjects by a variety of administration modes, including, for example, by intramuscular, subcutaneous, intravenous, intra-atrial, intra-articular, parenteral, intranasal, intrapulmonary, transdermal, intrapleural, intrathecal, intratumoral, and oral routes of administration. For prevention and treatment purposes, an anti-DLL3 binding construct can be administered to a subject in a single bolus delivery, via continuous delivery (e.g., continuous transdermal delivery) over an extended time period, or in a repeated administration protocol (e.g., on an hourly, daily, weekly, or monthly basis).

Effective doses of the compositions of the present disclosure vary depending upon many different factors, including means of administration, target site, physiological state of the subject, whether the subject is human or an animal, other medications administered, whether treatment is prophylactic or therapeutic, as well as the specific activity of the composition itself and its ability to elicit the desired response in the individual. Usually, the subject is a human, but in some diseases, the subject can be a nonhuman mammal. Typically, dosage regimens are adjusted to provide an optimum therapeutic response, i.e., to optimize safety and efficacy.

Determination of effective dosages in this context is typically based on animal model studies followed up by human clinical trials and is guided by determining effective dosages and administration protocols that significantly reduce the occurrence or severity of the subject disorder in model subjects. Accordingly, a "therapeutically effective amount," as used herein, refers to an amount of a compound is an amount that achieves the desired biologic or therapeutic effect, namely an amount that prevents, reduces or ameliorates one or more symptoms of the enumerated diseases being treated or prevented. For example, the therapeutically effective amount of the antibody, or antigen-binding fragment thereof, will depend on the condition to be treated, the severity and course of the condition, whether the antibody is administered for preventive or therapeutic purposes, previous therapy, the subject's clinical history and response to the antibody, the type of antibody, or antigen-binding fragment thereof, used, and the discretion of the attending physician. The anti-DLL3 binding construct is suitably administered to the patent at one time or over a series of treatments and may be administered to the patent at any time from diagnosis onwards. The anti-DLL3 binding construct may be administered as the sole treatment or in conjunction with other drugs or therapies (such as an oncolytic virus) useful in treating the condition in question.

In some embodiments, the therapeutically effective amount of the anti-DLL3 binding construct is between about 1 ng/kg body weight/day to about 100 mg/kg body weight/day. In some embodiments, the range of antibody administered is from about 1 ng/kg body weight/day to about 1 µg/kg body weight/day, 1 ng/kg body weight/day to about 100 ng/kg body weight/day, 1 ng/kg body weight/day to about 10 ng/kg body weight/day, 10 ng/kg body weight/day to about 1 µg/kg body weight/day, 10 ng/kg body weight/day to about 100 ng/kg body weight/day, 100 ng/kg body weight/day to about 1 µg/kg body weight/day, 100 ng/kg body weight/day to about 10 pg/kg body weight/day, 1 µg/kg body weight/day to about 10 pg/kg body weight/day, 1 µg/kg body weight/day to about 100 pg/kg body weight/day, 10 pg/kg body weight/day to about 100 pg/kg body weight/day, 10 pg/kg body weight/day to about 1 mg/kg body weight/day, 100 µg/kg body weight/day to about 10 mg/kg body weight/day, 1 mg/kg body weight/day to about 100 mg/kg body weight/day and 10 mg/kg body weight/day to about 100 mg/kg body weight/day. Dosages within this range can be achieved by single or multiple administrations, including, e.g., multiple administrations per day or daily, weekly, bi-weekly, or monthly administrations. The anti-DLL3 binding construct may be administered, as appropriate or indicated, as a single dose by bolus or by continuous infusion, or as multiple doses by bolus or by continuous infusion. Multiple doses may be administered, for example, multiple times per day, once daily, every 2, 3, 4, 5, 6 or 7 days, weekly, every 2, 3, 4, 5 or 6 weeks or monthly. However, other dosage regimens may be useful. The progress of this therapy is easily monitored by conventional techniques.

For administration to a human adult subject, the therapeutically effective amount may be administered in doses in the range of 0.0006 mg to 1000 mg per dose, including but not limited to 0.0006 mg per dose, 0.001 mg per dose, 0.003 mg per dose, 0.006 mg per dose, 0.01 mg per dose, 0.03 mg per dose, 0.06 mg per dose, 0.1 mg per dose, 0.3 mg per dose, 0.6 mg per dose, 1 mg per dose, 3 mg per dose, 6 mg per dose, 10 mg per dose, 30 mg per dose, 60 mg per dose, 100 mg per dose, 300 mg per dose, 600 mg per dose and 1000 mg per dose, and multiple, usually consecutive daily doses may be administered in a course of treatment. The anti-DLL3 antibody or antigen-fragment thereof can be administered at different times of the day. In one embodiment the optimal therapeutic dose can be administered in the evening. In another embodiment the optimal therapeutic dose can be administered in the morning. As expected, the dosage will be dependent on the condition, size, age, and condition of the subject.

Dosage of the pharmaceutical composition comprising the anti-DLL3 binding construct can be varied by the attending clinician to maintain a desired concentration at a target site. Higher or lower concentrations can be selected based on the mode of delivery, e.g., trans-epidermal delivery versus delivery to a mucosal surface. Dosage should also be adjusted based on the release rate of the administered formulation, e.g., nasal spray versus powder, sustained release oral or injected particles, transdermal formulations, etc.

Pharmaceutical compositions comprising the anti-DLL3 binding construct can be supplied as a kit comprising a container that comprises the pharmaceutical composition as described herein. A pharmaceutical composition can be provided, for example, in the form of an injectable solution for single or multiple doses, or as a sterile powder that will be reconstituted before injection. Alternatively, such a kit can include a dry-powder disperser, liquid aerosol generator, or nebulizer for administration of a pharmaceutical composition. Such a kit can further comprise written information on indications and usage of the pharmaceutical composition The disclosure relates to a method of treating cancer in a subject in need thereof, comprising administering a prophylactically effective amount or a therapeutically effective amount of an oncolytic virus, a viral stock, or a composition as described herein to the subject.

In some embodiments, the present disclosure provides methods of treating cancer comprising administration of a therapeutically effective amount of an anti-DLL3 binding construct described herein in combination with one or more additional therapeutic agents. In some embodiments, these two therapeutic agents are administered concurrently or sequentially In concurrent administration, these two therapeutic agents are administered at the same time or within a short time frame (for example, within 10 minutes, within 20 minutes, within 30 minutes, within 1 hour, within 2 hours, within 4 hours, within 6 hours, within 12 hours, or within 24 hours, including all ranges and subranges therebetween). In sequential administration, one of the therapeutic agents is administered before the other, for example, at least 2 hours before, at least 4 hours before, at least 6 hours before, at least 12 hours before, at least 1 day before, at least 2 days before, at least 3 days before, at least 4 days before, at least 5 days before, at least 6 days before, at least 1 week before, at least 2 weeks before, at least 3 weeks before, at least 4 weeks before, at least 1 month before, at least 2 months before, or at least 3 months before, including all ranges and sub ranges therebetween.

In some embodiments, the additional therapeutic agent is selected from a chemotherapeutic agent, an immune checkpoint inhibitor, an oncolytic virus or polynucleotide encoding the same, and an engineered immune cell comprising an engineered antigen receptor.

Engineered antigen receptors refer to non-naturally occurring antigen-specific receptors such as a chimeric antigen receptors (CARs) or a recombinant T cell receptor (TCRs). In some embodiments, the engineered antigen receptor is a CAR comprising an extracellular antigen binding domain fused via hinge and transmembrane domains to a cytoplasmic domain comprising a signaling domain. In some embodiments, the CAR extracellular domain binds to an antigen expressed by a target cell in an WIC-independent manner leading to activation and proliferation of the engineered immune cell. In some embodiments, the extracellular domain of a CAR recognizes a tag fused to an antibody or antigen-binding fragment thereof. In such embodiments, the antigen-specificity of the CAR is dependent on the antigen-specificity of the labeled antibody, such that a single CAR construct can be used to target multiple different antigens by substituting one antibody for another (See e.g., U.S. Pat. Nos. 9,233,125 and 9,624,279; US Patent Application Publication Nos. 20150238631 and 20180104354). In some embodiments, the extracellular domain of a CAR may comprise an antigen binding fragment derived from an antibody. In some embodiments, the extracellular antigen binding domain is an anti-DLL3 antigen binding construct.

In some embodiments, the present disclosure provides a CAR comprising an extracellular antigen binding domain, a hinge, a transmembrane domain, and a cytoplasmic domain wherein the extracellular antigen binding domain is a binding construct described herein. In some embodiments, the extracellular antigen binding domain is an anti-DLL3 antigen binding construct. In some embodiments, the extracellular antigen binding domain is an anti-DLL3 VHH sdAb described herein.

In some embodiments, the intracellular signaling domain of a CAR may be derived from the TCR complex zeta chain (such as CD3$\xi$ signaling domains), Fc$\gamma$RIII, Fc$\epsilon$RI, or the T-lymphocyte activation domain. In some embodiments, the intracellular signaling domain of a CAR further comprises a costimulatory domain, for example a 4-1BB, CD28, CD40, MyD88, or CD70 domain. In some embodiments, the intracellular signaling domain of a CAR comprises two costimulatory domains, for example any two of 4-1BB, CD28, CD40, MyD88, or CD70 domains. Exemplary CAR structures and intracellular signaling domains are known in the art (See e.g., WO 2009/091826; US 20130287748; WO 2015/142675; WO 2014/055657; and WO 2015/090229, incorporated herein by reference).

CARs specific for a variety of tumor antigens are known in the art, for example CD171-specific CARs (Park et al., Mol Ther (2007) 15(4):825-833), EGFRvIII-specific CARs (Morgan et al., Hum Gene Ther (2012) 23(10):1043-1053), EGF-R-specific CARs (Kobold et al., J Natl Cancer Inst (2014) 107(1):364), carbonic anhydrase K-specific CARs (Lamers et al., Biochem Soc Trans (2016) 44(3):951-959), FR-$\alpha$-specific CARs (Kershaw et al., Clin Cancer Res (2006) 12(20):6106-6015), HER2-specific CARs (Ahmed et al., J Clin Oncol (2015) 33(15)1688-1696; Nakazawa et al., Mol Ther (2011) 19(12):2133-2143; Ahmed et al., Mol Ther (2009) 17(10):1779-1787; Luo et al., Cell Res (2016) 26(7): 850-853; Morgan et al., Mol Ther (2010) 18(4):843-851; Grada et al., Mol Ther Nucleic Acids (2013) 9(2):32), CEA-specific CARs (Katz et al., Clin Cancer Res (2015) 21(14):3149-3159), IL13R$\alpha$2-specific CARs (Brown et al.,

61

Clin Cancer Res (2015) 21(18):4062-4072), GD2-specific CARs (Louis et al., Blood (2011) 118(23):6050-6056; Caruana et al., Nat Med (2015) 21(5):524-529), ErbB2-specific CARs (Wilkie et al., J Clin Immunol (2012) 32(5): 1059-1070), VEGF-R-specific CARs (Chinnasamy et al., Cancer Res (2016) 22(2):436-447), FAP-specific CARs (Wang et al., Cancer Immunol Res (2014) 2(2):154-166), MSLN-specific CARs (Moon et al, Clin Cancer Res (2011) 17(14):4719-30), NKG2D-specific CARs (VanSeggelen et al., Mol Ther (2015) 23(10):1600-1610), CD19-specific CARs (Axicabtagene ciloleucel (Yescarta®) and Tisagenlecleucel (Kymriah®). See also, Li et al., J Hematol and Oncol (2018) 11(22), reviewing clinical trials of tumor-specific CARs.

In some embodiments, the engineered antigen receptor is an engineered TCR. Engineered TCRs comprise TCRα and/or TCRβ chains that have been isolated and cloned from T cell populations recognizing a particular target antigen. For example, TCRα and/or TCRβ genes (i.e., TRAC and TRBC) can be cloned from T cell populations isolated from individuals with particular malignancies or T cell populations that have been isolated from humanized mice immunized with specific tumor antigens or tumor cells. Engineered TCRs recognize antigen through the same mechanisms as their endogenous counterparts (e.g., by recognition of their cognate antigen presented in the context of major histocompatibility complex (MHC) proteins expressed on the surface of a target cell). This antigen engagement stimulates endogenous signal transduction pathways leading to activation and proliferation of the TCR-engineered cells.

Engineered TCRs specific for tumor antigens are known in the art, for example WT1-specific TCRs (JTCR016, Juno Therapeutics; WT1-TCRc4, described in US Patent Application Publication No. 20160083449), MART-1 specific TCRs (including the DMF4T clone, described in Morgan et al., Science 314 (2006) 126-129); the DMF5T clone, described in Johnson et al., Blood 114 (2009) 535-546); and the ID3T clone, described in van den Berg et al., Mol. Ther. 23 (2015) 1541-1550), gp100-specific TCRs (Johnson et al., Blood 114 (2009) 535-546), CEA-specific TCRs (Parkhurst et al., Mol Ther. 19 (2011) 620-626), NY-ESO and LAGE-1 specific TCRs (1G4T clone, described in Robbins et al., J Clin Oncol 26 (2011) 917-924; Robbins et al., Clin Cancer Res 21 (2015) 1019-1027; and Rapoport et al., Nature Medicine 21 (2015) 914-921), and MAGE-A3-specific TCRs (Morgan et al., J Immunother 36 (2013) 133-151) and Linette et al., Blood 122 (2013) 227-242). (See also, Debets et al., Seminars in Immunology 23 (2016) 10-21).

In some embodiments, the engineered antigen receptor is directed against a target antigen selected from a cluster of differentiation molecule, such as CD3, CD4, CD8, CD16, CD24, CD25, CD33, CD34, CD45, CD64, CD71, CD78, CD80 (also known as B7-1), CD86 (also known as B7-2), CD96, CD116, CD117, CD123, CD133, and CD138, CD371 (also known as CLL1); a tumor-associated surface antigen, such as 5T4, BCMA (also known as CD269 and TNFRSF17, UniProt #Q02223), carcinoembryonic antigen (CEA), carbonic anhydrase 9 (CAIX or MN/CAIX), CD19, CD20, CD22, CD30, CD40, disialogangliosides such as GD2, ELF2M, ductal-epithelial mucin, ephrin B2, epithelial cell adhesion molecule (EpCAM), ErbB2 (HER2/neu), FCRL5 (UniProt #Q68SN8), FKBP11 (UniProt #Q9NYL4), glioma-associated antigen, glycosphingolipids, gp36, GPRC5D (UniProt #Q9NZD1), mut hsp70-2, intestinal carboxyl esterase, IGF-I receptor, ITGA8 (UniProt #P53708), KAMP3, LAGE-1a, MAGE, mesothelin, neutrophil elastase, NKG2D, Nkp30, NY-ESO-1, PAP, prostase, prostate-carcinoma tumor antigen-1 (PCTA-1), prostate specific antigen (PSA), PSMA, prostein, RAGE-1, ROR1, RU1 (SFMBT1), RU2 (DCDC2), SLAMF7 (UniProt #Q9NQ25), survivin, TAG-72, and telomerase; a major histocompatibility complex (MHC) molecule presenting a tumor-specific peptide epitope; tumor stromal antigens, such as the extra domain A (EDA) and extra domain B (EDB) of fibronectin; the A1 domain of tenascin-C (TnC A1) and fibroblast associated protein (FAP); cytokine receptors, such as epidermal growth factor receptor (EGFR), EGFR variant III (EGFRvIII), TFGβ-R or components thereof such as endoglin; a major histocompatibility complex (MHC) molecule; a virus-specific surface antigen such as an HIV-specific antigen (such as HIV gp120); an EBV-specific antigen, a CMV-specific antigen, a HPV-specific antigen, a Lassa virus-specific antigen, an Influenza virus-specific antigen as well as any derivate or variant of these surface antigens.

In some embodiments, the immune checkpoint inhibitor is an antibody or an antigen binding fragment thereof. In some embodiments, the immune checkpoint inhibitor binds to PD-1 (e.g., the inhibitor is an anti-PD-1 antibody). Anti-PD1 antibodies are known in the art, for example, Nivolumab, Pembrolizumab, Lambrolizumab, Pidilzumab, Cemiplimab, and AMP-224 (AstraZeneca/MedImmune and GlaxoSmithKline), JTX-4014 by Jounce Therapeutics, Spartalizumab (PDR001, Novartis), Camrelizumab (SHR1210, Jiangsu HengRui Medicine Co., Ltd), Sintilimab (IBI308, Innovent and Eli Lilly), Tislelizumab (BGB-A317), Toripalimab (JS 001), Dostarlimab (TSR-042, WBP-285, GlaxoSmithKline), INCMGA00012 (MGA012, Incyte and MacroGenics), and AMP-514 (MEDI0680, AstraZeneca). In some embodiments, the immune checkpoint inhibitor binds to PD-L1 (e.g., the inhibitor is an anti-PD-L1 antibody). Anti-PDL1 antibodies are known in the art, for example, MEDI-4736, MPDL3280A, Atezolizumab (Tecentriq, Roche Genentech), Avelumab (Bavencio, Merck Serono and Pfizer), and Durvalumab (Imfinzi, AstraZeneca). In some embodiments, the immune checkpoint inhibitor binds to CTLA4 (e.g., the inhibitor is an anti-CTLA4 antibody). Anti-CTLA4 antibodies are known in the art, for example, ipilumumab, tremelimumab, or any of the antibodies disclosed in WO2014/207063. In some embodiments, the immune checkpoint inhibitor is an anti-TIGIT antibody or fragment thereof. Anti-TIGIT antibodies are known in the art, for example tiragolumab (Roche), EOS-448 (iTeos Therapeutics), Vibostolimab (Merck), Domvanalimab (Arcus, Gilead), BMS-986207 (BMS), Etigilimab (Mereo), COM902 (Compugen), ASP8374 (Astellas), SEA-TGT (Seattle Genetics) BGB-A1217 (BeiGene), IBI-939 (Innovent), and M6223 (EMD Serono).

In some embodiments, the method of treating cancer comprises administering to the subject 1) a therapeutically effective amount of an oncolytic virus or polynucleotide encoding the same; and 2) a therapeutically effective amount of a polypeptide comprising an anti-DLL3 binding construct or polynucleotide encoding the same. In some embodiments, the oncolytic virus or polynucleotide encoding the same is administered before the polypeptide comprising an anti-DLL3 binding construct or polynucleotide encoding the same. In some embodiments, the polypeptide comprising an anti-DLL3 binding construct or polynucleotide encoding the same is administered before the oncolytic virus or polynucleotide encoding the same. In some embodiments, the oncolytic virus is a picornavirus. In some embodiments, the picornavirus is a Seneca Valley Virus (SVV) or a Coxsackie virus (CVA).

In some embodiments, the polypeptide comprising an anti-DLL3 binding construct or polynucleotide encoding the same is administered once. In some embodiments, the polypeptide comprising an anti-DLL3 binding construct or polynucleotide encoding the same is administered multiple times or repeatedly. In some embodiments, the oncolytic virus or polynucleotide encoding the same is administered once. In some embodiments, the oncolytic virus or polynucleotide encoding the same is administered multiple times or repeatedly. In some embodiments, repeated administration (e.g., of a polypeptide comprising an anti-DLL3 antigen-binding fragment) is performed every about 3 hours, 6 hours, 12 hours, 1 day, 2 days, 3 days, 4 days, 5 days, 6 days, a week, 2 weeks, 3 weeks, 4 weeks, 1 month, or longer, including all ranges and subranges therebetween, for a duration of time. In some embodiments, the duration of time is about 12 hours, 1 day, 2 days, 3 days, 4 days, 5 days, 6 days, a week, 2 weeks, 3 weeks, 4 weeks, 1 month, 2 months, 3 months, 4 months, 5 months, 6 months, or longer, including all ranges and subranges therebetween.

"Administration" refers herein to introducing a therapeutic agent, a polypeptide, a vector, an oncolytic virus, a viral stock, a conjugate thereof, or a composition thereof into a subject or contacting a therapeutic agent, a polypeptide, a vector, an oncolytic virus, a viral stock, a conjugate thereof, or a composition thereof with a cell and/or tissue. Administration can occur by injection, irrigation, inhalation, consumption, electro-osmosis, hemodialysis, iontophoresis, and other methods known in the art. The route of administration will vary, naturally, with the location and nature of the disease being treated, and may include, for example auricular, buccal, conjunctival, cutaneous, dental, endocervical, endosinusial, endotracheal, enteral, epidural, interstitial, intra-articular, intra-arterial, intra-abdominal, intraauricular, intrabiliary, intrabronchial, intrabursal, intracavernous, intracerebral, intracisternal, intracorneal, intracronal, intracoronary, intracranial, intradermal, intradiscal, intraductal, intraduodenal, intraduodenal, intradural, intraepicardial, intraepidermal, intraesophageal, intragastric, intragingival, intrahepatic, intraileal, intralesional, intralingual, intraluminal, intralymphatic, intramammary, intramedulleray, intrameningeal, instramuscular, intranasal, intranodal, intraocular, intraomentum, intraovarian, intraperitoneal, intrapericardial, intrapleural, intraprostatic, intrapulmonary, intraruminal, intrasinal, intraspinal, intrasynovial, intratendinous, intratesticular, intratracheal, intrathecal, intrathoracic, intratubular, intratumoral, intratympanic, intrauterine, intraperitoneal, intravascular, intraventricular, intravesical, intravestibular, intravenous, intravitreal, larangeal, nasal, nasogastric, oral, ophthalmic, oropharyngeal, parenteral, percutaneous, periarticular, peridural, perineural, periodontal, respiratory, retrotubular, rectal, spinal, subarachnoid, subconjunctival, subcutaneous, subdermal, subgingival, sublingual, submucosal, subretinal, topical, transdermal, transendocardial, transmucosal, transplacental, trantracheal, transtympanic, ureteral, urethral, and/or vaginal perfusion, lavage, direct injection, and oral administration.

In some embodiments, the polypeptide comprising an anti-DLL3 binding construct, or the polynucleotide encoding the same, is administered systemically. In some embodiments, the polypeptide or polynucleotide encoding the same is administered parenterally. In some embodiments, the polypeptide or polynucleotide encoding the same is administered intravenously. In some embodiments, the polypeptide or polynucleotide encoding the same is administered locally. In some embodiments, the polypeptide or polynucleotide encoding the same is administered intratumorally. In some embodiments, the polypeptide is a trispecific binding construct comprising an anti-DLL3 binding domain of the disclosure.

In some embodiments, the oncolytic virus or polynucleotide encoding the same is administered systemically. In some embodiments, the oncolytic virus or polynucleotide encoding the same is administered parenterally. In some embodiments, the oncolytic virus or polynucleotide encoding the same is administered intravenously. In some embodiments, the oncolytic virus or polynucleotide encoding the same is administered locally. In some embodiments, the oncolytic virus or polynucleotide encoding the same is administered intratumorally.

In some embodiments, the polynucleotide encoding the oncolytic virus (e.g., a RNA molecule encoding SVV viral genome or Coxsackievirus viral genome) is encapsulated in a lipid nanoparticle (LNP). In some embodiments, administering the polynucleotide encoding the oncolytic virus comprises administering the LNP containing the polynucleotide.

In some embodiments, the oncolytic virus is a picornavirus. In some embodiments, the oncolytic virus is a Seneca Valley virus (SVV). In some embodiments, the oncolytic virus is a coxsackievirus. In some embodiments, the coxsackievirus is a coxsackievirus A type (CVA)—for example, CVA21. In some embodiments, the oncolytic virus is a herpes simplex virus.

Further Numbered Embodiments

Further numbered embodiments of the present disclosure are provided as follows:

Embodiment 1: A single domain antibody (sdAb) comprising a complementarity determining region (CDR) 1, a CDR2, and a CDR3, wherein: the CDR1 comprises an amino acid sequence selected from SEQ ID NOs: 1, 6, 10, 14, 18, 22, 26, 30, 33, 36, 39, 46, 52, 60, 65, 69, 73, 77, and 83; the CDR2 comprises an amino acid sequence selected from SEQ ID NOs: 2, 7, 11, 15, 19, 23, 27, 40, 43, 47, 53, 61, 66, 74, 78, 81, and 82; and the CDR3 comprises an amino acid sequence selected from SEQ ID NOs: 3, 8, 12, 16, 20, 24, 28, 31, 34, 37, 41, 44, 48, 54, 62, 67, 71, 75, 79, and 84.

Embodiment 2: The sdAb of Embodiment 1, wherein: the CDR1 comprises an amino acid sequence of SEQ ID NO: 46; the CDR2 comprises an amino acid sequence of SEQ ID NO: 47; and the CDR3 comprises an amino acid sequence of SEQ ID NO: 48.

Embodiment 3: The sdAb of Embodiment 1, wherein: the CDR1 comprises an amino acid sequence of SEQ ID NO: 52; the CDR2 comprises an amino acid sequence of SEQ ID NO: 53; and the CDR3 comprises an amino acid sequence of SEQ ID NO: 54.

Embodiment 4: The sdAb of Embodiment 1, wherein: the CDR1 comprises an amino acid sequence of SEQ ID NO: 18; the CDR2 comprises an amino acid sequence of SEQ ID NO: 19; and the CDR3 comprises an amino acid sequence of SEQ ID NO: 20.

Embodiment 5: The sdAb of Embodiment 1, wherein: the CDR1 comprises an amino acid sequence of SEQ ID NO: 83; the CDR2 comprises an amino acid sequence of SEQ ID NO: 2; and the CDR3 comprises an amino acid sequence of SEQ ID NO: 84.

Embodiment 6: The sdAb of Embodiment 1, wherein: the CDR1 comprises an amino acid sequence of SEQ ID NO:

60; the CDR2 comprises an amino acid sequence of SEQ ID NO: 61; and the CDR3 comprises an amino acid sequence of SEQ ID NO: 62.

Embodiment 7: The sdAb of Embodiment 1, wherein: the CDR1 comprises an amino acid sequence of SEQ ID NO: 65; the CDR2 comprises an amino acid sequence of SEQ ID NO: 66; and the CDR3 comprises an amino acid sequence of SEQ ID NO: 67.

Embodiment 8: The sdAb of Embodiment 1, wherein: the CDR1 comprises an amino acid sequence of SEQ ID NO: 69; the CDR2 comprises an amino acid sequence of SEQ ID NO: 23; and the CDR3 comprises an amino acid sequence of SEQ ID NO: 24.

Embodiment 9: The sdAb of Embodiment 1, wherein: the CDR1 comprises an amino acid sequence of SEQ ID NO: 14; the CDR2 comprises an amino acid sequence of SEQ ID NO: 43; and the CDR3 comprises an amino acid sequence of SEQ ID NO: 71.

Embodiment 10: The sdAb of Embodiment 1, wherein: the CDR1 comprises an amino acid sequence of SEQ ID NO: 73; the CDR2 comprises an amino acid sequence of SEQ ID NO: 74; and the CDR3 comprises an amino acid sequence of SEQ ID NO: 75.

Embodiment 11. The sdAb of Embodiment 1 comprising an amino acid sequence that is at least 95%, at least 96%, at least 97%, at least 98%, or at least 99% identical to an amino acid sequence selected from SEQ ID NOs: 4, 5, 9, 13, 17, 21, 25, 29, 32, 35, 38, 42, 45, 49, 55, 59, 63, 64, 68, 70, 72, and 76.

Embodiment 12. The sdAb of Embodiment 1 comprising or consisting of an amino acid sequence selected from SEQ ID NOs: 4, 5, 9, 13, 17, 21, 25, 29, 32, 35, 38, 42, 45, 49, 55, 59, 63, 64, 68, 70, 72, and 76.

Embodiment 13. A single domain antibody sdAb comprising (a) human framework region sequence and (b) a complementarity determining region (CDR) 1, a CDR2, and a CDR3, wherein (i) the CDR1 comprises an amino acid sequence selected from SEQ ID NOs: 1, 6, 10, 14, 18, 22, 26, 30, 33, 36, 39, 46, 52, 60, 65, 69, 73, 77, and 83; (ii) the CDR2 comprises an amino acid sequence selected from SEQ ID NOs: 2, 7, 11, 15, 19, 23, 27, 40, 43, 47, 53, 61, 66, 74, 78, 81, and 82; and (iii) the CDR3 comprises an amino acid sequence selected from SEQ ID NOs: 3, 8, 12, 16, 20, 24, 28, 31, 34, 37, 41, 44, 48, 54, 62, 67, 71, 75, 79, and 84.

Embodiment 14: The sdAb of Embodiment 13, wherein: the CDR1 comprises an amino acid sequence of SEQ ID NO: 46; the CDR2 comprises an amino acid sequence of SEQ ID NO: 47; and the CDR3 comprises an amino acid sequence of SEQ ID NO: 48.

Embodiment 15: The sdAb of Embodiment 13, wherein: the CDR1 comprises an amino acid sequence of SEQ ID NO: 52; the CDR2 comprises an amino acid sequence of SEQ ID NO: 53; and the CDR3 comprises an amino acid sequence of SEQ ID NO: 54.

Embodiment 16: The sdAb of Embodiment 13, wherein: the CDR1 comprises an amino acid sequence of SEQ ID NO: 18; the CDR2 comprises an amino acid sequence of SEQ ID NO: 19; and the CDR3 comprises an amino acid sequence of SEQ ID NO: 20.

Embodiment 17: The sdAb of Embodiment 13, wherein: the CDR1 comprises an amino acid sequence of SEQ ID NO: 83; the CDR2 comprises an amino acid sequence of SEQ ID NO: 2; and the CDR3 comprises an amino acid sequence of SEQ ID NO: 84.

Embodiment 18: The sdAb of Embodiment 13, wherein: the CDR1 comprises an amino acid sequence of SEQ ID NO: 60; the CDR2 comprises an amino acid sequence of SEQ ID NO: 61; and the CDR3 comprises an amino acid sequence of SEQ ID NO: 62.

Embodiment 19: The sdAb of Embodiment 13, wherein: the CDR1 comprises an amino acid sequence of SEQ ID NO: 65; the CDR2 comprises an amino acid sequence of SEQ ID NO: 66; and the CDR3 comprises an amino acid sequence of SEQ ID NO: 67.

Embodiment 20: The sdAb of Embodiment 13, wherein: the CDR1 comprises an amino acid sequence of SEQ ID NO: 69; the CDR2 comprises an amino acid sequence of SEQ ID NO: 23; and the CDR3 comprises an amino acid sequence of SEQ ID NO: 24.

Embodiment 21: The sdAb of Embodiment 13, wherein: the HCDR1 comprises an amino acid sequence of SEQ ID NO: 14; the HCDR2 comprises an amino acid sequence of SEQ ID NO: 43; and the HCDR3 comprises an amino acid sequence of SEQ ID NO: 71.

Embodiment 22: The sdAb of Embodiment 13, wherein: the CDR1 comprises an amino acid sequence of SEQ ID NO: 73; the CDR2 comprises an amino acid sequence of SEQ ID NO: 74; and the CDR3 comprises an amino acid sequence of SEQ ID NO: 75.

Embodiment 23: The sdAb of Embodiment 13, comprising an amino acid sequence that is at least 95%, at least 96%, at least 97%, at least 98%, or at least 99% identical to an amino acid sequence selected from SEQ ID NOs: 50, 51, 56, 57 and 58.

Embodiment 24: The sdAb of Embodiment 13, comprising or consisting of an amino acid sequence selected from SEQ ID NOs: 50, 51, 56, 57 and 58.

Embodiment 25: The sdAb of any one of Embodiments 1-24, specifically binding to a Delta-like ligand 3 (DLL3) protein.

Embodiment 26: The sdAb of Embodiment 25, wherein the DLL3 protein is a human DLL3 protein.

Embodiment 27: A chimeric antigen receptor (CAR) comprising an extracellular antigen binding domain, a hinge, a transmembrane domain, and a cytoplasmic domain wherein the extracellular antigen binding domain is the sdAb of any one of Embodiments 1-26.

Embodiment 28: A biomolecule comprising the sdAb of any one of Embodiments 1-26.

Embodiment 29: A polynucleotide encoding the sdAb of any one of Embodiments 1-26, the CAR of Embodiment 27, or the biomolecule of Embodiment 28.

Embodiment 30: The polynucleotide of Embodiment 29, wherein the polynucleotide is an mRNA molecule.

Embodiment 31: A vector comprising the polynucleotide of Embodiment 29 or Embodiment 30.

Embodiment 32: A binding construct comprising the sdAb of any one of Embodiments 1-26.

Embodiment 33: A binding construct comprising the sdAb of any one of Embodiments 1-26 and an Fc domain.

Embodiment 34: A bispecific binding construct comprising a first binding domain and a second binding domain, wherein the first binding domain comprises the sdAb of any one of Embodiments 1-26; and wherein the second binding domain is selected from a antigen binding domain that specifically binds to CD3, CD16 or NKp46, or human serum albumin (HSA), or an Fc domain.

Embodiment 35: A trispecific binding construct comprising a first binding domain, a second binding domain and a third binding domain, wherein the first binding domain comprises the sdAb of any one of Embodiments 1-26; wherein the second binding domain comprises an Fc domain or an antigen binding domain that specifically binds to human serum albumin (HSA); and wherein the third binding domain is an antigen binding domain specifically binds to CD3, CD16 or NKp46.

Embodiment 36: The trispecific binding construct of Embodiment 35, wherein the second binding domain is an antigen binding domain that specifically binds to HSA, and the third binding domain is an antigen binding domain that specifically binds to CD3.

Embodiment 37: A polynucleotide encoding the binding construct of Embodiment 32 or 33, the bispecific binding construct of Embodiment 34, or the trispecific binding construct of any one of Embodiments 35-36.

Embodiment 38: The polynucleotide of Embodiment 37, wherein the polynucleotide is an mRNA molecule.

Embodiment 39: A vector comprising the polynucleotide of Embodiment 37.

Embodiment 40: A method of treating cancer in a subject in need thereof, comprising administering the sdAb of any one of Embodiments 1-26, the CAR of Embodiment 27, the biomolecule of Embodiment 28, the binding construct of Embodiment 32 or 33, the bispecific binding construct of Embodiment 34, or the trispecific binding construct of any one of Embodiments 35-36 to the subject.

Embodiment 41: Use of the sdAb of any one of Embodiments 1-26, the CAR of Embodiment 27, the biomolecule of Embodiment 28, the binding construct of Embodiment 32 or 33, the bispecific binding construct of Embodiment 34, or the trispecific binding construct of any one of Embodiments 35-36, for treating cancer in a subject in need thereof.

Embodiment 42: Use of the sdAb of any one of Embodiments 1-26, the CAR of Embodiment 27, the biomolecule of Embodiment 28, the binding construct of Embodiment 32 or 33, the bispecific binding construct of Embodiment 34, or the trispecific binding construct of any one of Embodiments 35-36 in the manufacture of a medicament for treating cancer in a subject in need thereof.

Embodiment 43: The method of Embodiment 40 or use of Embodiment 41 or 42, wherein the cancer is selected from non-small cell lung cancer (NSCLC), small cell lung cancer (SCLC), small cell bladder cancer, large cell neuroendocrine carcinoma (LCNEC), castration-resistant small cell neuroendocrine prostate cancer (CRPC-NE), carcinoid (e.g., pulmonary carcinoid), glioblastoma multiforme-IDH mutant (GBM-IDH mutant), Merkel cell carcinoma, and Gastric neuroendocrine cancer.

Embodiment 44: The method of Embodiment 40 or 43, or the use of any one of Embodiments 41-43, wherein the sdAb or the binding construct is administered in combination with an oncolytic virus or a polynucleotide encoding the oncolytic virus.

Embodiment 45: The method or use of Embodiment 44, wherein the sdAb or the binding construct, and the oncolytic virus or the polynucleotide encoding the oncolytic virus, are administered concurrently.

Embodiment 46: The method or use of Embodiment 44, wherein the sdAb or the binding construct, and the oncolytic virus or the polynucleotide encoding the oncolytic virus, are administered sequentially.

Embodiment 47: The method or use of any one of Embodiments 44-46, wherein the oncolytic virus is a picornavirus.

Embodiment 48: The method or use of Embodiment 47, wherein the picornavirus is a Coxsackievirus.

Embodiment 49: The method or use of Embodiment 47, wherein the picornavirus is a Seneca Valley virus.

Embodiment 50: The method or use of any one of Embodiments 44-49, wherein the polynucleotide encoding the oncolytic virus is encapsulated in a lipid nanoparticle.

Embodiment 51: An oncolytic virus expressing one or more payload molecules, wherein the one or more payload molecules comprise the sdAb of any one of Embodiments 1-26, the binding construct of Embodiment 32 or 33, the bispecific binding construct of Embodiment 34 or 34.b, or the trispecific binding construct of any one of Embodiments 35-36.

Embodiment 52: The oncolytic virus of Embodiment 51, wherein the virus is selected from a herpes simplex virus, an adenovirus, a polio virus, a vaccinia virus, a measles virus, a vesicular stomatitis virus, an orthomyxovirus, a parvovirus, a maraba virus, a picornavirus, a togaviriadae virus, a semliki forest virus, a sindbis virus, a paramyxoviridae virus, and a sendai virus.

Embodiment 53: The oncolytic virus of Embodiment 52, wherein the picornavirus is a coxsackievirus or a seneca valley virus.

Embodiment 54: A method of treating cancer in a subject in need thereof, comprising administering the oncolytic virus of any one of Embodiments 51-53 to the subject.

Embodiment 55: Use of the oncolytic virus of any one of Embodiments 51-53 for treating cancer in a subject in need thereof.

Embodiment 56: Use of the oncolytic virus of any one of Embodiments 51-53 in the manufacture of a medicament for treating cancer in a subject in need thereof.

Embodiment 57: A messenger RNA (mRNA) polynucleotide encoding the sdAb of any one of Embodiments 1-26, the binding construct of Embodiment 32 or 33, the bispecific binding construct of Embodiment 34 or 34.b, or the trispecific binding construct of any one of Embodiments 35-36.

Embodiment 58: A method of treating cancer in a subject in need thereof, comprising administering the mRNA polynucleotide of Embodiment 57 to the subject.

Embodiment 59: Use of the mRNA polynucleotide of Embodiment 57 for treating cancer in a subject in need thereof.

Embodiment 60: Use of the mRNA polynucleotide of Embodiment 57 in the manufacture of a medicament for treating cancer in a subject in need thereof.

Embodiment 61: The method of Embodiment 58 or the use of Embodiment 59 or 60, wherein the mRNA polynucleotide is administered in combination with an oncolytic virus.

Embodiment 62: The method of Embodiment 58 or the use of Embodiment 59 or 60, wherein the mRNA polynucleotide is administered in combination with a polynucleotide encoding an oncolytic virus.

EXAMPLES

Example 1: Cytotoxicity of Anti-DLL3/Anti-CD3 Bispecific Binding Constructs

Experiments were performed to assess the cytotoxicity of multiple anti-DLL3/anti-CD3 bispecific binding constructs. The bispecific binding constructs used in this example comprised an anti-DLL3 VHH domain linked to an anti-CD3 scFv (also referred to herein as a LiTE construct). The anti-DLL3 VHH domains used are the 2HCE27 (SEQ ID NO: 49), 3HCE56 (SEQ ID NO: 55), and 3HCE4 (SEQ ID NO: 21). Human CD3 T cells were incubated with CHO cells expressing human DLL3 at an effector-to-target (E:T) of 10:1. Different dilutions of each LiTEs were tested as indicated in FIG. 1. The Caspase 3/7 area/Phase area % was measured according to the IncuCyte® immune cell killing assay protocol (Essen Bioscience) at 72 hours to determine the cytotoxicity % and the EC50 of each LiTE was determined. Results are shown in FIG. 1. All constructs display cytotoxicity. Among all the VHH clones, 2HCE27-CD3v1 displayed the best activity in the killing assay. CD3v1 was better than CD3v2 at induce the killing of the target cells when combined with 2HCE27 VHH.

Figure 2:
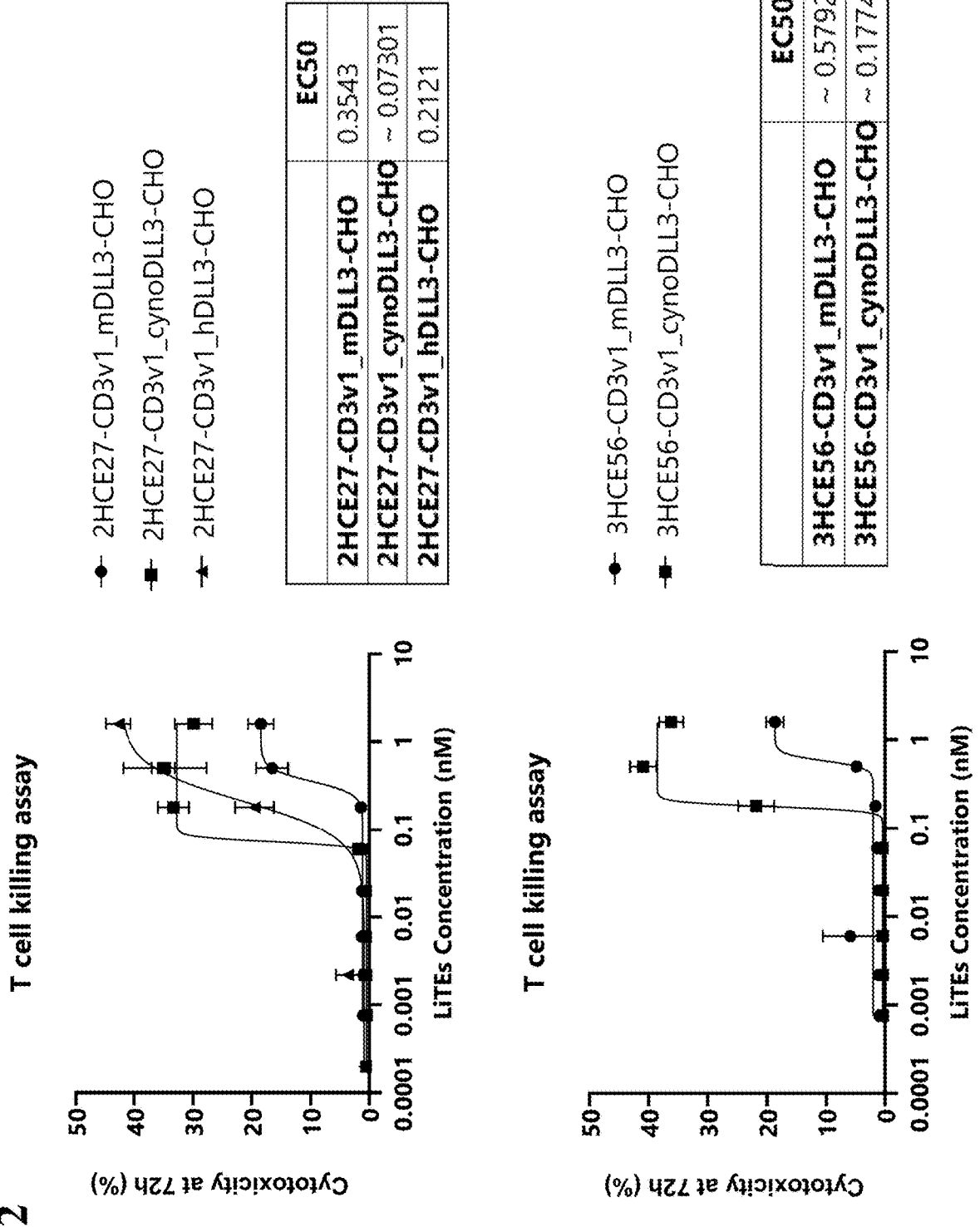
FIG. 2 illustrates the species cross-reactivity of two different anti-DLL3/anti-CD3 bispecific binding constructs.

Example 2: Cross-Reactivity of Anti-DLL3/Anti-CD3 Bispecific Binding Constructs The 2HCE27 and 3HCE56 LiTE constructs described in Example 1 were tested in an in vitro assay to determine the ability of each to bind to murine, human, or cynomolgus DLL3. Human CD3 T cells were incubated with CHO cells expressing either human DLL3 or mouse DLL3 or cyno DLL3 at an E:T 10:1. Different dilution of LiTEs were tested. At 72 hours the Caspase 3/7 area/Phase area % was measured according to the IncuCyte® immune cell killing assay protocol (Essen Bioscience) to reflect the cytotoxicity %. Results are shown in FIG. 2. Both 2HCE27 and 3HCE56 LiTEs induced killing of target cells expressing cyno or mouse DLL3, demonstrating that both anti-human VHHs can cross-react with cyno and mouse DLL3.

Example 3: Binding Properties of Anti-DLL3 Constructs

Antibody binning experiments were carried out for 5 anti-DLL3 VHHs and an anti-human DLL3 BiTE (SEQ ID NO: 756). The target antigen was coated on a series of Octet SA tips. Each series of tips was first soaked in a periplasmic extract containing one specific VHH. After the response signals reached saturation, the tips were transferred to a mix of PEs containing again the first VHH (at the same concentration) plus a different VHH (termed secondary VHH) for each tip of the series. Secondary VHH that still bind the target antigen in the presence of the first VHH will show an increased response, as compared to the binding response of the first VHH alone. This was repeated for each VHH as primary VHH until all VHH were tested against each other in both directions (as primary and as secondary binder). From the response data, the bins were deduced for each VHH. Results are shown in Table 9 below. 2HCE117 and 3HCE4 show competition with the human DLL3 BiTEs, whereas 3HCE56 and 3HCE87 show a partial competition. 2HCE27 does not compete with the human DLL3 BiTE, suggesting that their binding epitopes on DLL3 are different.

DLL3. To obtain off-rate ($k_{off}$), human biotinylated DLL3 was immobilized on Octet SA tips, and cynomolgus or mouse DLL3 was immobilized on Octet AR2G tips. For each DLL3 protein, the binding to a dilution series of each anti-DLL3 construct was measured using Fortebio Octet Red. The dissociation constant ($K_D$), off-rate ($k_{off}$) and other kinetic parameters for each anti-DLL3 construct were calculated using a 1:1 binding model. In addition, binding of these anti-DLL3 constructs to CHO cells expressing human, cyno or mouse DLL3 protein was analyzed using flow cytometry (FACS). Results are shown in FIG. 3, which demonstrates that all anti-DLL3 constructs tested (2HCE27, 3HCE4, 3HCE56, 3HCE87 and 2HCE117) have high affinity binding to human DLL3 protein, as well as binding to cyno and mouse DLL3 proteins.

Figure 10:
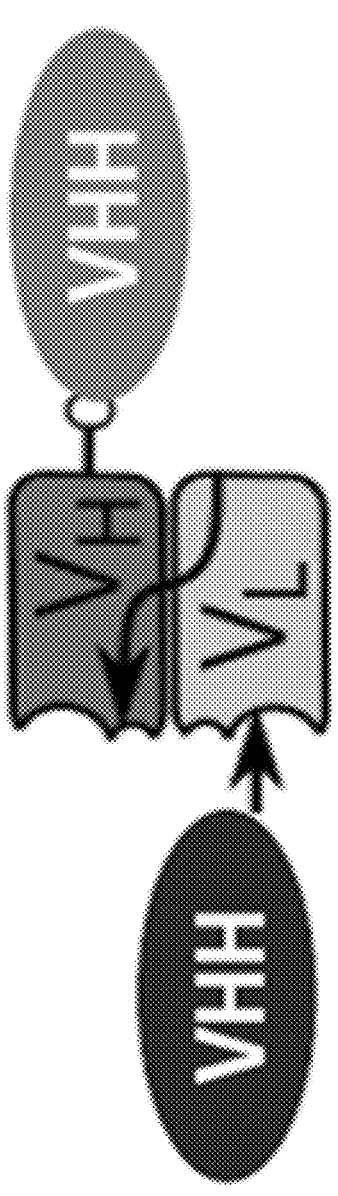
FIG. 10 illustrates a trispecific binding construct of the present disclosure.

Example 4: Binding and Cross-Reactivity of an Anti-DLL3/Anti-CD3/Anti-HSA Trispecific Binding Construct Experiments were performed to assess the binding and cross-reactivity of an anti-DLL3/anti-CD3/anti-HSA tri specific binding construct. The domain organization of the tri specific binding construct is shown in FIG. 10. The anti-DLL3 VHH domain in the trispecific binding construct is 2HCE27 (SEQ ID NO: 49).

Surface Plasmon Resonance (SPR) was used to assess the binding kinetics and binding affinity. Kinetic rate coefficients were recovered from binding analysis experiments performed with a Biacore 3000 biosensor. Concentrations of the anti-DLL3/anti-CD3/anti-HSA trispecific binding construct ranging from 1.23 nM to 300 nM were run against the SPR sensorgram surfaces immobilized with recombinant human CD3 (rhu CD3) or recombinant HSA (rHSA). Concentrations of recombinant human DLL3 (rhu DLL3) ranging from 1.23 nM to 100 nM were run against the SPR sensorgram surface immobilized with the anti-DLL3/anti-CD3/anti-HSA trispecific binding construct. The association and dissociation phase data were globally fit to a 1:1 model to determine the association rate coefficient ($k_{on}$), dissociation rate coefficient ($k_{off}$), the Rmax value, and the dissociation constant ($K_D$). Results were reported as the global fits to 1:1 model±standard error. The control groups were the three corresponding individual binding constructs. The results are shown in Table 10 below. All three antigen

TABLE 9

| | | | BIN 6 | BIN 5 | | |
| | DLL3 BiTEs | 2HCE27 | 3HCE4 | 3HCE56 | 3HCE87 | 2HCE117 |
| --- | --- | --- | --- | --- | --- | --- |
| DLL3 BiTEs | 0.00 | 82.52 | 121.36 | 1501.59 | 125.35 | 1279.87 |
| 2HCE27 | 83.38 | 0.00 | 53.42 | 6495.12 | 87.49 | 19919.16 |
| 3HCE4 | 9.03 | 346.55 | 0 | 406.99 | 120.36 | 3507.51 |
| 3HCE56 | 44.06 | −3.58 | −79.59 | 0.00 | −99.14 | 1114.98 |
| 3HCE87 | 68.35 | −48.19 | −54.40 | 203.52 | 0.00 | 1210.99 |
| 2HCE117 | −23.17 | −73.01 | −90.13 | −206.97 | −98.70 | 0.00 |

Binning of Anti-DLL3 Antibodies

Additional experiments were carried out to further characterize the binding properties of the anti-DLL3 constructs. Binding properties tested include dissociation constant ($K_D$), off-rate ($k_{off}$), binding to DLL3 protein by ELISA and binding to CHO cells expressing human, cyno or mouse binding domains in the trispecific binding construct retain binding to the corresponding antigen. The anti-DLL3 binding domain in the trispecific binding construct shows comparable dissociation constant ($K_D$) as the isolated anti-DLL3 binding construct.

TABLE 10

Comparison of Binding Properties of the anti-DLL3/anti-CD3/anti-
HSA trispecific Binding Construct with Corresponding Individual
Binding Constructs

| Binding Construct | Ligand | $k_{on}$ 1 × $10^4$ ($M^{-1}s^{-1}$) | $k_{off}$ 1 × $10^{-3}$ ($s^{-1}$) | Rmax (RU) | $K_D$ (nM) |
|---|---|---|---|---|---|
| anti-DLL3/ anti-CD3/ anti-HSA trispecific binding construct | rhu CD3 | 33.67 ± 0.03 | 0.39 ± 0.01 | 50.18 ± 0.01 | 1.15 ± 0.01 |
| | rHSA | 2.7 ± 0.01 | 1.75 ± 0.01 | 83.73 ± 0.07 | 64.7 ± 0.1 |
| | rhu DLL3 | 9.84 ± 0.02 | 0.64 ± 0.001 | 43.27 ± 0.04 | 6.47 ± 0.01 |
| anti-CD3 | rhu CD3 | 510 | 0.57 | 11.1 | 0.112 |
| anti-HSA | rHSA | | | | 0.91 |
| anti-DLL3 (2HCE27) | rhu DLL3 | 8 ± 0.01 | 0.64 ± 0.001 | | 7.89 ± 0.01 |

Cell binding assays were performed to determine the ability of the anti-DLL3/anti-CD3/anti-HSA trispecific binding construct to bind to human or cynomolgus (cyno) DLL3 and CD3.

$5 \times 10^4$ CHO or cancer cells/well were plated in a 96 well round plate. Cells were incubated for 30 min at 4° C. with 0.02 mL block solution (10% goat+10% rabbit serum diluted in Flow media (PBS, 1% BSA)) and then washed. The trispecific binding construct was titrated from 120 nM to 0.1 nM in serial 3-fold dilutions in Flow media, added to the cells at a volume of 30 μL/well, and incubated for 30 min at 4° C. The cells were then washed in Flow media and stained with an anti-His APC conjugated antibody (cat #IC050A, R&D systems) for 20 min at 4° C. to detect the His-tagged trispecific binding construct.

Figure 4A:
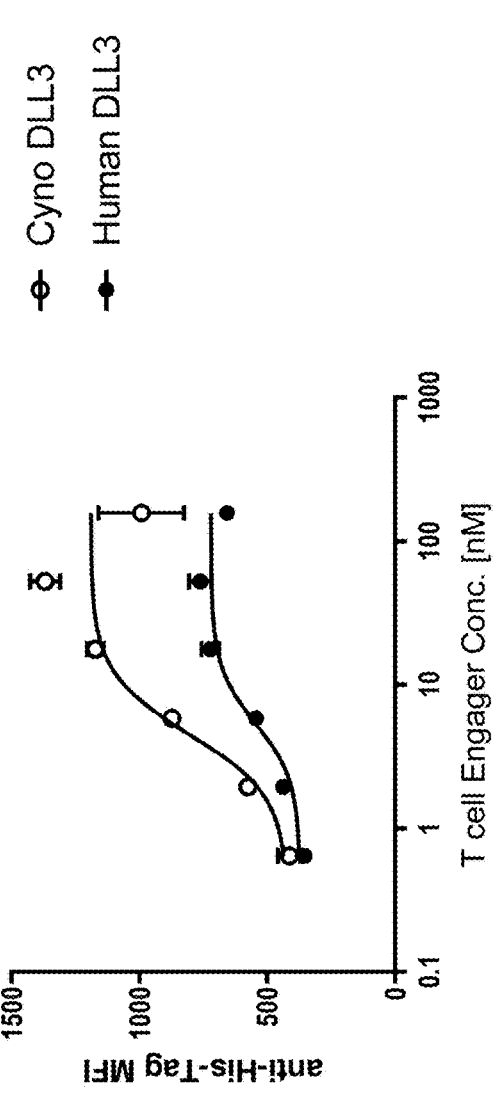
FIG. 4A illustrates the species cross-reactivity of the anti-DLL3/anti-CD3/anti-HSA trispecific binding construct on Cyno-DLL3-CHO cells and human-DLL3-CHO cells measured by flowcytometry.

Flow cytometry was used to analyze the presence of the trispecific binding construct on cell surface. CHO cells expressing either human DLL3 or cynomolgus DLL3 were washed 2×0.2 mL with Flow media and then 100 μL Flow media was added. 5 μL 7AAD was added 5 min before plate analyzing to enable gating of live versus dead cells. Data were acquired on a BD LSRFortessa using BD FACSDiva software, and analyzed using FlowJo software. The EC50 values of the trispecific binding construct were calculated by measuring the APC MFI in the live cells gate. The results (FIG. 4A) show that the trispecific binding construct binds to human DLL3 and cynomolgus DLL3 on the cell surface with similar EC50.

Figure 4B:
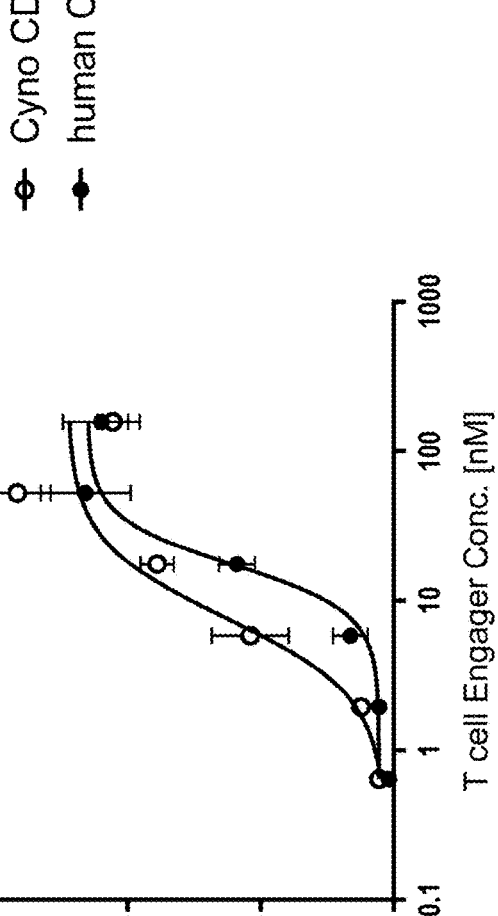
FIG. 4B illustrates the species cross-reactivity of the anti-DLL3/anti-CD3/anti-HSA trispecific binding construct on human and Cyno CD8 T cells measured by flow cytometry.

For the CD8 human and cyno T cell binding assays, the procedure was similar, but the staining with the anti-His APC conjugated antibody was done in presence of anti-human CD8-PE (clone SK1, Cat #12-087-41, eBioscience), anti-human CD14-BV421 (clone HCD14, Cat #325628, Biolegend), and anti-human CD4-BV605 (clone RPA-T4, Cat #562659BD, Biosciences). The EC50 values of the trispecific binding construct were calculated by measuring the APC MFI in the live cells CD8+ gate. The results (FIG. 4B) show that the trispecific binding construct binds to human CD3 and cynomolgus CD3 on the cell surface with similar EC50.

Figures 5A, 5B, 5C:
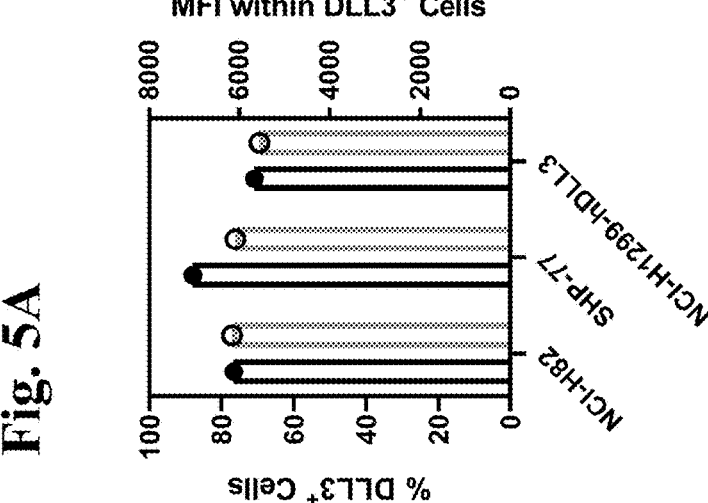
FIG. 5A illustrates the expression of DLL3 on SHP-77, NCI-H82 and NCI-H1299 cells transduced with human DLL3. The percent of cells expressing DLL3 and the mean fluorescence intensity (MFI) within the positive cells were measured by flow cytometry.
FIG. 5B illustrates the binding of the anti-DLL3/anti-CD3/anti-HSA trispecific binding construct on the NSCLC cell line NCI-H1299, or NCI-H1299 cells transduced with human DLL3, as measured by flow cytometry.
FIG. 5C illustrates the binding of the anti-DLL3/anti-CD3/anti-HSA trispecific binding construct on the NSCLC cell lines NCI-H82 and SHP-77, as measured by flow cytometry.

Additional experiments were performed to analyze the binding of the anti-DLL3/anti-CD3/anti-HSA trispecific binding construct to multiple cancer cell lines including NCI-H1299 parental, NCI-H1299 transduced with human DLL3 (NCI-H1299-hDLL3), SHP-77 and NCI-H82. Firstly, the cancer cell lines were stained for human DLL3 expression. For each cell line, 5×104 cells/well were plated in a 96 well round plate. Cells were incubated for 15 min at 4° C.

with 30 μL/well of anti-DLL3 antibody (Biolegend, clone RMD3-13, cat #154004) in Flow media (PBS, 1% BSA). Samples were washed with 0.25 mL Flow media, then 100 μL Flow media was added. 5 μL 7AAD was added 5 min before plate analyzing to enable live/dead gating. Data were acquired on a BD LSRFortessa using BD FACSDiva software, and analyzed using FlowJo software. The results are shown in FIG. 5A. The analyzed cell lines express DLL3 in about 70%-90% of the cell population, with about 5000-7000 mean fluorescence intensity (MFI) within the positive cells. Binding assay was performed following procedures similar to the CHO cells above, and the results are shown in FIG. 5B and FIG. 5C. The anti-DLL3/anti-CD3/anti-HSA trispecific binding construct binds to all DLL3 expressing cell lines.

Table 11 below summarizes the binding EC50 values of the trispecific binding construct to DLL3 in various cell lines used in this example.

TABLE 11

EC50 of Trispecific Binding Construct Binding to DLL3 in Various Cell
Lines

| DLL3 binding | EC50 [nM] |
|---|---|
| CHO-human DLL3 | 5.56 ± 0.22 |
| CHO-Cyno DLL3 | 5.51 ± 1.35 |
| NCI-H1299-human DLL3 | 10.47 ± 1.5 |
| NCI-H82 | 9.96 ± 8.9 |
| SHP-77 | 12.36 ± 7.12 |

Table 12 below summarize the binding EC50 values of the trispecific binding construct to CD3 in various cell lines used in this example.

TABLE 12

EC50 of Trispecific Binding Construct Binding to CD3 in Various Cell
Lines

| CD3 binding | EC50 [nM] |
|---|---|
| Human CD4 T Cell | 17.97 ± 1.58 |
| Human CD8 T Cell | 18.11 ± 0.86 |
| Cyno CD4 T Cell | 7.29 ± 1.57 |
| Cyno CD8 T Cell | 6.57 ± 0.94 |

Example 5: Cytotoxicity of the
Anti-DLL3/Anti-CD3/Anti-HSA Trispecific Binding
Construct Experiments were performed to analyze the in vitro cytotoxicity of the anti-DLL3/anti-CD3/anti-HSA trispecific binding construct at the presence of T cells.

Protocol for CHO cells expressing human DLL3 or cyno, or NCI-H1299 cell line transduced with human DLL3. The day before the cytotoxicity assay, target cells were plated 5000 target cells/well in the 96 well plate. On the day of the assay, purified CD3 T cells (effector cell) from human or Cyno PBMCs were plated 50 000 cells/well, to obtain an Effector:Target cell ratio of 10:1. The trispecific binding construct was titrated from 20 nM to 0.1 nM, serial 3-fold dilutions in media and was added to the wells, then IncuCyte® Caspase-3/7 Green Reagent for Apoptosis (Essen BioScience, Inc. cat #4668) was added to the wells to measure cytotoxicity. The plates were scanned every 3 hours for 96 hours in the presence of IncuCyte®. The data was analyzed, and best time point was used to calculate the EC50 values. The results are shown in FIG. 6A and FIG. 6B.

Protocol for NCI-H82 and SHP-77 cell lines: NCI-H82 or SHP-77 target cells were plated at a density of 20000 and 3000 target cells/well, respectively, in flat bottom 96 well plate. Purified CD3 T cells from human PBMCs were plated to obtain an Effector:Target cell ratio of 5:1. The trispecific binding construct was titrated from 20 nM to 0.1 nM, serial 3-fold dilutions in media and was added to the wells. The cytotoxicity was measured 72 h later using the CytoTox 96® Non-Radioactive Cytotoxicity Assay (Promega, cat #G1780). The data was analyzed according to the manufacturer recommendations and EC50 values were calculated. The results are shown in FIG. 6C.

Figures 6A, 6B:
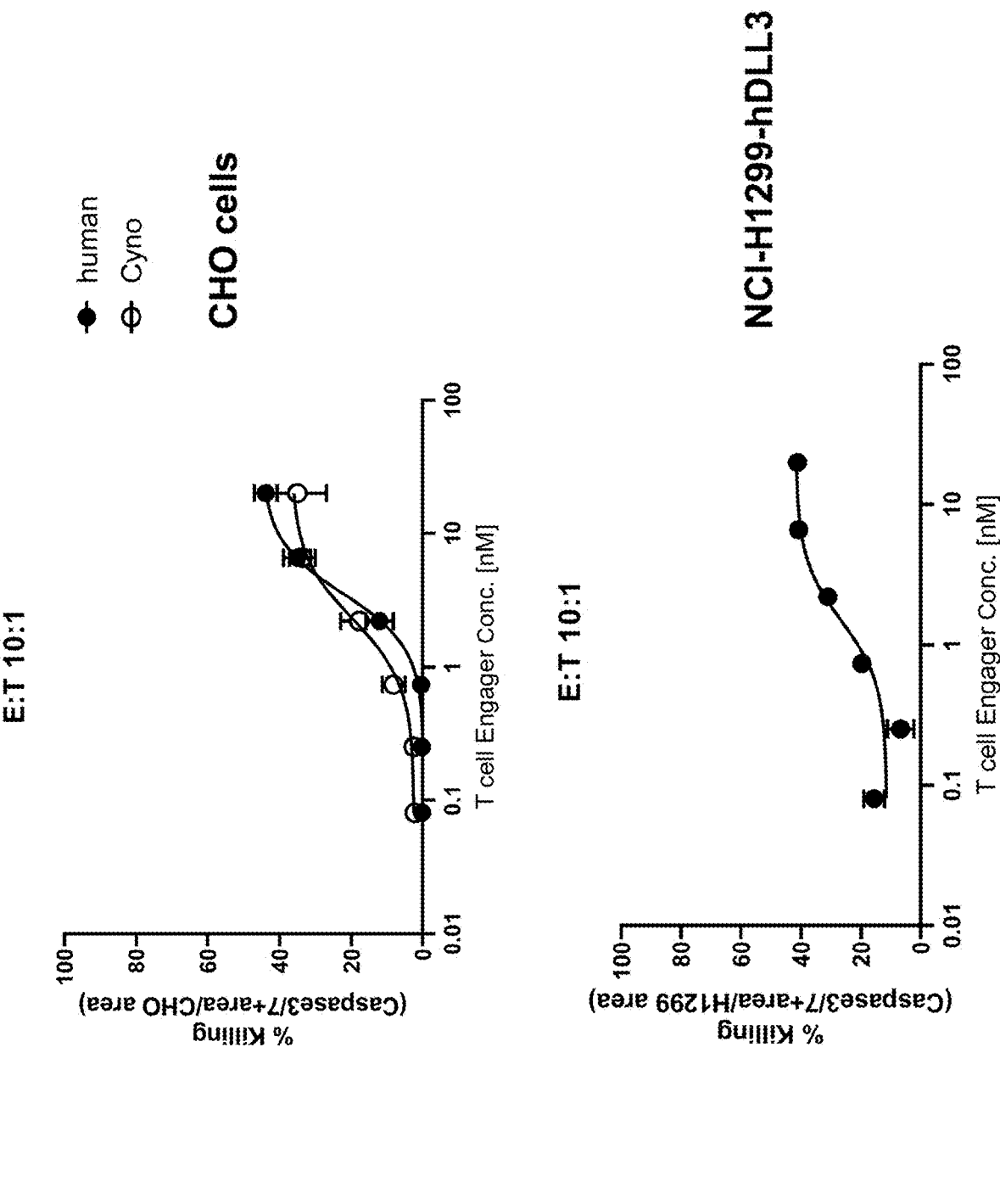
FIG. 6A illustrates the cytotoxicity of the anti-DLL3/anti-CD3/anti-HSA trispecific binding construct on Cyno-DLL3-expressing CHO cells and human-DLL3-expressing CHO cells by cyno or human T cells, respectively.
FIG. 6B illustrates the cytotoxicity of the anti-DLL3/anti-CD3/anti-HSA trispecific binding construct on the NSCLC cell line NCI-H1299 transduced with human DLL3 by human T cells.
Figure 6C:
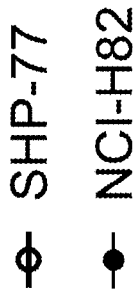
FIG. 6C illustrates the cytotoxicity of the anti-DLL3/anti-CD3/anti-HSA trispecific binding construct on NSCLC cell line NCI-H82 and SHP-77 by human T cells.
Figure 6C:
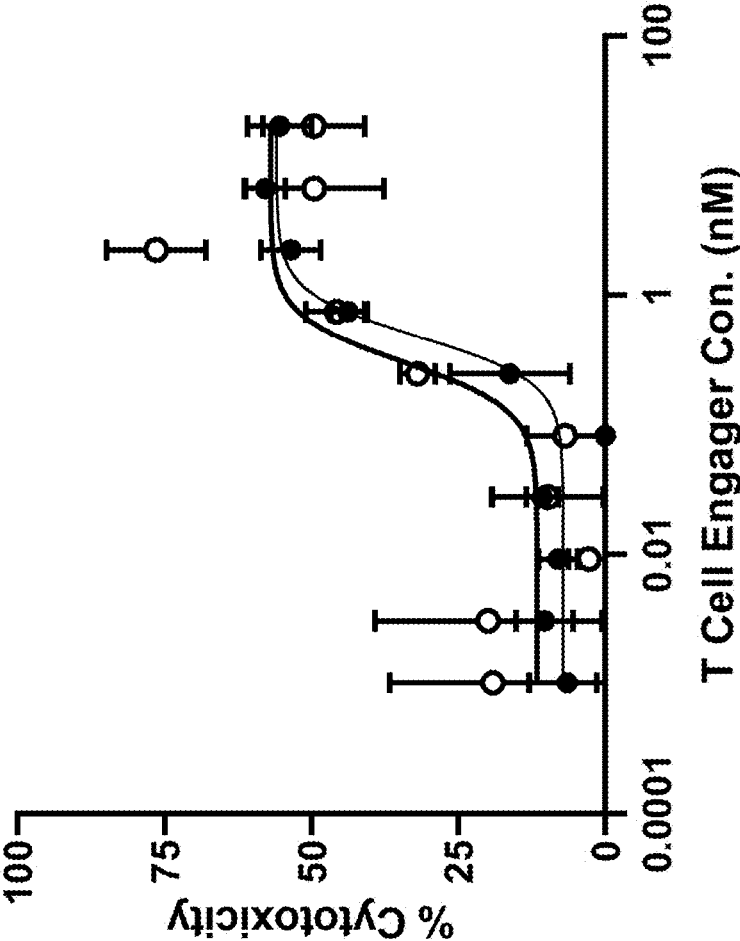

The results in FIG. 6A-6C demonstrate that the anti-DLL3/anti-CD3/anti-HSA trispecific binding construct is able to mediate potent cell killing activity of the DLL3 expressing target cells by T cells. The EC50 values of cytotoxicity evaluated in this example are summarized in Table 13 below.

TABLE 13

| Cytotoxicity EC50 of Trispecific Binding Construct | |
| --- | --- |
| Target cells | EC50 [nM] |
| CHO-human DLL3 | 1.79 ± 0.9 |
| CHO-Cyno DLL3 | 1.58 ± 0.84 |
| NCI-H1299-human DLL3 | 1.49 ± 0.44 |
| NCI-H82 | 0.36 ± 0.19 |
| SHP-77 | 0.43 ± 0.28 |

Example 6: Pharmacokinetics (PK) Study of the Anti-DLL3/Anti-CD3/Anti-HSA Trispecific Binding Construct Experiments were performed to evaluate the pharmacokinetics of the trispecific binding construct and the effect of the anti-HSA binding domain.

Figure 7:
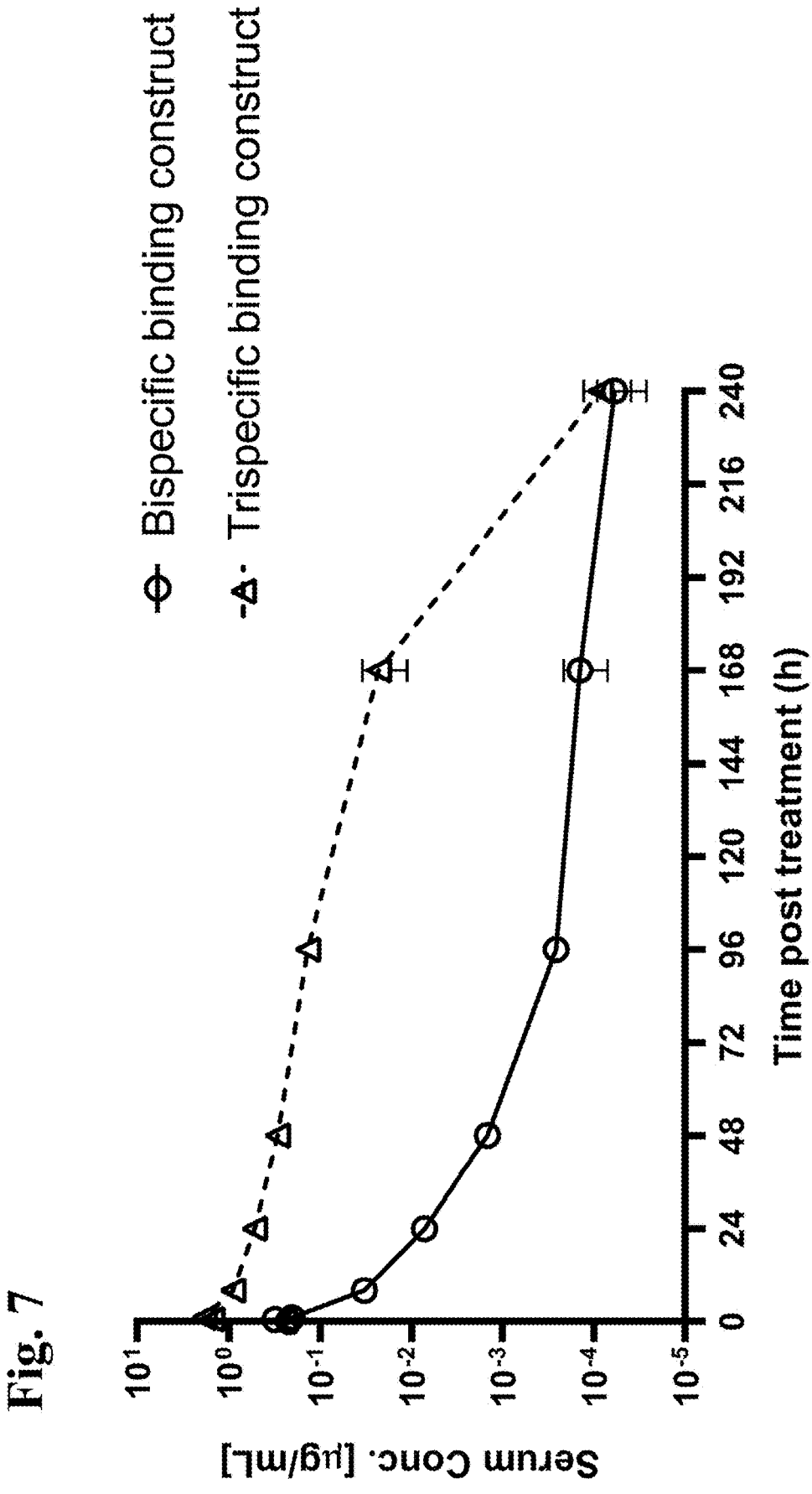
FIG. 7 illustrates the pharmacokinetics (PK) of the anti-DLL3/anti-CD3/anti-HSA trispecific binding construct compared to the anti-DLL3/anti-CD3 bispecific construct in mouse.

Balb/c mice were dosed with 1 mg/kg, single intravenous injection, 5 ml/kg volume, of either the anti-DLL3/anti-CD3/anti-HSA trispecific binding construct, or an anti-DLL3/anti-CD3 bispecific binding construct. Blood was collected at 5 min (Cmax), 1 hr, 8 hrs, 24 hrs, 48 hrs, 72 hrs, 96 hrs, 7 days, and 10 days post-injection. The serum was frozen before quantification. The concentrations of the binding constructs were measured using an in-house developed immunoassay on the MSD platform. Biotinylated capture antibody (anti-VHH, Genscript, #A02015) was linked to a streptavidin small spot plate (MSD, #R92TG). Detection anti-His-tag antibody (THE anti-HIS, Genscript, #A00186-100) was conjugated to a SULFO-TAG-NHS-Ester label (MSD, R31AA). Standard curve was generated using the same binding constructs used in the study at a concentration range from 10,000 pg/ml to 2.44 pg/ml. Mouse plasma samples were diluted with assay diluent (MSD Blocker A, #R93BA in PBS) as necessary for quantification within the range of detection, with a minimum dilution of 1:10. Samples were analyzed on the Quickplex SQ120. Standard curves and data analysis were generated using the MSD Discovery Workbench Analysis Software, v.4. The results are shown in FIG. 7 and Table 14 below.

TABLE 14

| PK of Trispecific Binding Construct vs Bispecific Binding Construct | | |
| --- | --- | --- |
| | anti-DLL3/anti-CD3/anti-HSA trispecific binding construct | anti-DLL3/anti-CD3 bispecific binding construct |
| T1/2 (h) | 33.281 | 9.02 |
| AUC∞ (h * μg/mL) | 45.959 | 1.33 |
| Cl (mL/h/kg) | 21.76 | 751.32 |
| Vss (mL/kg) | 866.28 | 8259.21 |

T1/2: serum half-life;
AUC∞: cumulative area under curve;
Cl: clearance rate;
Vss: steady state volume of distribution.

The results demonstrate that the presence of anti-HSA binding domain significantly increases the serum retention time of the binding construct.

Figure 8B:
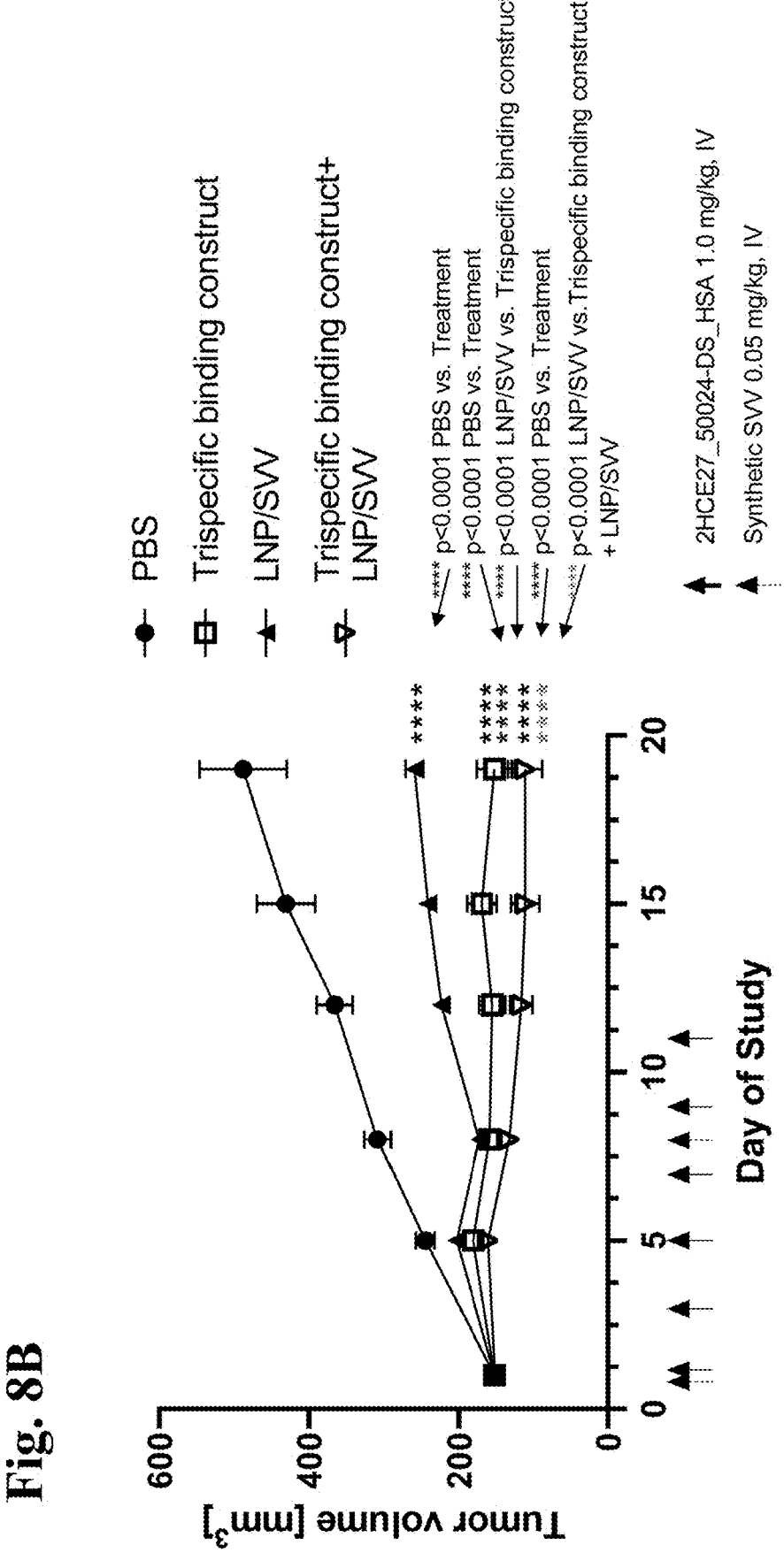
FIG. 8B illustrates the in vivo efficacy of the anti-DLL3/anti-CD3/anti-HSA trispecific binding construct and/or LNP containing synthetic SVV RNA viral genome in an NCI-H1299-hDLL3 tumor model using humanized-NSG mice.

Example 7: In Vivo Efficacy Studies of the Anti-DLL3/Anti-CD3/Anti-HSA Trispecific Binding Construct NSG mice (The Jackson Laboratory) 8 weeks old were injected with $5 \times 10^6$-NCI-H82 or NCI-H1299hDLL3-tumor cells. $10 \times 10^6$ freshly isolated PBMCs were intravenously injected 7 days prior treatment initiation. Treatments were initiated when mice reached an average tumor size of approximately 150 mm³. Mice were dosed with the anti-DLL3/anti-CD3/anti-HSA trispecific binding construct intravenously at 1.0 mg/kg every 2 days for 6 injections, and/or dosed twice with lipid nanoparticles (LNPs) containing synthetic SVV RNA viral genomes intravenously at 0.05 mg/kg every 7 days. Tumor volume and body weight were measured twice a week. Study endpoint was reached when the tumor volume reached 2000 mm³, or >20% body weight loss occurred, or tumors had open ulcerations, or mice reached 21 or 28 days from treatment initiation. The results are shown in FIG. 8A (for NCI-H82 tumor model) and FIG. 8B (for NCI-H1299-hDLL3 tumor model).

Figure 9:
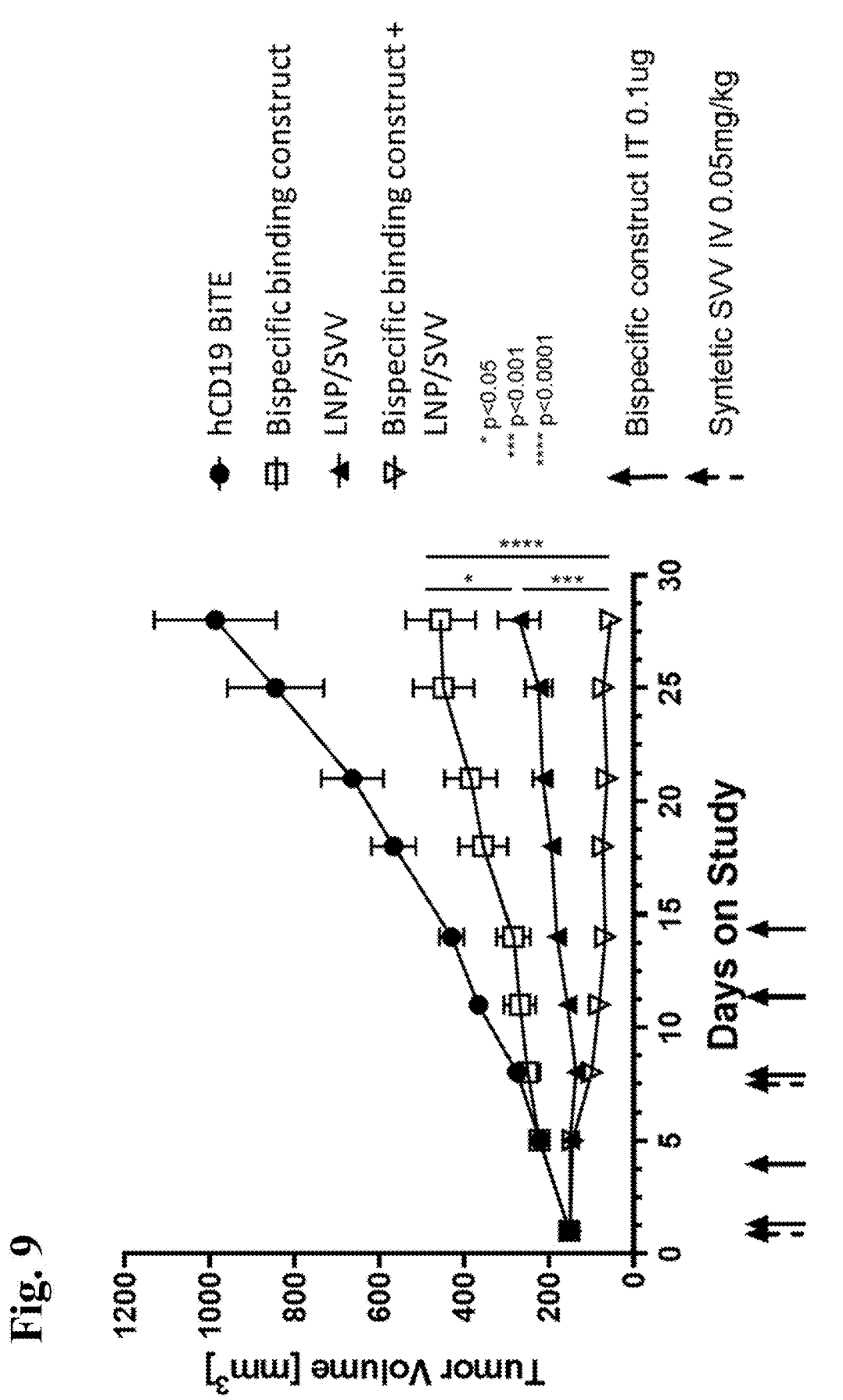
FIG. 9 illustrates the in vivo efficacy of the anti-DLL3/anti-CD3 bispecific binding construct and/or LNP containing synthetic SVV RNA viral genome in an NCI-H1299-hDLL3 tumor model using humanized-NSG mice.

In another set of experiments, NSG mice (The Jackson Laboratory) 8 weeks old were injected with $5 \times 10^6$ NCI-H1299-hDLL3 tumor cells. $10 \times 10^6$ freshly isolated PBMCs were intravenously injected 7 days prior treatment initiation. Treatments were initiated when mice reached an average tumor size of approximately 150 mm³. Mice were dosed with an anti-DLL3/anti-CD3 bispecific binding construct intratumorally at 0.1 μg every 3 days for 5 injections, and/or dosed twice with lipid nanoparticles containing synthetic SVV RNA viral genome intravenously at 0.05 mg/kg every 7 days. A human CD19 BiTE was used as a control group. Tumor volume and body weight were measured twice a week. Study endpoint was reached when the tumor volume reached 2000 mm3, or >20% body weight loss occurred, or tumors had open ulcerations, or mice reached 21 or 28 days from treatment initiation. The results are shown in FIG. 9.

These results demonstrate that a T-cell engager molecule comprising a DLL3 binding domain and a CD3 binding domain can effectively mediate the killing of cancer cells in an NCI-H1299-hDLL3 lung cancer model, and its anticancer effect is synergistic with the treatment of an oncolytic virus such as SVV.

Example 8: In Vivo Efficacy of Lipid Nanoparticles Comprising Oncolytic Virus-Encoding RNA Molecules in Combination with an Anti-DLL3 Antibody in Lung Cancer The ability of anti-DLL3 antibodies (exemplary forms include full length monoclonal antibody, T-cell engager, T-cell engager with extended half-life, NK engager, or NK engager with extended half-life) to enhance the efficacy of a lipid nanoparticles comprising Coxsackie A virus (CVA)-encoding RNA molecules to inhibit lung tumor growth in vivo are evaluated.

Briefly, 8-week-old NSG mice are injected with human PBMC on day 1, 2 and 3. On day 10, NCI-H1299-hDLL3 cells ($5\times10^6$ cells/0.1 mL in a 1:1 mixture of serum-free PBS and Matrigel®) are implanted subcutaneously in the right flank of PBMC-humanized mice. When median tumor size is approximately 150 mm$^3$ (120-180 mm$^3$ range), mice are cohorted in groups of 8-10 mice per treatment arm. Mice are treated with the anti-DLL3 antibody (via intravenous or intratumoral administration) and/or intravenous administration of CVA-RNA lipid nanoparticles. Tumor volume is measured 2 times a week to assess the efficacy of each treatment arm.

Example 9: In Vivo Efficacy of Lipid Nanoparticles Comprising Oncolytic Virus-Encoding RNA Molecules in Combination with Anti-DLL3 Antibody Encoded by an mRNA in Lung Cancer mRNA encoding an anti-DLL3 antibody (exemplary forms include full-length monoclonal antibody, T-cell engager, T-cell engager with extended half-life, NK engager, or NK engager with extended half-life) and SVV-RNA or CVA-RNA are co-formulated in lipid nanoparticles to evaluate their efficacy to inhibit lung tumor growth in vivo.

Briefly, 8-week-old NSG mice are injected with human PBMC on day 1, 2 and 3. On day 10, NCI-H1299-hDLL3 cells ($5\times10^6$ cells/0.1 mL in a 1:1 mixture of serum-free PBS and Matrigel®) are implanted subcutaneously in the right flank of PBMC-humanized mice. When median tumor size is approximately 150 mm$^3$ (120-180 mm$^3$ range), mice are cohorted in groups of 8-10 mice per treatment arm. Mice are treated with intravenous administration of SVV-RNA or CVA-RNA lipid nanoparticles or SVV-RNA or CVA-RNA lipid nanoparticles co-formulated with mRNA encoding the anti-DLL3 antibody. Tumor volume is measured 2 times a week to assess the efficacy of each treatment arm.

Example 10: In Vivo Efficacy of Lipid Nanoparticles Comprising Oncolytic Virus-Encoding RNA Molecules in Lung Cancer An oncolytic virus-RNA genome (e.g., SVV-RNA or CVA-RNA) comprising a transgene encoding an anti-DLL3 antibodies (for example, in the form of T-cell engager, or NK engager) is formulated in a lipid nanoparticle. Alternatively, a replicon comprising a transgene encoding an anti-DLL3 antibody is co-formulated with oncolytic virus-encoding RNA (e.g., SVV-RNA or CVA-RNA) in a lipid nanoparticle. These lipid nanoparticles are evaluated for their efficacy to inhibit lung tumor growth in vivo.

Briefly, 8-week-old NSG mice are injected with human PBMC on day 1, 2 and 3. On day 10, NCI-H1299-hDLL3 cells ($5\times106$ cells/0.1 mL in a 1:1 mixture of serum-free PBS and Matrigel®) are implanted subcutaneously in the right flank of PBMC-humanized mice. When median tumor size reached approximately 150 mm$_3$ (120-180 mm$_3$ range), mice are cohorted in groups of 8-10 mice per treatment arm. Mice are treated with intravenous administration of lipid nanoparticles containing oncolytic virus-encoding RNA (without transgene encoding the anti-DLL3 antibody), lipid nanoparticles containing oncolytic virus-encoding RNA comprising a transgene encoding the anti-DLL3 antibody, or lipid nanoparticles co-formulated with oncolytic virus-encoding RNA and replicons comprising a transgene encoding the anti-DLL3 antibody. Tumor volume is measured 2 times a week to assess the efficacy of each treatment arm.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

---

The invention claimed is:

1. A protein binding construct comprising a DLL3-binding domain that is capable of specifically binding DLL3 or an epitope of DLL3 comprising a heavy chain variable region (VH) comprising a complementarity determining region (CDR) 1, a CDR2, and a CDR3, wherein the CDR1, CDR2, and CDR3 comprise the amino acid sequences as set forth in any one of the following sets of SEQ ID NOs:

a) SEQ ID NOs: 46, 47, and 48, respectively;
b) SEQ ID NOs: 52, 53, and 54, respectively;
c) SEQ ID NOs: 18, 19, and 20, respectively;
d) SEQ ID NOs: 83, 2, and 84, respectively;
e) SEQ ID NOs: 60, 61, and 62, respectively;
f) SEQ ID NOs: 65, 66, and 67, respectively;
g) SEQ ID NOs: 69, 23, and 24, respectively;
h) SEQ ID NOs: 14, 43, and 71, respectively;
i) SEQ ID NOs: 73, 74, and 75, respectively;
j) SEQ ID NOs: 77, 78, and 79, respectively;
k) SEQ ID NOs: 1, 2, and 3, respectively;
l) SEQ ID NOs: 6, 7, and 8, respectively;
m) SEQ ID NOs: 10, 11, and 12, respectively;
n) SEQ ID NOs: 14, 15, and 16, respectively;
o) SEQ ID NOs: 22, 23, and 24, respectively;
p) SEQ ID NOs: 26, 27, and 28, respectively;
g) SEQ ID NOs: 30, 2, and 31, respectively;
r) SEQ ID NOs: 33, 81, and 34, respectively;
S) SEQ ID NOs: 36, 82, and 37, respectively;
t) SEQ ID NOs: 39, 40, and 41, respectively; and
u) SEQ ID NOs: 14, 43, and 44, respectively.

2. The protein binding construct of claim 1, wherein:
the CDR1 comprises an amino acid sequence of SEQ ID NO: 52;
the CDR2 comprises an amino acid sequence of SEQ ID NO: 53; and
the CDR3 comprises an amino acid sequence of SEQ ID NO: 54.

3. The protein binding construct of claim 1, wherein:
the CDR1 comprises an amino acid sequence of SEQ ID NO: 18;
the CDR2 comprises an amino acid sequence of SEQ ID NO: 19; and
the CDR3 comprises an amino acid sequence of SEQ ID NO: 20.

4. The protein binding construct of claim 1, wherein:
the CDR1 comprises an amino acid sequence of SEQ ID NO: 83;
the CDR2 comprises an amino acid sequence of SEQ ID NO: 2; and
the CDR3 comprises an amino acid sequence of SEQ ID NO: 84.

5. The protein binding construct of claim 1, wherein:
the CDR1 comprises an amino acid sequence of SEQ ID NO: 60;
the CDR2 comprises an amino acid sequence of SEQ ID NO: 61; and
the CDR3 comprises an amino acid sequence of SEQ ID NO: 62.

6. The protein binding construct of claim 1, wherein:
the CDR1 comprises an amino acid sequence of SEQ ID NO: 65;
the CDR2 comprises an amino acid sequence of SEQ ID NO: 66; and
the CDR3 comprises an amino acid sequence of SEQ ID NO: 67.

7. The protein binding construct of claim 1, wherein:
the CDR1 comprises an amino acid sequence of SEQ ID NO: 69;
the CDR2 comprises an amino acid sequence of SEQ ID NO: 23; and
the CDR3 comprises an amino acid sequence of SEQ ID NO: 24.

8. The protein binding construct of claim 1, wherein:
the CDR1 comprises an amino acid sequence of SEQ ID NO: 14;
the CDR2 comprises an amino acid sequence of SEQ ID NO: 43; and
the CDR3 comprises an amino acid sequence of SEQ ID NO: 71.

9. The protein binding construct of claim 1, wherein:
the CDR1 comprises an amino acid sequence of SEQ ID NO: 73;
the CDR2 comprises an amino acid sequence of SEQ ID NO: 74; and
the CDR3 comprises an amino acid sequence of SEQ ID NO: 75.

10. The protein binding construct of claim 1, comprising or consisting of an amino acid sequence that is at least 95%, at least 96%, at least 97%, at least 98%, or at least 99% identical to an amino acid sequence selected from SEQ ID NOs: 4, 5, 9, 13, 17, 21, 25, 29, 32, 35, 38, 42, 45, 49, 55, 59, 63, 64, 68, 70, 72, and 76.

11. The protein binding construct of claim 1, further comprising a human framework region sequence.

12. The protein binding construct of claim 11, wherein:
the CDR1 comprises an amino acid sequence of SEQ ID NO: 46;
the CDR2 comprises an amino acid sequence of SEQ ID NO: 47; and
the CDR3 comprises an amino acid sequence of SEQ ID NO: 48.

13. The protein binding construct of claim 11, wherein:
the CDR1 comprises an amino acid sequence of SEQ ID NO: 52;
the CDR2 comprises an amino acid sequence of SEQ ID NO: 53; and
the CDR3 comprises an amino acid sequence of SEQ ID NO: 54.

14. The protein binding construct of claim 11, wherein:
the CDR1 comprises an amino acid sequence of SEQ ID NO: 18;
the CDR2 comprises an amino acid sequence of SEQ ID NO: 19; and
the CDR3 comprises an amino acid sequence of SEQ ID NO: 20.

15. The protein binding construct of claim 11, wherein:
the CDR1 comprises an amino acid sequence of SEQ ID NO: 83;
the CDR2 comprises an amino acid sequence of SEQ ID NO: 2; and
the CDR3 comprises an amino acid sequence of SEQ ID NO: 84.

16. The protein binding construct of claim 11, wherein:
the CDR1 comprises an amino acid sequence of SEQ ID NO: 60;
the CDR2 comprises an amino acid sequence of SEQ ID NO: 61; and
the CDR3 comprises an amino acid sequence of SEQ ID NO: 62.

17. The protein binding construct of claim 11, wherein:
the CDR1 comprises an amino acid sequence of SEQ ID NO: 65;
the CDR2 comprises an amino acid sequence of SEQ ID NO: 66; and the CDR3 comprises an amino acid sequence of SEQ ID NO: 67.

18. The protein binding construct of claim 11, wherein:
the CDR1 comprises an amino acid sequence of SEQ ID NO: 69;
the CDR2 comprises an amino acid sequence of SEQ ID NO: 23; and
the CDR3 comprises an amino acid sequence of SEQ ID NO: 24.

19. The protein binding construct of claim 11, wherein:
the CDR1 comprises an amino acid sequence of SEQ ID NO: 14;
the CDR2 comprises an amino acid sequence of SEQ ID NO: 43; and
the CDR3 comprises an amino acid sequence of SEQ ID NO: 71.

20. The protein binding construct of claim 11, wherein:
the CDR1 comprises an amino acid sequence of SEQ ID NO: 73;
the CDR2 comprises an amino acid sequence of SEQ ID NO: 74; and
the CDR3 comprises an amino acid sequence of SEQ ID NO: 75.

21. The protein binding construct of claim 11, comprising or consisting of an amino acid sequence that is at least 95%, at least 96%, at least 97%, at least 98%, or at least 99% identical to an amino acid sequence selected from SEQ ID NOs: 50, 51, 56, 57 and 58.

22. A chimeric antigen receptor (CAR) comprising the protein binding construct of claim 1.

23. A method of treating cancer in a subject in need thereof, comprising administering an effective amount of the protein binding construct of claim 11 to the subject, thereby treating the subject.

24. The protein binding construct of claim 1, wherein:
the CDR1 comprises an amino acid sequence of SEQ ID NO: 46;
the CDR2 comprises an amino acid sequence of SEQ ID NO: 47; and
the CDR3 comprises an amino acid sequence of SEQ ID NO: 48.

* * * * *